US011497724B2

(12) United States Patent
Kovacs

(10) Patent No.: US 11,497,724 B2
(45) Date of Patent: Nov. 15, 2022

(54) CCL5 INHIBITORS

(71) Applicant: LAPKO INC., Las Vegas, NV (US)

(72) Inventor: Bruce Kovacs, Irvine, CA (US)

(73) Assignee: LAPKO INC, Las Vegas, NV (US)

( * ) Notice: Subject to any disclaimer, the term of this patent is extended or adjusted under 35 U.S.C. 154(b) by 0 days.

(21) Appl. No.: 17/580,429

(22) Filed: Jan. 20, 2022

(65) Prior Publication Data

US 2022/0142961 A1 May 12, 2022

Related U.S. Application Data

(63) Continuation of application No. 17/191,196, filed on Mar. 3, 2021, now Pat. No. 11,318,111, which is a continuation of application No. 16/724,235, filed on Dec. 21, 2019, now Pat. No. 10,940,132, which is a continuation of application No. PCT/US2019/037240, filed on Jun. 14, 2019.

(60) Provisional application No. 62/685,455, filed on Jun. 15, 2018.

(51) Int. Cl.
*A61K 31/216* (2006.01)
*A61P 17/02* (2006.01)
*A61K 45/00* (2006.01)

(52) U.S. Cl.
CPC ............ *A61K 31/216* (2013.01); *A61K 45/00* (2013.01); *A61P 17/02* (2018.01)

(58) Field of Classification Search
None
See application file for complete search history.

(56) References Cited

U.S. PATENT DOCUMENTS

| 2010/0256118 | A1 | 10/2010 | Isobe et al. |
| 2010/0297048 | A1 | 11/2010 | Moussou et al. |
| 2014/0037564 | A1 | 2/2014 | Chung et al. |
| 2014/0228419 | A1 | 8/2014 | Kalbe et al. |
| 2020/0138766 | A1 | 5/2020 | Kovacs |

FOREIGN PATENT DOCUMENTS

| WO | WO-03106384 A2 * | 12/2003 | ............ C07F 5/025 |
| WO | 2004080478 A1 | 9/2004 | |
| WO | 2012130850 A1 | 10/2012 | |
| WO | 2016202341 A1 | 12/2016 | |

OTHER PUBLICATIONS

Xu et al. "Copper-promoted trifluoromethylation of primary and secondary alkylboronic acids," Angewandte Chemie, International Edition (2012), 51(50), 12551-12554 (Year: 2012).*
U.S. Appl. No. 16/724,235, filed Dec. 21, 2019.
U.S. Appl. No. 17/191,196, filed Mar. 3, 2021.
Allen SJ et al, "Chemokine: Receptor Structure, Interactions, and Antagonism", Annu Rev Immunol, 2007, vol. 25:787-820.
Antinolo G et al, "Evaluation of germline sequence variants within the promoter region of RANTES gene in a cohort of women with endometriosis from Spain", Molecular Human Reproduction, 2003, vol. 9(8):491-495.
Camargo JF et al, "CCR5 Expression Levels Influence NFAT Translocation, IL-2 Production, and Subsequent Signaling Events during T Lymphocyte Activation1", Journal of Immunology, 2009, vol. 182:171-182.
Chen Y et al, "Chemokine gene polymorphisms associate with gender in patients with uveitis", Tissue Antigens, 2004, vol. 63:41-45.
Chirhara J et al, "Elevation of the plasma level of RANTES during asthma attacks", J Allergy Clin Immunol, 1997, vol. 100(6), Part 2:S53-S55.
Fukaya et al, "Topical clofibrate improves symptoms in patients with atopic dermatitis and reduces serum TARC levels: a randomized, double-blind, placebo-controlled pilot study," J Drugs Dermatol, 2014, vol. 13(3):259-63.
Iijima W et al, "Infiltrating CD8+ T Cells in Oral Lichen Planus Predominantly Express CCR5 and CXCR3 and Carry Respective Chemokine Ligands RANTES/CCL5 and IP-10/CXCL10 in Their Cytolytic GranulesA Potential Self-Recruiting Mechanism", American Journal of Pathology, 2003, vol. 163(1):261-268.
International Search Report dated Oct. 17, 2019.
Kaur G and Dufour JM, "Cell lines Valuable tools or useless artifacts", Spermatogenesis, 2012, vol. 2(1):1-5.
Lin S et al, "Chemokine C-C motif receptor 5 and C-C motif ligand 5 promote cancer cell migration under hypoxia", Cancer Sci, 2012. vol. 103(5):904-912.
Makki RF et al, "RANTES gene polymorphism in polymyalgia rheumatica, giant cell arteritis and rheumatoid arthritis", Clinical and Experimental Rheumatology, 2000, vol. 18:391-393.
Marques RE et al, "Targeting CCL5 in inflammation", Expert Opinion on Therapeutic Targets, 2013, vol. 17(12):1-22.
Mitchell D and Olive C, "Regulation of Toll-like receptor-induced chemokine production in murine dendritic cells by mitogen-activated protein kinases", Molecular Immunology, 2010, vol. 47:2065-2073.
Murdoch C and Finn A, "Chemokine receptors and their role in inflammation and infectious diseases", Blood, 2000, vol. 95(10):3032-3043.
Murphy PM, "International Union of Pharmacology. XXX. Update on Chemokine Receptor Nomenclature", Pharmacol Rev, 2002, vol. 54:227-229.
Murphy PM, "The Molecular Biology of Leukocyte Chemoattractant Receptors1", Annu Rev Immunol, 1994, vol. 12:593-633.
Nickel RG et al, "Atopic Dermatitis Is Associated with a Functional Mutation in the Promoter of the C-C Chemokine RANTES1", The Journal of Immunology, 2000, vol. 164:1612-1616.
Rival Y et al, "PPARa and PPARd activators inhibit cytokine-induced nuclear translocation of NF-kB and expression of VCAM-1 in EAhy926 endothelial cells", European Journal of Pharmacology, 2002, vol. 435:143-151.

(Continued)

Primary Examiner — Jeffrey S Lundgren
Assistant Examiner — Michael J Schmitt
(74) Attorney, Agent, or Firm — Gorman IP Law, APC

(57) ABSTRACT

Compounds, pharmaceutically acceptable salts, esters, prodrugs, and pharmaceutical compositions thereof are disclosed that are useful for inhibition of the biological activity of CCL5 on mammalian cells, as well as methods of treatment for diseases involving the increased biological activity of CCL5.

10 Claims, 6 Drawing Sheets

(56) References Cited

OTHER PUBLICATIONS

Figure 1A:
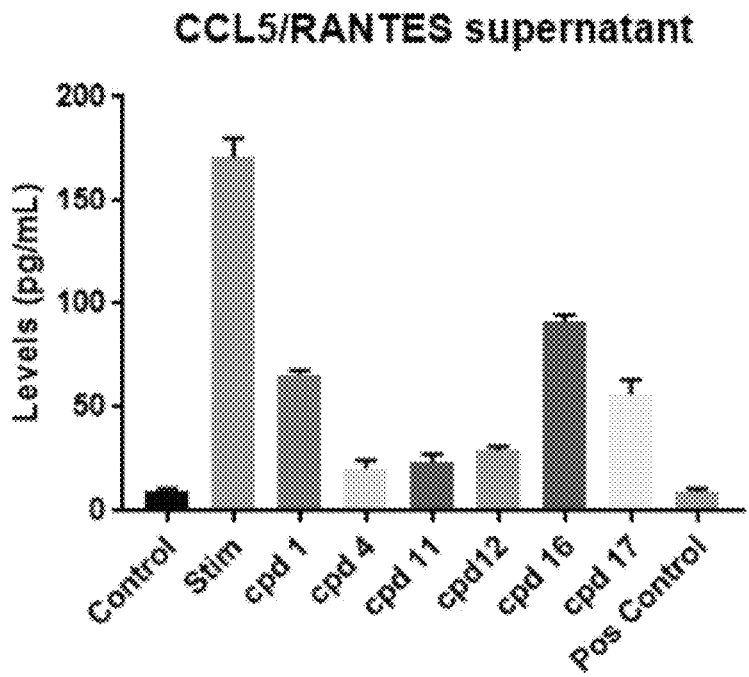

Russo CR et al, "Anti-inflammatory drug development: Broad or specific chemokine receptor antagonists?", Current Opinion in Drug Discovery & Development, 2010, vol. 13(4):414-427.
Schall TJ et al, "A human T cell-specific molecule is a member of a new gene family.", J Immunol, 1988, vol. 141:1018-1025.
Sheu et al, "Topical Peroxisome Proliferator Activated Receptor-a Activators Reduce Inflammation in Irritant and Allergic Contact Dermatitis Models," J. Invest. Dermatol, 2002 vol. 118:94-101.
Szodoray P et al, "Circulating Cytokines in Primary Sjogren's Syndrome Determined by a Multiplex Cytokine Array System", Scandinavian Journal of Immunology, 2004, vol. 59:592-599.
Tanaka K et al, "Upregulating promoter polymorphisms of RANTES relate to atopic dermatitis", International Journal of Immunogenetics, 2006, vol. 33:423-428.
Toebak MJ et al, "CXCL8 secretion by dendritic cells predicts contact allergens from irritants", Toxicology in Vitro, 2006, vol. 20:117-124.
Turner MD et al, "Cytokines and chemokines: At the crossroads of cell signalling and inflammatory disease", Biochimica et Biophysica Acta, 2014, vol. 1843:2563-2582.
Villarroel M et al, "Fenofibric acid prevents retinal pigment epithelium disruption induced by interleukin-1$\beta$ by suppressing AMP-activated protein kinase (AMPK) activation", Diabetologia, 2011, vol. 54:1543-1553.
Wesler J, "Primary Cells Versus Cell Lines", ScienCell Research Laboratories Online, 2015, pp. 1-2.
Yamamoto M et al, "Serum cytokines correlated with the disease severity of generalized pustular psoriasis", Disease Markers, 2013, vol. 34:153-161.
Zhebrun et al, "Synthesis of Some CC Chemokines and Their Receptors in the Synovium in Rheumatoid Arthritis", Bulletin of Experimental Biology and Medicine, 2014, vol. 158(2):192-196.

\* cited by examiner

CCL5 INHIBITORS

This Non-Provisional application is a Continuation application of application Ser. No. 17/191,196 filed on Mar. 3, 2021, which is a Continuation application of application Ser. No. 16/724,235 filed Dec. 21, 2019, which is a Continuation application of PCT International Application No. PCT/US2019/037240 filed on Jun. 14, 2019, which claims priority under 35 U.S.C. § 119 to Provisional Application No. 62/685,455 filed in the United States on Jun. 15, 2018, the entire contents of each of which are hereby incorporated by reference.

FIELD OF THE INVENTION

This invention pertains to inhibitors of the biological effects of CCL5 on mammalian cells. The invention provides compounds and methods useful for inhibition of the biological effects of CCL5 on mammalian cells and for the treatment of dermatologic, ocular, respiratory, and other diseases associated with increased CCL5 biological activity on human cells and tissues.

BACKGROUND OF THE INVENTION

Chemokines constitute a family of chemoattractant cytokines and are subdivided into four families on the basis of the number and spacing of the conserved cysteine residues in the N-terminus of the protein. Chemokines play a major role in selectively recruiting monocytes, neutrophils, and lymphocytes, as well as in inducing chemotaxis through the activation of G-protein-coupled receptors. CCL5 (also known as RANTES) belongs to the C—C chemokine subfamily, whose chemokines present adjacent cysteines, and comprises the majority of the chemokines [1, 2]. This chemokine plays an important role in leukocyte biology and disease pathogenesis by controlling cell recruitment and activation in basal and in inflammatory circumstances. In addition, because chemokine receptors are expressed on other cell types, chemokines have multiple other roles, including angiogenesis, tissue and vascular remodeling, pathogen elimination, antigen presentation, leukocyte activation and survival, chronic inflammation, tissue repair/healing, fibrosis, embryogenesis and tumorigenesis [3,4]. The many biologic effects of chemokines are mediated by their interaction with chemokine receptors on the cell surface. The most relevant known receptors for CCL5 are CCR1, CCR3, and CCR5[1].

CCL5 has been shown to induce the in vitro migration and recruitment of T cells, dendritic cells, eosinophils, NK cells, mast cells, and basophils. Although initially considered to be a T cell-specific cytokine (hence the original name, RANTES; regulated upon activation, normal T cell expressed and secreted) [5], CCL5 is produced by platelets, macrophages, eosinophils, fibroblasts, endothelium, epithelial, and endometrial cells. The variety of cells that express and mediate CCL5 effects implicates this chemokine in multiple biological processes, from pathogen control to enhancement of inflammation in several disorders, such as: arthritis, asthma, cancer, dermatitis, endometriosis, lichen planus, psoriasis, Sjogren syndrome, uveitis, and others [6, 7, 8, 9, 10, 11, 12, 13, 14, 15, 16].

Certain types of normal mammalian and human cells such as; endothelial, epithelial, fibroblast, keratinocyte, smooth muscle, mesangial, astrocyte, monocyte, and microglial cells can be induced to produce and secrete high levels of CCL5 by stimulation with various substances and under a variety of stress conditions. In the resting state of these cells the level of CCL5 is barely detectable. However, exposure of these cells to various stimulants alone or in combination, such as cytokines; IL-1b, and TNF-alpha, cause increase in production of CCL5 [17]. When these types of cells are subjected to stress conditions such as low oxygen levels (hypoxia) they respond by producing increased amounts of CCL5 [18]. In addition, when these types of cells are exposed to various bacterial antigens or components of bacterial cell breakdown such as lipoteichoic acid, flagellin, and lipopolysaccharide (LPS) they are induced to produce and secrete increased amount of CCL5. In addition, substances that mimic bacterial, viral and fungal components such as Poly(I:C) and Pam3Cys also induce these types of mammalian cells to produce increased amounts of CCL5 [19].

CCL5 binds to and transduces signals through the G-protein-coupled receptors, such as; CCR5, CCR3, and CCR4. These receptors are present on many types of human cells such as: leukocytes, peripheral blood mononuclear cells (PBMCs), fibroblasts, vascular smooth muscle cells, endothelial cells, and astrocytes [20].

When CCL5 binds to its cell surface receptors on leukocytes it causes them to produce cytokines such as; IL-1 alpha (Interleukin 1 alpha), IL-1 beta (Interleukin 1 beta), IFN-gamma (Interferon gamma), CCL2 (chemokine motif ligand 2), and IL-8 (Interleukin 8) [21], which participate in increasing inflammatory response and contribute to tissue damage, pain, and loss of function in several inflammatory diseases. Binding of CCL5 to its receptors on endothelial cells causes them to produce VEGF-A, an angiogenic protein.

Increased CCL5 production by human endothelial, epithelial, fibroblasts, keratinocytes, smooth muscle, mesangial, astrocytic, monocytic, and microglial cells promotes inflammation, inflammation-dependent disease progression, subsequent tissue destruction, and loss of function in various human tissues such as the dermis, epidermis, ocular uvea, and pulmonary bronchial epithelium by serving to attract monocytes, T-lymphocytes, and natural killer cells, and by increasing the production of pro-fibrosis genes in fibroblasts. Increased production of CCL5 by cells and tissues leads to increased blood levels of CCL5. An inherited genetic variant in the CCL5 gene promotor region is associated with several diseases [22, 23]. Therefore, CCL5 is an important therapeutic target to treat inflammatory diseases such as those referenced herein. There are no approved drugs on the market that reduce cellular production of CCL5 [24]. Thus, there is a need for chemical compounds that inhibit the production of CCL5 by mammalian cells, especially those in epithelial tissues such as; skin, lung, gastrointestinal tract, eye, genito-urinary tract and endocrine glands, as well as in endothelial tissues.

SUMMARY OF THE INVENTION

According to one embodiment of the present invention, there is provided a compound of Formula 1 below:

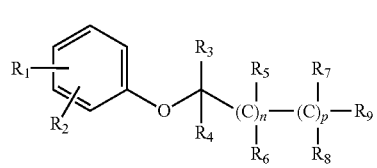

Formula 1 wherein:

n and p are independently selected from 0 or 1;

$R_1$ and $R_2$ are independently selected from H, OH, F, Cl, Br, I, (halogen)alkyl, $C_1$-$C_8$ straight or branched chain alkyl, $C_1$-$C_8$ cycloalkyl, heterocycloalkyl, alkylheterocycloalkyl, optionally substituted $C_1$-$C_8$ alkenyl, optionally substituted $C_1$-$C_8$ alkynyl, optionally substituted aryl, optionally substituted alkylaryl, optionally substituted heteroaryl, optionally substituted alkylheteroaryl, O-alkyl, O-cycloalkyl, O-alkylcycloalkyl, O-aryl, O-optionally substituted aryl, alkyl-O-aryl, alkyl-O-optionally substituted aryl, C(O)-aryl, C(O)-optionally substituted aryl, $CH_2C(O)$-aryl, $CH_2C(O)$-optionally substituted aryl, O-(halogen)alkyl; $R_3$, $R_4$, $R_5$, $R_6$, $R_7$, and $R_8$, if present, are independently selected from H, $C_1$-$C_8$ straight or branched chain alkyl, $C_1$-$C_8$ cycloalkyl, heterocycloalkyl, alkylheterocycloalkyl, optionally substituted $C_1$-$C_8$ alkenyl, optionally substituted $C_1$-$C_8$ alkynyl, optionally substituted aryl, optionally substituted alkylaryl, optionally substituted heteroaryl, or optionally substituted alkylheteroaryl, and/or adjacent substituents $R_1$ and $R_2$, $R_3$ and $R_4$, $R_5$ and $R_6$, $R_7$ and $R_8$, if present, may form a saturated or unsaturated 3-7 membered carbocyclic or heterocyclic ring; $R_9$ is selected from COOH, COO-straight or branched chain alkyl, $B(OH)_2$, $B(OR_{10})(OR_{11})$;

$R_{10}$ and $R_{11}$, if present, are independently selected from optionally substituted alkyl, cycloalkyl, alkylcycloalkyl, and/or when $R_{10}$ and $R_{11}$ are present and adjacent to each other can together form an alkyl bridged 5 or 6 membered heterocyclic ring, or a pharmaceutically acceptable salt, ester or prodrug form thereof with the proviso that when n and p are both 0, $R_1$ is H, $R_3$ is methyl, $R_4$ is methyl, and $R_9$ is COOH, $COOCH_3$, or $COOC_2H_5$, then $R_2$ cannot be Cl, and when and p are both 0, $R_2$ is H, $R_3$ is methyl, $R_4$ is methyl, and $R_9$ COOH, $COOCH_3$, or $COOC_2H_5$, then $R_1$ cannot be Cl.

Additional embodiments of the invention include a pharmaceutical composition comprising a compound as defined above and a pharmaceutically acceptable carrier and/or diluent for topical application.

Another embodiment of the invention is the inhibition of the production of CCL5 by cells comprising mammalian epithelial tissues by topical application of a compound or compounds according to Formula 1, either alone or in combination with other bioactive substances.

Yet another embodiment of the invention is the inhibition of the production of CCL5 by cells comprising mammalian vascular endothelial tissues by application of a compound or compounds according to Formula 1, either alone or in combination with other bioactive substances, by directly contacting the endothelial cells.

An additional embodiment of the invention is the inhibition of the biological effect of CCL5 on mammalian cells such as, but not limited to, epithelial cells, monocytic cells, and endothelial cells, as well as tissues containing these cells, by application of a compound or compounds according to Formula 1, either alone or in combination with other bioactive substances.

A further embodiment of the invention is the use of a compound as defined above in the manufacture of a medicament for the treatment of a mammal at risk for or having at least one disease or disorder associated with elevated CCL5 levels. Non-limiting examples of such disorders are: inflammatory skin disorders and/or diseases; urticarial conditions; respiratory ailments; airway and pulmonary conditions; gastrointestinal disorders; genito-urinary disorders; allergic diseases; atopic disorders; infection-based diseases; trauma and tissue injury-based conditions; fibrotic diseases; and/or ophthalmic/ocular diseases.

BRIEF DESCRIPTIONS OF THE DRAWINGS

Figure 1B:
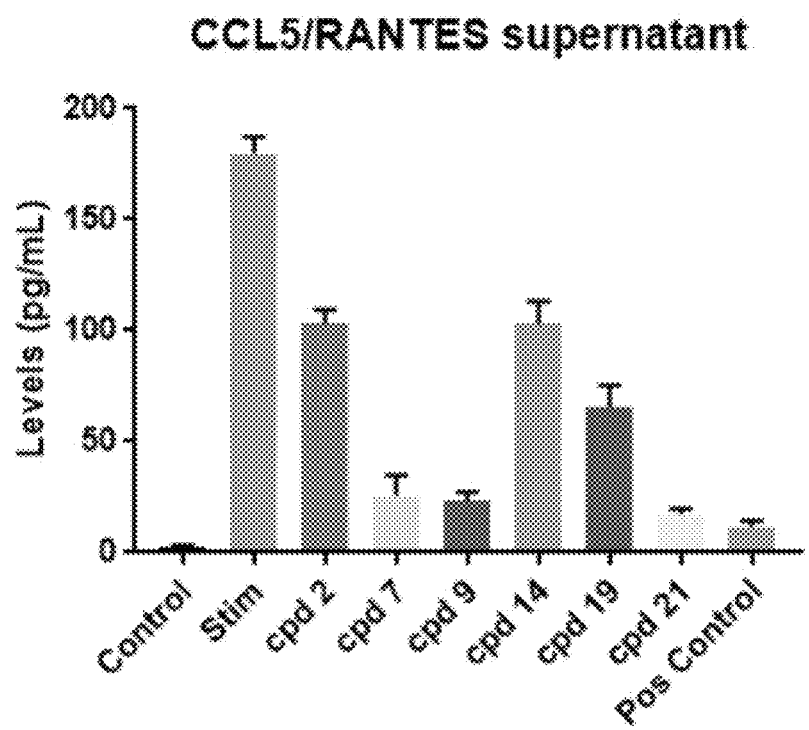

FIG. 1a-b: Reduced production of CCL5 by human keratinocyte cells after treatment with compounds of Formula 1. FIG. 1a: cells were stimulated with Poly (I:C). FIG. 1b: cells were stimulated with Flagellin.

Figure 2A:
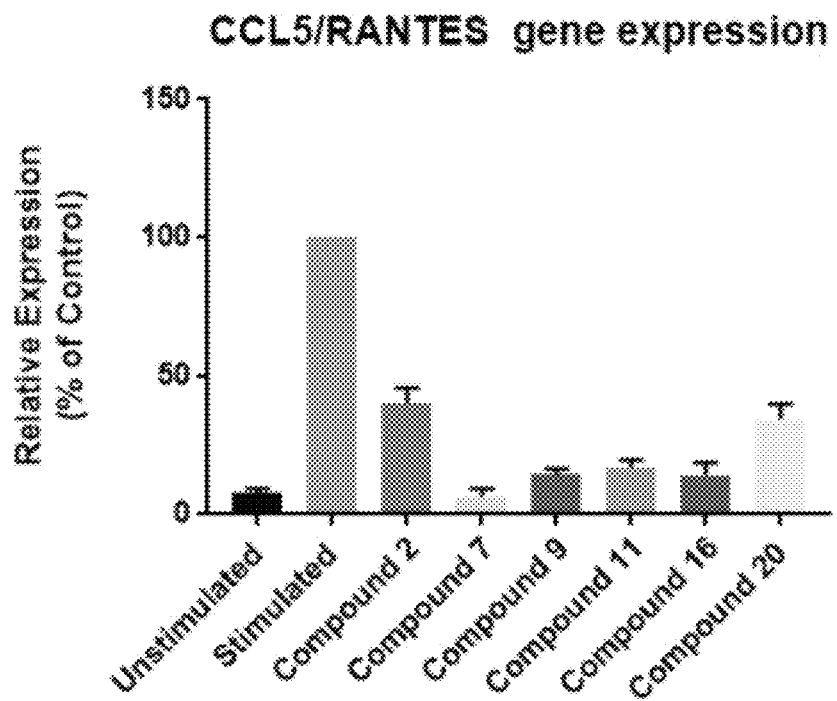
Figure 2B:
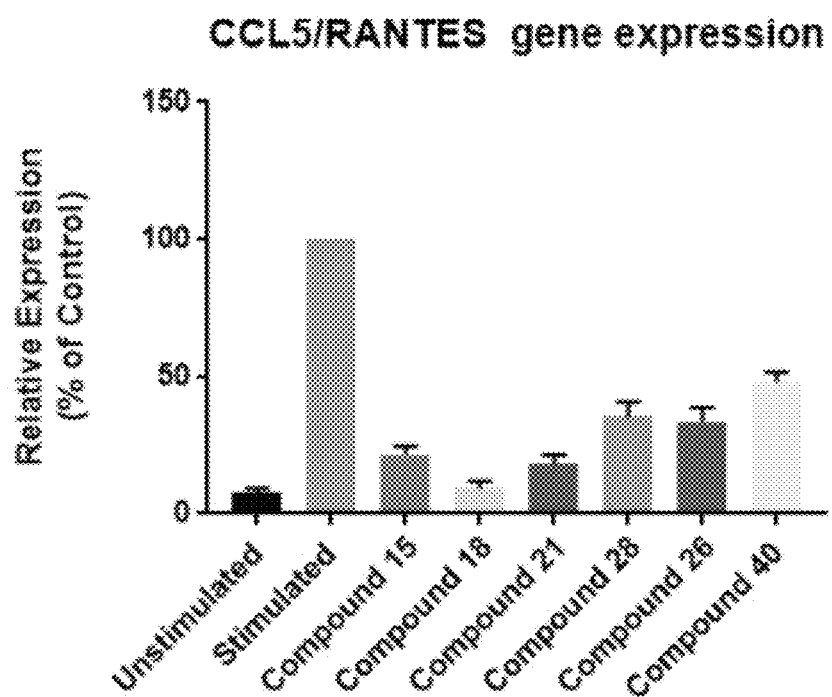

FIG. 2a-b: Decreased expression of the CCL5 gene in human keratinocyte cells and human bronchial epithelial cells after treatment with compounds of Formula 1. FIG. 2a: HEHK cells were stimulated with Poly (I:C). FIG. 2b: NHBE cells were stimulated with TNF-alpha.

Figure 3:
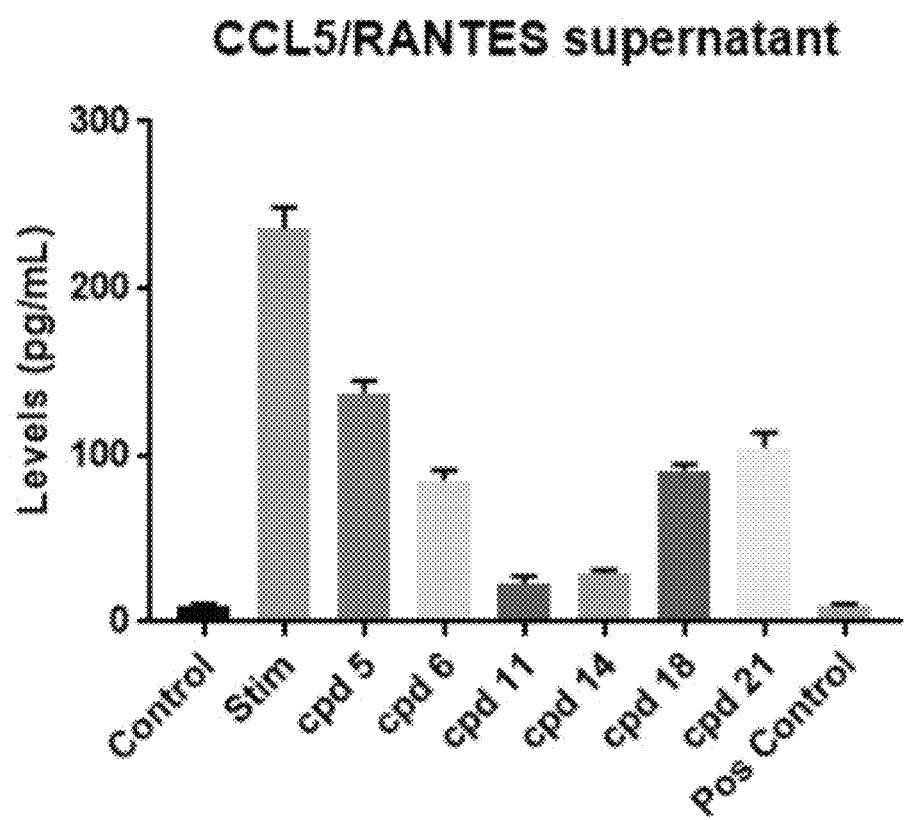

FIG. 3: Reduced production of CCL5 induced by stimulation of human keratinocyte cells with TNF-alpha after treatment with compounds of Formula 1.

Figure 4:
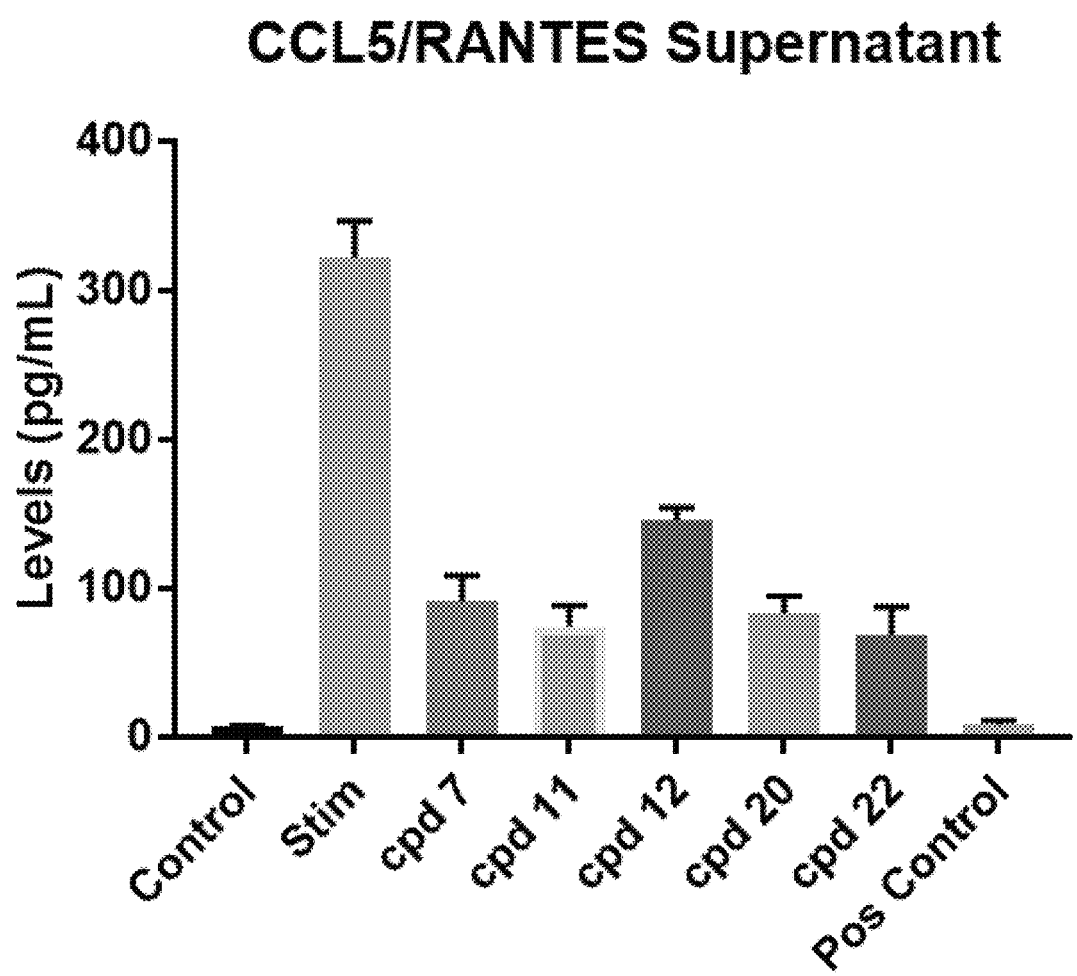

FIG. 4: Reduced production of CCL5 induced by stimulation of human umbilical vein endothelial cells (HUVEC) with TNF-alpha after treatment with compounds of Formula 1.

Figure 5A:
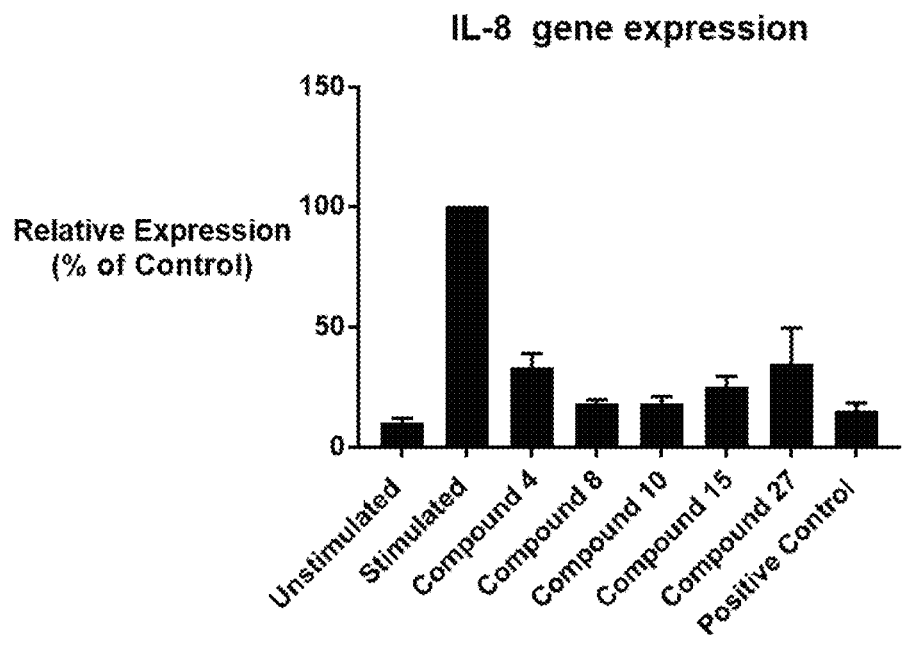
Figure 5B:
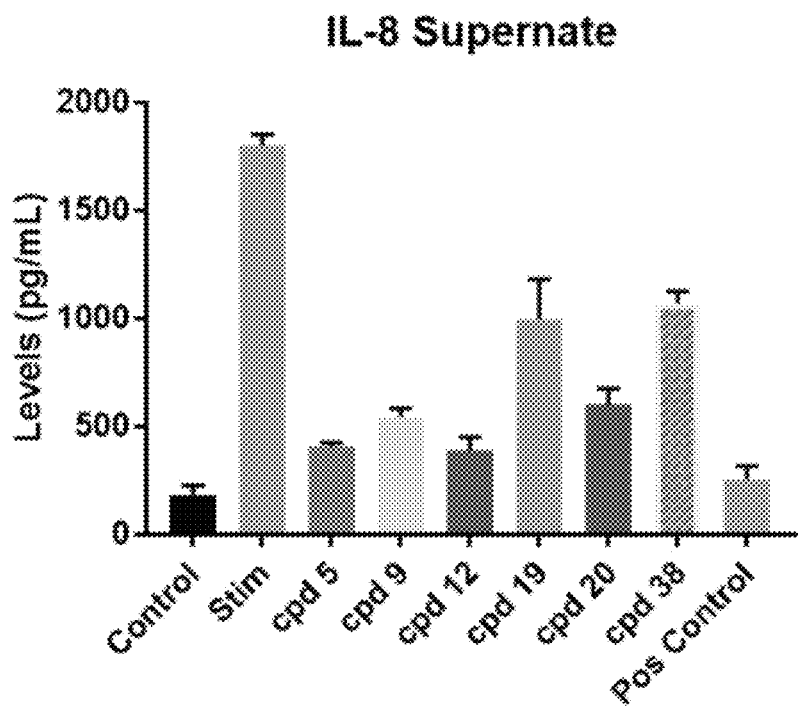
Figure 5C:
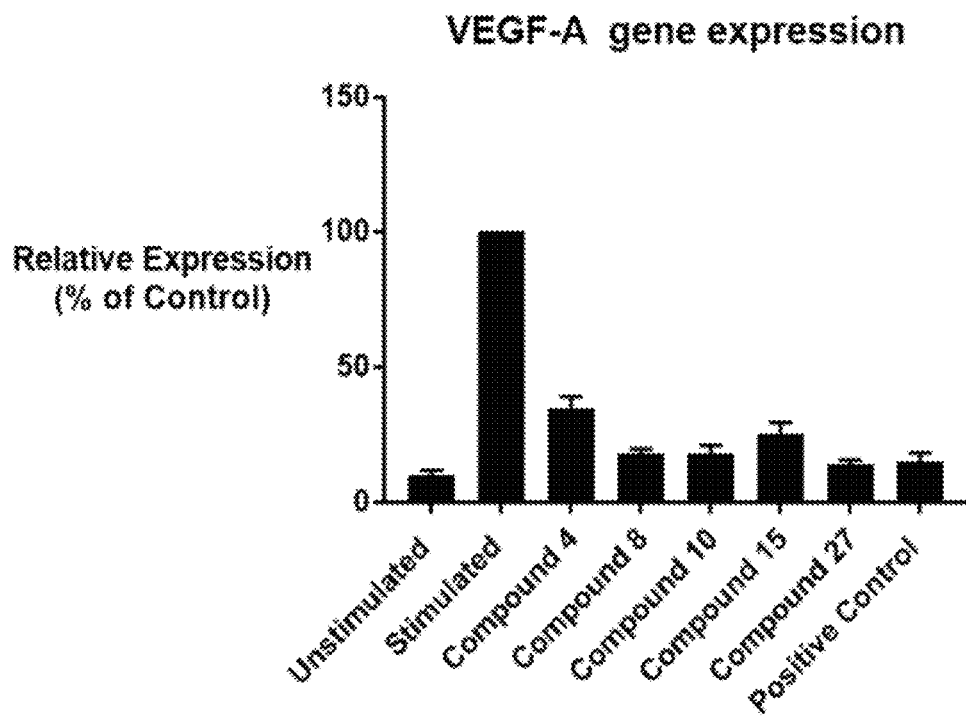
Figure 5D:
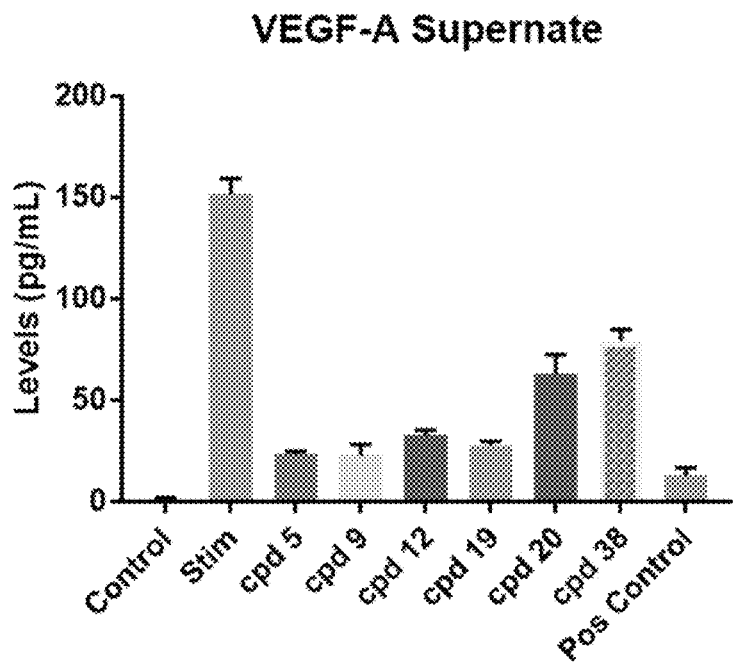

FIG. 5a-d: Reduced production of IL-8 by human peripheral blood monocyte cells (PBMCs) and reduced production of VEGF-A by human umbilical vein endothelial cells (HUVEC) induced by stimulation with recombinant human CCL5/RANTES after treatment with compounds of Formula 1. FIG. 5a: IL-8 gene expression. FIG. 5b: IL-8 Supernate. FIG. 5c: VEGF-A gene expression. FIG. 5d: VEGF-A Supernate.

DETAILED DESCRIPTION OF THE INVENTION

Compounds embodied by Formula 1 may have one or several asymmetric centers and therefore can exist in different stereoisomeric configurations. Consequently, the compound of Formula 1 can occur as individual (pure) enantiomers, individual pure enantiomeric diastereomers as well as a mixture of enantiomers or diastereomers. The scope of the present invention includes both single enantiomers and mixtures thereof in all ratios. The scope of the present invention further includes all tautomeric forms ("tautomers") of the compounds of Formula 1, and all mixtures thereof in any ratio. It will be appreciated by one skilled in the art that a single compound may exhibit more than one type of isomerism.

The enantiomeric compounds of Formula 1 may be resolved into their pure enantiomers by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, specific stereoisomers may be synthesized by using an optically active starting material, by asymmetric synthesis using optically active reagents, substrates, catalysts or solvents, or by converting one stereoisomer into the other by asymmetric transformation or inversion.

The compounds of the present invention may exist in unsolvated as well as a variety of solvated forms with pharmaceutically acceptable solvents such as water, ethanol, and the like. In general, the solvated forms are considered equivalent to the unsolvated forms for the purposes of the present invention. It should be understood that pharmaceutically acceptable solvents further include isotopically substituted solvents such as $D_2O$, dimethyl sulfoxide-d6, and the like. The term 'solvate' is used herein to describe a complex comprising the compound of the invention and one or more pharmaceutically acceptable solvent molecules, including water. As such, all manner of hydrates of the compound are included by the term 'solvate'. It is intended that the present invention embrace unsolvated forms, solvated forms and mixtures of solvated forms in any ratio.

The compound of the present invention and/or its salts and/or solvate may exist as amorphous solids or may exist in one or more crystalline states, i.e. polymorphs. Polymorphs of the compound of Formula 1 are encompassed in the present invention and may be prepared by crystallization under a number of different conditions such as, for example, using different solvents or different solvent mixtures; crystallization at different temperatures; and using various modes of cooling ranging from very fast to very slow during crystallization. Polymorphs may also be obtained by heating or melting a compound of Formula 1 followed by gradual or fast cooling. The presence of polymorphs may be determined by solid NMR spectroscopy, IR spectroscopy, differential scanning calorimetry, powder x-ray diffraction or other techniques. It should be understood that all such crystalline and amorphous forms of the compound of Formula 1, and its salts, solvates, and prodrugs thereof are encompassed by the invention and the claims.

The present invention also includes all pharmaceutically acceptable isotopically labeled variations of the compound of Formula 1. Such isotopically labeled variations are compounds having the same Formula and molecular formula as the compound of Formula 1 but wherein one or more atoms are replaced by atoms having an atomic mass or mass number different from the atomic mass or mass number usually found in nature. Examples of isotopes that may be incorporated into the compound of the present invention include isotopes of hydrogen, carbon, fluorine, nitrogen, and oxygen, such as $^2H$, $^3H$, $^{11}C$, $^{13}C$, $^{14}C$, $^{18}F$, $^{13}N$, $^{15}N$, $^{17}O$, and $^{18}O$, respectively.

Certain isotopically labeled variations of the compound of the present invention such as, for example, those incorporating a radioactive isotope such as $^3H$ and $^{14}C$, are useful in drug and/or substrate tissue distribution studies. Tritium, i.e. $^3H$, and carbon-14, i.e. $^{14}C$, are particularly preferred due their ease of preparation and detection. Further, substitution with heavier isotopes such as deuterium, i.e. $^2H$, can afford certain therapeutic advantages resulting from greater metabolic stability, for example, increased in vivo half-life or reduced dosage requirements, and hence may be preferred in some circumstances. Isotopically labeled compounds of Formula 1 of this invention and prodrugs thereof can generally be prepared by carrying out the procedures disclosed in the Schemes and/or in the Examples by substituting a readily available isotopically labeled reagent for a non-isotopically labeled reagent.

"Alkyl" means a straight or branched chain, saturated hydrocarbon radical. By way of example, the hydrocarbon chain may have from one to twenty carbons, one to sixteen carbons, one to fourteen carbons, one to twelve carbons, one to ten carbons, one to eight carbons, one to six carbons, one to four carbons, etc. "Lower alkyl" may refer to alkyls having, e.g., one to six carbons, one to four carbons, etc. In certain examples, a straight chain alkyl may have from one to six carbon atoms and a branched alkyl three to six carbon atoms, e.g., methyl, ethyl, propyl, 2-propyl, butyl (including all isomeric forms), pentyl (including all isomeric forms), and the like. "Me" means methyl, "Et" means ethyl, and "iPr" means isopropyl. Alkyl may be optionally substituted, e.g., optionally substituted with oxygen, silicon, sulphur or optionally substituted with OH, O-alkyl, SH, S-alkyl, $NH_2$, and/or NH-alkyl. In another example, alkyl may be $C_1$ to $C_{12}$ straight chain or branched chain alkyl optionally substituted with oxygen, silicon, sulphur, or optionally substituted with OH, O-alkyl, SH, S-alkyl, $NH_2$, and/or NH-alkyl.

"Alkylene" means a divalent alkyl, with alkyl as defined above.

"Aryl" means a monocyclic or bicyclic aromatic hydrocarbon radical, e.g., having from 6 to 20 or 6 to 10 ring atoms e.g., phenyl or naphthyl. Aryl may be optionally substituted, e.g., substituted phenyl or substituted naphthyl.

"Alkylaryl" means a (alkylene)-R radical where R is aryl as defined above. Alkylaryl may be optionally substituted. In certain examples, alkylaryl may be alkylphenyl, alkylsubstituted phenyl, alkylnaphthyl or alkylsubstituted naphthyl.

"Alkenyl" means a straight or branched chain, saturated hydrocarbon radical which contains a carbon-carbon double bond. By way of example, the hydrocarbon chain may have from two to twenty carbons, two to sixteen carbons, two to fourteen carbons, two to twelve carbons, two to ten carbons, two to eight carbons, two to six carbons, two to four carbons, etc. "Lower alkenyl" may refer to alkenyls having, e.g., two to six carbons, two to four carbons, etc. In certain examples, a straight chain alkenyl may have from two to six carbon atoms and a branched alkyl three to six carbon atoms, e.g., a vinyl group, an allyl group, butene (including all isomeric forms), pentene (including all isomeric forms), and the like. Alkenyl may be optionally substituted. In certain examples, alkenyl may be a $C_2$ to $C_{12}$ straight chain or branched chain hydrocarbon containing a carbon-carbon double bond, optionally substituted with oxygen, silicon or sulphur, or optionally substituted with OH, O-alkyl, SH, S-alkyl, $NH_2$, or NH-alkyl.

"Alkynyl" means a straight or branched chain, saturated hydrocarbon radical which contains a carbon-carbon triple bond. By way of example, the hydrocarbon chain may have from two to twenty carbons, two to sixteen carbons, two to fourteen carbons, two to twelve carbons, two to ten carbons, two to eight carbons, two to six carbons, two to four carbons, etc. "Lower alkynyl" may refer to alkynyls having, e.g., two to six carbons, two to four carbons, etc. In certain examples, a straight chain alkynyl may have from two to six carbon atoms and a branched alkyl three to six carbon atoms, e.g., an acetylene group, a propargyl group, butyne (including all isomeric forms), pentyne (including all isomeric forms), and the like. Alkynyl may be optionally substituted. In certain examples, alkynyl may be a $C_2$ to $C_{12}$ straight chain or branched chain hydrocarbon containing a carbon-carbon triple bond, optionally substituted with oxygen, silicon or sulphur, or optionally substituted with OH, O-alkyl, SH, S-alkyl, $NH_2$, or NH-alkyl.

"Cycloalkyl" means a cyclic saturated or partially saturated hydrocarbon radical (or an alicyclic radical). By way of example, the cycloalkyl may have from three to twenty carbon atoms, from three to sixteen carbon atoms, from three to fourteen carbon atoms, from three to twelve carbon atoms, from three to ten carbon atoms, from three to eight carbon atoms, from three to seven carbon atoms, from three to six carbon atoms, etc., wherein one or two carbon atoms may be replaced by an oxo group, e.g., adamantanyl, cyclopropyl, cyclobutyl, cyclopentyl, cyclohexyl, cyclohexenyl, indanyl, and the like.

"Alkylcycloalkyl" means a (alkylene)-R radical where R is cycloalkyl as defined above; e.g., cyclopropylmethyl, cyclobutylmethyl, cyclopentylethyl, or cyclohexylmethyl, and the like. In another example, alkylcycloalkyl has four to twelve carbon atoms, i.e., $C_4$-$C_{12}$ alkylcycloalkyl.

"O-alkyl" or "Alkoxy" means an (oxygen)-R radical where R is alkyl as defined above. For example, O-alkyl may be an oxygen atom bonded to a $C_1$ to $C_6$ straight chain or branched chain alkyl. Alkoxy groups have the general formula: R—O.

"O-cycloalkyl" means an (oxygen)-R radical where R is cycloalkyl as defined above. For example, O-cycloalkyl is an oxygen atom bonded to a $C_3$ to $C_7$ cycloalkyl.

"O-alkylcycloalkyl" means an (oxygen)-R radical where R is alkylcycloalkyl as defined above. For example, O-cycloalkyl is an oxygen atom bonded to a $C_4$ to $C_8$ alkylcycloalkyl.

"Heterocyclyl" or "heterocycloalkyl" means a saturated or unsaturated monocyclic group, in which one or two ring atoms are heteroatom selected from N, O, or S, the remaining ring atoms being C. Heterocyclyl and heterocycloalkyl includes, e.g., where the heterocycle comprises one or two hetero atoms selected from O, S, or N, including a $C_2$ to $C_6$ heterocycloalkyl. The heterocyclyl ring is optionally fused to a (one) aryl or heteroaryl ring as defined herein. The heterocyclyl ring fused to monocyclic aryl or heteroaryl ring is also referred to in this application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds. When the heterocyclyl group contains at least one nitrogen atom, it is also referred to herein as heterocycloamino and is a subset of the heterocyclyl group. When the heterocyclyl group is a saturated ring and is not fused to aryl or heteroaryl ring as stated above, it is also referred to herein as saturated monocyclic heterocyclyl.

"Alkylheterocycloalkyl" means an -(alkylene)-R radical where R is heterocyclyl ring as defined above e.g., tetraydrofuranylmethyl, piperazinylmethyl, morpholinylethyl, and the like. Alkylheterocycloalkyl also includes, e.g., where the heterocycle comprises one or two hetero atoms selected from O, S, or N and has three to eleven carbon atoms, i.e., $C_3$ to $C_{11}$ alkylheterocycloalkyl, and includes when N is present in the heterocyclic ring the nitrogen atom may be in the form of an amide, carbamate, or urea.

"Heteroaryl" means a monocyclic or bicyclic aromatic radical, where one or more, preferably one, two, or three, ring atoms are heteroatom selected from N, O, or S, the remaining ring atoms being carbon. Representative examples include, but are not limited to, pyrrolyl, thienyl (thiophenyl), thiazolyl, imidazolyl, furanyl, indolyl, isoindolyl, oxazolyl, isoxazolyl, diazolyl, pyrazolyl, triazolyl, benzothiazolyl, benzoxazolyl, quinolinyl, isoquinolinyl, pyridinyl (pyridyl), pyrimidinyl, pyrazinyl, pyridazinyl, tetrazolyl, and the like. Heteroaryl may be optionally substituted.

"Oxo" or "carbonyl" means a =(O) group or C=O group, respectively.

The term "substituted" means that the referenced group is substituted with one or more additional group(s) individually and independently selected from groups described herein. In some embodiments, an optional substituent is selected from oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoroalkyl, substituted or unsubstituted heteroalkyl, substituted or unsubstituted alkoxy, fluoroalkoxy, —S— alkyl, —S(O)$_2$-alkyl, —CONH ((substituted or unsubstituted alkyl) or (substituted or unsubstituted phenyl)), —CON(H or alkyl)$_2$, —OCON (substituted or unsubstituted alkyl)$_2$, —NHCONH ((substituted or unsubstituted alkyl) or (substituted or unsubstituted phenyl)), —NHCOalkyl, —N(substituted or unsubstituted alkyl) CO (substituted or unsubstituted alkyl), —NHCOO (substituted or unsubstituted alkyl), —C(OH)(substituted or unsubstituted alkyl)$_2$, and —C(NH$_2$)(substituted or unsubstituted alkyl)$_2$. In some embodiments, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(O)$_2$—CH$_3$, —CONH$_2$, —CONHCH$_3$, —NHCONHCH$_3$, —COCH$_3$, —COOH, and the like. In some embodiments, substituted groups are substituted with one, two, or three of the preceding groups. In some embodiments, substituted groups are substituted with one or two of the preceding groups. In some embodiments, substituted groups are substituted with one of the preceding groups. Further, unless stated to the contrary, a formula with chemical bonds shown only as solid lines and not as wedges or dashed lines contemplates each possible isomer, e.g., each enantiomer and diastereomer, and a mixture of isomers, such as racemic or scalemic mixtures.

In some embodiments, a compound of the disclosure is present in a composition as a salt. In some embodiments, salts are obtained by reacting a compound of the disclosure with acids. In some other embodiments, pharmaceutically acceptable salts are obtained by reacting a compound of the disclosure with a base. In other embodiments, the compounds are used as free-acid or free-base form in the manufacture of the compositions described herein. The type of salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium or calcium), or an aluminum ion. In some cases, the lipid modulating compound described herein are reacted with an organic base, such as, but not limited to, ethanolamine, diethanolamine, triethanolamine, methylamine, dimethylamine, trimethylamine, ethylamine, diethylamine, triethylamine, N-methylglucamine, dicyclohexylamine, tris(hydroxymethyl)methylamine. In other cases, the compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

"Addition compound" refers to a complex of two or more complete molecules in which each preserves its fundamental structure and no covalent bonds are made or broken (for example, hydrates of salts, adducts).

"Aliphatic acid" refers to acids of nonaromatic hydrocarbons. Examples of aliphatic acids include, but are not limited to, butyric acid, hexanoic acid, propionic acid, octanoic acid, and acetic acid.

"Alkene" refers to an unsaturated linear divalent hydrocarbon moiety of one to twelve, typically one to six, carbon atoms or a saturated branched divalent hydrocarbon moiety of three to twelve, typically three to six, carbon atoms. Exemplary alkene groups include, but are not limited to, methylene, ethylene, propylene, butylene, pentylene, and the like.

"Antagonist" refers to a compound or a composition that attenuates the effect of an agonist. The antagonist can directly bind reversibly or irreversibly to a region of the receptor in common with an agonist. An antagonist can also bind at a different site on the receptor or an associated ion channel. Thus, the term "antagonist" includes a functional antagonist. A "functional antagonist" refers to a compound and/or composition that reverses the effects of an agonist by means other than acting at the same receptor as the agonist, i.e., a functional antagonist causes a response in the tissue or animal which opposes the action of an agonist. Examples include agents which have opposing effects on an intracellular second messenger or on a physiologic state in an animal (for example, blood pressure).

"Biological activity" as used herein means having an effect on or eliciting or preventing a response from a living cell, tissue, organ or physiologic activity, such as, but not limited to, altering gene and/or protein expression, protein phosphorylation, cellular behavior, and/or organ function.

"Biomarker" as used herein means a measurable indicator of the severity or the presence of a particular disease state. More generally a biomarker is anything that can be used as an indicator of a particular disease state or some other physiological state of an organism.

"Carboxyl" refers to an organic functional group consisting of a carbon atom double bonded to an oxygen atom and single bonded to a hydroxyl group.

"Chiral center" (i.e., stereochemical center, stereocenter, or stereogenic center) refers to an asymmetrically substituted atom, e.g., a carbon atom to which four different groups are attached. The ultimate criterion of a chiral center, however, is nonsuperimposability of its mirror image. If an asymmetric center is present in one or more substituents, the compound may be in the form of a racemic mixture, a single enantiomer, a diastereoisomeric mixture, an enantiomeric diastereomer, a meso compound, a pure epimer, or a mixture of epimers thereof.

"Derivative" refers to a compound that is derived from some parent compound where one atom is replaced with another atom or group of atoms and usually maintains its general structure. For example, trichloromethane (chloroform) is a derivative of methane.

"Dermatitis" as used herein refers to a general or localized inflammation of the skin, either due to an inherent skin defect, direct contact with an irritating substance, virus, bacteria, animal parasite, fungus or to an allergic reaction. Symptoms of dermatitis include: redness, itching, exudations, pain, fissures, cracks, ulcers, and in some cases blistering of the skin.

"Eczema" as used herein refers to an inflammatory condition of the skin characterized by redness, itching, and oozing vesicular lesions which become scaly, crusted, or hardened.

"Epithelium (epithelia, plural) or epithelial tissues" as used herein means a type of animal tissue made up of densely packed cells that rest on a basement membrane to act as a covering of a free surface such as, but not limited to the surface of the human body; or lining of various bodily surfaces, such as but not limited to the eyes; or lining various body cavities such as but not limited the abdominal cavity; or lining the lumina of tubular structures within organs, such as but not limited to the respiratory epithelium, urogenital epithelium.

"Enantiomeric excess" refers to the difference between the amounts of enantiomers. The percentage of enantiomeric excess (% ee) can be calculated by subtracting the percentage of one enantiomer from the percentage of the other enantiomer. For example, if the % of (R)-enantiomer is 99% and % of (S)-enantiomer is 1%, the % ee of (R)-isomer is 99%-1% or 98%.

The terms "halo," "halogen" and "halide" are used interchangeably herein and refer to fluoro, chloro, bromo, or iodo.

"Haloalkyl" refers to an alkyl group as defined herein in which one or more hydrogen atom is replaced by the same or different halo atoms. The term "haloalkyl" also includes perhalogenated alkyl groups in which all alkyl hydrogen atoms are replaced by halogen atoms. Exemplary haloalkyl groups include, but are not limited to: —$CH_2F$, —$CH_2Cl$, —$CF_3$, —$CH_2CF_3$, —$CH_2CCl_3$, and the like.

"Hetero-substituted alkyl" refers to an alkyl group, as defined herein, that contains one or more heteroatoms such as N, O, or S. Such heteroatoms can be hydroxy, alkoxy, amino, mono-, di-alkyl amino, thiol, alkylthiol, etc.

"Hydroxyalkyl" refers to an alkyl group, as defined herein, having one or more hydroxyl substituent(s).

"Keto acid" refers to organic compounds that contain a carboxylic acid group and a ketone group.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N, O-dimethylhydroxylamino, and the like.

"Leukocyte or leukocytes" as used herein refer to a colorless cell that circulates in the blood and body fluids and is involved in counteracting foreign substances and infectious disease as well as being causative of inflammatory diseases. They have also been referred to as white (blood) cells. There are several types, all are amoeboid cells with a nucleus, including lymphocytes, granulocytes, monocytes, and macrophages.

"Ligand" as used herein means a biochemical substance in the form of a nucleic acid, protein or peptide that forms a complex with another biomolecule in a cell or tissue to serve a biological purpose.

"Moderate" as used herein means to decrease or increase the quality, quantity, intensity or duration of a biological product or process.

"Peripheral blood mononuclear cell (PBMC)" as used herein means any peripheral blood cell having a round nucleus. These cells are a subset of leukocytes and consist of lymphocytes (T cells, B cells, NK cells) and monocytes, whereas erythrocytes and platelets have no nuclei and granulocytes (neutrophils, basophils, and eosinophils) have multilobed nuclei.

"Pharmaceutically acceptable excipient" refers to an excipient that is useful in preparing a pharmaceutical composition that is generally safe, non-toxic, and neither biologically nor otherwise undesirable, and includes excipients that are acceptable for veterinary use as well as human pharmaceutical use.

"Pharmaceutically acceptable salt" of a compound means a salt that is pharmaceutically acceptable and that possesses the desired pharmacological activity of the parent compound. Such salts include: acid addition salts formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. A "pharmaceutically acceptable salt" of a compound also includes salts formed when an acidic proton present in the parent compound is either replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Pharmaceutically acceptable vehicle means a carrier or inert medium used as a solvent (or diluent) in which the medicinally active agent is formulated and or administered.

The terms "pro-drug" and "prodrug" are used interchangeably herein and refer to any compound which releases an active parent drug according to Formula 1, or a pharmaceutically acceptable salt or solvate of Formula 1, in vivo when such prodrug is administered to a mammalian subject. Prodrugs of a compound of Formula 1 are prepared by modifying one or more functional group(s) present in the compound of Formula 1 in such a way that the modification(s) may be cleaved in vivo to release the parent compound. Prodrugs include compounds of Formula 1 wherein a hydroxy group in a compound of Formula 1 is bonded to any group that may be cleaved in vivo to regenerate the free hydroxyl, aliphatic alcohol, amino, or sulfhydryl group, respectively. Examples of prodrugs include, but are not limited to, esters (e.g., acetate, formate, glycol and benzoate derivatives of Formula 1) and the like. For example, the compound according to Formula 1 that is methyl 3-(4-hydroxyphenoxy)-3-methyl-butanoate can be reacted under acidic conditions with 2-hydroxybenzoic acid to produce, [4-(3-methoxy-1,-1-dimethyl-3oxo-propoxy)2-hydroxybenzoate an ester prodrug that will be hydrolyzed to 2-hydroxybenzoic acid and the starting compound by esterase enzymes in tissues. The transformation from prodrug to a compound of Formula 1, or a pharmaceutically acceptable salt or solvate thereof, may occur by various mechanisms, such as via hydrolysis in blood. A prodrug of the compound of Formula 1 may be formed in a conventional manner according to methods known in the art. A thorough discussion of prodrugs is provided by V. Stella in *Pro-drugs as Novel Delivery Systems*, Vol. 14 of the A.C.S. Symposium Series (Stella (1975)), and in *Bioreversible Carriers in Drug Design* (Roche (1987)), both of which are incorporated herein by reference.

"Pro-inflammatory cytokine" refers to a type of cytokine (i.e. a protein signaling molecule) that is secreted from leukocytes, monocytes and other non-leukocyte cell types; such as but not limited epithelial cells, that promote inflammation by their biological effect on other cells and tissue in mammalian organisms. Non-limiting examples of pro-inflammatory cytokines are: Interleukin 1 (IL-1; IL-1a & IL-1b), Interleukin 6 (IL-6), Interleukin 13 (IL-13), Tumor Necrosis Factor alpha (TNF-alpha), Interferon gamma (IFN-gamma), and Interleukin 8 (IL-8).

The term "prophylaxis" of a state, disorder, disease or condition as used herein refers to prevention of the appearance of clinical symptoms of the state, disorder, disease or condition developing in a patient that is predisposed to the state, disorder, disease, or condition.

"Protecting group" refers to a moiety, with the exception of alkyl groups, that when attached to a reactive group in a molecule masks, reduces, or prevents that reactivity. Examples of protecting groups can be found in T. W. Greene and P. G. M. Wuts, Protective Groups in Organic Synthesis, 3rd edition, John Wiley & Sons, New York, 1999, and Harrison and Harrison et al., Compendium of Synthetic Organic Methods, Vols. 1-8 (John Wiley and Sons, 1971-1996), which are incorporated by reference herein in their entirety. Representative hydroxy protecting groups include acyl groups, benzyl and trityl ethers, tetrahydropyranyl ethers, trialkylsilyl ethers, and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P, or S) to which it is attached.

"Signal transduction" or "signaling pathway activity" refers to a biochemical causal relationship generally initiated by a protein-protein interaction such as binding of a biological active factor to a receptor, resulting in transmission of a signal from one portion of a cell to another portion of a cell. In general, the transmission can involve specific phosphorylation of one or more tyrosine, serine, or threonine residues on one or more protein components such as enzymes or transcription factors (i.e. intracellular secondary messengers) in the series of reactions causing signal transduction (often referred to as a cascade) that results in measurable changes to the cell. Penultimate cellular processes typically include nuclear events, resulting in a change in gene expression. Terminal events of signal transduction cascade result in changes in cellular activity such as but not limited to, alterations in protein products produced and/or secreted by the cell, changes in cellular behavior characteristics of division, motility, adherence, etc.

"Stereoisomer" means molecules that have the same molecular formula, molecular weight and sequence of bonded atoms (constitution), but differ in the three-dimensional orientations of their atoms in space. By definition, molecules that are stereoisomers of each other represent the same structural isomer. The chemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994.

"A therapeutically effective amount" means the amount of a compound that, when administered to an individual for treating a disease, is sufficient to effect such treatment for the disease, as defined below. The "therapeutically effective amount" will vary depending on the compound, the disease and its severity or affected organ or tissue and the age, weight, etc., of the individual to be treated.

"Tautomer" or "tautomeric form" means structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons. The compounds of the present invention according to Formula 1 can exist in different tautomeric states depending on the environment of the particular compound, such as the acidity or alkalinity (i.e. pH) of the solution in which they are dissolved.

"Topical or topically applied" as used herein means the direct delivery or application of the active drug ingredient such as compounds according to Formula 1 directly to the surface of the epithelial tissue by means of a spray, cream, ointment, shampoo, lotion, solution or other suitable delivery solvent or vehicle. Various methods of topical drug delivery such as; but not limited to mechanical application, instillation, inhalation, patches, and the like are known to those skilled in the art, are commonly used for topical application, and are implicit in the concept of topical application as used herein.

"Treating" or "treatment" of a disease means inhibiting the disease, i.e., arresting or reducing the pathophysiologic process or processes of the disease or its clinical symptoms; or relieving the disease, i.e., causing regression of the pathophysiologic process or processes of disease or reducing the clinical manifestations of the pathophysiologic process or processes of the specific disease.

In some embodiments, a compound of the disclosure is present in a composition as a salt. In some embodiments, salts are obtained by reacting a compound of the disclosure with acids. In some other embodiments, pharmaceutically acceptable salts are obtained by reacting a compound of the disclosure with a base. In other embodiments, the compounds are used as free-acid or free-base form in the manufacture of the compositions described herein. The type of salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, the lipid modulating compound described herein are reacted with an organic base, such as, but not limited to, ethanolamine, diethanolamine, triethanolamine, methylamine, dimethylamine, trimethylamine, ethylamine, diethylamine, triethylamine, N-methylglucamine, dicyclohexylamine, tris (hydroxymethyl)methylamine. In other cases, the compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

In the scope of the embodiments, the compounds described herein include further forms of the compounds such as pharmaceutically acceptable salts, solvates (including hydrates), amorphous phases, partially crystalline and crystalline forms (including all polymorphs), prodrugs, metabolites, N-oxides, isotopically-labeled, epimers, pure epimers, epimer mixtures, enantiomers including, but not limited to, single enantiomers and enantiomeric diastereomers, meso compounds, stereoisomers, racemic mixtures, and diastereoisomeric mixtures. Compounds described herein having one or more double bonds include cis/trans isomers, E/Z isomers and geometric isomers.

In some embodiments, sites on the compounds disclosed herein are susceptible to various metabolic reactions. Therefore, incorporation of appropriate substituents at the places of metabolic reactions will reduce, minimize or eliminate the metabolic pathways. In specific embodiments, the appropriate substituent to decrease or eliminate the susceptibility of the aromatic ring to metabolic reactions is, by way of example only, a halogen, deuterium, or an alkyl group. Examples of such substituents can be found in Burger's Medicinal Chemistry, Drug Discovery and Development, 8 Volume Set (Abraham (2010)) and in Foye's Principles of Medicinal Chemistry (Lemke (2012)).

In some embodiments, sites on the compounds disclosed herein are not susceptible to various metabolic reactions. Therefore, incorporation of appropriate substituents at or near or distant from the places of a lack of metabolic reactions will modulate, enhance, or maximize the metabolic pathways. In specific embodiments, the appropriate substituent (metabolic handle) to enhance, or maximize the susceptibility of the aromatic ring to metabolic reactions is, by way of example only, is a phenolic or methoxy or carboxylate group. Examples of such substituents can be found in Burger's Medicinal Chemistry, Drug Discovery and Development, 8 Volume Set (Abraham (2010)) and in Foye's Principles of Medicinal Chemistry (Lemke (2012)).

Throughout the specification, groups and substituents thereof can be chosen by one skilled in the field to provide stable moieties and compounds.

I. METHODS OF SYNTHESIS

The compounds of Formula 1 may be prepared by the methods described below, together with synthetic methods known in the art of organic chemistry, or modifications and transformations that are familiar to those of ordinary skill in the art. Various starting materials, intermediates, and reagents may be purchased from commercial sources or made according to literature methods or adaptations thereof. Although other reagents, compounds or methods can be used in practice or testing, generalized methods for the preparation of the compound of Formula 1 are illustrated by the following descriptions and reaction Schemes. The methods disclosed herein, including those outlined in the Schemes, descriptions, and Examples are for intended for illustrative purposes and are not to be construed in any manner as limitations thereon. Various changes and modifications will be obvious to those of skill in the art given the benefit of the present disclosure and are deemed to be within the spirit and scope of the present disclosure as further defined in the appended claims.

Although specific embodiments of various aspects of the invention will be described with reference to the Schemes, Preparations, and/or Examples, it should be understood that such embodiments are by way of example only and are merely illustrative of a small number of the many possible specific embodiments which can represent applications of the principles of the present disclosure. The starting materials used for the synthesis of compounds described herein can be obtained from commercial sources, such as Aldrich Chemical Co. (Milwaukee, Wis.), Sigma Chemical Co. (St. Louis, Mo.), or the starting materials can be synthesized. The compounds described herein and other related compounds having different substituents can be synthesized using techniques and materials known to those of skill in the art, such as described, for example, in March's Advanced Organic Chemistry: Reactions, Mechanisms, and Formula (Smith (2013)), Design and Strategy in Organic Synthesis (Hanessian (2013)) Greene's Protective Groups in Organic Synthesis (Wuts (2006)) and Fiesers' Reagents for Organic Synthesis (Volumes 1-27) (Ho (2013)), each of which are incorporated by reference in their entirety.

General methods for the preparation of the compounds as disclosed herein may be derived from known reactions in the field and the reactions may be modified by the use of appropriate reagents and conditions, as would be recognized by the skilled person, for the introduction of the various moieties found in the formulae as provided herein.

The intermediate products described can be recovered by extraction, evaporation, or other techniques known in the art. The crude materials may then be optionally purified by chromatography, HPLC, recrystallization, trituration, distillation, or other techniques known in the art. In the discussions below, the following abbreviations were used: THF (tetrahydrofuran), DMF (N,N-dimethylformamide), BOC (tert-butoxycarbonyl), Cbz (carbobenzoxy), $Cs_2CO_3$ (Cesium Carbonate), DEPC (diethylcyano-phosphate), LDA (lithium Diisopropylamide), NMP (N-Methyl-2-pyrrolidone), TEA or $NEt_3$ (triethyl amine), p-TsOH (p-toluene sulfonic acid), i-PrOAc (isopropyl acetate), HOBT (1-hydroxybenzo-triazole), EDC (1-ethyl-3-(3-dimethylaminopropyl) carbodiimide), and EtOH (ethanol).

As would be appreciated by those skilled in the art, some of the methods useful for the preparation of such compounds, as discussed above, may require protection of a particular functionality, e.g., to prevent interference by such functionality in reactions at other sites within the molecule or to preserve the integrity of such functionality. The need for, and type of, such protection is readily determined by one skilled in the art and will vary depending on, for example, the nature of the functionality and the conditions of the selected preparation method. Methods of introducing and removing protecting groups are well known to those of ordinary skill in the art and are described in Greene's Protective Groups in Organic Synthesis (Wuts (2006)). Alternate reagents, starting materials, as well as methods for optimizing or adapting the procedures described herein would also be readily determined by one skilled in the art.

Scheme 1

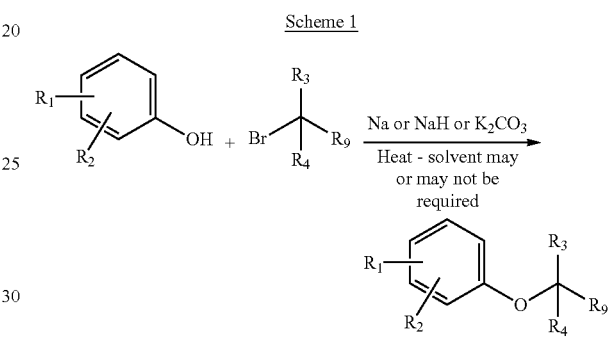

In Scheme 1 a variety of means are used to generate a phenolate from a commercially available phenol which then displaces the bromine of the $R_3$ $R_4$ intermediate to give the product shown. Other phenols are easily available by synthesis to those skilled in the art. Other atoms to be displaced from the $R_3$ $R_4$ component are also envisaged including chlorine, iodine and the so-called Mitsonobu adduct derived from treatment of the corresponding alcohol with DEAD (diazoethyldicarboxylate).

Scheme 2

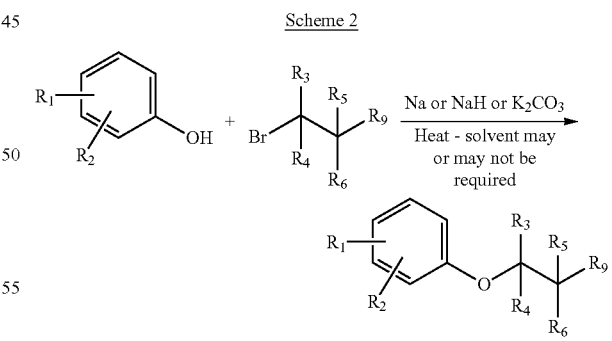

Scheme 2 outlines a similar set of transformations. Again, a variety of means are used to generate a phenolate from a commercially available phenol which then displaces the bromine of the $R_3$ $R_4$ intermediate to give the product shown. Other phenols are easily available by synthesis to those skilled in the art. Other atoms to be displaced from the $R_3$ $R_4$ component are also envisaged including chlorine, iodine and the so-called Mitsonobu adduct derived from treatment of the corresponding alcohol with DEAD.

Scheme 3

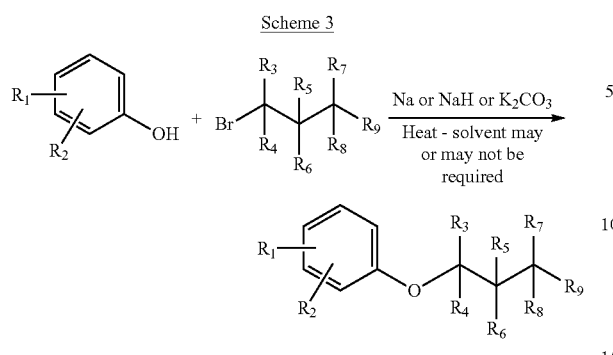

Scheme 3 outlines the general synthesis of representative compounds. Again, a variety of means are used to generate a phenolate from a commercially available phenol which then displaces the bromine of the $R_3$ $R_4$ intermediate to give the product shown. Other phenols are easily available by synthesis to those skilled in the art. Other atoms to be displaced from the $R_3$ $R_4$ component are also envisaged including chlorine, iodine and the so-called Mitsonobu adduct derived from treatment of the corresponding alcohol with DEAD.

The transformations shown in either Scheme 1 or Scheme 2 or Scheme 3 can be carried out with racemic material or material which has partial enrichment of one enantiomer over the other as well as optically pure materials.

Scheme 4

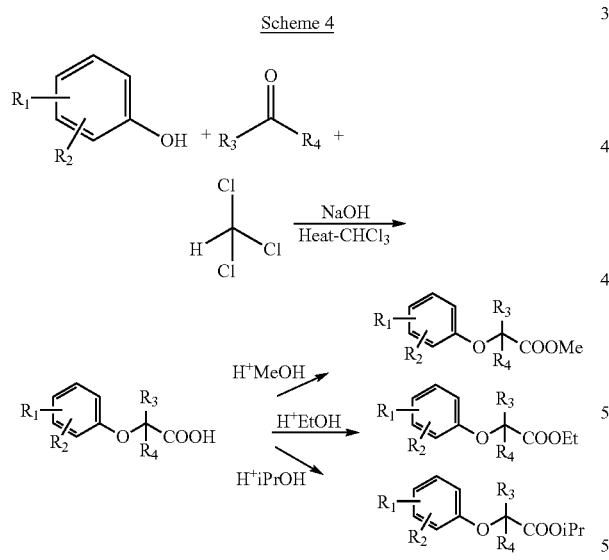

Scheme 4 is an alternative synthesis which is only suitable for the limited case where n and p=0 in the generic structure, Formula 1, and is not suitable for the generation of enantiomers at the possible asymmetric center adjacent to $R_3$ and $R_4$. In this case the phenolate generated reacts with a ketone carrying $R_3$ and $R_4$ followed by reaction of the intermediate with the anion derived from chloroform and hydrolysis to give the desired carboxylic acid. Acid catalyzed esterification then gives the esters shown.

Scheme 5

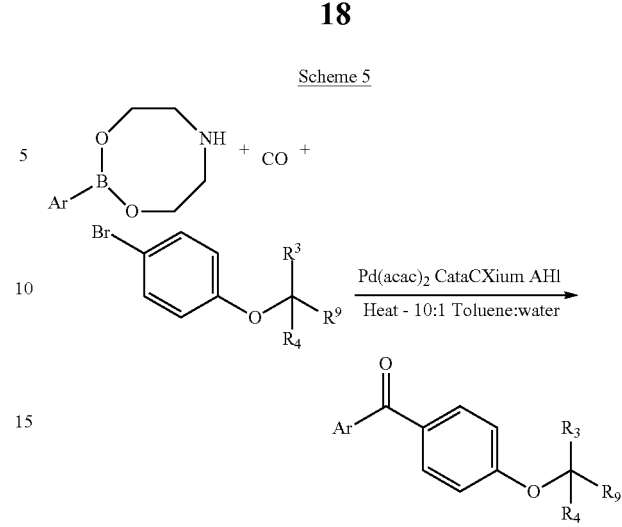

Scheme 6

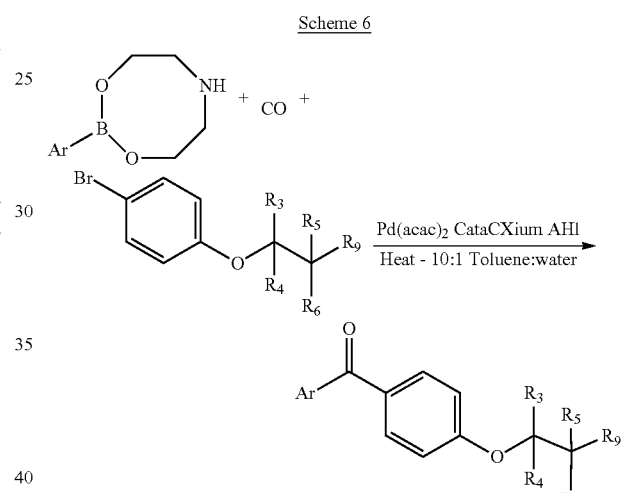

Scheme 7

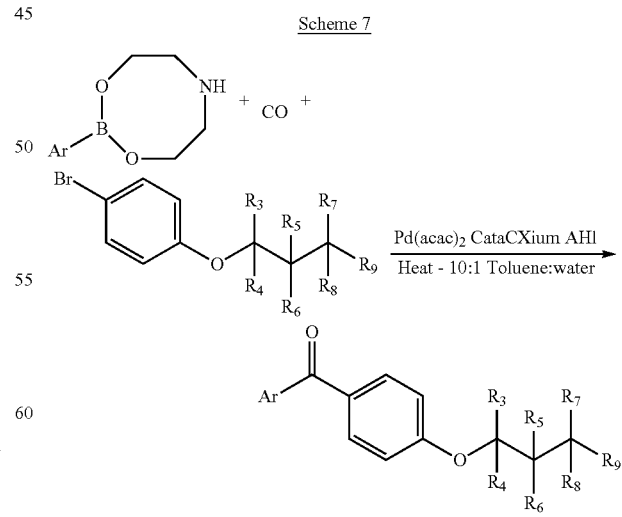

Scheme 5, Scheme 6, and Scheme 7 illustrate how the Suzuki-Miyaura reaction (Molander et al. (2014)) can be used to handle some of the more challenging substituents envisaged for the central aryl ring without going through the phenol as the penultimate/final intermediate. The optimally substituted aryl boronate and the suitably substituted aryl bromide participate in a CO trapping reaction assisted by Pd(acac)$_2$.

Again, these transformations can be carried out with racemic materials, partially optically enriched materials and optically pure materials.

Preparation of the example compounds were prepared as set forth above and/or with standard procedures well known to those skilled in the art. Example compounds are set forth in Tables 1-13.

TABLE 1

Structure

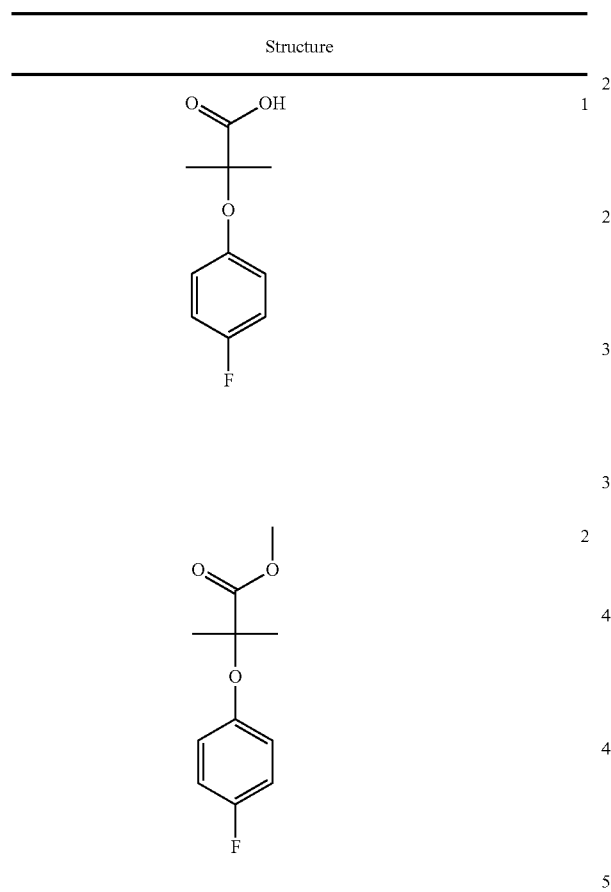

TABLE 1-continued

Structure

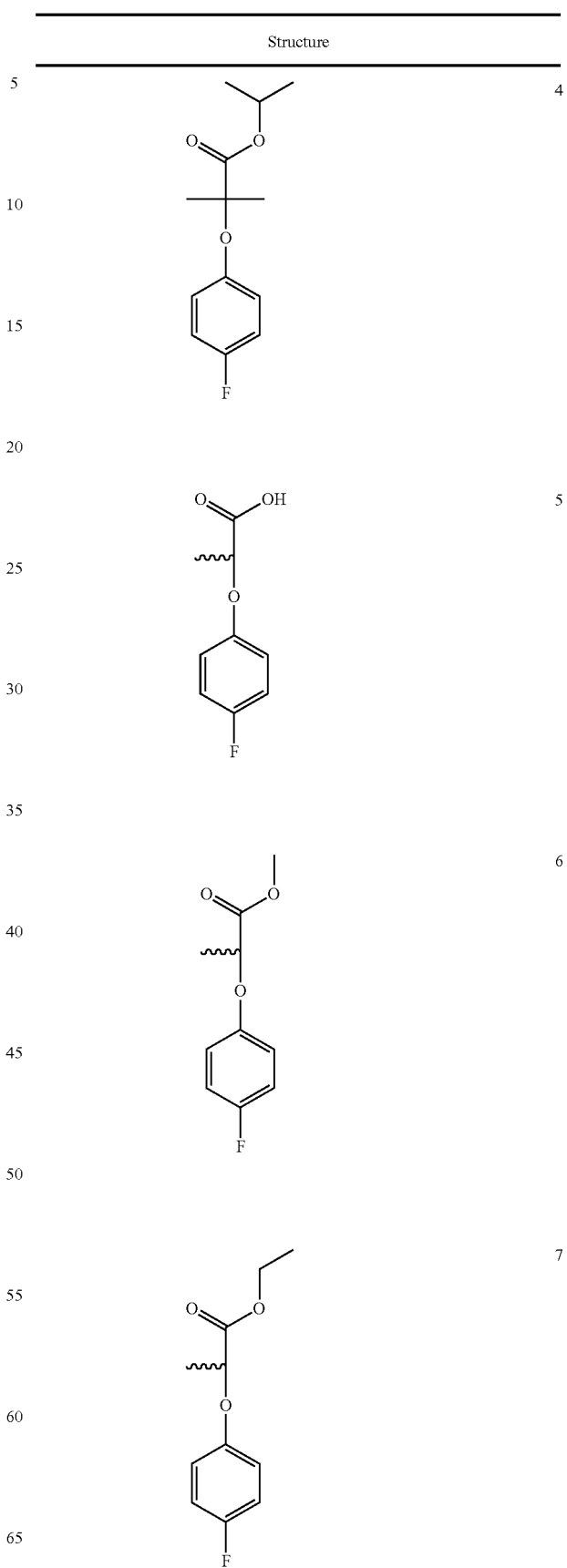

TABLE 1-continued
| Structure | |
|---|---|
| 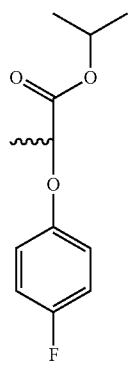 [SMILES: CC(C)OC(=O)C(C)Oc1ccc(F)cc1] | 8 |
| 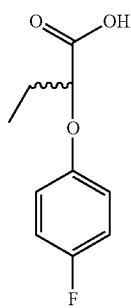 | 9 |
| 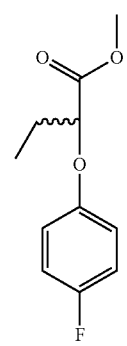 | 10 |
| 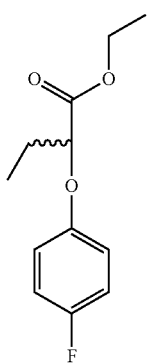 | 11 |
TABLE 1-continued
| Structure | |
|---|---|
| 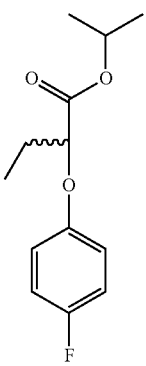 [SMILES: CCOC(=O)C(CC)Oc1ccc(F)cc1] | 12 |
| 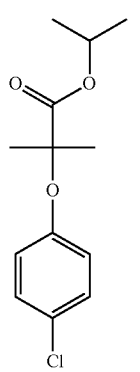 | 13 |
| 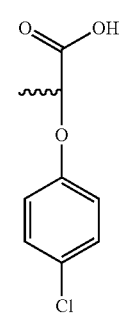 | 14 |
| 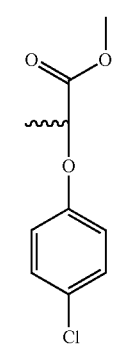 | 15 |

TABLE 1-continued
| Structure | |
|---|---|
| 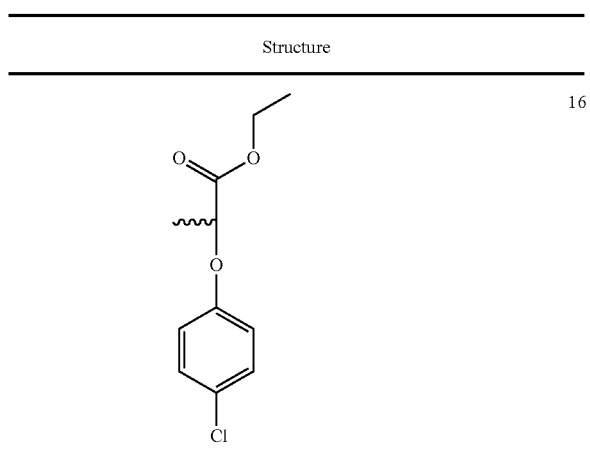 | 16 |
| 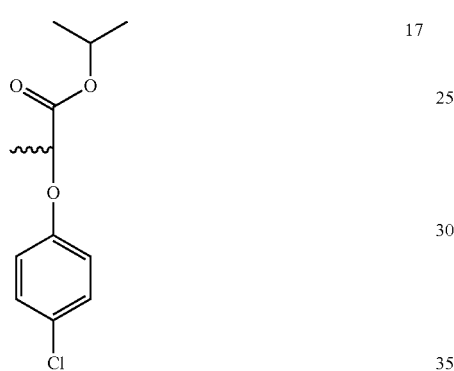 | 17 |
| 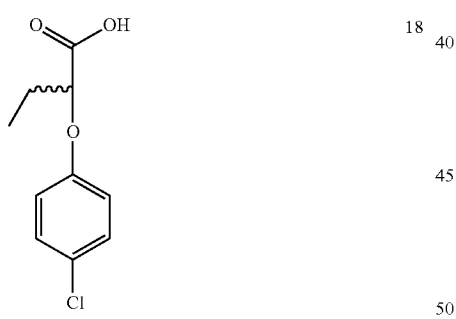 | 18 |
| 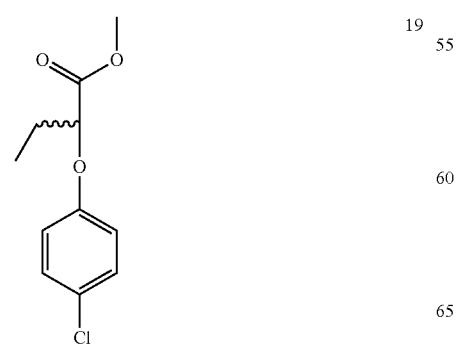 | 19 |
TABLE 1-continued
| Structure | |
|---|---|
| 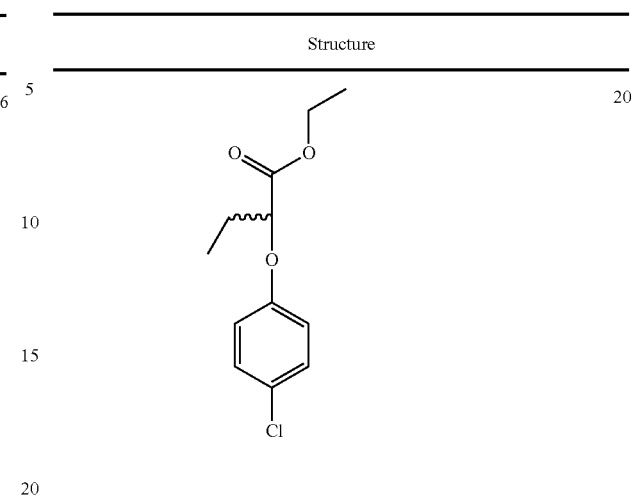 | 20 |
| 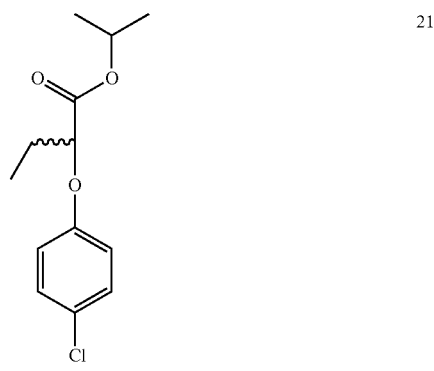 | 21 |
| 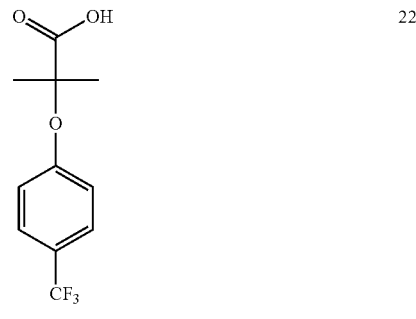 | 22 |
| 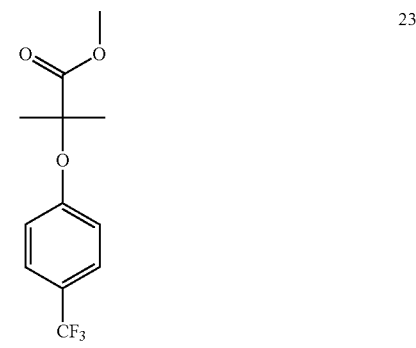 | 23 |

TABLE 1-continued
| Structure | |
|---|---|
| 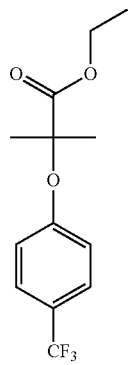 [SMILES: CCOC(=O)C(C)(C)Oc1ccc(C(F)(F)F)cc1] | 24 |
| 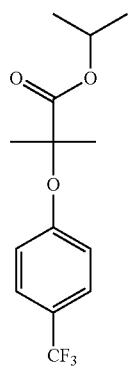 [SMILES: CC(C)OC(=O)C(C)(C)Oc1ccc(C(F)(F)F)cc1] | 25 |
| 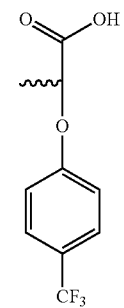 | 26 |
| 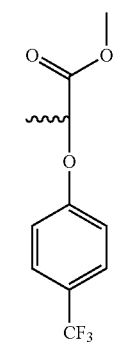 | 27 |
TABLE 1-continued
| Structure | |
|---|---|
| 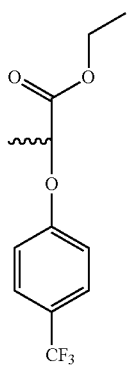 [SMILES: CCOC(=O)C(C)Oc1ccc(C(F)(F)F)cc1] | 28 |
| 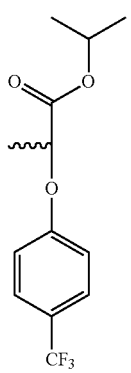 [SMILES: CC(C)OC(=O)C(C)Oc1ccc(C(F)(F)F)cc1] | 29 |
| 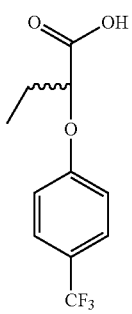 [SMILES: CCC(Oc1ccc(C(F)(F)F)cc1)C(=O)O] | 30 |
| 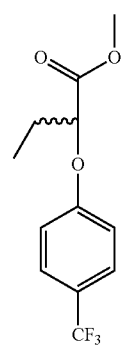 | 31 |

TABLE 1-continued
| Structure | |
|---|---|
| 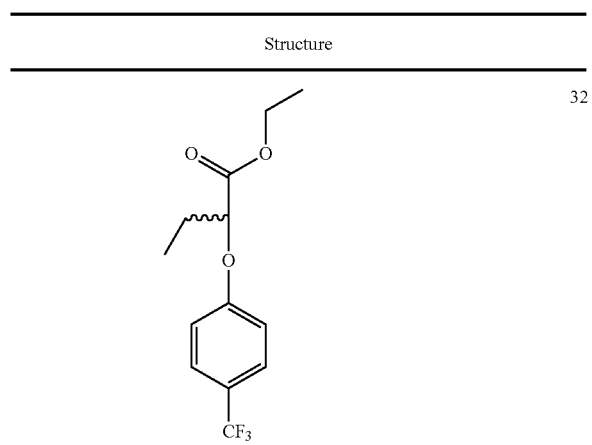 | 32 |
| 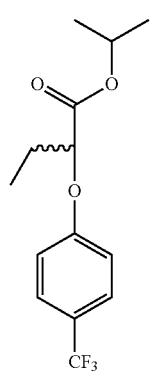 [SMILES: CCC(Oc1ccc(C(F)(F)F)cc1)C(=O)OC(C)C] | 33 |
| 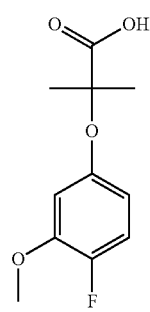 [SMILES: COc1cc(OC(C)(C)C(=O)O)ccc1F] | 34 |
| 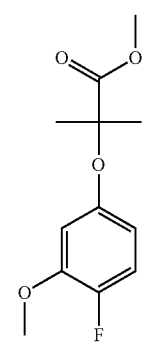 [SMILES: COC(=O)C(C)(C)Oc1ccc(F)c(OC)c1] | 35 |
TABLE 1-continued
| Structure | |
|---|---|
| 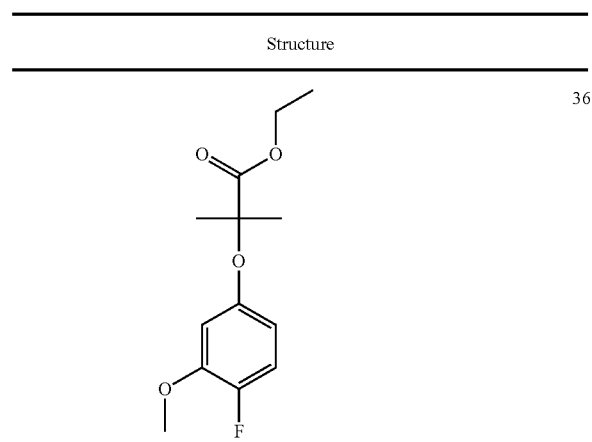 | 36 |
| 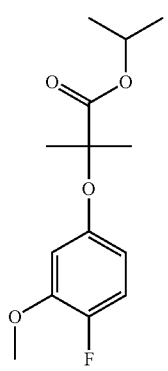 [SMILES: COc1cc(OC(C)(C)C(=O)OC(C)C)ccc1F] | 37 |
| 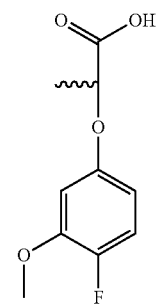 | 38 |
| 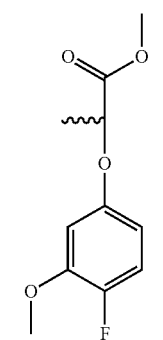 | 39 |

TABLE 1-continued
| Structure | |
|---|---|
| 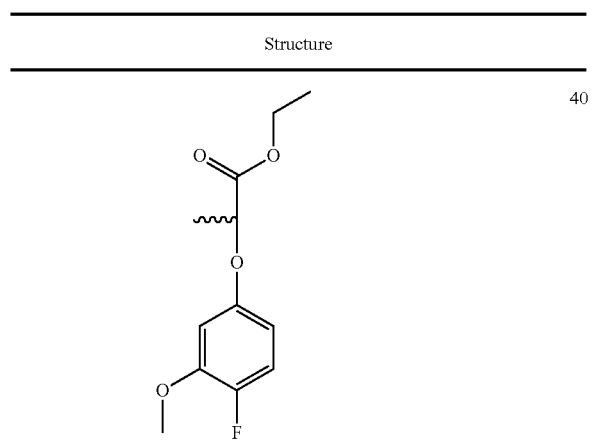 | 40 |
| 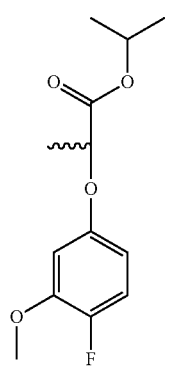 [SMILES: COc1cc(OC(C)C(=O)OC(C)C)ccc1F] | 41 |
| 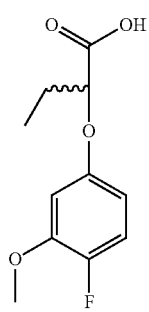 [SMILES: CCC(Oc1ccc(F)c(OC)c1)C(=O)O] | 42 |
| 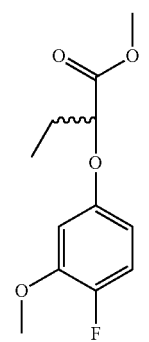 | 43 |
TABLE 1-continued
| Structure | |
|---|---|
| 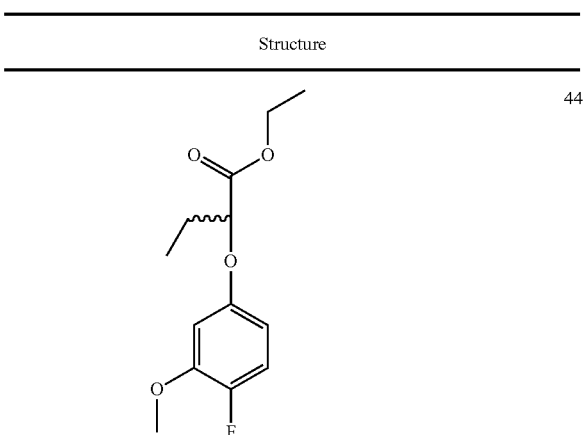 | 44 |
| 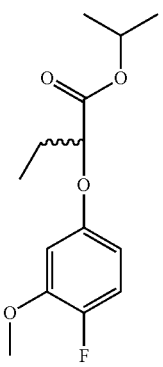 [SMILES: CCC(Oc1ccc(F)c(OC)c1)C(=O)OC(C)C] | 45 |
| 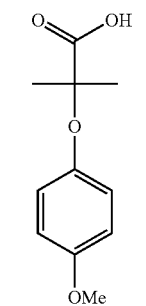 | 46 |
| 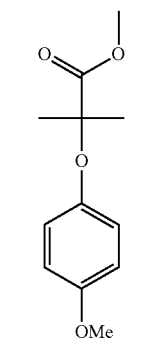 | 47 |

TABLE 1-continued
| Structure | |
|---|---|
| 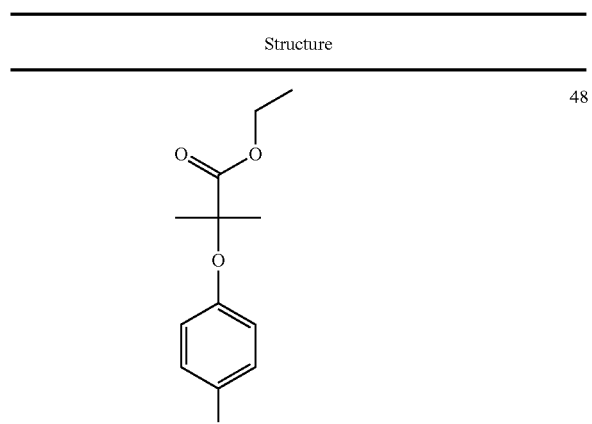 | 48 |
| 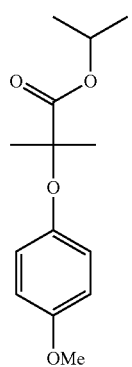 [SMILES: COc1ccc(OC(C)(C)C(=O)OC(C)C)cc1] | 49 |
| 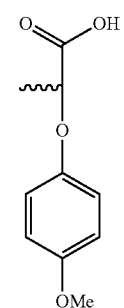 | 50 |
| 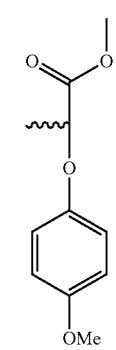 | 51 |
TABLE 1-continued
| Structure | |
|---|---|
| 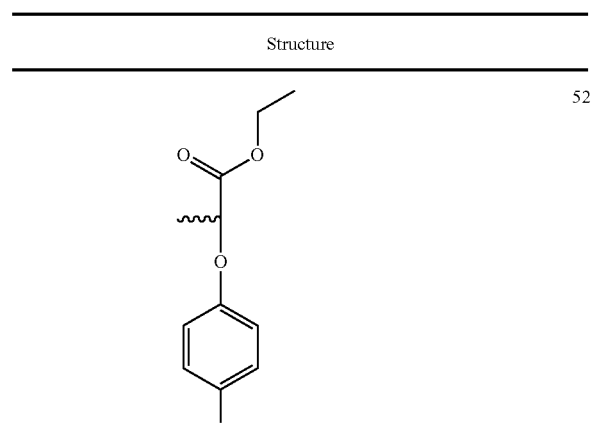 | 52 |
| 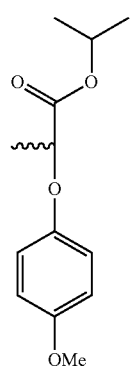 [SMILES: COc1ccc(OC(C)C(=O)OC(C)C)cc1] | 53 |
| 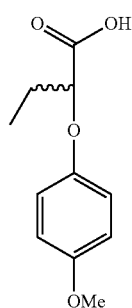 | 54 |
| 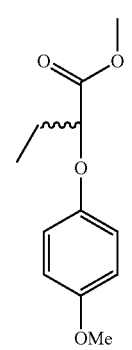 | 55 |

TABLE 1-continued

| Structure | |
|---|---|
| (structure of ethyl 2-(4-methoxyphenoxy)butanoate) | 56 |
| (structure of isopropyl 2-(4-methoxyphenoxy)butanoate) | 57 |
| (structure of 2-(2,5-dimethylphenoxy)-2-methylpropanoic acid) | 58 |
| (structure of methyl 2-(2,5-dimethylphenoxy)-2-methylpropanoate) | 59 |
| (structure of ethyl 2-(2,5-dimethylphenoxy)-2-methylpropanoate) | 60 |
| (structure of isopropyl 2-(2,5-dimethylphenoxy)-2-methylpropanoate) | 61 |
| (structure of 2-(2,5-dimethylphenoxy)acetic acid) | 62 |
| (structure of methyl 2-(2,5-dimethylphenoxy)acetate) | 63 |
| (structure of ethyl 2-(2,5-dimethylphenoxy)acetate) | 64 |
| (structure of isopropyl 2-(2,5-dimethylphenoxy)acetate) | 65 |

TABLE 1-continued

| Structure | |
|---|---|
| (compound 66: 2,5-dimethylphenoxy-CH(Et)-COOH) | 66 |
| (compound 67: methyl 2-(2,5-dimethylphenoxy)butanoate) | 67 |
| (compound 68: ethyl 2-(2,5-dimethylphenoxy)butanoate) | 68 |
| (compound 69: isopropyl 2-(2,5-dimethylphenoxy)butanoate) | 69 |

TABLE 2

| Structure | |
|---|---|
| (compound 70: 2-(4-bromophenoxy)-2-methylpropanoic acid) | 70 |

TABLE 2-continued

| Structure | |
|---|---|
| (compound 71: methyl 2-(4-bromophenoxy)-2-methylpropanoate) | 71 |
| (compound 72: ethyl 2-(4-bromophenoxy)-2-methylpropanoate) | 72 |
| (compound 73: isopropyl 2-(4-bromophenoxy)-2-methylpropanoate) | 73 |
| (compound 74: 2-(4-bromophenoxy)propanoic acid) | 74 |

TABLE 2-continued
Structure
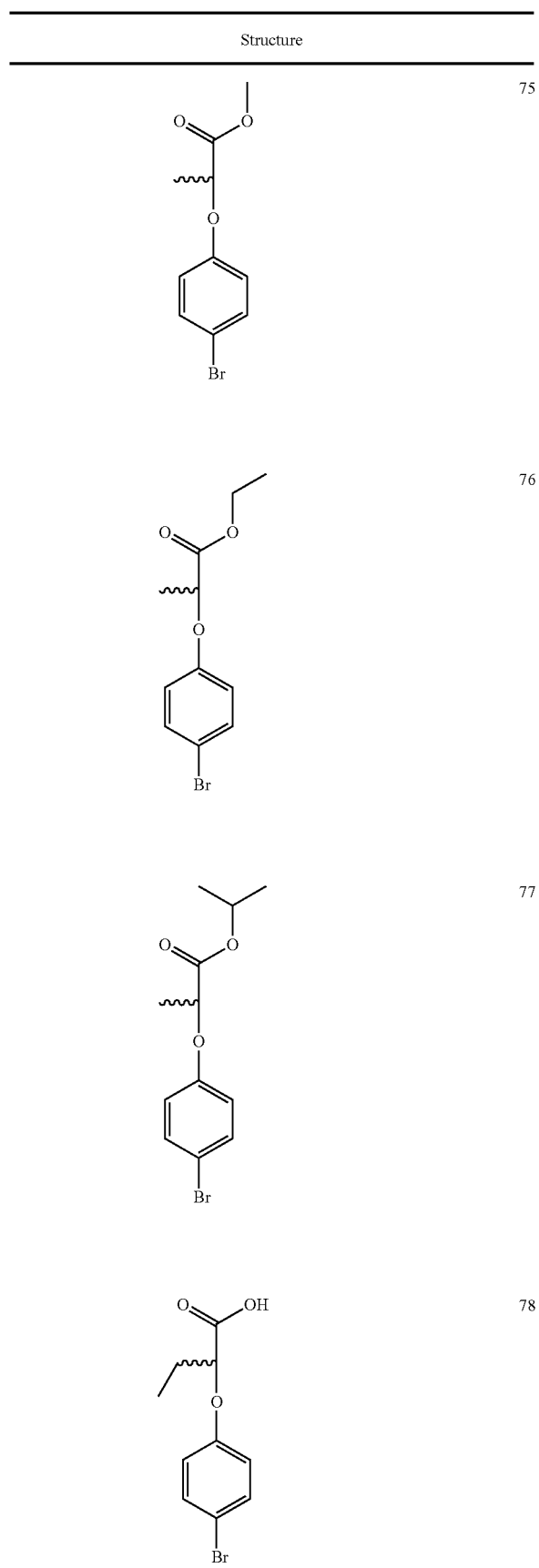
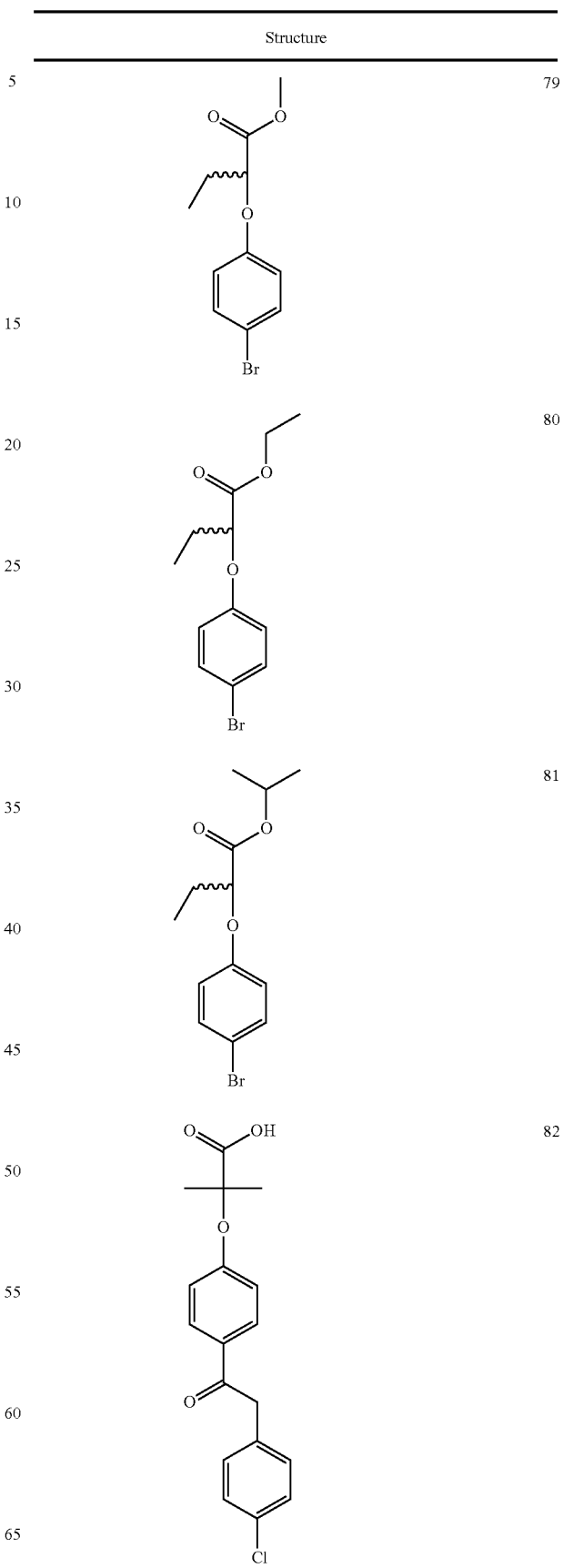

TABLE 2-continued
| Structure | |
|---|---|
| 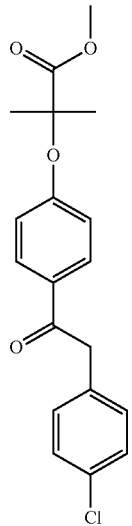 [SMILES: COC(=O)C(C)(C)Oc1ccc(C(=O)Cc2ccc(Cl)cc2)cc1] | 83 |
| 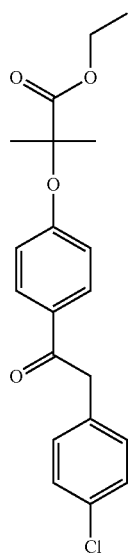 [SMILES: CCOC(=O)C(C)(C)Oc1ccc(C(=O)Cc2ccc(Cl)cc2)cc1] | 84 |
TABLE 2-continued
| Structure | |
|---|---|
| 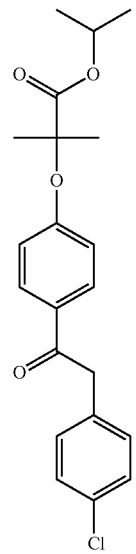 [SMILES: CC(C)OC(=O)C(C)(C)Oc1ccc(C(=O)Cc2ccc(Cl)cc2)cc1] | 85 |
| 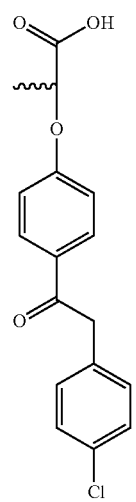 [SMILES: CC(Oc1ccc(C(=O)Cc2ccc(Cl)cc2)cc1)C(=O)O] | 86 |
| 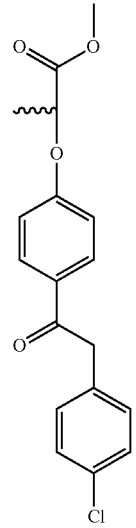 [SMILES: COC(=O)C(C)Oc1ccc(C(=O)Cc2ccc(Cl)cc2)cc1] | 87 |

TABLE 2-continued
| Structure | |
|---|---|
| 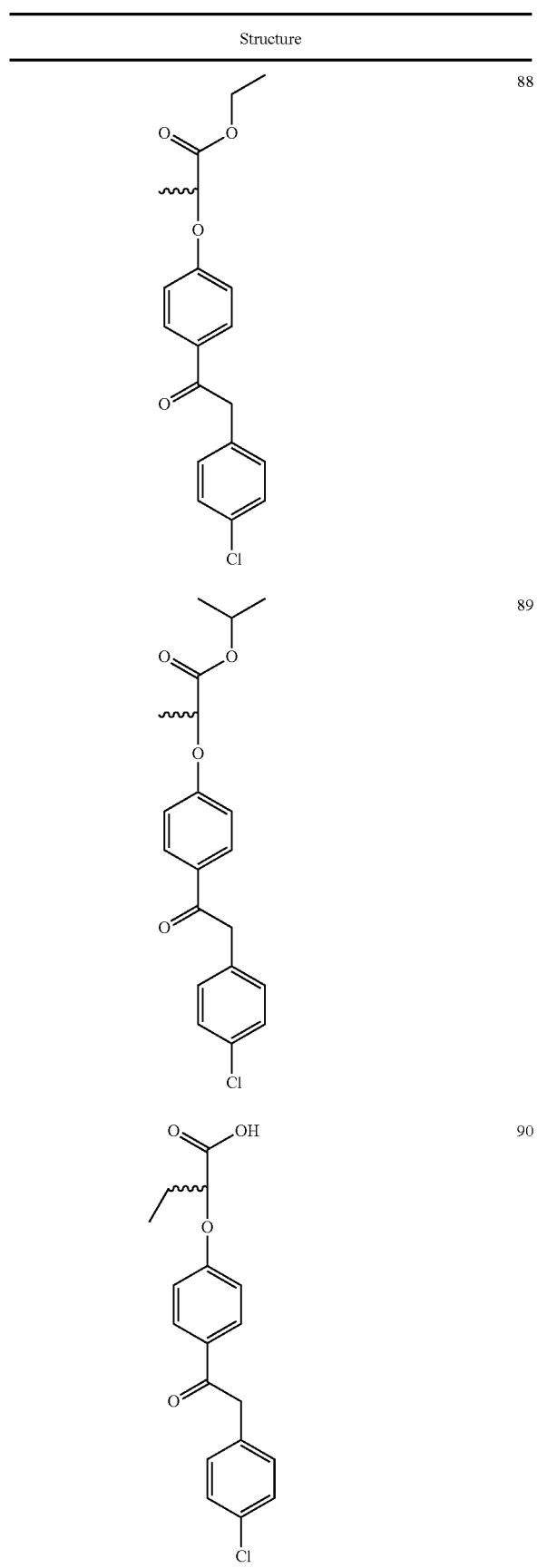 | 88 |
| 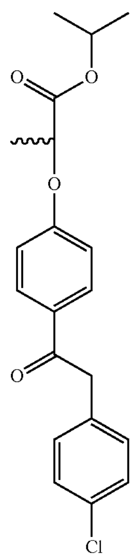 [SMILES: CC(C)OC(=O)C(C)Oc1ccc(C(=O)Cc2ccc(Cl)cc2)cc1] | 89 |
| 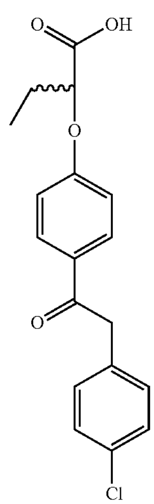 [SMILES: CCC(Oc1ccc(C(=O)Cc2ccc(Cl)cc2)cc1)C(=O)O] | 90 |
TABLE 2-continued
| Structure | |
|---|---|
| 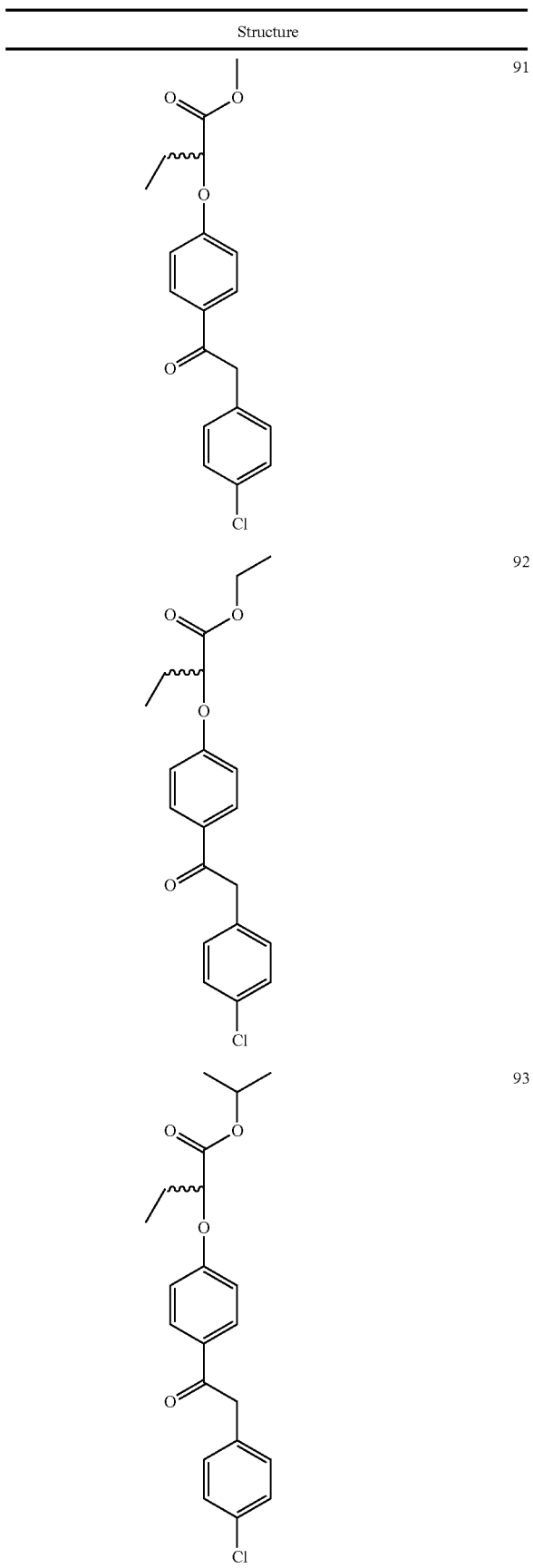 | 91 |
| 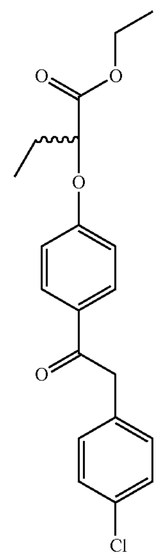 [SMILES: CCOC(=O)C(CC)Oc1ccc(C(=O)Cc2ccc(Cl)cc2)cc1] | 92 |
| 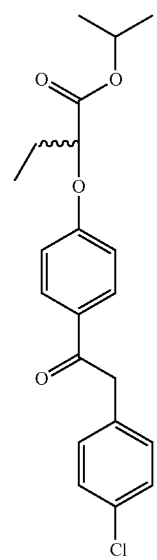 [SMILES: CCC(Oc1ccc(C(=O)Cc2ccc(Cl)cc2)cc1)C(=O)OC(C)C] | 93 |

TABLE 2-continued
| Structure | |
|---|---|
| 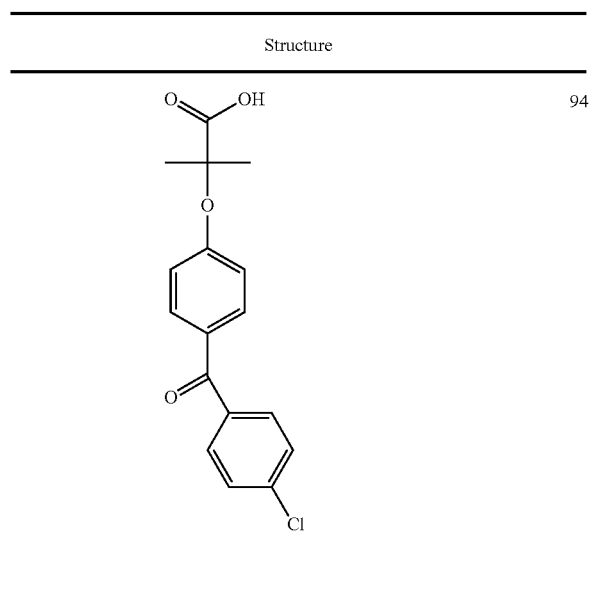 | 94 |
| 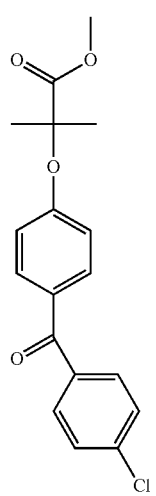 | 95 |
| 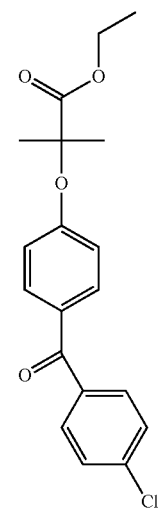 | 96 |
TABLE 2-continued
| Structure | |
|---|---|
| 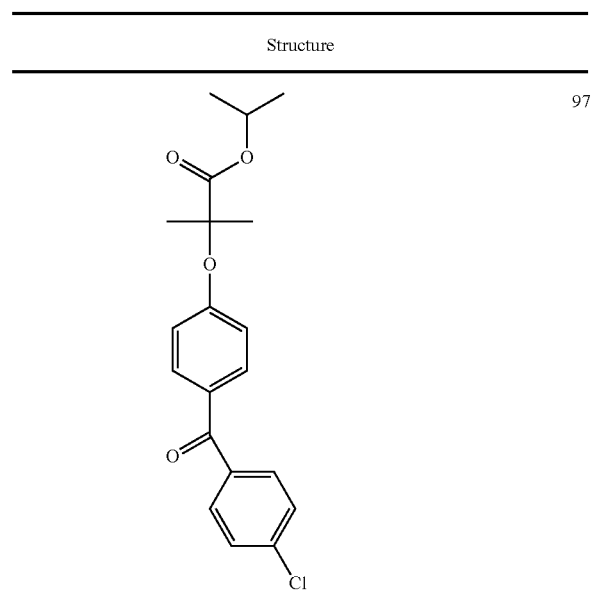 | 97 |
| 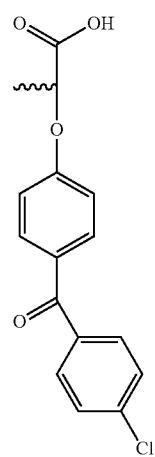 [SMILES: CC(Oc1ccc(C(=O)c2ccc(Cl)cc2)cc1)C(=O)O] | 98 |
| 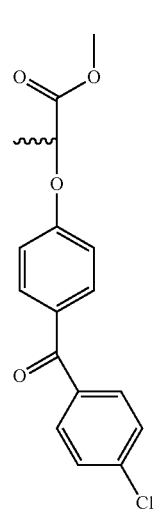 [SMILES: COC(=O)C(C)Oc1ccc(C(=O)c2ccc(Cl)cc2)cc1] | 99 |

TABLE 2-continued
| Structure | |
|---|---|
| 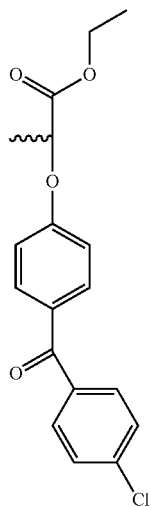 [SMILES: CCOC(=O)C(C)Oc1ccc(C(=O)c2ccc(Cl)cc2)cc1] | 100 |
| 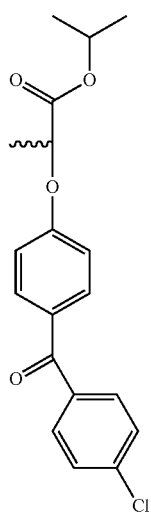 [SMILES: CC(C)OC(=O)C(C)Oc1ccc(C(=O)c2ccc(Cl)cc2)cc1] | 101 |
| 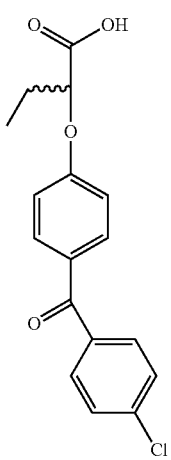 [SMILES: CCC(Oc1ccc(C(=O)c2ccc(Cl)cc2)cc1)C(=O)O] | 102 |
TABLE 2-continued
| Structure | |
|---|---|
| 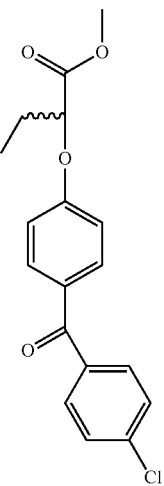 [SMILES: CCC(Oc1ccc(C(=O)c2ccc(Cl)cc2)cc1)C(=O)OC] | 103 |
| 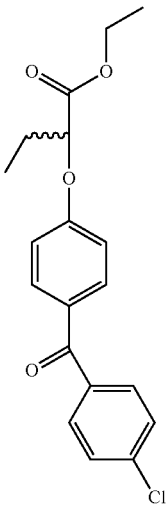 [SMILES: CCOC(=O)C(CC)Oc1ccc(C(=O)c2ccc(Cl)cc2)cc1] | 104 |
| 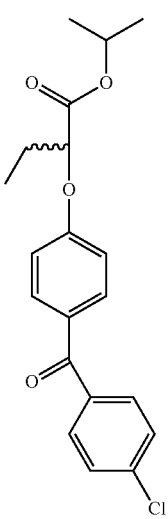 [SMILES: CCC(Oc1ccc(C(=O)c2ccc(Cl)cc2)cc1)C(=O)OC(C)C] | 105 |

TABLE 3
| Structure | |
|---|---|
| 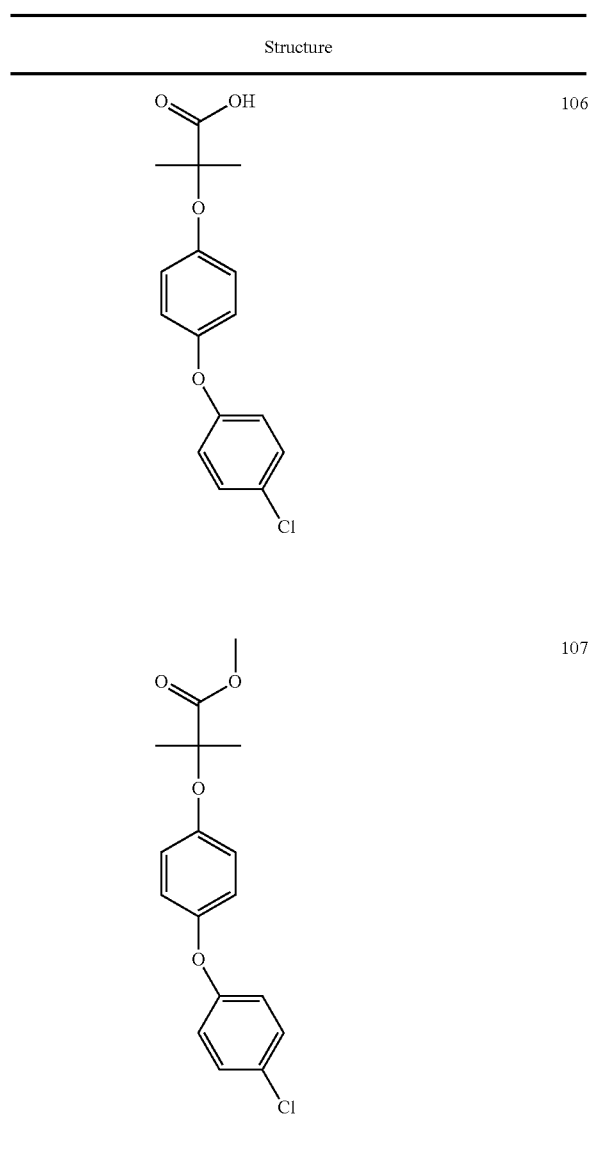 | 106 |
| | 107 |
| | 108 |
TABLE 3-continued
| Structure | |
|---|---|
| 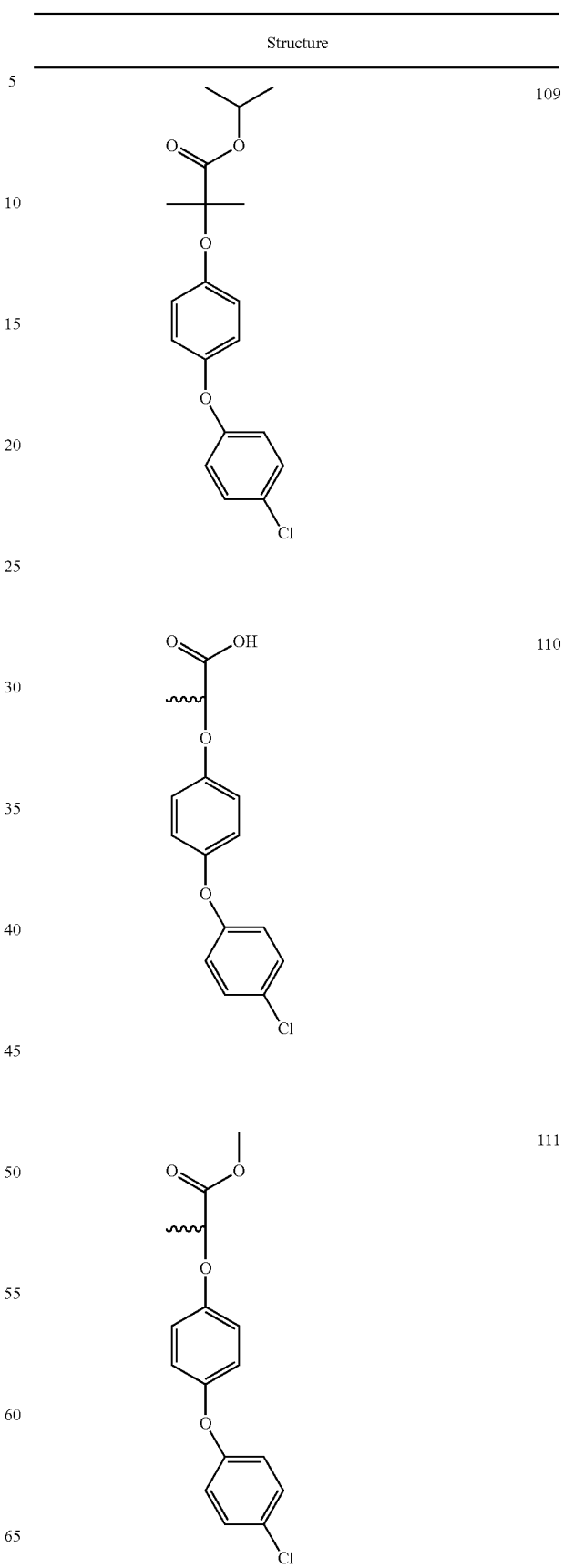 | 109 |
| | 110 |
| | 111 |

TABLE 3-continued
| Structure | |
|---|---|
| 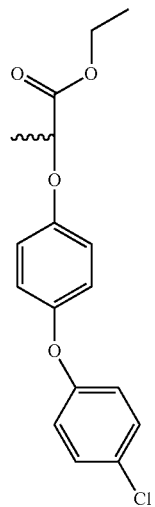 [SMILES: CCOC(=O)C(C)Oc1ccc(Oc2ccc(Cl)cc2)cc1] | 112 |
| 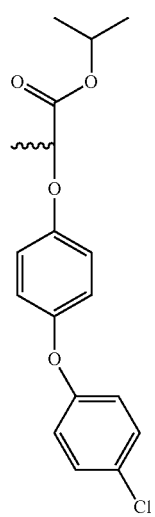 [SMILES: CC(C)OC(=O)C(C)Oc1ccc(Oc2ccc(Cl)cc2)cc1] | 113 |
| 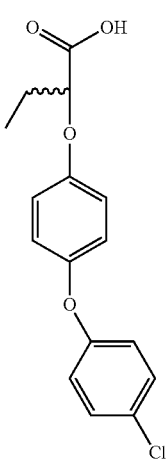 [SMILES: CCC(Oc1ccc(Oc2ccc(Cl)cc2)cc1)C(=O)O] | 114 |
| 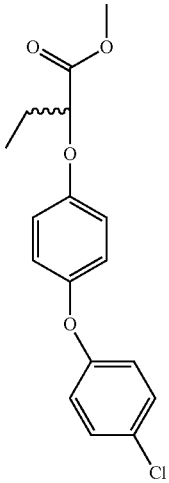 [SMILES: CCC(Oc1ccc(Oc2ccc(Cl)cc2)cc1)C(=O)OC] | 115 |
| 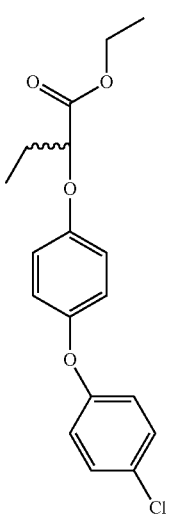 [SMILES: CCOC(=O)C(CC)Oc1ccc(Oc2ccc(Cl)cc2)cc1] | 116 |
| 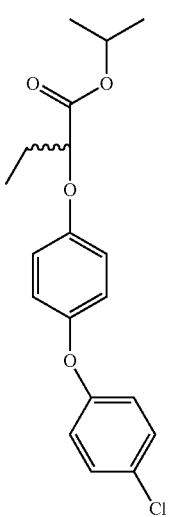 [SMILES: CCC(Oc1ccc(Oc2ccc(Cl)cc2)cc1)C(=O)OC(C)C] | 117 |

TABLE 3-continued
| Structure | |
|---|---|
| 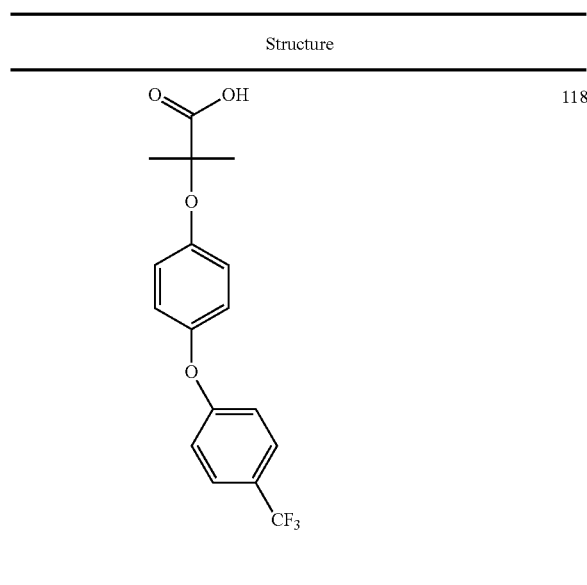 | 118 |
| | 119 |
| 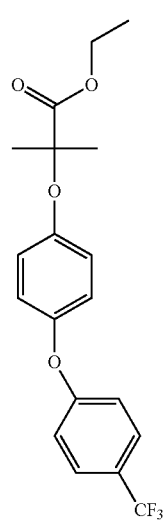 | 120 |
TABLE 3-continued
| Structure | |
|---|---|
| 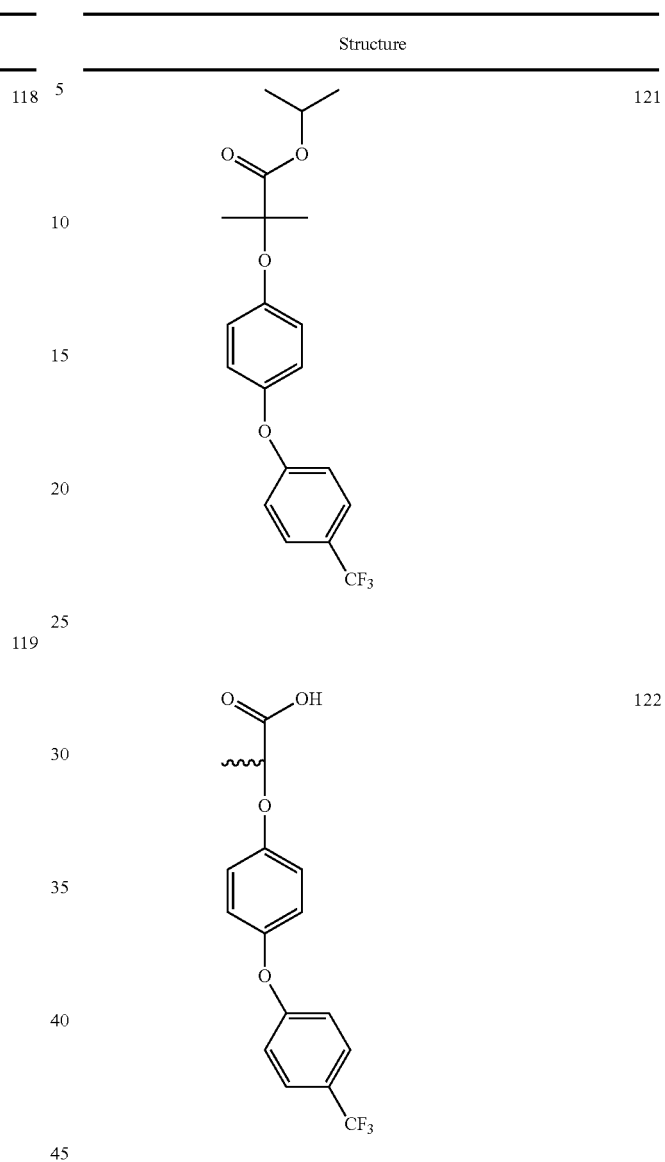 | 121 |
| | 122 |
| 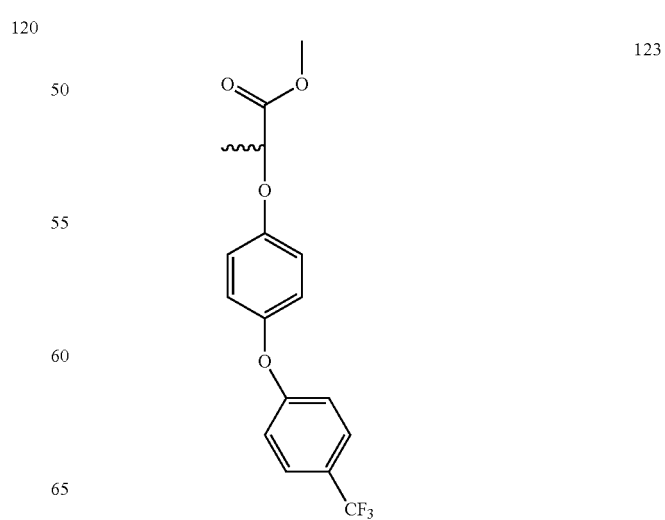 | 123 |

TABLE 3-continued
| Structure | |
|---|---|
| 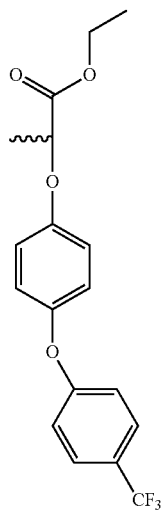 [SMILES: CCOC(=O)C(C)Oc1ccc(Oc2ccc(C(F)(F)F)cc2)cc1] | 124 |
| 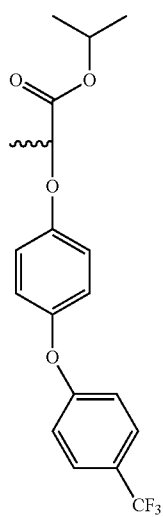 [SMILES: CC(C)OC(=O)C(C)Oc1ccc(Oc2ccc(C(F)(F)F)cc2)cc1] | 125 |
| 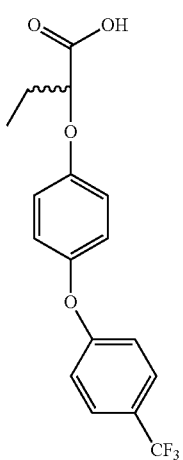 [SMILES: CCC(Oc1ccc(Oc2ccc(C(F)(F)F)cc2)cc1)C(=O)O] | 126 |
| 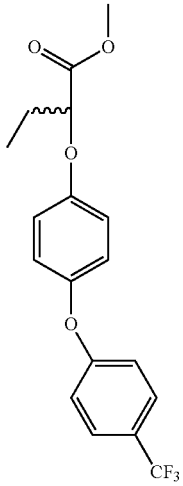 [SMILES: CCC(Oc1ccc(Oc2ccc(C(F)(F)F)cc2)cc1)C(=O)OC] | 127 |
| 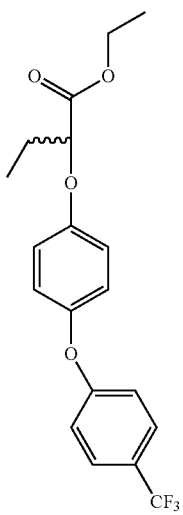 [SMILES: CCOC(=O)C(CC)Oc1ccc(Oc2ccc(C(F)(F)F)cc2)cc1] | 128 |
|  | 129 |

TABLE 3-continued
| Structure | |
|---|---|
| 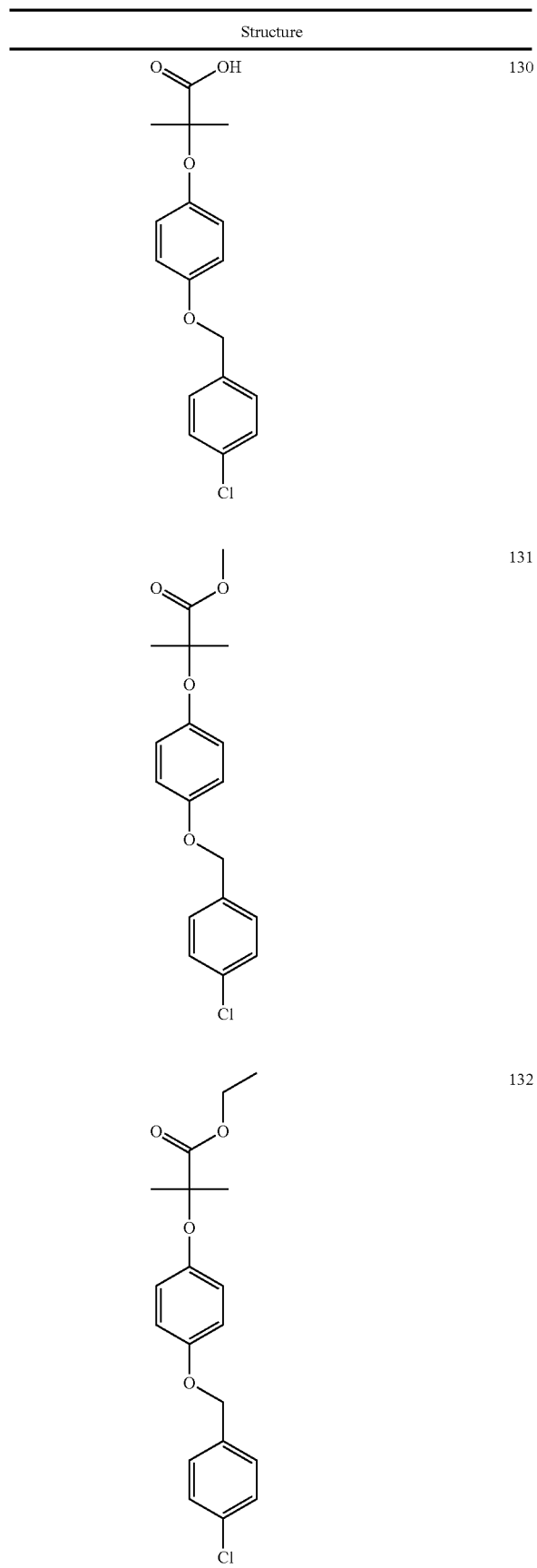 | 130 |
| | 131 |
| | 132 |
| Structure | |
|---|---|
| 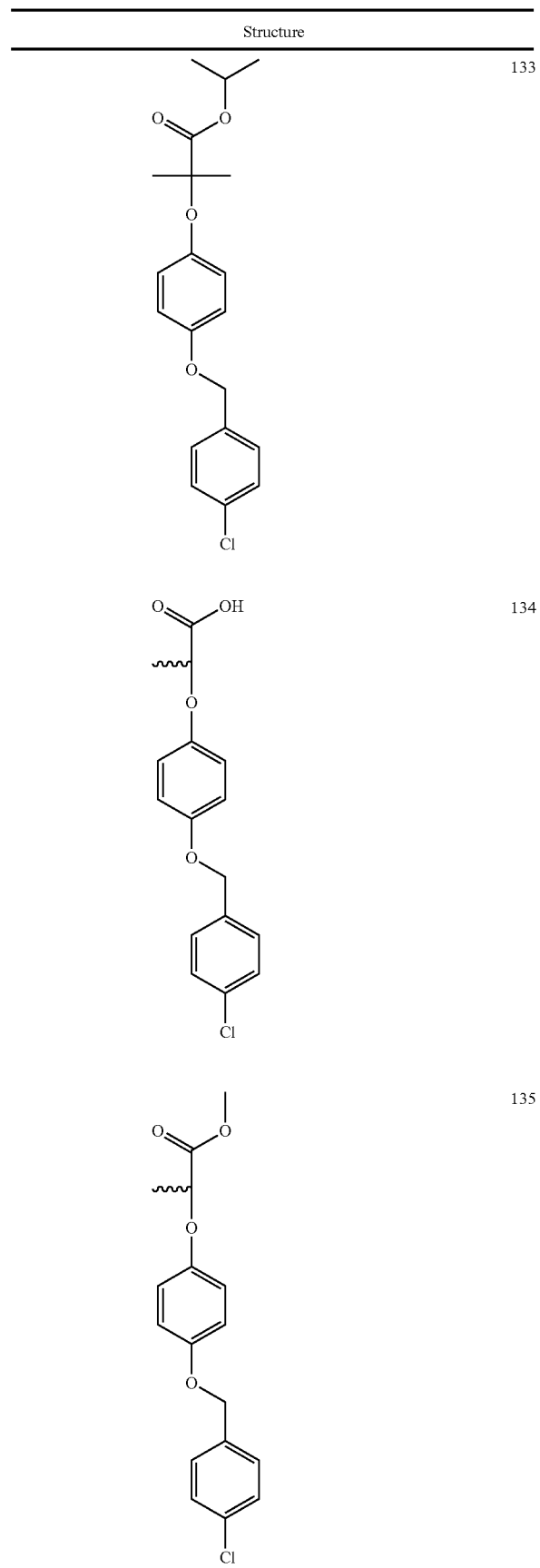 | 133 |
| | 134 |
| | 135 |

TABLE 3-continued
| Structure | |
|---|---|
| 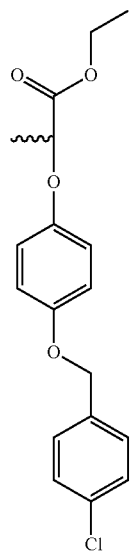 [SMILES: CCOC(=O)C(C)Oc1ccc(OCc2ccc(Cl)cc2)cc1] | 136 |
| 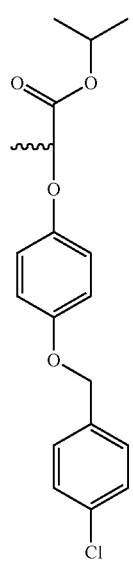 [SMILES: CC(C)OC(=O)C(C)Oc1ccc(OCc2ccc(Cl)cc2)cc1] | 137 |
| 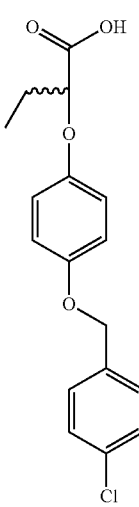 | 138 |
| 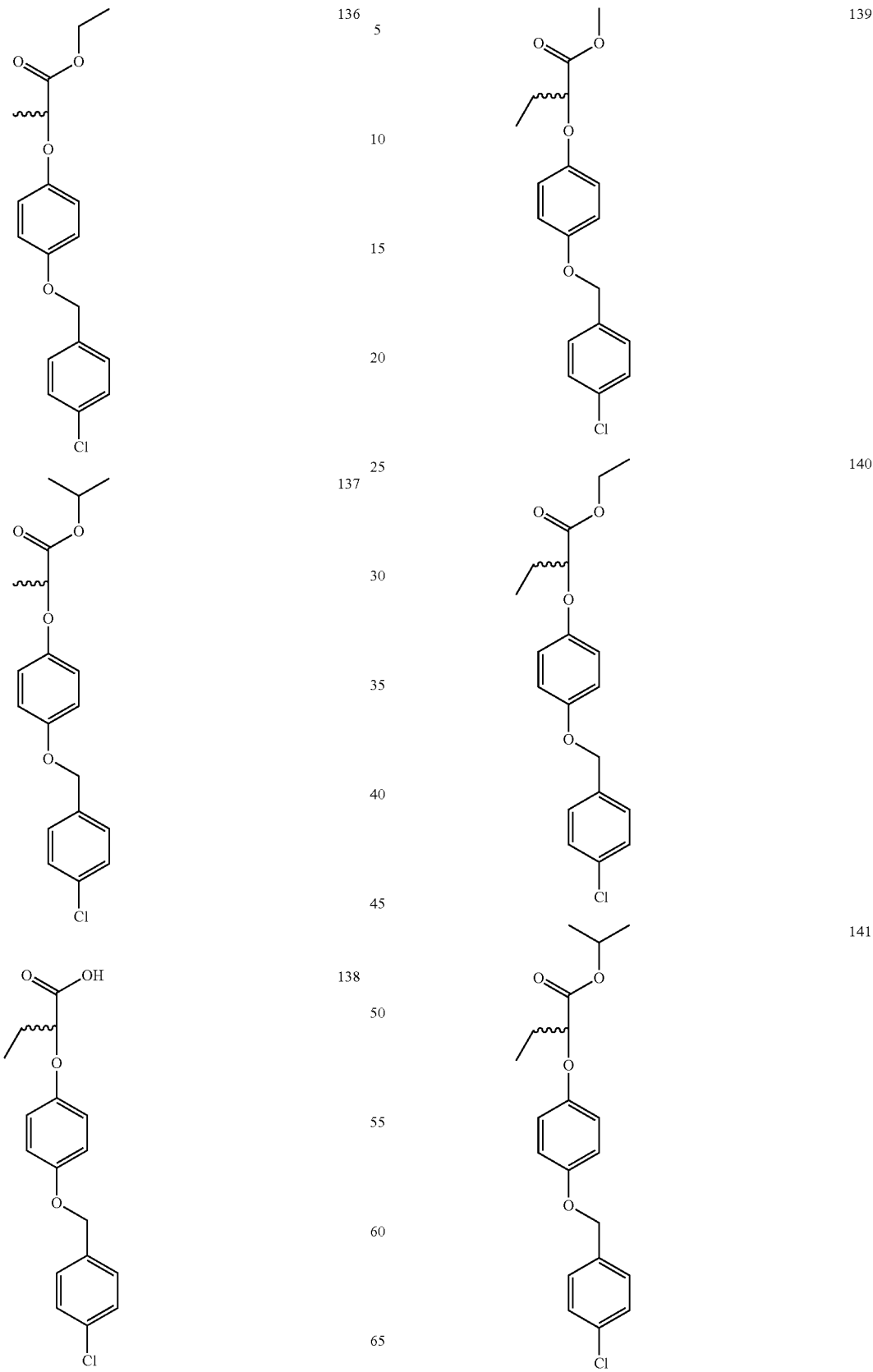 | 139 |
| | 140 |
| | 141 |

TABLE 3-continued
| Structure | |
|---|---|
| 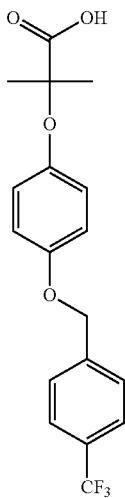 [SMILES: CC(C)(Oc1ccc(OCc2ccc(C(F)(F)F)cc2)cc1)C(=O)O] | 142 |
| 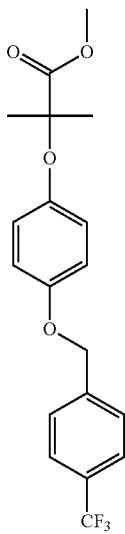 [SMILES: COC(=O)C(C)(C)Oc1ccc(OCc2ccc(C(F)(F)F)cc2)cc1] | 143 |
| 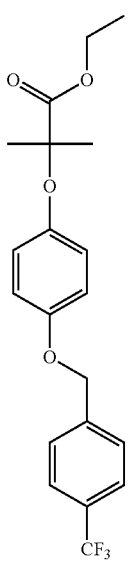 [SMILES: CCOC(=O)C(C)(C)Oc1ccc(OCc2ccc(C(F)(F)F)cc2)cc1] | 144 |
TABLE 3-continued
| Structure | |
|---|---|
| 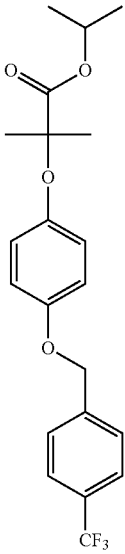 [SMILES: CC(C)OC(=O)C(C)(C)Oc1ccc(OCc2ccc(C(F)(F)F)cc2)cc1] | 145 |
| 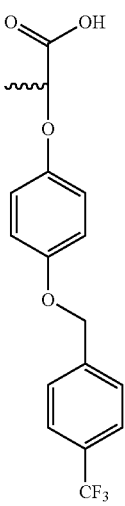 [SMILES: CC(Oc1ccc(OCc2ccc(C(F)(F)F)cc2)cc1)C(=O)O] | 146 |
|  | 147 |

TABLE 3-continued
| Structure | |
|---|---|
| 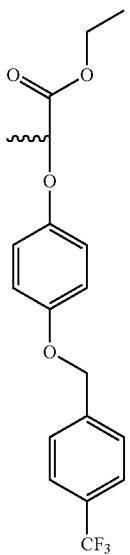 [SMILES: CCOC(=O)C(C)Oc1ccc(OCc2ccc(C(F)(F)F)cc2)cc1] | 148 |
| 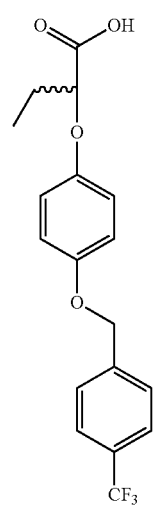 [SMILES: CCC(Oc1ccc(OCc2ccc(C(F)(F)F)cc2)cc1)C(=O)O] | 149 |
| 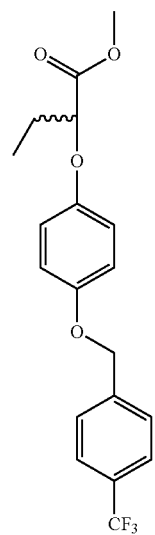 [SMILES: CCC(Oc1ccc(OCc2ccc(C(F)(F)F)cc2)cc1)C(=O)OC] | 150 |
TABLE 3-continued
| Structure | |
|---|---|
| 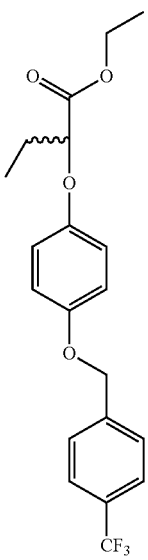 | 151 |
| 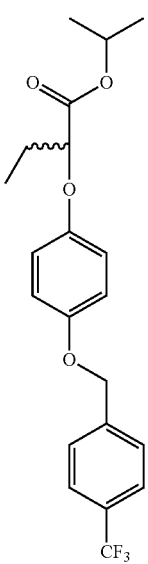 [SMILES: CCC(Oc1ccc(OCc2ccc(C(F)(F)F)cc2)cc1)C(=O)OC(C)C] | 152 |
TABLE 4
| Structure | |
|---|---|
| 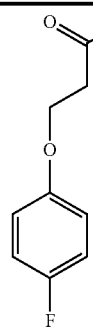 | 153 |

TABLE 4-continued
| Structure | |
|---|---|
| 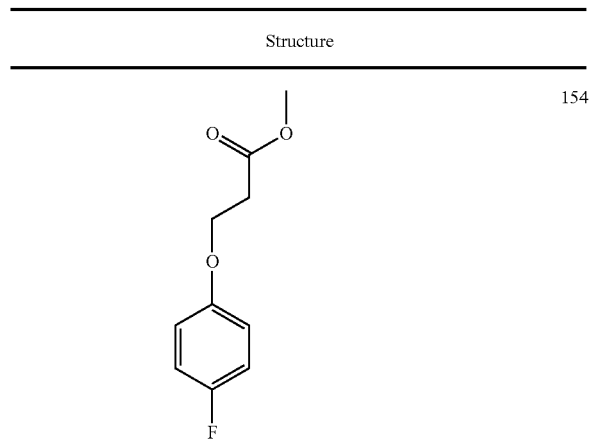 | 154 |
| 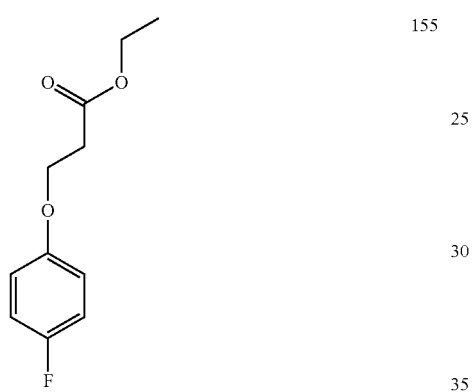 | 155 |
| 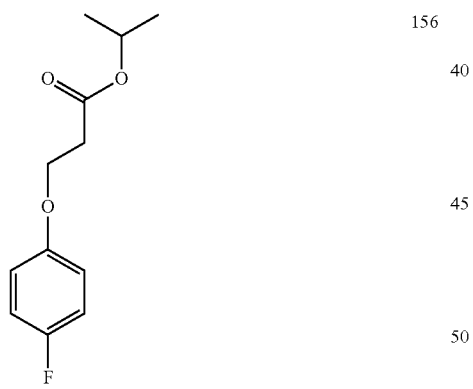 | 156 |
| 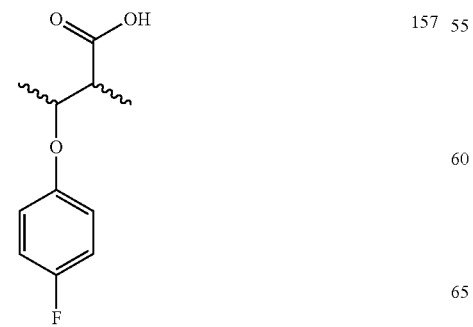 | 157 |
| 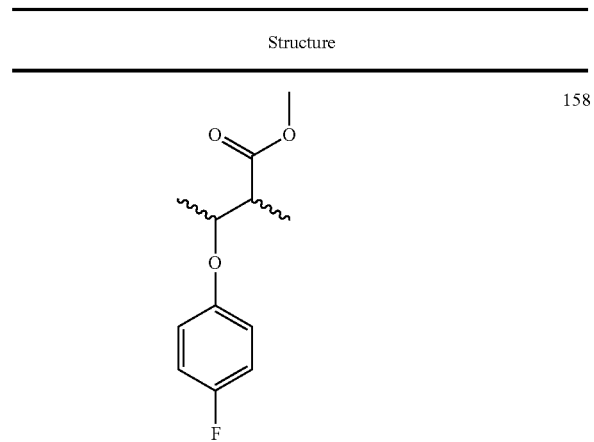 | 158 |
| 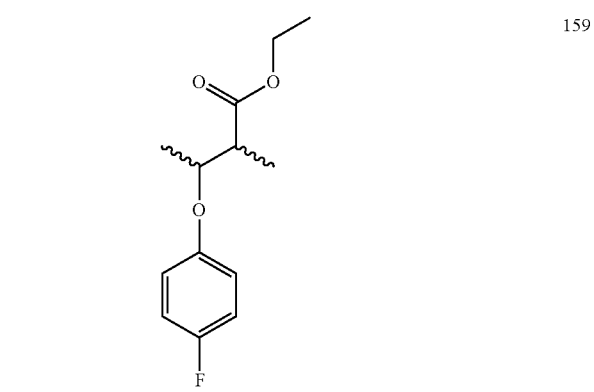 | 159 |
| 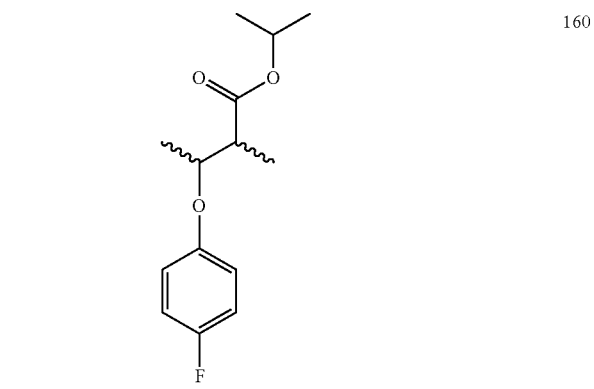 | 160 |
| 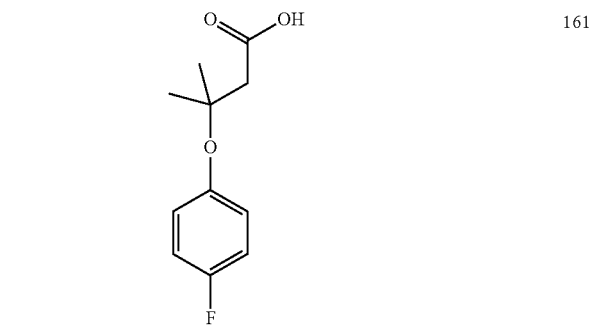 | 161 |

TABLE 4-continued
| Structure | |
|---|---|
| 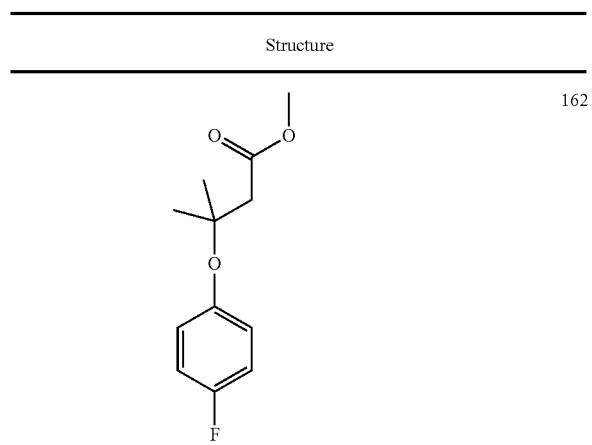 | 162 |
| 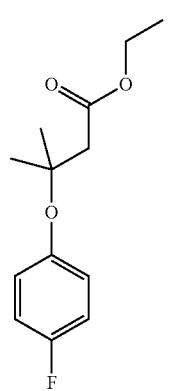 [SMILES: CCOC(=O)CC(C)(C)Oc1ccc(F)cc1] | 163 |
| 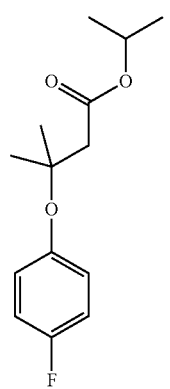 [SMILES: CC(C)OC(=O)CC(C)(C)Oc1ccc(F)cc1] | 164 |
| 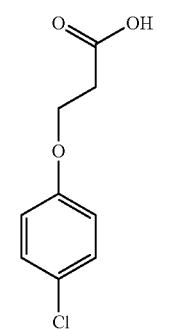 | 165 |
TABLE 4-continued
| Structure | |
|---|---|
| 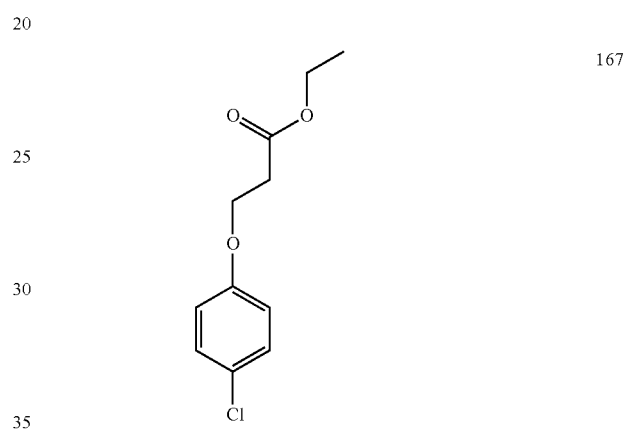 | 166 |
| | 167 |
| | 168 |
| 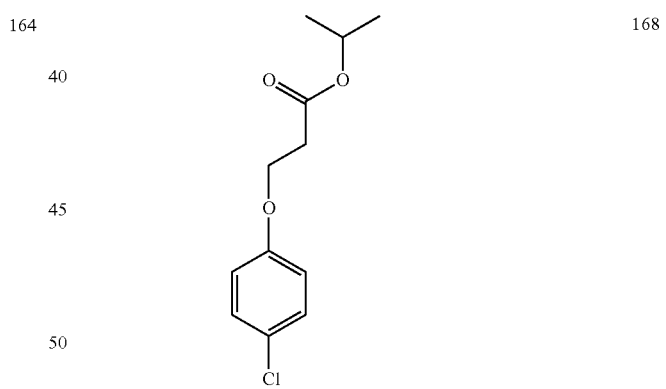 | |
| 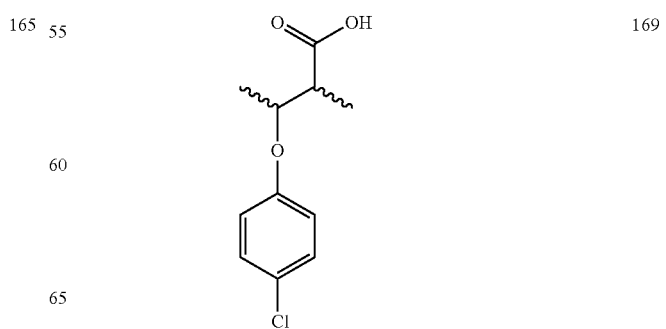 | 169 |

TABLE 4-continued
| Structure | |
|---|---|
| 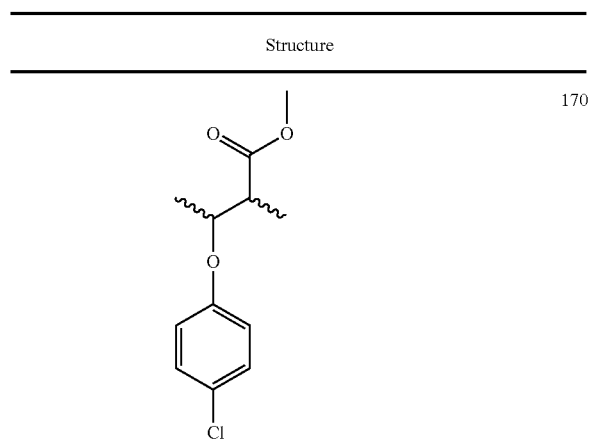 | 170 |
| 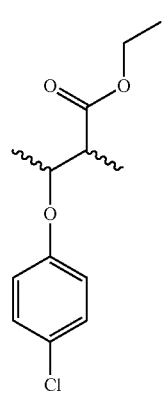 | 171 |
| 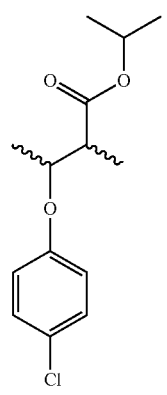 | 172 |
| 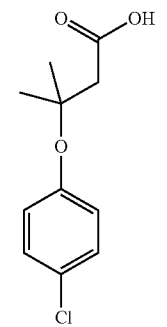 | 173 |
TABLE 4-continued
| Structure | |
|---|---|
| 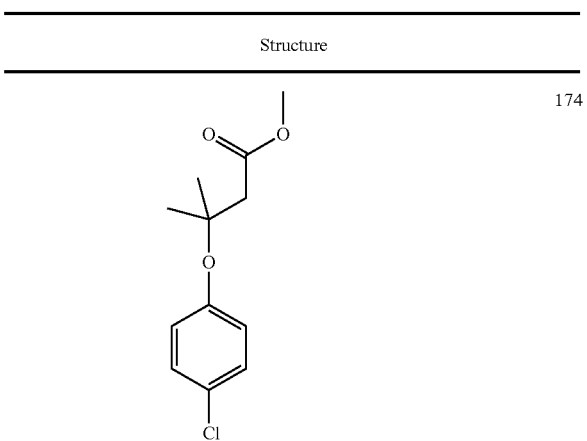 | 174 |
| 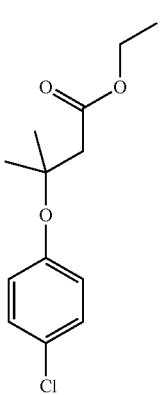 [SMILES: CCOC(=O)CC(C)(C)Oc1ccc(Cl)cc1] | 175 |
| 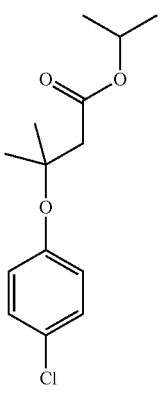 [SMILES: CC(C)OC(=O)CC(C)(C)Oc1ccc(Cl)cc1] | 176 |
| 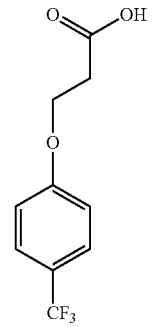 [SMILES: O=C(O)CCOc1ccc(C(F)(F)F)cc1] | 177 |

TABLE 4-continued
| Structure | |
|---|---|
| 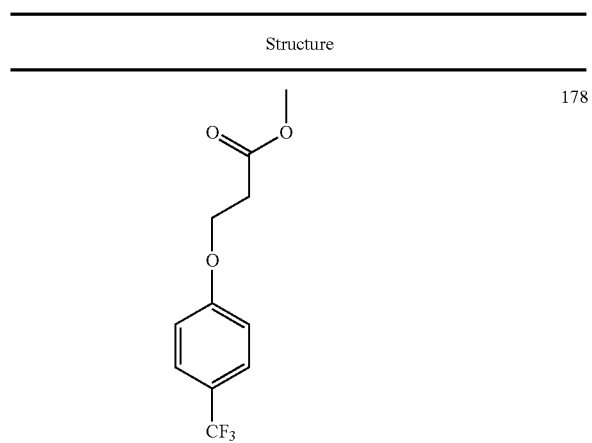 | 178 |
| 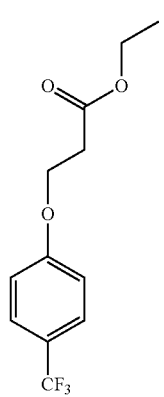 [SMILES: CCOC(=O)CCOc1ccc(C(F)(F)F)cc1] | 179 |
| 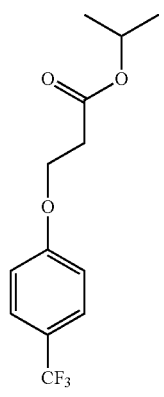 [SMILES: CC(C)OC(=O)CCOc1ccc(C(F)(F)F)cc1] | 180 |
| 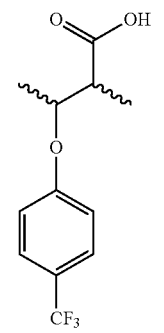 | 181 |
TABLE 4-continued
| Structure | |
|---|---|
| 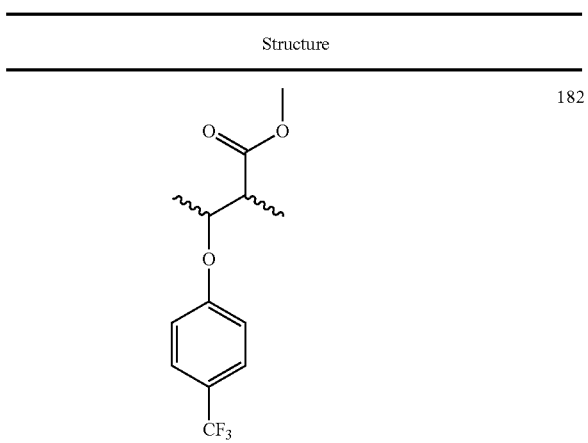 | 182 |
| 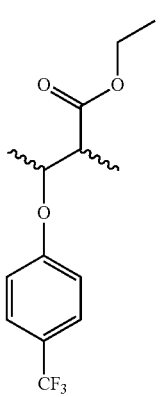 | 183 |
| 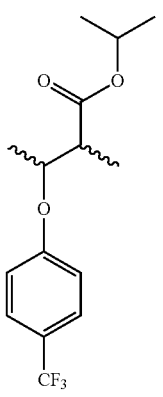 | 184 |
| 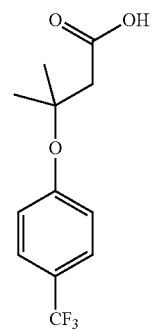 | 185 |

TABLE 4-continued
| Structure | |
|---|---|
| 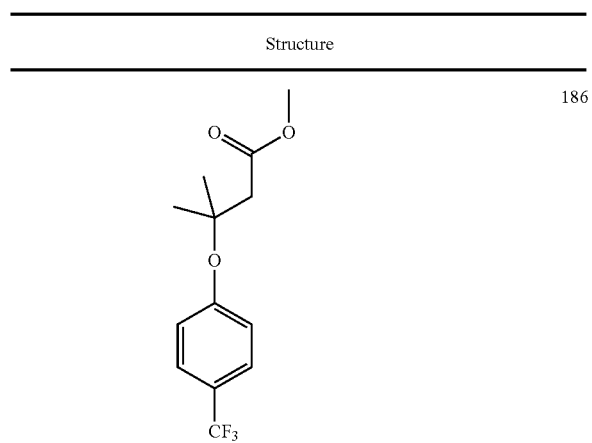 | 186 |
| 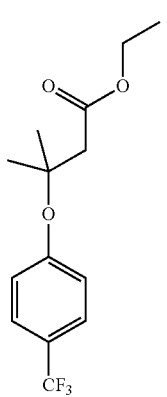 [SMILES: CCOC(=O)CC(C)(C)Oc1ccc(C(F)(F)F)cc1] | 187 |
| 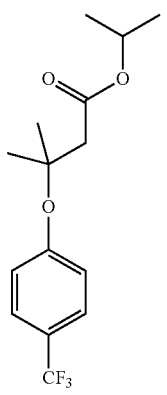 [SMILES: CC(C)OC(=O)CC(C)(C)Oc1ccc(C(F)(F)F)cc1] | 188 |
| 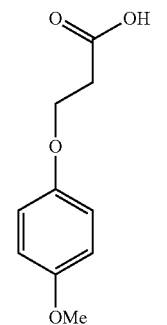 | 189 |
TABLE 4-continued
| Structure | |
|---|---|
| 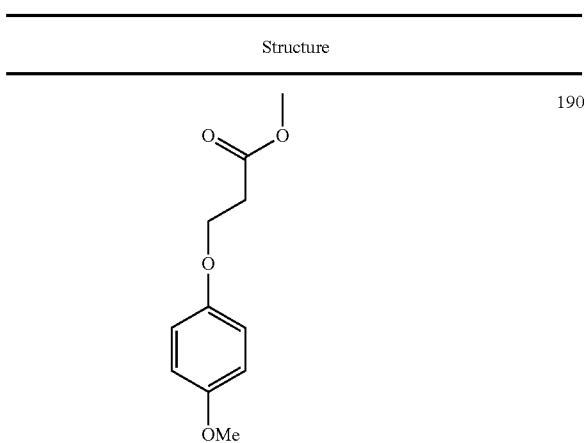 | 190 |
| 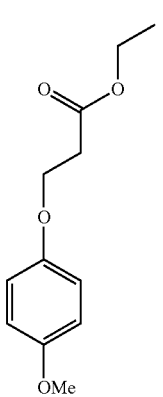 | 191 |
| 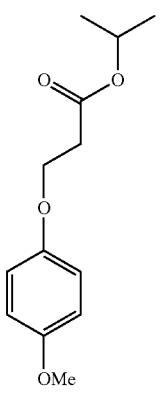 [SMILES: COc1ccc(OCCC(=O)OC(C)C)cc1] | 192 |
| 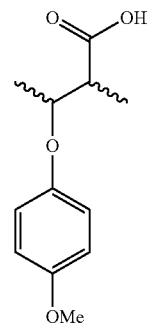 | 193 |

TABLE 4-continued
| Structure | |
|---|---|
| 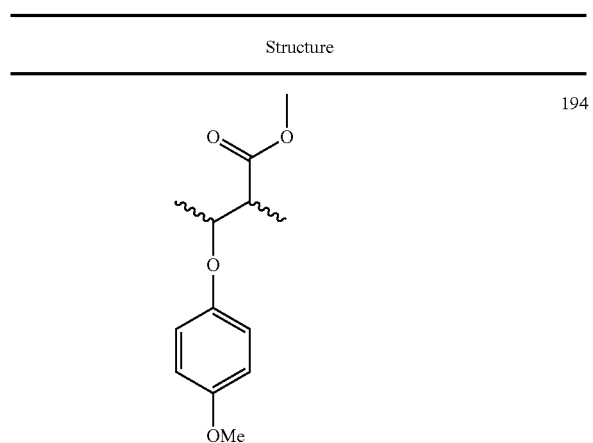 | 194 |
| 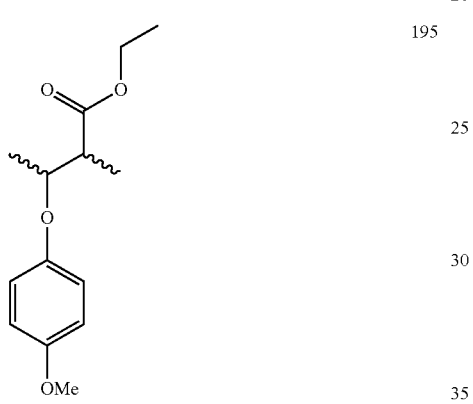 | 195 |
| 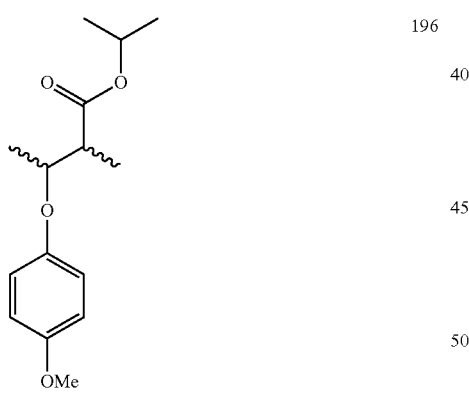 | 196 |
| 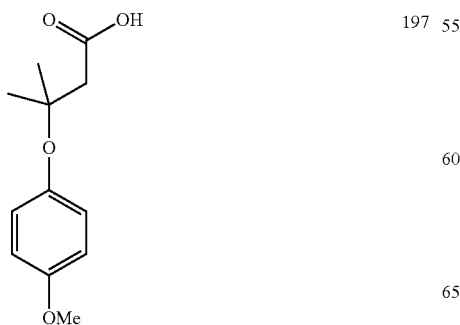 | 197 |
TABLE 4-continued
| Structure | |
|---|---|
| 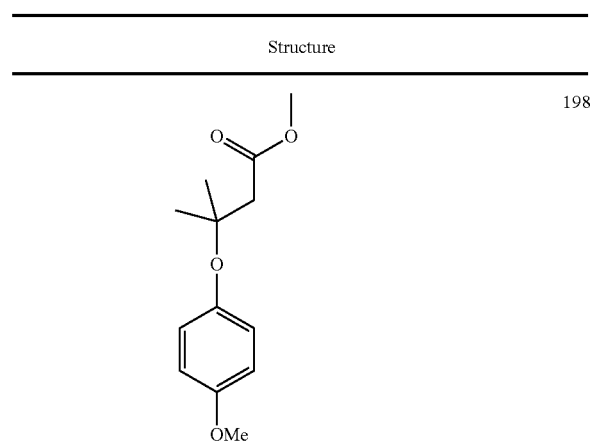 | 198 |
| 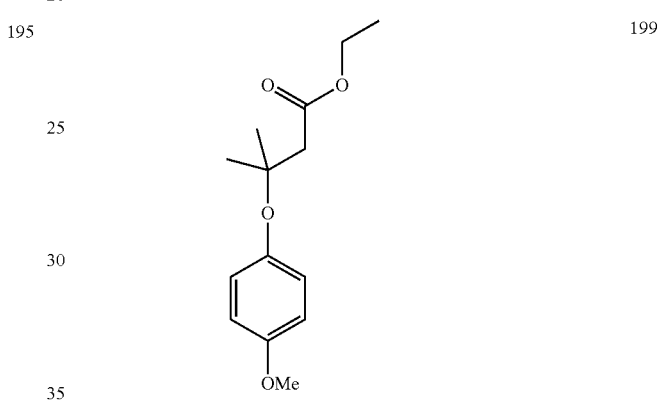 | 199 |
| 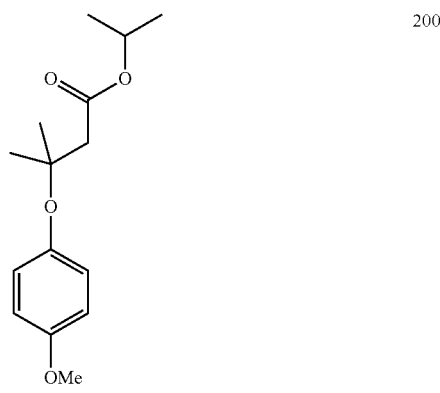 | 200 |
| 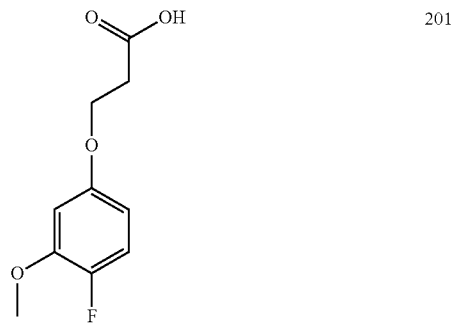 | 201 |

TABLE 4-continued
| Structure | |
|---|---|
| 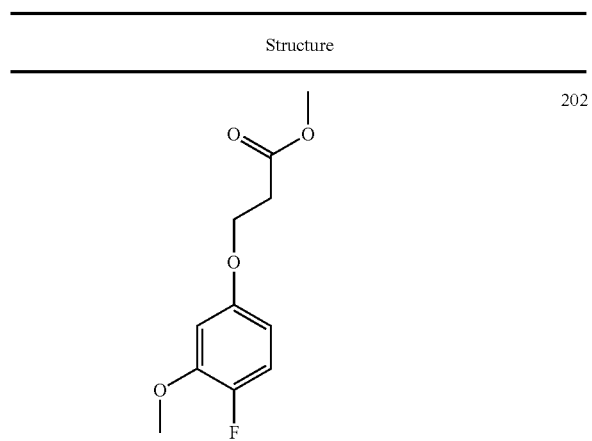 | 202 |
| 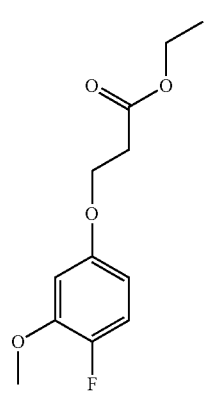 [SMILES: CCOC(=O)CCOc1ccc(F)c(OC)c1] | 203 |
| 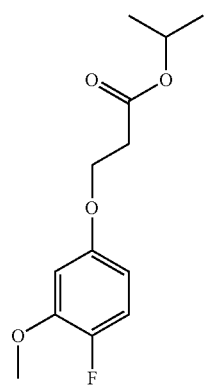 [SMILES: COc1cc(OCCC(=O)OC(C)C)ccc1F] | 204 |
| 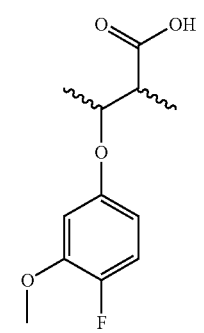 | 205 |
TABLE 4-continued
| Structure | |
|---|---|
| 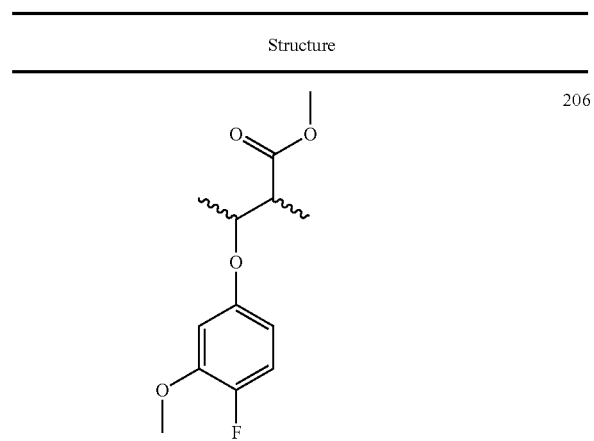 | 206 |
| 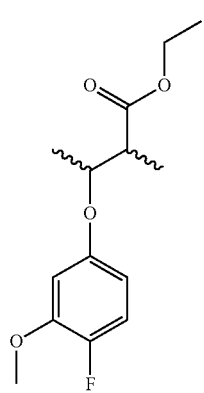 | 207 |
| 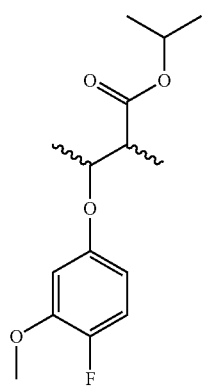 | 208 |
| 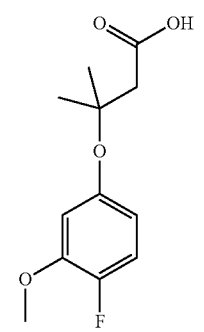 [SMILES: COc1cc(OC(C)(C)CC(=O)O)ccc1F] | 209 |

TABLE 4-continued
| Structure | |
|---|---|
| 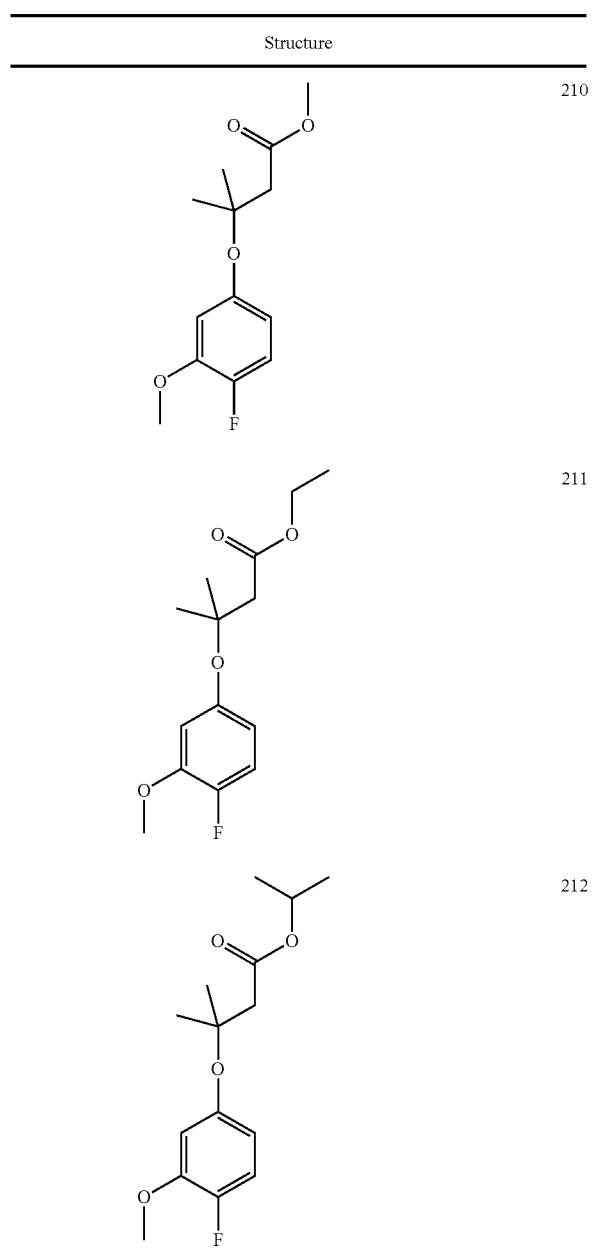 | 210 |
| 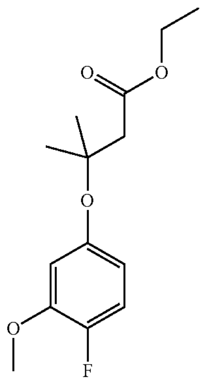 [SMILES: CCOC(=O)CC(C)(C)Oc1ccc(F)c(OC)c1] | 211 |
| 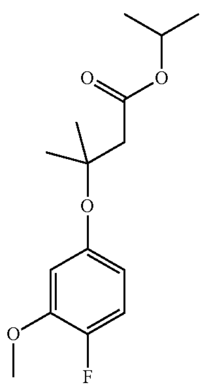 [SMILES: COc1cc(OC(C)(C)CC(=O)OC(C)C)ccc1F] | 212 |
TABLE 5
| Structure | |
|---|---|
| 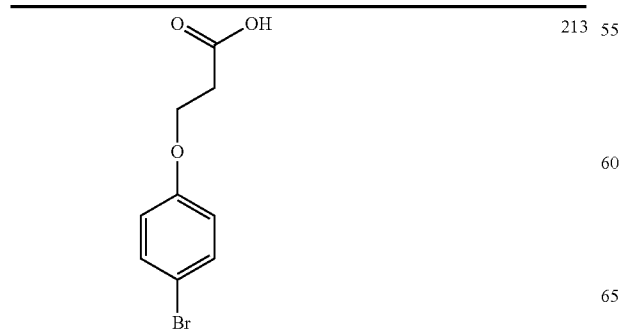 | 213 |
TABLE 5-continued
| Structure | |
|---|---|
| 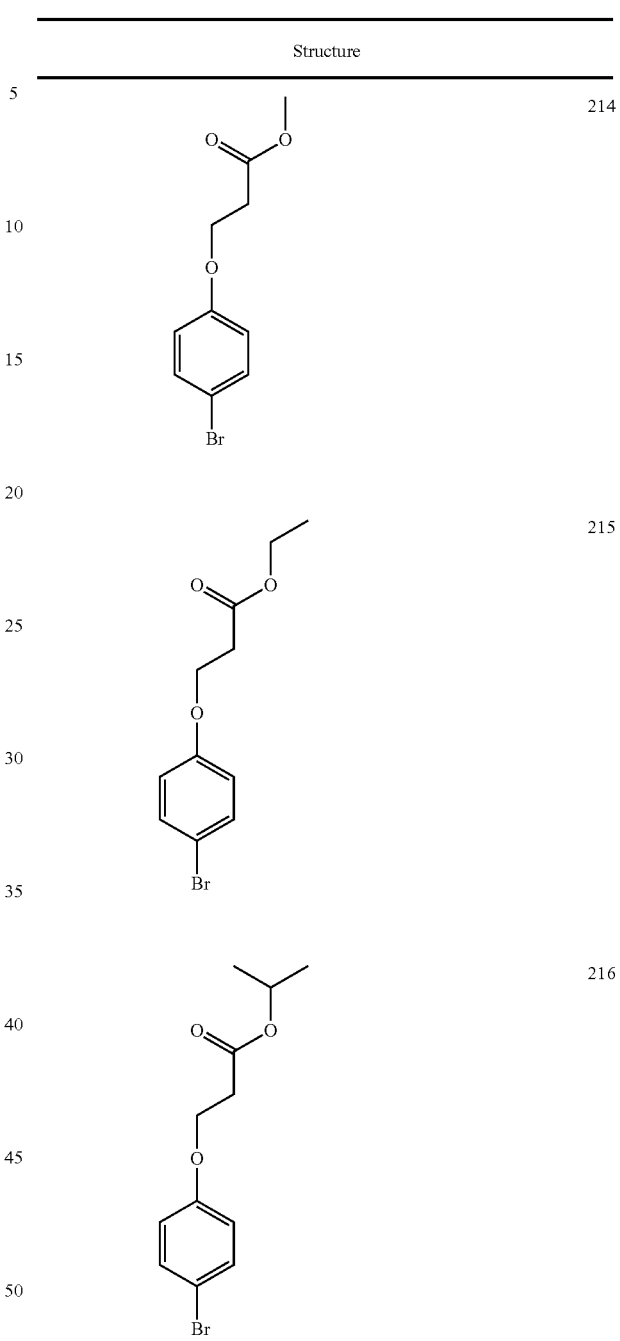 | 214 |
| 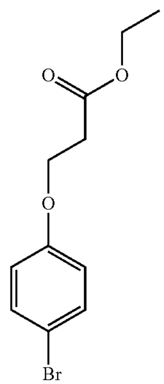 | 215 |
| 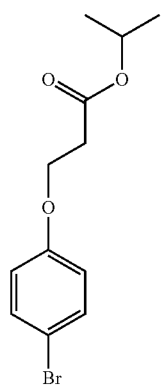 [SMILES: CC(C)OC(=O)CCOc1ccc(Br)cc1] | 216 |
| 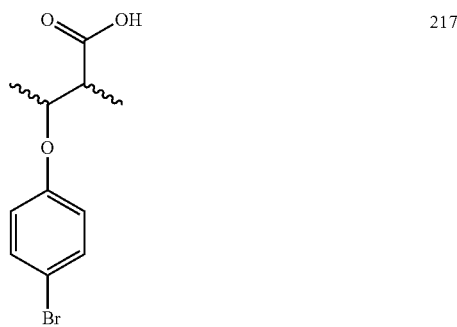 | 217 |

TABLE 5-continued
| Structure | |
|---|---|
| 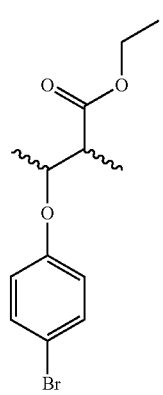 | 218 |
| 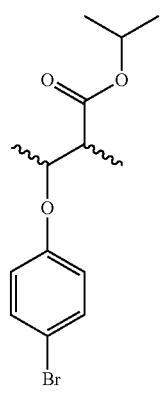 | 219 |
| 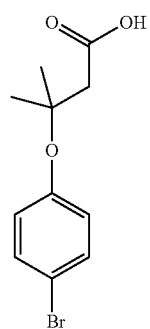 | 220 |
| 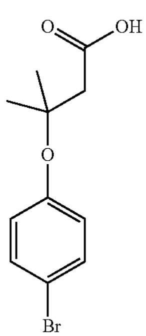 | 221 |
TABLE 5-continued
| Structure | |
|---|---|
| 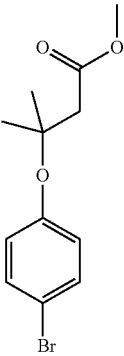 [SMILES: COC(=O)CC(C)(C)Oc1ccc(Br)cc1] | 222 |
| 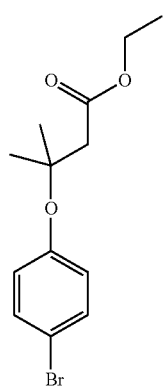 [SMILES: CCOC(=O)CC(C)(C)Oc1ccc(Br)cc1] | 223 |
| 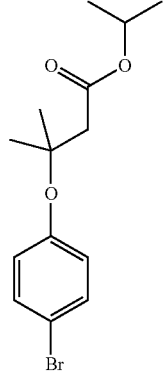 [SMILES: CC(C)OC(=O)CC(C)(C)Oc1ccc(Br)cc1] | 224 |
| 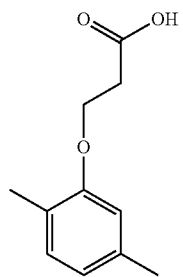 | 225 |
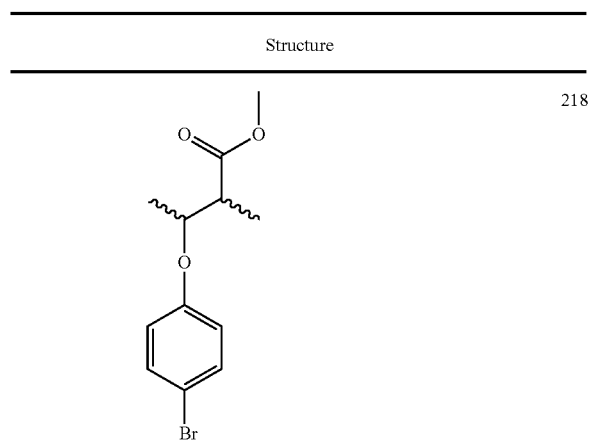

TABLE 5-continued
| Structure | |
|---|---|
| 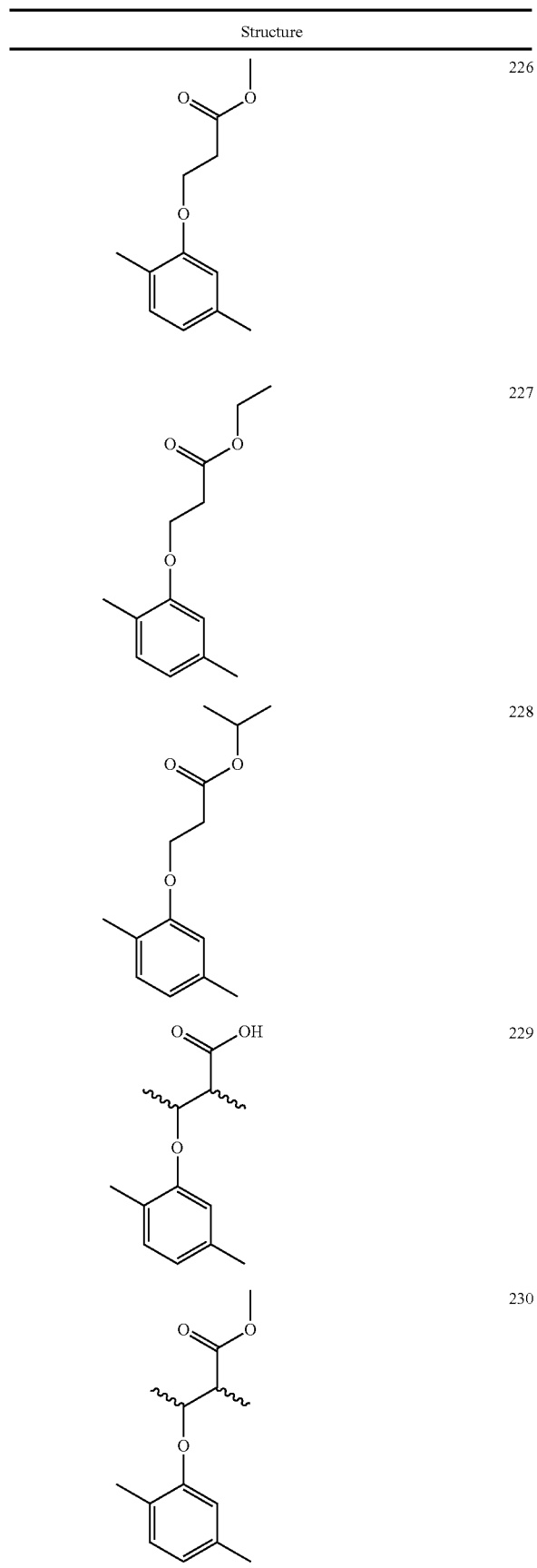 | 226 227 228 229 230 |
| 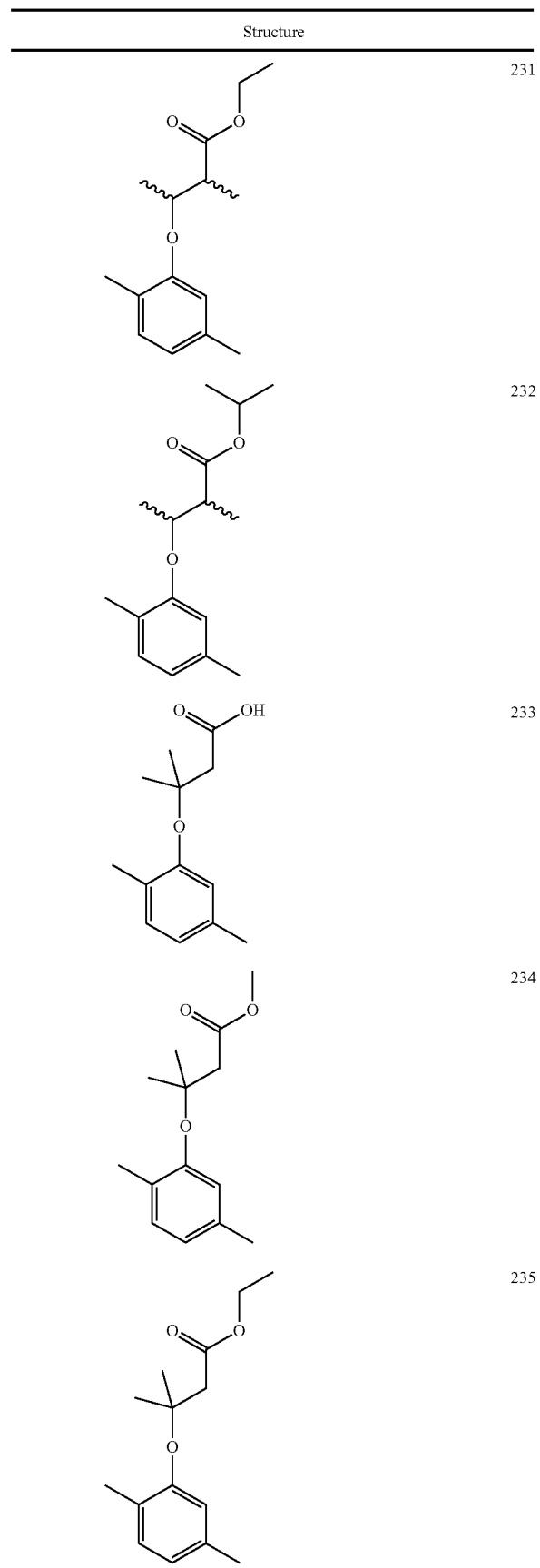 | 231 232 233 234 235 |

TABLE 5-continued
| Structure | |
|---|---|
| 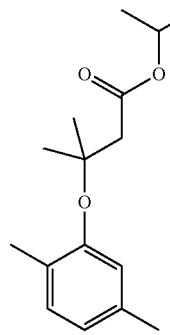 | 236 |
| 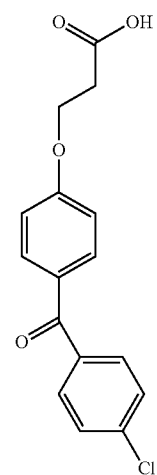 [SMILES: O=C(O)CCOc1ccc(C(=O)c2ccc(Cl)cc2)cc1] | 237 |
| 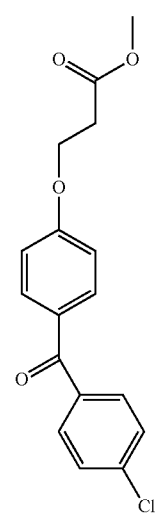 [SMILES: COC(=O)CCOc1ccc(C(=O)c2ccc(Cl)cc2)cc1] | 238 |
TABLE 5-continued
| Structure | |
|---|---|
| 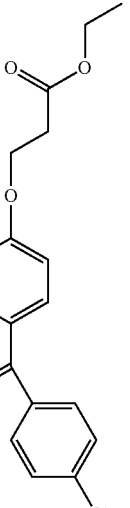 | 239 |
| 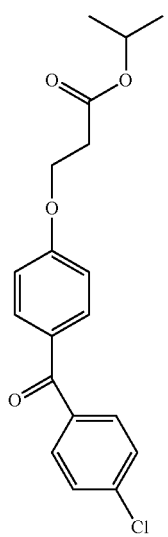 [SMILES: CC(C)OC(=O)CCOc1ccc(C(=O)c2ccc(Cl)cc2)cc1] | 240 |
| 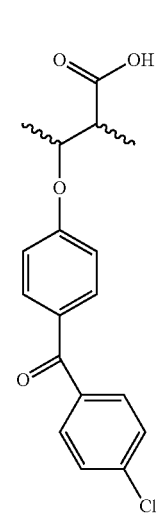 | 241 |

TABLE 5-continued
| Structure | |
|---|---|
| 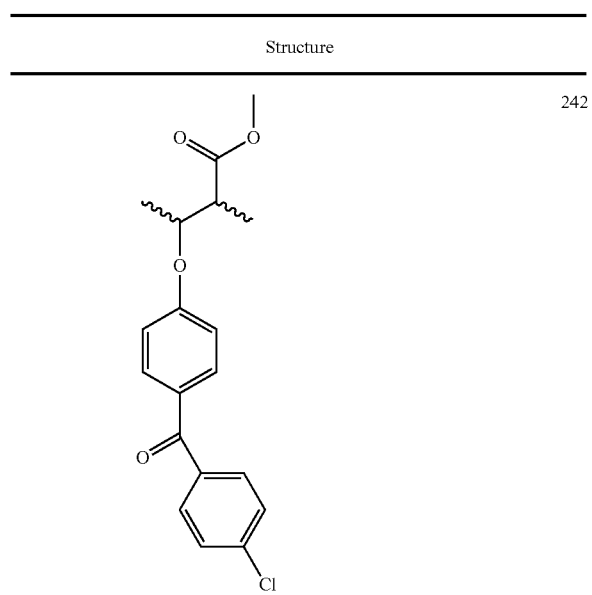 | 242 |
| 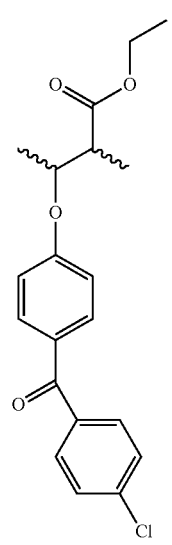 | 243 |
| 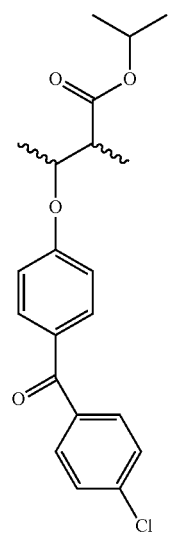 | 244 |
| 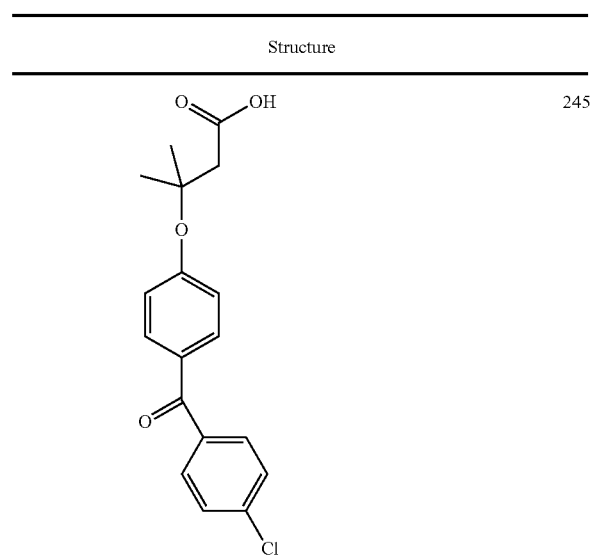 | 245 |
| 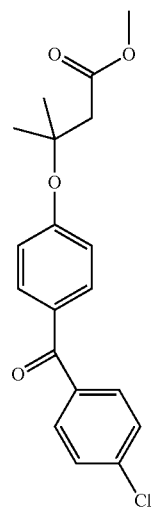 [SMILES: COC(=O)CC(C)(C)Oc1ccc(C(=O)c2ccc(Cl)cc2)cc1] | 246 |
| 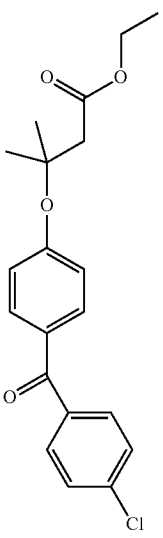 [SMILES: CCOC(=O)CC(C)(C)Oc1ccc(C(=O)c2ccc(Cl)cc2)cc1] | 247 |

TABLE 5-continued
| Structure | |
|---|---|
| 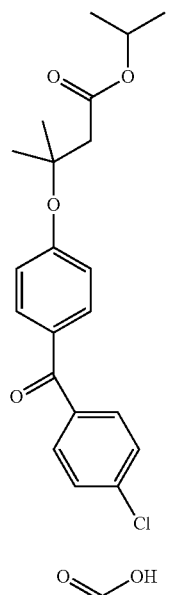 | 248 |
| 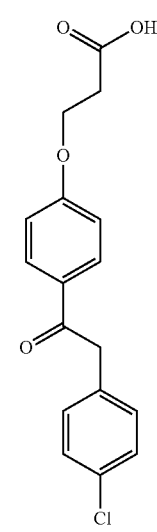 [SMILES: O=C(O)CCOc1ccc(C(=O)Cc2ccc(Cl)cc2)cc1] | 249 |
| 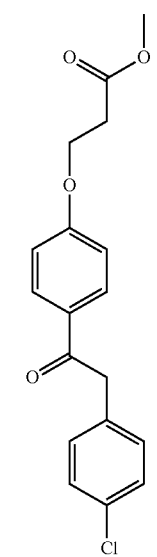 | 250 |
TABLE 5-continued
| Structure | |
|---|---|
| 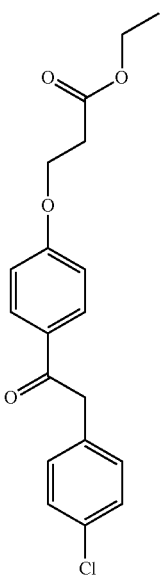 [SMILES: CCOC(=O)CCOc1ccc(C(=O)Cc2ccc(Cl)cc2)cc1] | 251 |
| 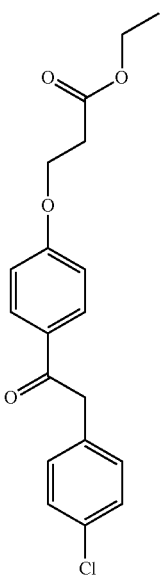 [SMILES: CCOC(=O)CCOc1ccc(C(=O)Cc2ccc(Cl)cc2)cc1] | 252 |

TABLE 5-continued
| Structure | |
|---|---|
| 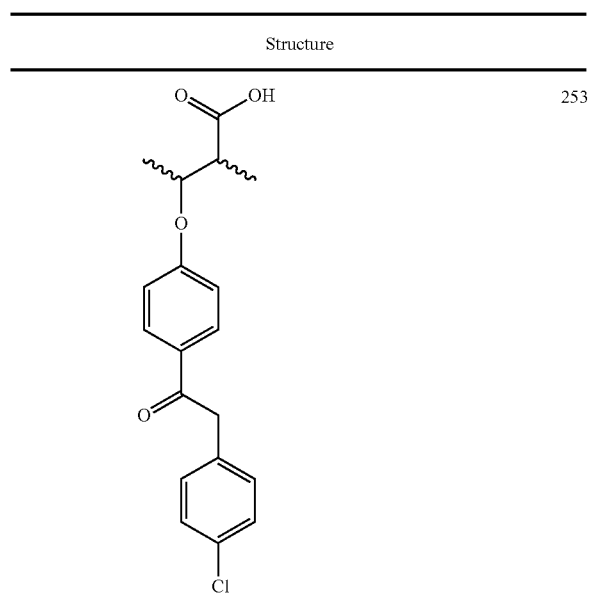 | 253 |
| 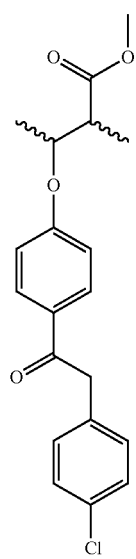 | 254 |
| 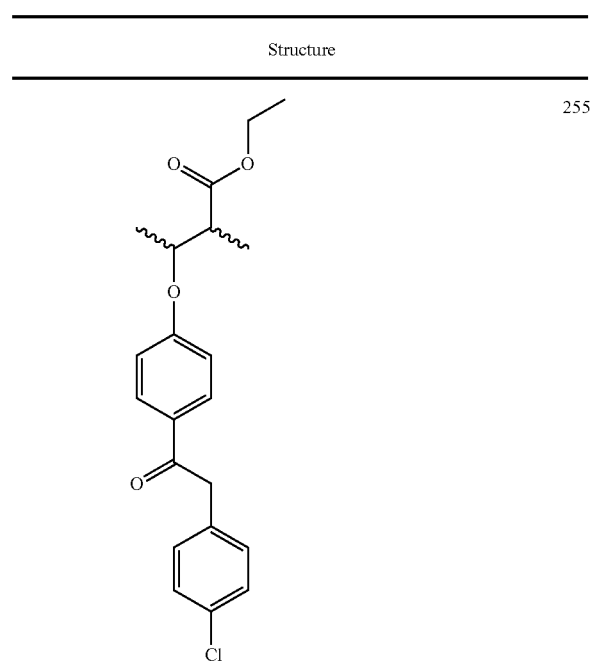 | 255 |
| 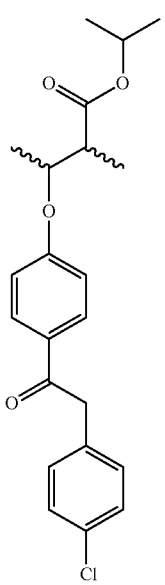 | 256 |

TABLE 5-continued
| Structure | |
|---|---|
| 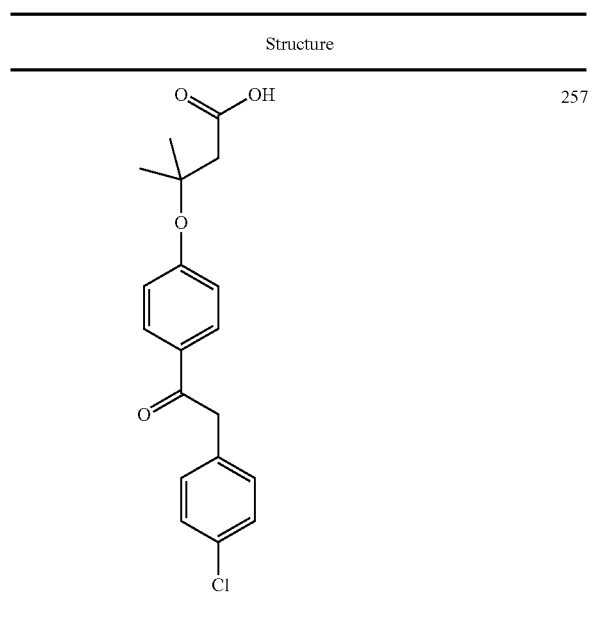 | 257 |
| 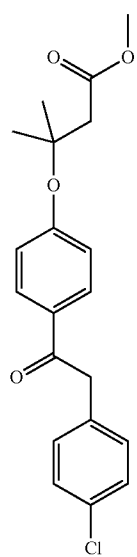 [SMILES: COC(=O)CC(C)(C)Oc1ccc(C(=O)Cc2ccc(Cl)cc2)cc1] | 258 |
TABLE 5-continued
| Structure | |
|---|---|
| 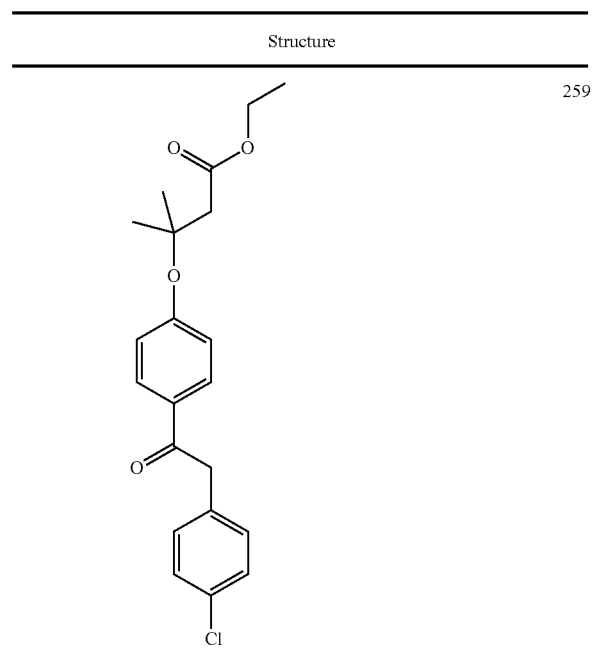 | 259 |
| 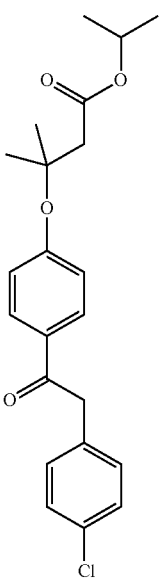 [SMILES: CC(C)OC(=O)CC(C)(C)Oc1ccc(C(=O)Cc2ccc(Cl)cc2)cc1] | 260 |

TABLE 6
| Structure | |
|---|---|
| 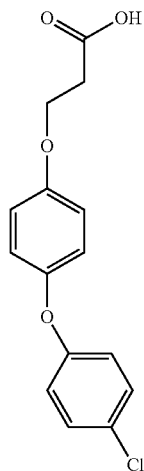 [SMILES: O=C(O)CCOc1ccc(Oc2ccc(Cl)cc2)cc1] | 261 |
| 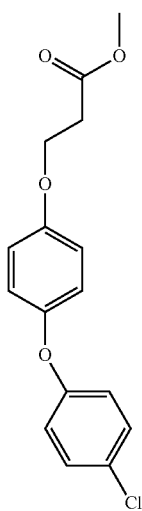 [SMILES: COC(=O)CCOc1ccc(Oc2ccc(Cl)cc2)cc1] | 262 |
| 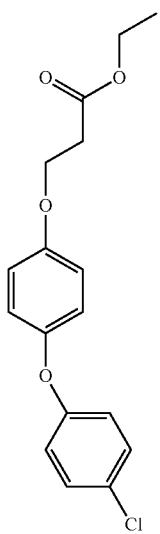 [SMILES: CCOC(=O)CCOc1ccc(Oc2ccc(Cl)cc2)cc1] | 263 |
TABLE 6-continued
| Structure | |
|---|---|
| 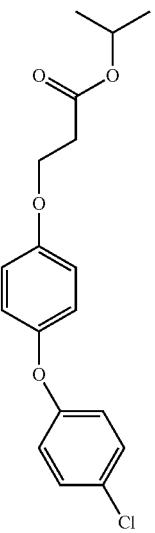 [SMILES: CC(C)OC(=O)CCOc1ccc(Oc2ccc(Cl)cc2)cc1] | 264 |
| 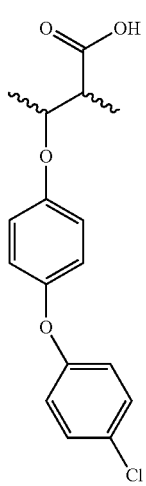 | 265 |
| 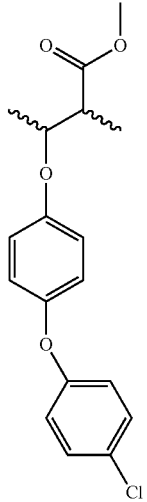 | 266 |

TABLE 6-continued
| Structure | |
|---|---|
| 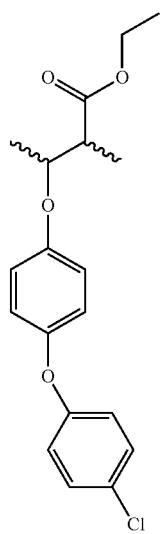 | 267 |
| 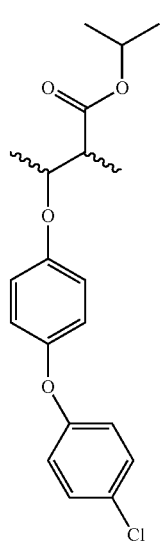 | 268 |
| 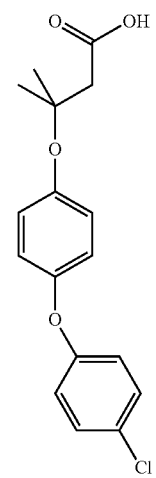 [SMILES: CC(C)(CC(=O)O)Oc1ccc(Oc2ccc(Cl)cc2)cc1] | 269 |
| 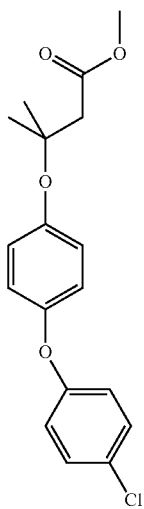 [SMILES: COC(=O)CC(C)(C)Oc1ccc(Oc2ccc(Cl)cc2)cc1] | 270 |
| 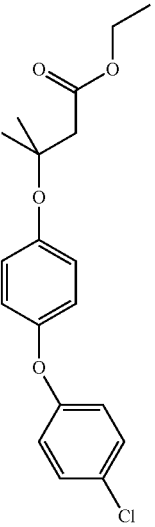 [SMILES: CCOC(=O)CC(C)(C)Oc1ccc(Oc2ccc(Cl)cc2)cc1] | 271 |
| 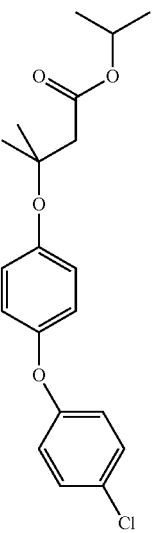 [SMILES: CC(C)OC(=O)CC(C)(C)Oc1ccc(Oc2ccc(Cl)cc2)cc1] | 272 |

TABLE 6-continued
| Structure | |
|---|---|
| 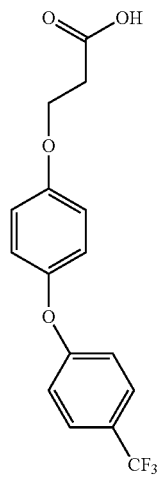 [SMILES: O=C(O)CCOc1ccc(Oc2ccc(C(F)(F)F)cc2)cc1] | 273 |
| 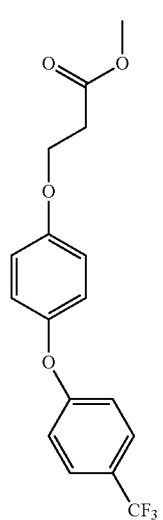 [SMILES: COC(=O)CCOc1ccc(Oc2ccc(C(F)(F)F)cc2)cc1] | 274 |
| 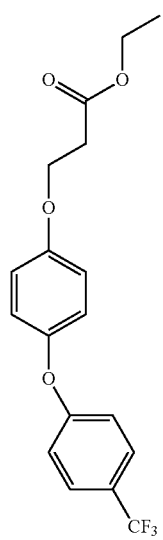 [SMILES: CCOC(=O)CCOc1ccc(Oc2ccc(C(F)(F)F)cc2)cc1] | 275 |
TABLE 6-continued
| Structure | |
|---|---|
| 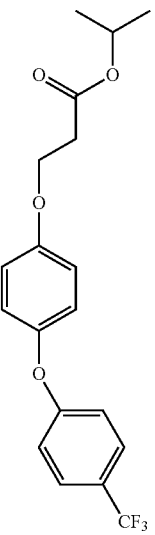 [SMILES: CC(C)OC(=O)CCOc1ccc(Oc2ccc(C(F)(F)F)cc2)cc1] | 276 |
| 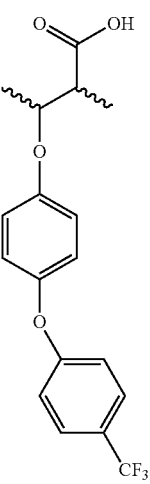 | 277 |
| 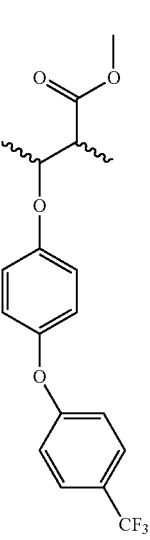 | 278 |

TABLE 6-continued
| Structure | |
|---|---|
| 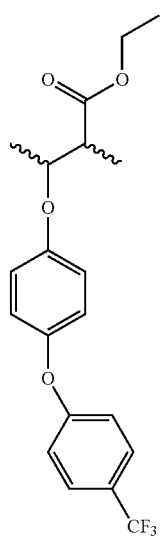 | 279 |
| 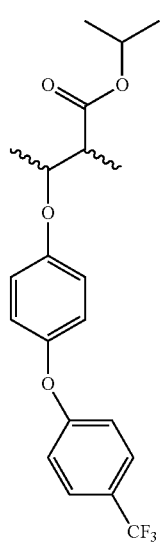 | 280 |
| 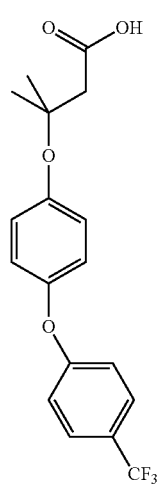 [SMILES: CC(C)(CC(=O)O)Oc1ccc(Oc2ccc(C(F)(F)F)cc2)cc1] | 281 |
TABLE 6-continued
| Structure | |
|---|---|
| 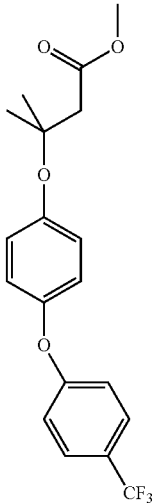 [SMILES: COC(=O)CC(C)(C)Oc1ccc(Oc2ccc(C(F)(F)F)cc2)cc1] | 282 |
| 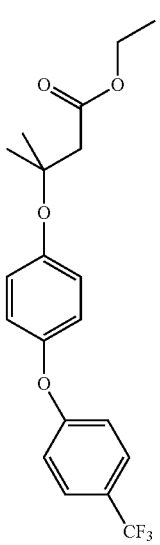 [SMILES: CCOC(=O)CC(C)(C)Oc1ccc(Oc2ccc(C(F)(F)F)cc2)cc1] | 283 |
| 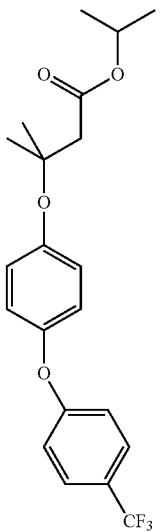 [SMILES: CC(C)OC(=O)CC(C)(C)Oc1ccc(Oc2ccc(C(F)(F)F)cc2)cc1] | 284 |

TABLE 6-continued
| Structure | |
|---|---|
| 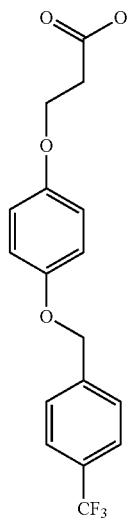 | 285 |
| 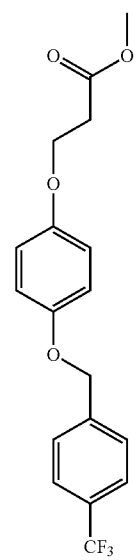 [SMILES: COC(=O)CCOc1ccc(OCc2ccc(C(F)(F)F)cc2)cc1] | 286 |
TABLE 6-continued
| Structure | |
|---|---|
| 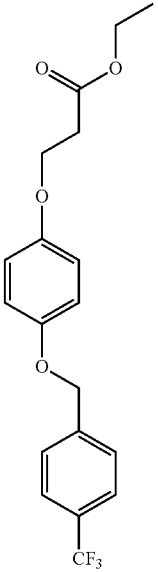 [SMILES: CCOC(=O)CCOc1ccc(OCc2ccc(C(F)(F)F)cc2)cc1] | 287 |
| 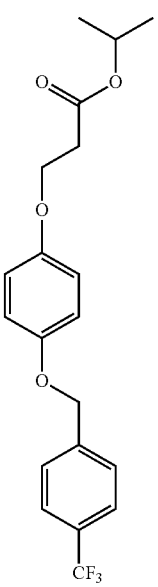 [SMILES: CC(C)OC(=O)CCOc1ccc(OCc2ccc(C(F)(F)F)cc2)cc1] | 288 |

TABLE 6-continued
| Structure | |
|---|---|
| 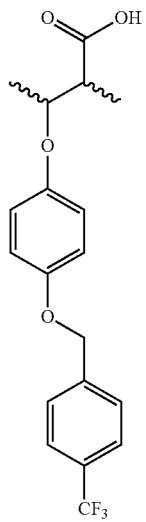 | 289 |
| 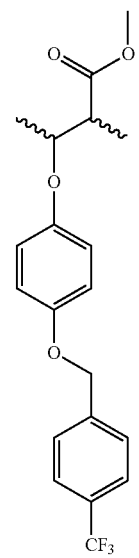 | 290 |
| 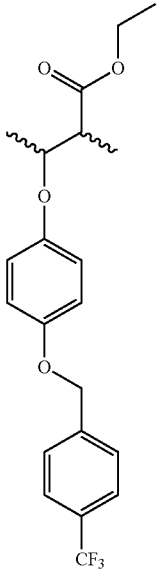 | 291 |
| 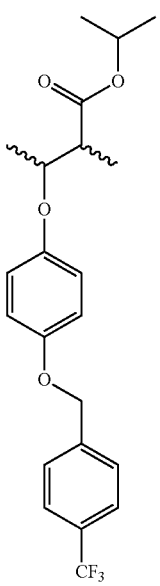 | 292 |

TABLE 6-continued
| Structure | |
|---|---|
| 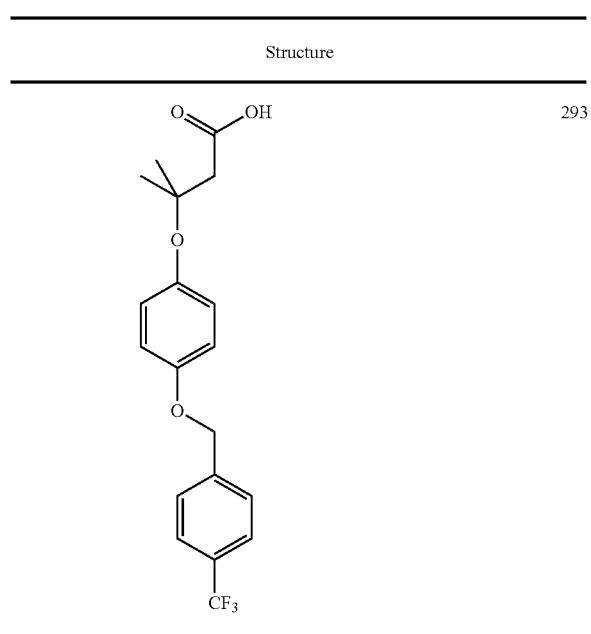 | 293 |
| 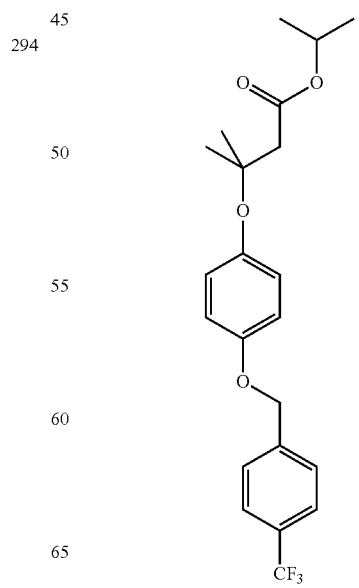 | 294 |
| 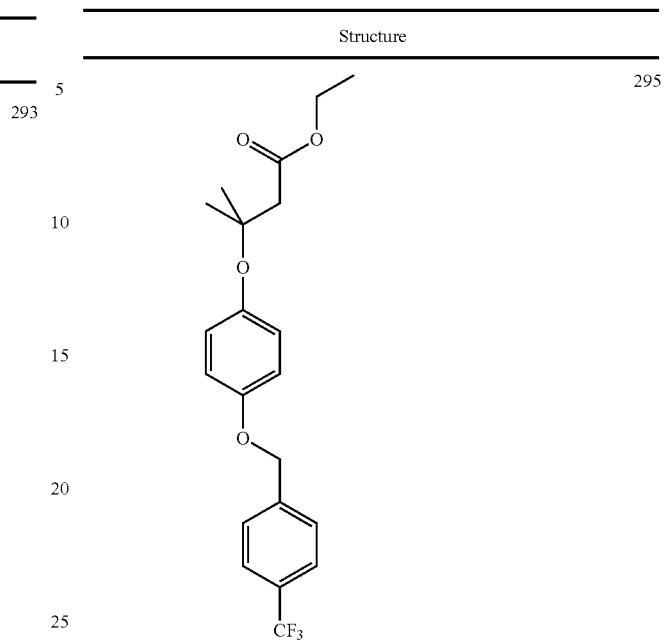 295, 296 | |

TABLE 6-continued
| Structure | |
|---|---|
| 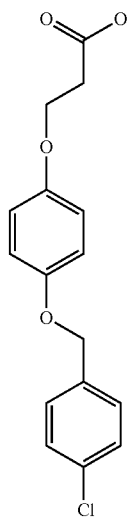 | 297 |
| 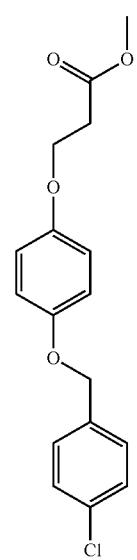 [SMILES: COC(=O)CCOc1ccc(OCc2ccc(Cl)cc2)cc1] | 298 |
| 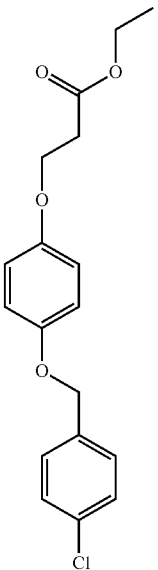 [SMILES: CCOC(=O)CCOc1ccc(OCc2ccc(Cl)cc2)cc1] | 299 |
| 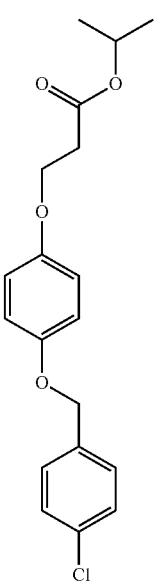 [SMILES: CC(C)OC(=O)CCOc1ccc(OCc2ccc(Cl)cc2)cc1] | 300 |

TABLE 6-continued
| Structure | |
|---|---|
| 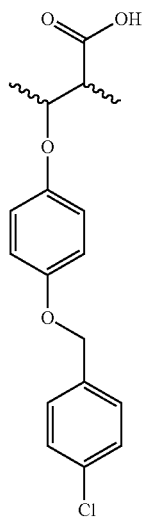 | 301 |
| 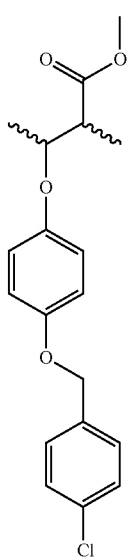 | 302 |
| 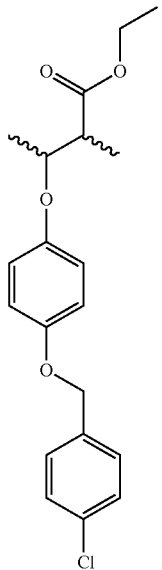 | 303 |
| 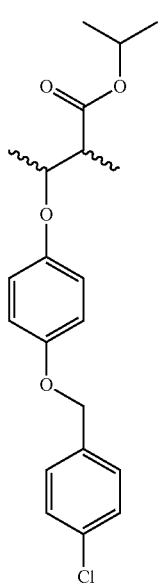 | 304 |

TABLE 6-continued

| Structure | |
|---|---|
| (structure of 3-methyl-3-[4-[(4-chlorobenzyl)oxy]phenoxy]butanoic acid) | 305 |
| (methyl ester of above) | 306 |
| (ethyl ester of above) | 307 |
| (isopropyl ester of above) | 308 |

TABLE 7

| Structure | |
|---|---|
| (3-[(4-fluorophenoxy)methyl]-3-methylbutanoic acid / 2,2-dimethyl-3-(4-fluorophenoxy)propanoic acid) | 309 |

TABLE 7-continued
| Structure | |
|---|---|
| 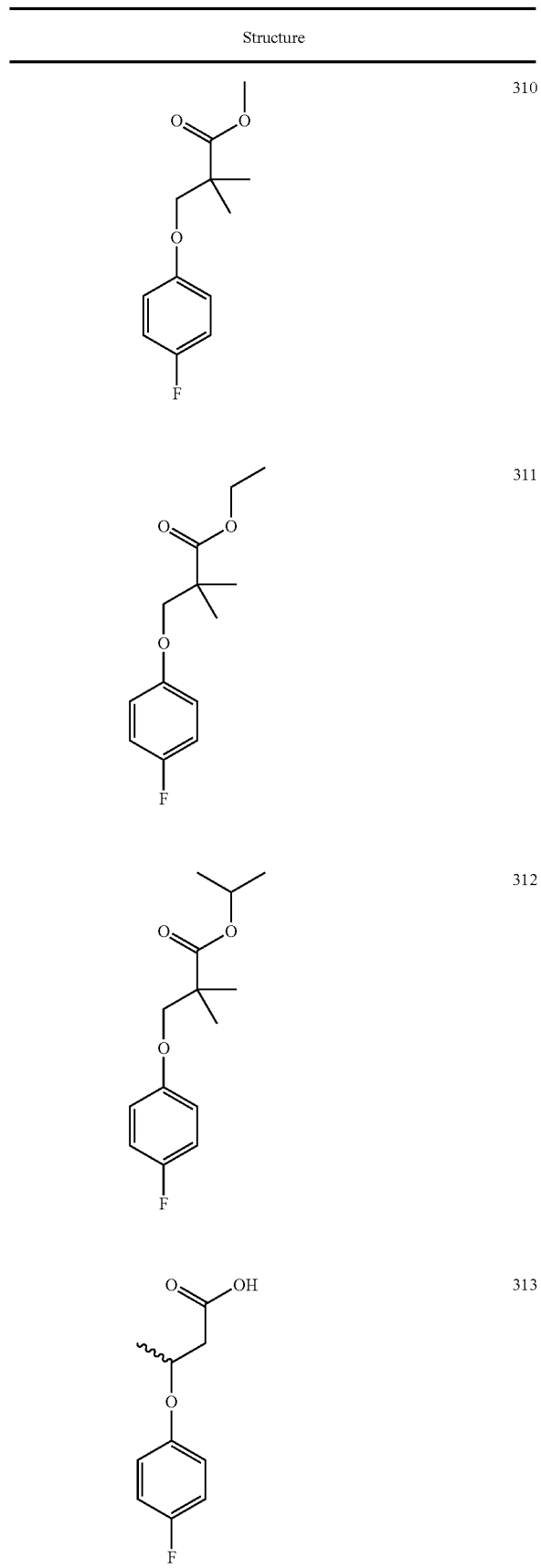 | 310 311 312 313 |
TABLE 7-continued
| Structure | |
|---|---|
| 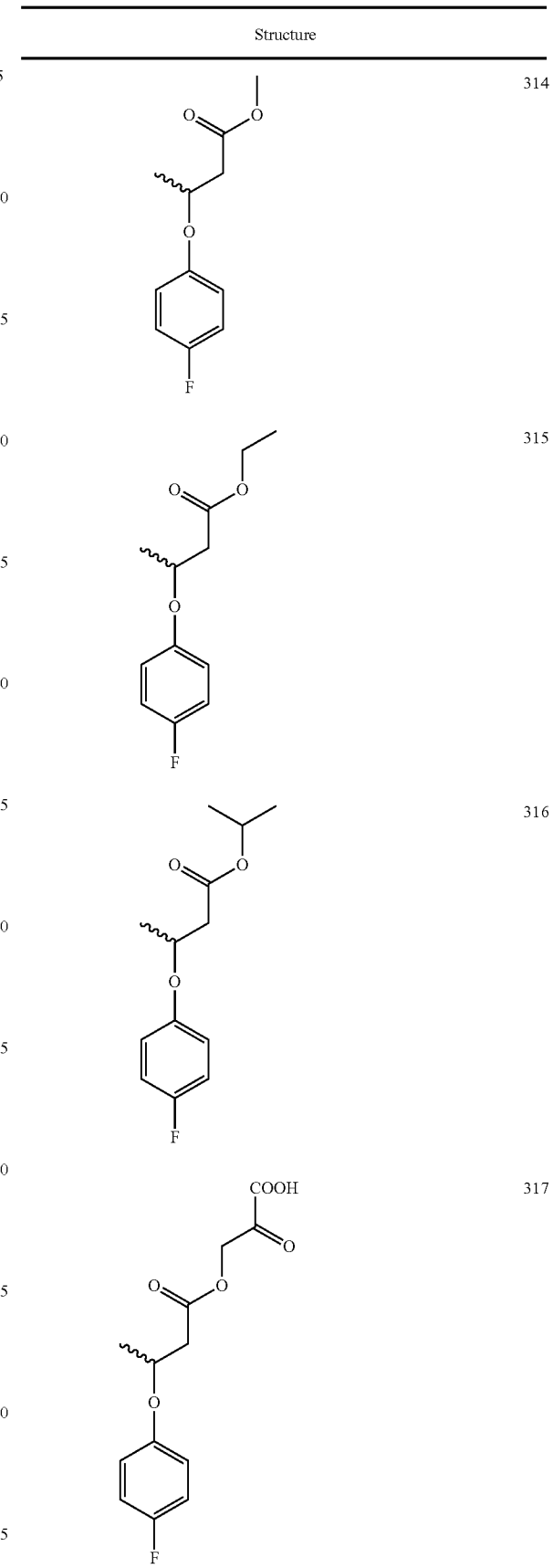 | 314 315 316 317 |

TABLE 7-continued
| Structure | |
|---|---|
| 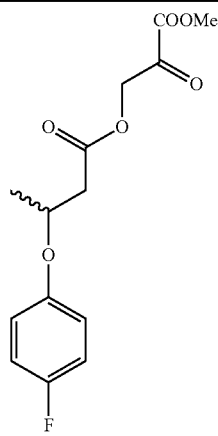 | 318 |
| 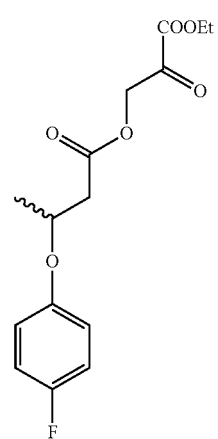 [SMILES: CCOC(=O)C(=O)COC(=O)CC(C)Oc1ccc(F)cc1] | 319 |
| 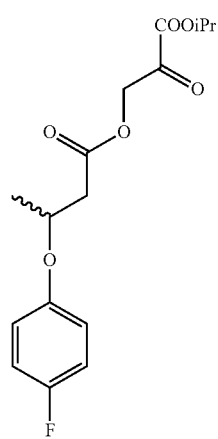 | 320 |
| 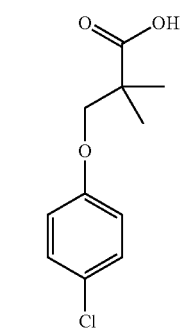 | 321 |
TABLE 7-continued
| Structure | |
|---|---|
| 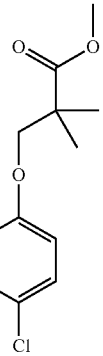 | 322 |
| 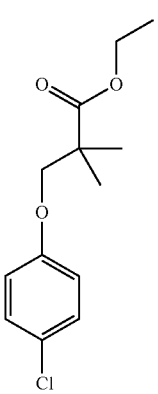 [SMILES: CCOC(=O)C(C)(C)COc1ccc(Cl)cc1] | 323 |
| 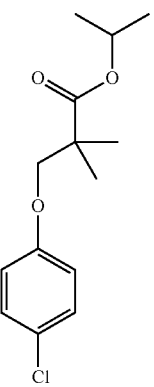 [SMILES: CC(C)OC(=O)C(C)(C)COc1ccc(Cl)cc1] | 324 |
| 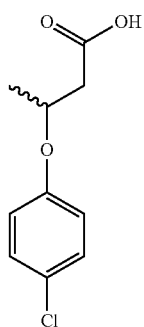 | 325 |

TABLE 7-continued
| Structure | |
|---|---|
| 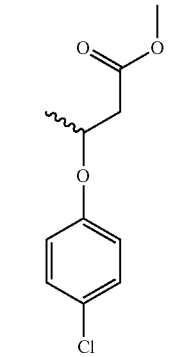 | 326 |
| 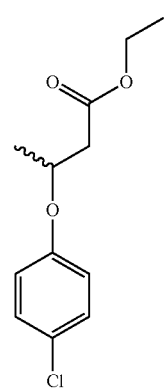 [SMILES: CCOC(=O)CC(C)Oc1ccc(Cl)cc1] | 327 |
| 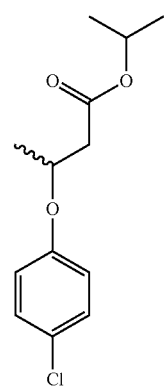 [SMILES: CC(C)OC(=O)CC(C)Oc1ccc(Cl)cc1] | 328 |
| 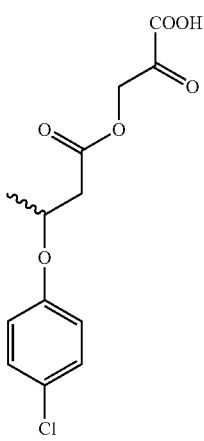 [SMILES: CC(CC(=O)OCC(=O)C(=O)O)Oc1ccc(Cl)cc1] | 329 |
| 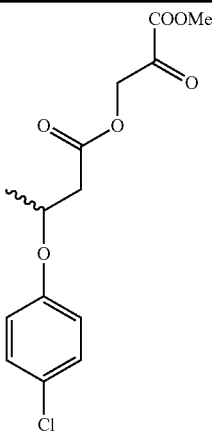 | 330 |
| 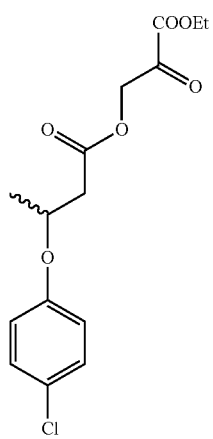 [SMILES: CCOC(=O)C(=O)COC(=O)CC(C)Oc1ccc(Cl)cc1] | 331 |
| 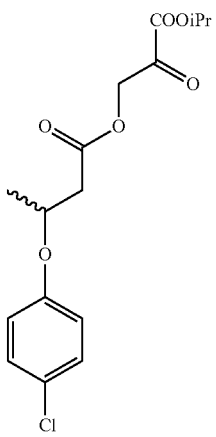 | 332 |
| 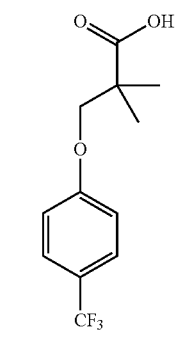 [SMILES: CC(C)(COc1ccc(C(F)(F)F)cc1)C(=O)O] | 333 |

TABLE 7-continued
| Structure | |
|---|---|
| 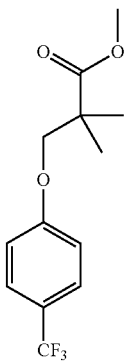 | 334 |
| 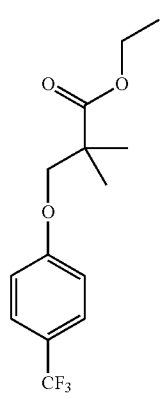 [SMILES: CCOC(=O)C(C)(C)COc1ccc(C(F)(F)F)cc1] | 335 |
| 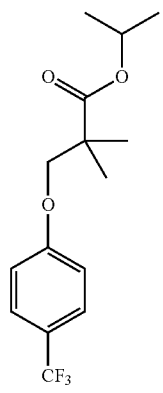 [SMILES: CC(C)OC(=O)C(C)(C)COc1ccc(C(F)(F)F)cc1] | 336 |
| 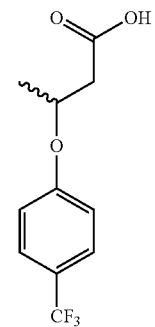 | 337 |
TABLE 7-continued
| Structure | |
|---|---|
| 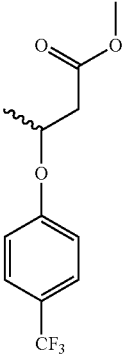 | 338 |
| 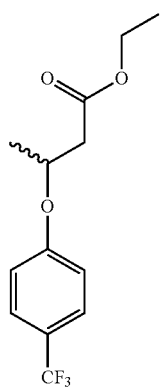 [SMILES: CCOC(=O)CC(C)Oc1ccc(C(F)(F)F)cc1] | 339 |
| 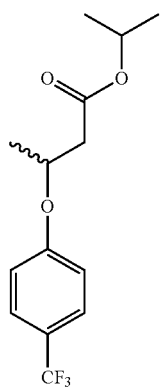 [SMILES: CC(C)OC(=O)CC(C)Oc1ccc(C(F)(F)F)cc1] | 340 |
| 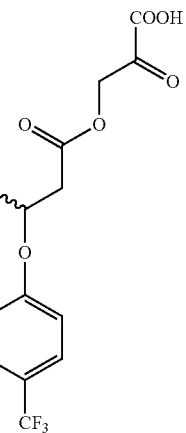 | 341 |

TABLE 7-continued
| Structure | |
|---|---|
| 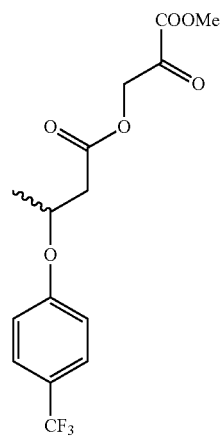 [SMILES: COC(=O)C(=O)COC(=O)CC(C)Oc1ccc(C(F)(F)F)cc1] | 342 |
| 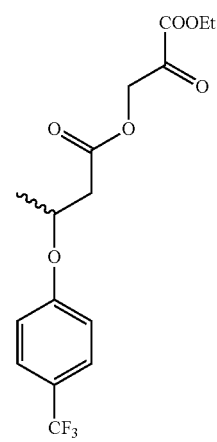 [SMILES: CCOC(=O)C(=O)COC(=O)CC(C)Oc1ccc(C(F)(F)F)cc1] | 343 |
| 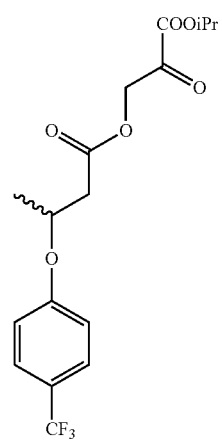 | 344 |
TABLE 7-continued
| Structure | |
|---|---|
| 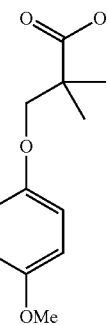 | 345 |
| 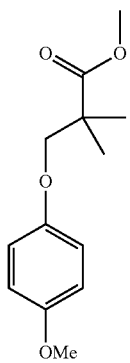 [SMILES: COC(=O)C(C)(C)COc1ccc(OC)cc1] | 346 |
| 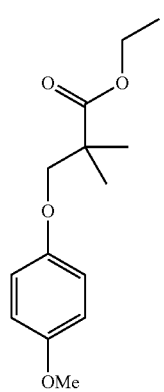 [SMILES: CCOC(=O)C(C)(C)COc1ccc(OC)cc1] | 347 |
| 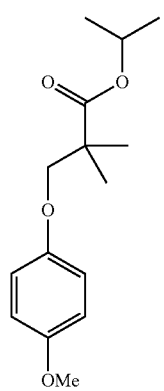 [SMILES: COc1ccc(OCC(C)(C)C(=O)OC(C)C)cc1] | 348 |

TABLE 7-continued
| Structure | |
|---|---|
| 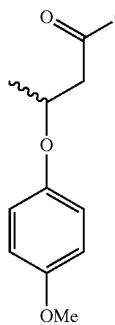 | 349 |
| 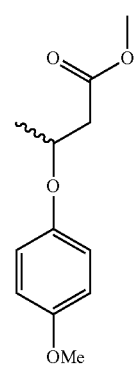 | 350 |
| 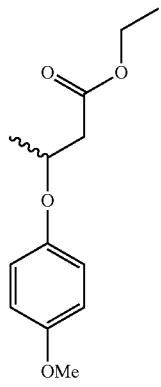 [SMILES: CCOC(=O)CC(C)Oc1ccc(OC)cc1] | 351 |
| 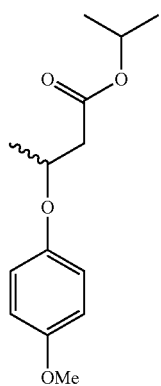 [SMILES: COc1ccc(OC(C)CC(=O)OC(C)C)cc1] | 352 |
TABLE 7-continued
| Structure | |
|---|---|
| 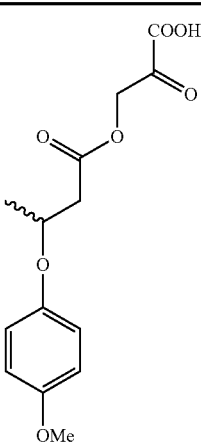 | 353 |
| 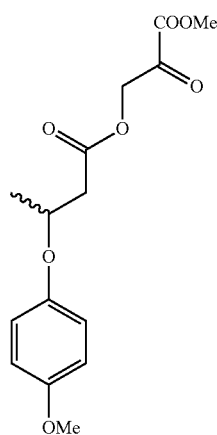 [SMILES: COC(=O)C(=O)COC(=O)CC(C)Oc1ccc(OC)cc1] | 354 |
| 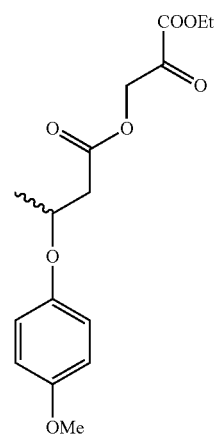 [SMILES: CCOC(=O)C(=O)COC(=O)CC(C)Oc1ccc(OC)cc1] | 355 |

TABLE 7-continued
| Structure | |
|---|---|
| 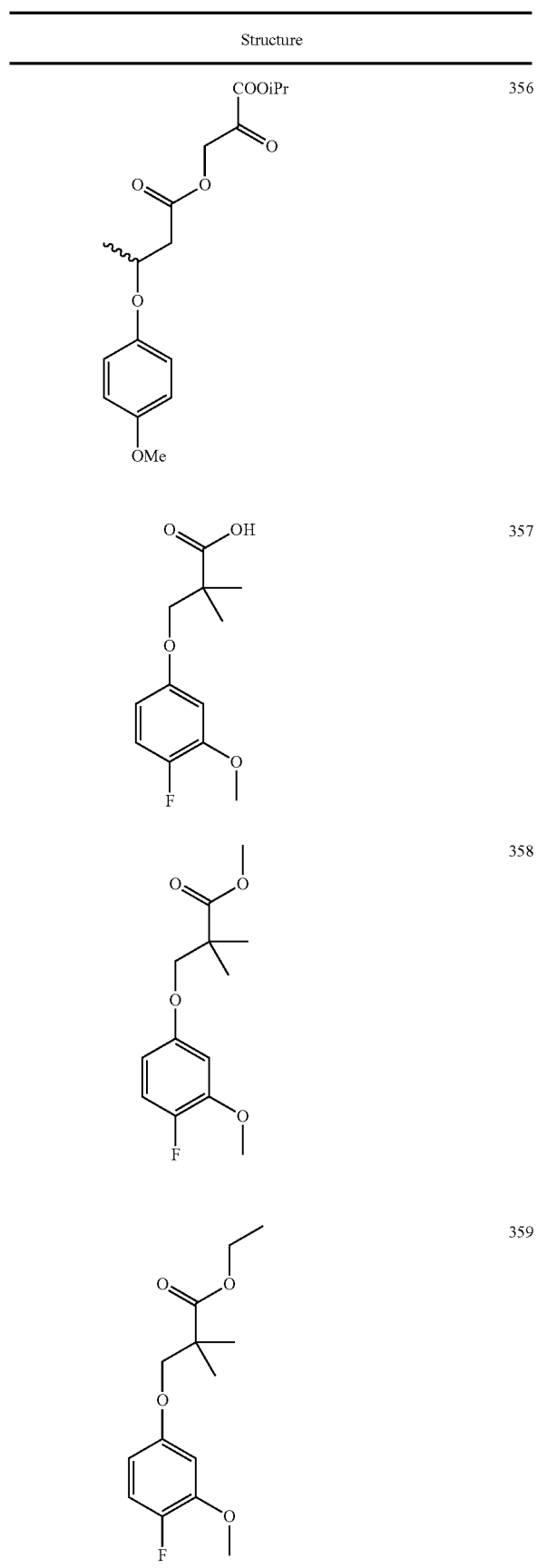 | 356 357 358 359 |
| 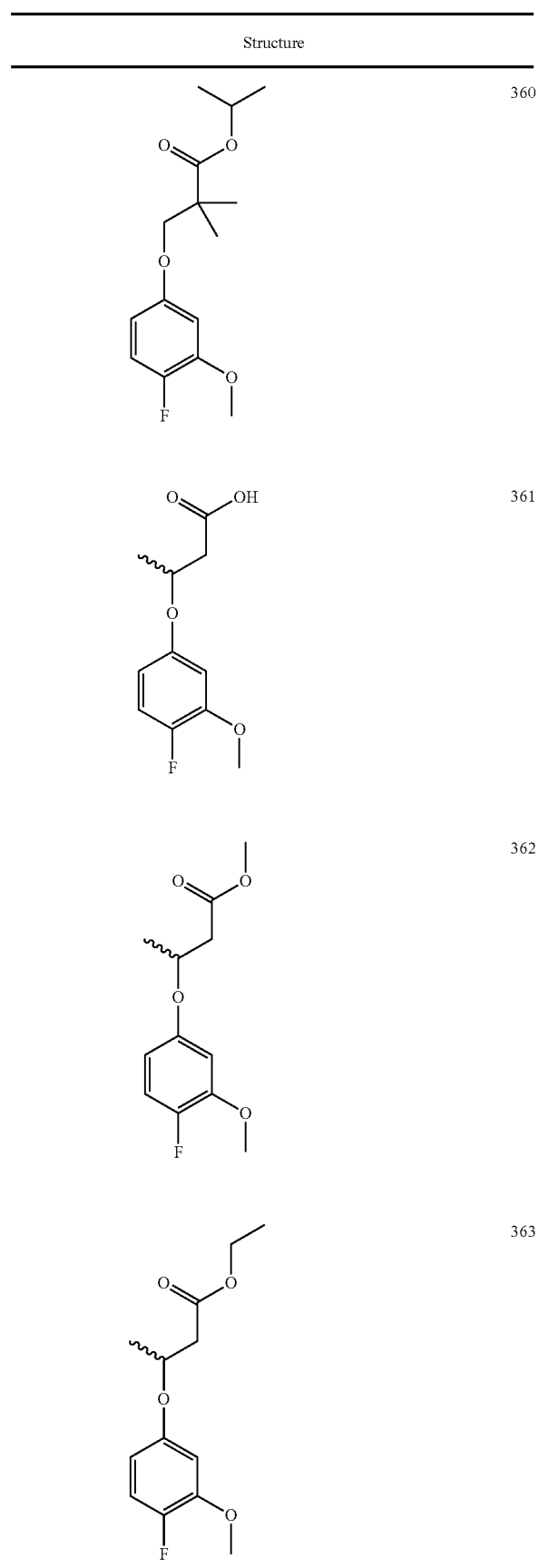 | 360 361 362 363 |

TABLE 7-continued
| Structure | |
|---|---|
| 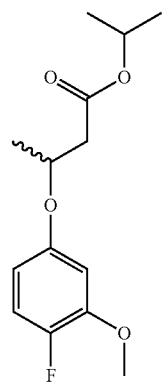 [SMILES: COc1cc(OC(C)CC(=O)OC(C)C)ccc1F] | 364 |
| 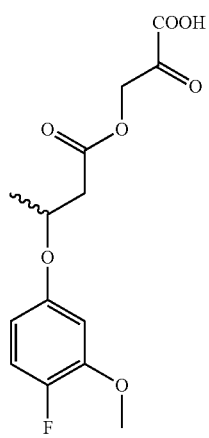 [SMILES: COc1cc(OC(C)CC(=O)OCC(=O)C(=O)O)ccc1F] | 365 |
| 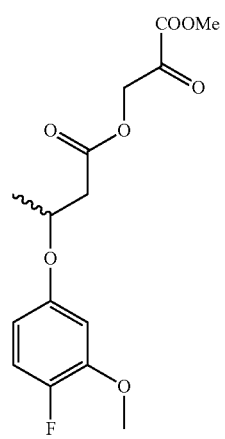 [SMILES: COC(=O)C(=O)COC(=O)CC(C)Oc1ccc(F)c(OC)c1] | 366 |
TABLE 7-continued
| Structure | |
|---|---|
| 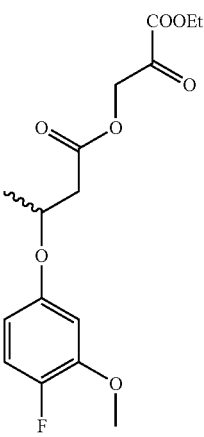 [SMILES: CCOC(=O)C(=O)COC(=O)CC(C)Oc1ccc(F)c(OC)c1] | 367 |
| 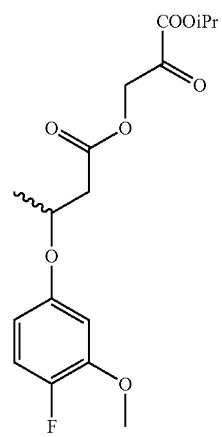 | 368 |
TABLE 8
| Structure | |
|---|---|
| 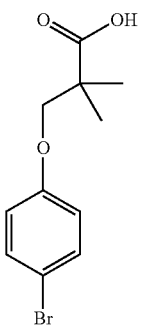 | 369 |

TABLE 8-continued
| Structure | |
|---|---|
| 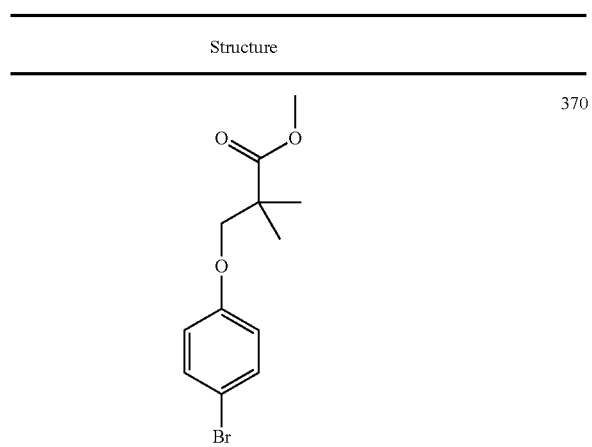 | 370 |
| 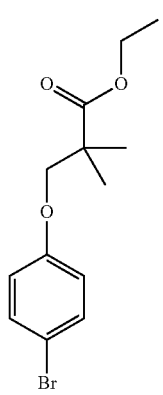 [SMILES: CCOC(=O)C(C)(C)COc1ccc(Br)cc1] | 371 |
| 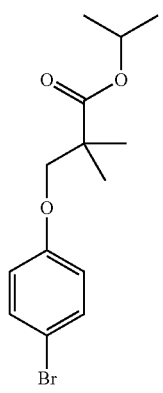 | 372 |
| 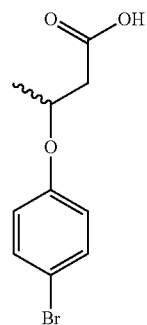 | 373 |
| 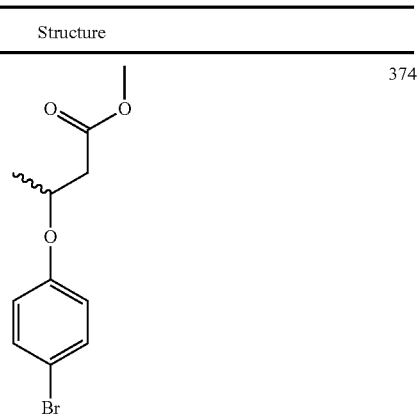 | 374 |
| 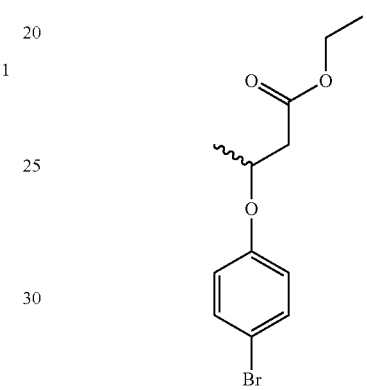 | 375 |
| 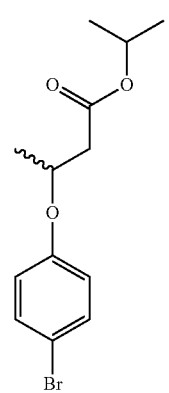 | 376 |
| 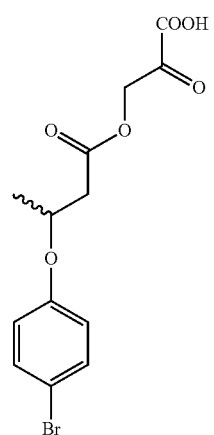 | 377 |

TABLE 8-continued

| Structure | |
|---|---|
| (structure) | 378 |
| (structure) | 379 |
| (structure) | 380 |
| (structure) | 381 |
| (structure) | 382 |
| (structure) | 383 |
| (structure) | 384 |
| (structure) | 385 |
| (structure) | 386 |

TABLE 8-continued
| Structure | |
|---|---|
| 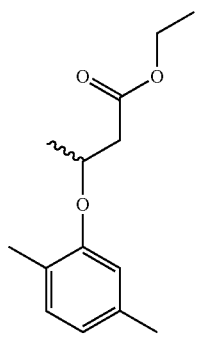 [SMILES: CCOC(=O)CC(C)Oc1cc(C)ccc1C] | 387 |
| 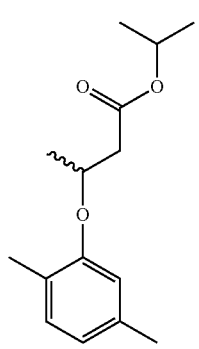 [SMILES: Cc1ccc(C)c(OC(C)CC(=O)OC(C)C)c1] | 388 |
| 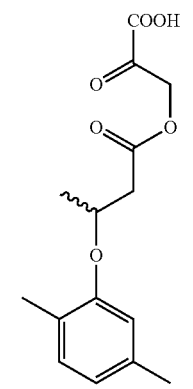 [SMILES: Cc1ccc(C)c(OC(C)CC(=O)OCC(=O)C(=O)O)c1] | 389 |
| 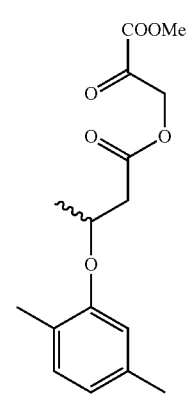 [SMILES: COC(=O)C(=O)COC(=O)CC(C)Oc1cc(C)ccc1C] | 390 |
TABLE 8-continued
| Structure | |
|---|---|
| 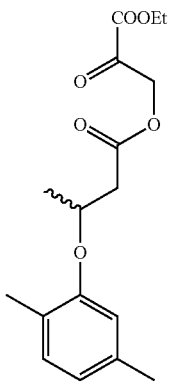 [SMILES: CCOC(=O)C(=O)COC(=O)CC(C)Oc1cc(C)ccc1C] | 391 |
| 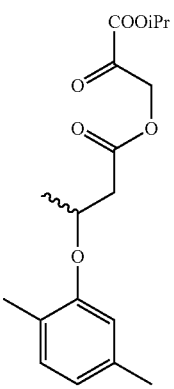 | 392 |
| 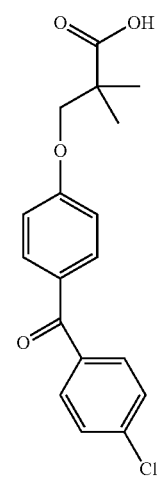 [SMILES: CC(C)(COc1ccc(C(=O)c2ccc(Cl)cc2)cc1)C(=O)O] | 393 |

TABLE 8-continued
| Structure | |
|---|---|
| 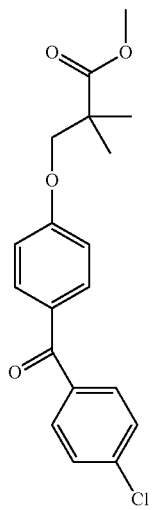 [SMILES: COC(=O)C(C)(C)COc1ccc(C(=O)c2ccc(Cl)cc2)cc1] | 394 |
| 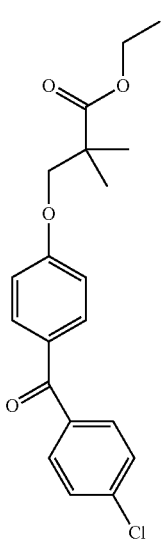 [SMILES: CCOC(=O)C(C)(C)COc1ccc(C(=O)c2ccc(Cl)cc2)cc1] | 395 |
| 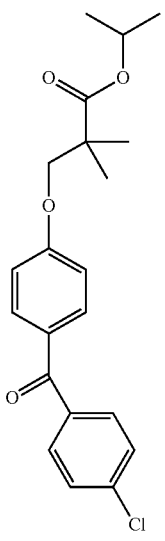 [SMILES: CC(C)OC(=O)C(C)(C)COc1ccc(C(=O)c2ccc(Cl)cc2)cc1] | 396 |
| 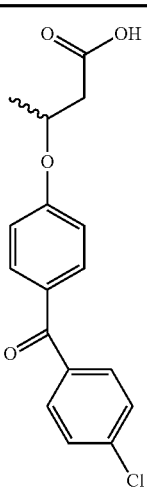 | 397 |
| 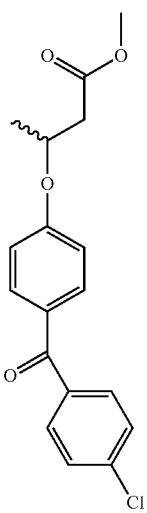 [SMILES: COC(=O)CC(C)Oc1ccc(C(=O)c2ccc(Cl)cc2)cc1] | 398 |
| 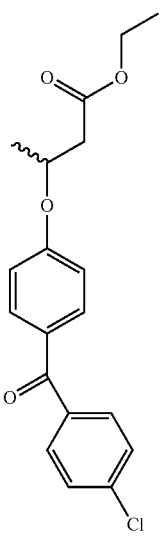 [SMILES: CCOC(=O)CC(C)Oc1ccc(C(=O)c2ccc(Cl)cc2)cc1] | 399 |

TABLE 8-continued
| Structure | |
|---|---|
| 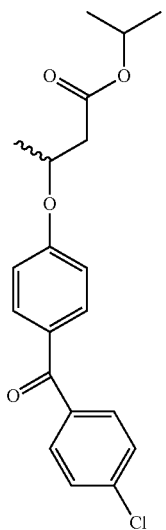 [SMILES: CC(C)OC(=O)CC(C)Oc1ccc(C(=O)c2ccc(Cl)cc2)cc1] | 400 |
| 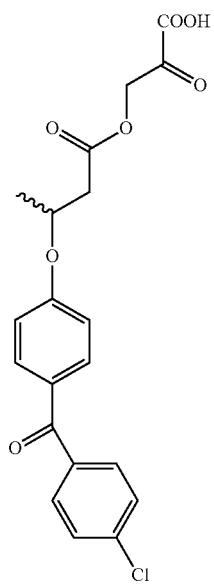 [SMILES: CC(CC(=O)OCC(=O)C(=O)O)Oc1ccc(C(=O)c2ccc(Cl)cc2)cc1] | 401 |
| 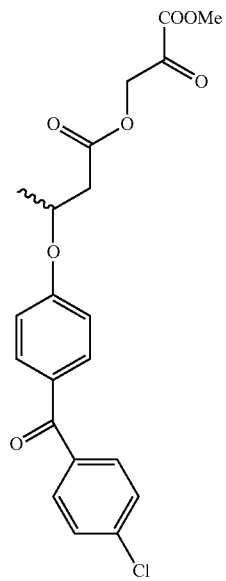 [SMILES: COC(=O)C(=O)COC(=O)CC(C)Oc1ccc(C(=O)c2ccc(Cl)cc2)cc1] | 402 |
| 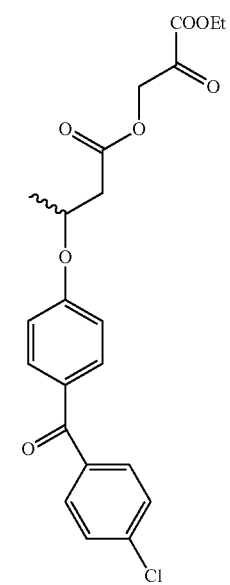 [SMILES: CCOC(=O)C(=O)COC(=O)CC(C)Oc1ccc(C(=O)c2ccc(Cl)cc2)cc1] | 403 |

TABLE 8-continued
| Structure | |
|---|---|
| 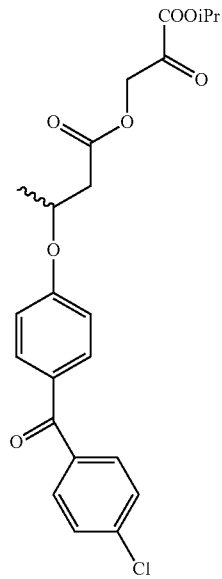 | 404 |
| 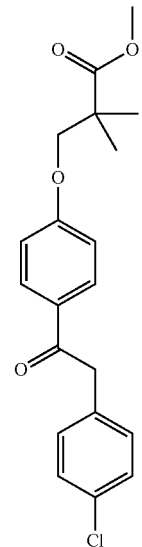 | 406 |
| 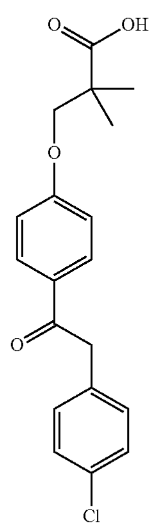 [SMILES: CC(C)(COc1ccc(C(=O)Cc2ccc(Cl)cc2)cc1)C(=O)O] | 405 |
| | 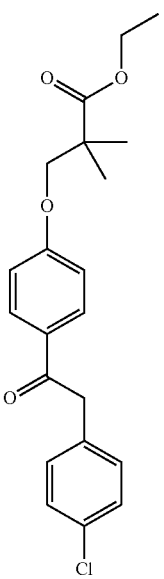 [SMILES: CCOC(=O)C(C)(C)COc1ccc(C(=O)Cc2ccc(Cl)cc2)cc1] 407 |

TABLE 8-continued
| Structure | |
|---|---|
| 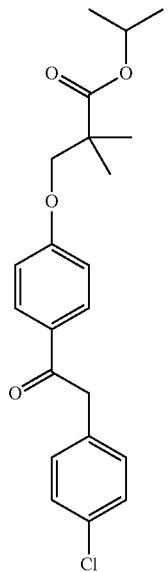 [SMILES: CC(C)OC(=O)C(C)(C)COc1ccc(C(=O)Cc2ccc(Cl)cc2)cc1] | 408 |
| 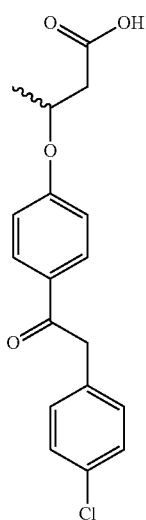 [SMILES: CC(CC(=O)O)Oc1ccc(C(=O)Cc2ccc(Cl)cc2)cc1] | 409 |
TABLE 8-continued
| Structure | |
|---|---|
| 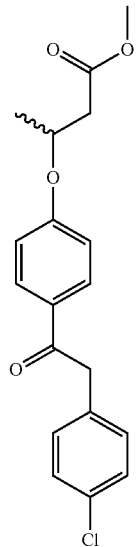 | 410 |
| 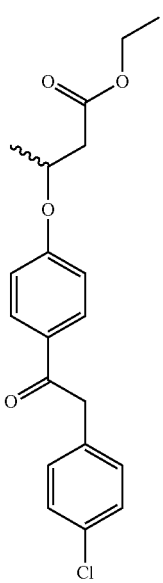 [SMILES: CCOC(=O)CC(C)Oc1ccc(C(=O)Cc2ccc(Cl)cc2)cc1] | 411 |

TABLE 8-continued
| Structure | |
|---|---|
| 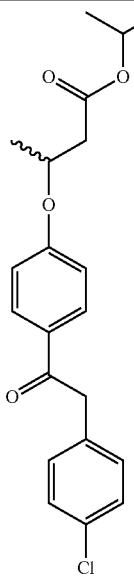 | 412 |
| 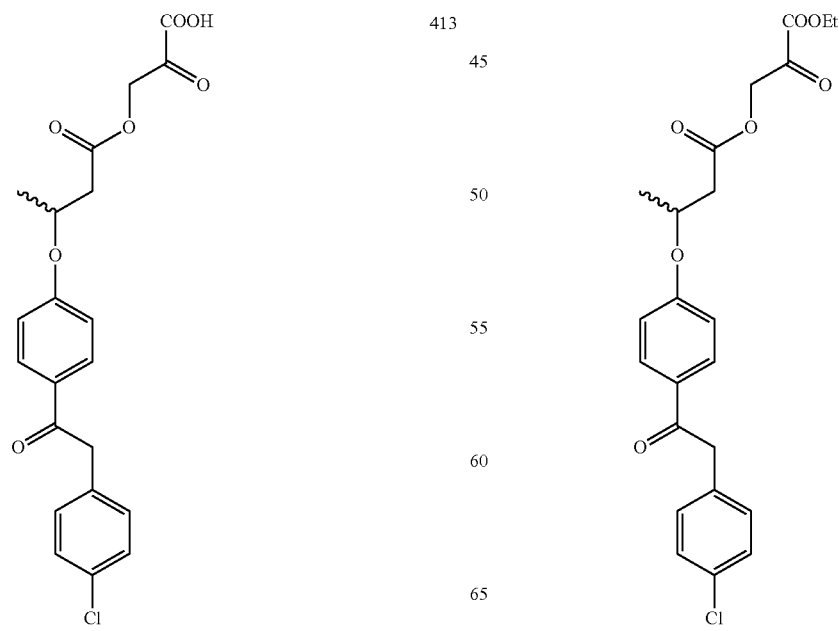 | 413 |
| 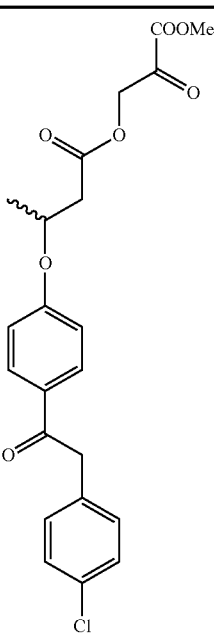 | 414 |
| 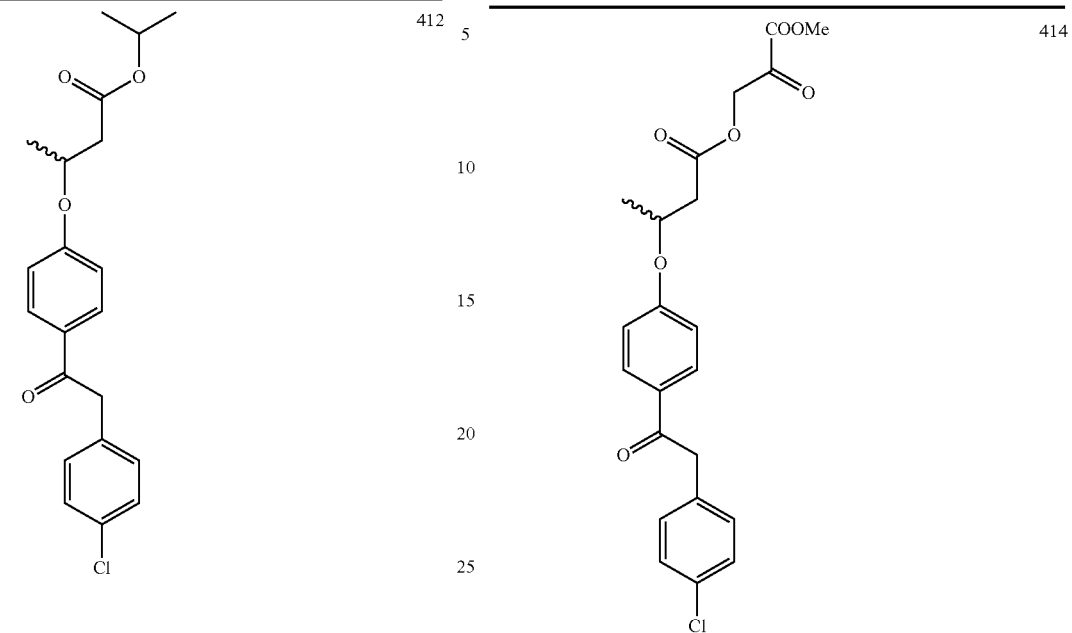 | 415 |

TABLE 8-continued
| Structure | |
|---|---|
| 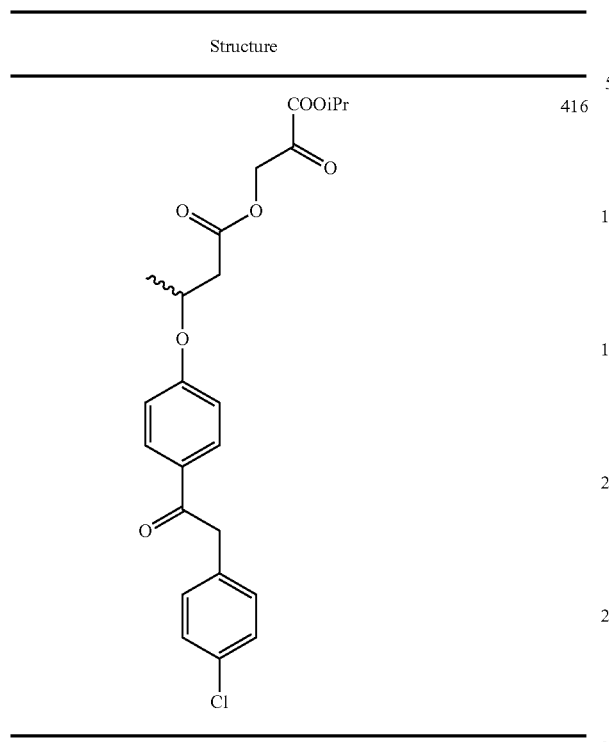 | 416 |
TABLE 9
| Structure | |
|---|---|
| 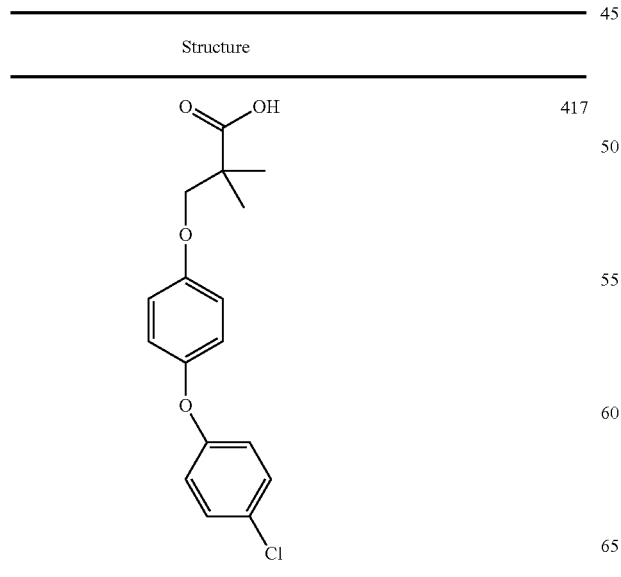 | 417 |
TABLE 9-continued
| Structure | |
|---|---|
| 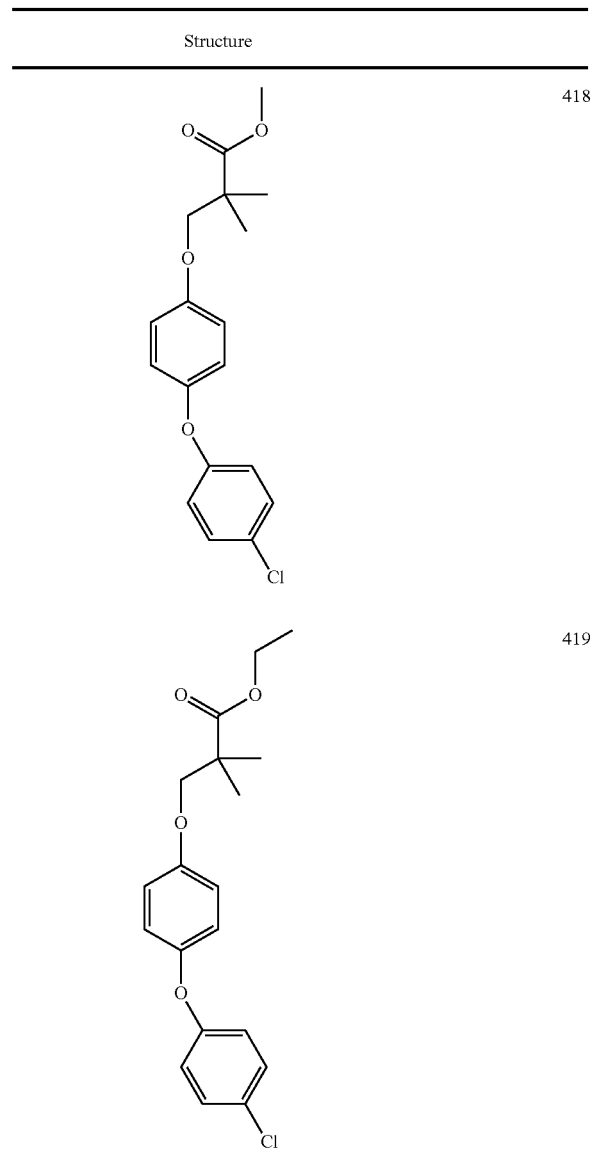 | 418 |
| 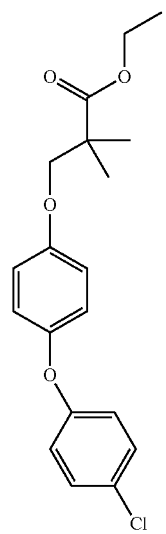 | 419 |
| 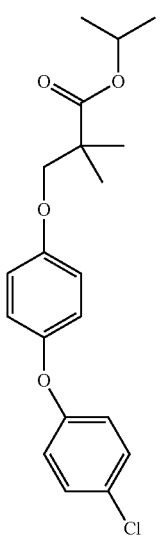 [SMILES: CC(C)OC(=O)C(C)(C)COc1ccc(Oc2ccc(Cl)cc2)cc1] | 420 |

TABLE 9-continued
| Structure | |
|---|---|
| 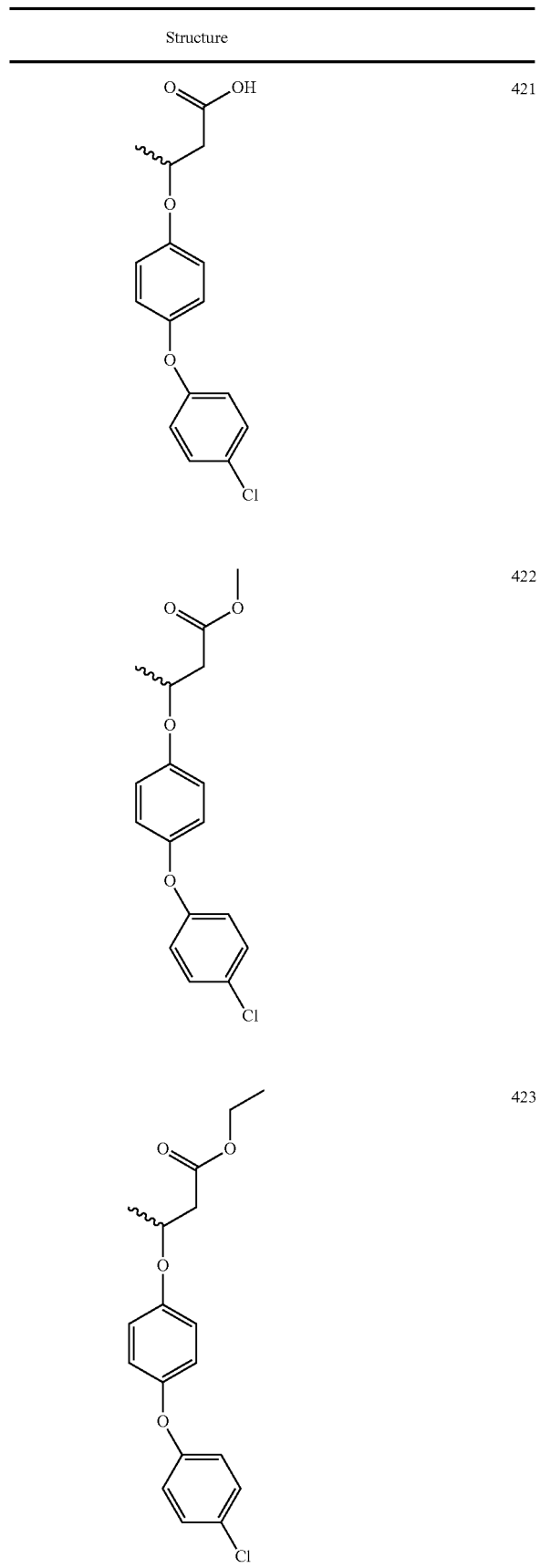 | 421 |
| 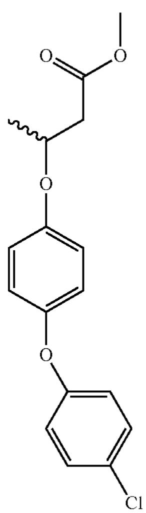 [SMILES: COC(=O)CC(C)Oc1ccc(Oc2ccc(Cl)cc2)cc1] | 422 |
| 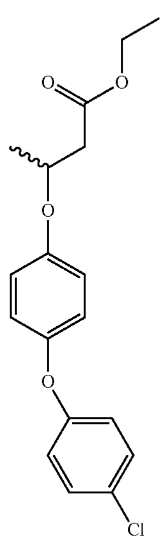 | 423 |
TABLE 9-continued
| Structure | |
|---|---|
| 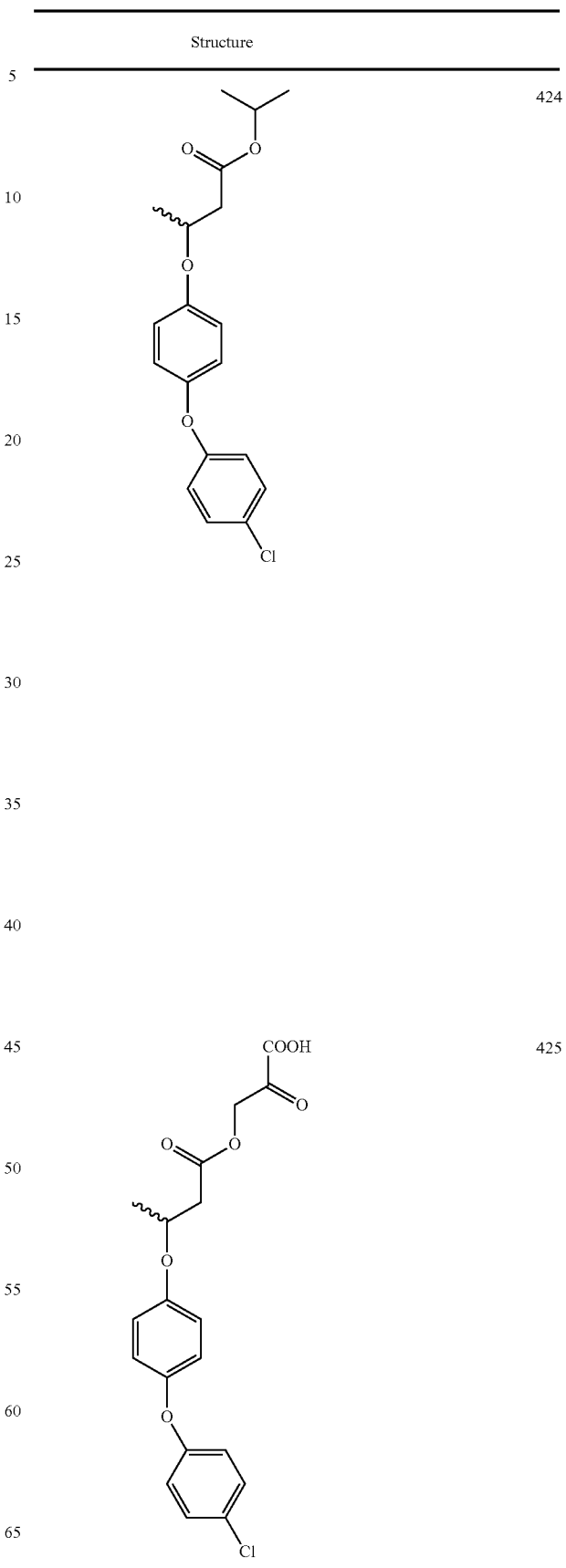 | 424 |
| 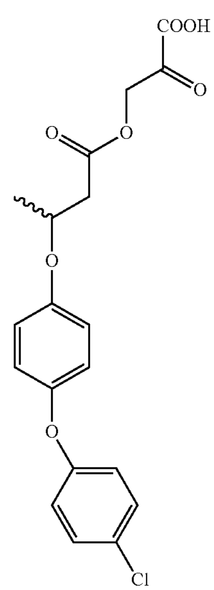 [SMILES: CC(CC(=O)OCC(=O)C(=O)O)Oc1ccc(Oc2ccc(Cl)cc2)cc1] | 425 |

TABLE 9-continued
| Structure | |
|---|---|
| 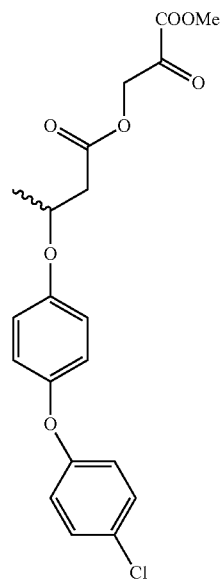 [SMILES: COC(=O)C(=O)COC(=O)CC(C)Oc1ccc(Oc2ccc(Cl)cc2)cc1] | 426 |
| 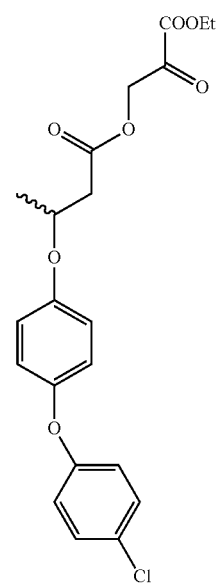 [SMILES: CCOC(=O)C(=O)COC(=O)CC(C)Oc1ccc(Oc2ccc(Cl)cc2)cc1] | 427 |
TABLE 9-continued
| Structure | |
|---|---|
| 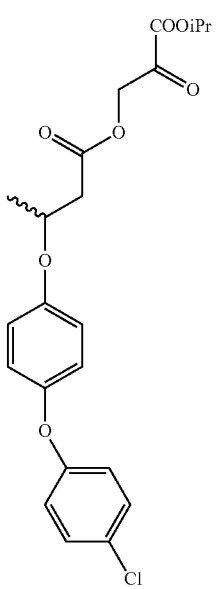 | 428 |
| 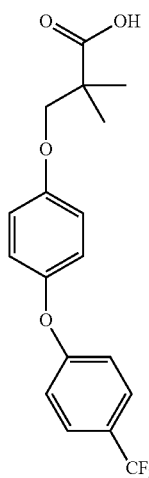 | 429 |
| 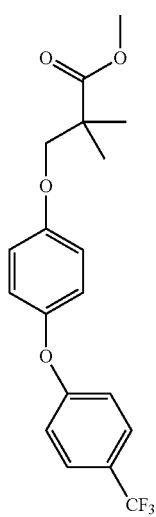 [SMILES: COC(=O)C(C)(C)COc1ccc(Oc2ccc(C(F)(F)F)cc2)cc1] | 430 |

TABLE 9-continued
| Structure | |
|---|---|
| 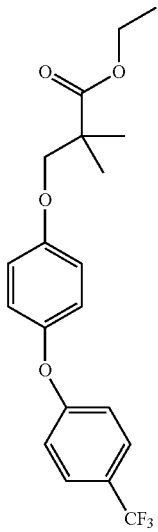 [SMILES: CCOC(=O)C(C)(C)COc1ccc(Oc2ccc(C(F)(F)F)cc2)cc1] | 431 |
| 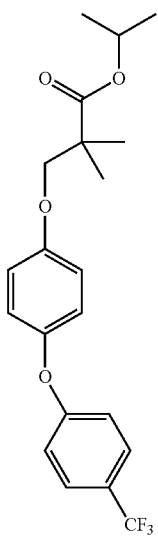 [SMILES: CC(C)OC(=O)C(C)(C)COc1ccc(Oc2ccc(C(F)(F)F)cc2)cc1] | 432 |
| 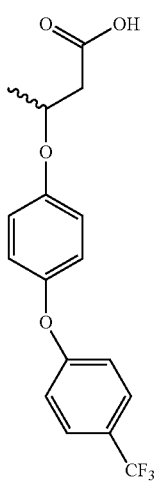 [SMILES: CC(CC(=O)O)Oc1ccc(Oc2ccc(C(F)(F)F)cc2)cc1] | 433 |「
TABLE 9-continued
| Structure | |
|---|---|
| 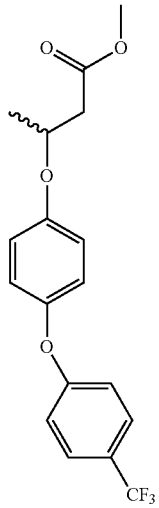 [SMILES: COC(=O)CC(C)Oc1ccc(Oc2ccc(C(F)(F)F)cc2)cc1] | 434 |
| 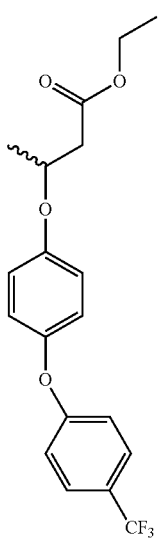 [SMILES: CCOC(=O)CC(C)Oc1ccc(Oc2ccc(C(F)(F)F)cc2)cc1] | 435 |
| 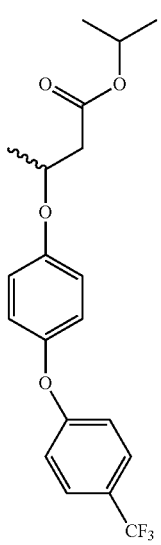 [SMILES: CC(C)OC(=O)CC(C)Oc1ccc(Oc2ccc(C(F)(F)F)cc2)cc1] | 436 |

TABLE 9-continued
| Structure | |
|---|---|
| 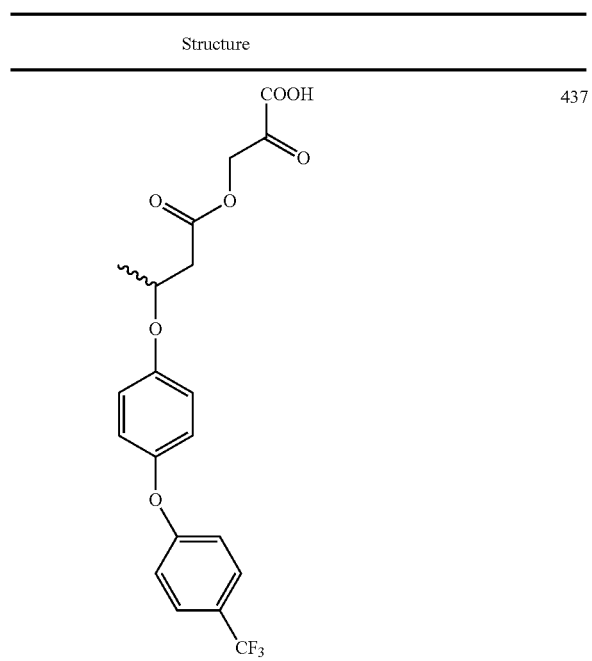 | 437 |
| 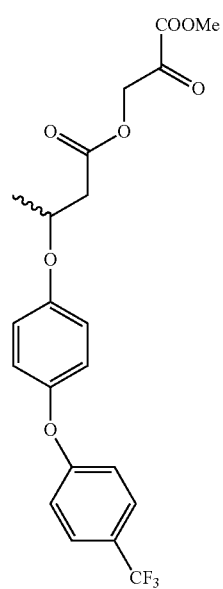 [SMILES: COC(=O)C(=O)COC(=O)CC(C)Oc1ccc(Oc2ccc(C(F)(F)F)cc2)cc1] | 438 |
TABLE 9-continued
| Structure | |
|---|---|
| 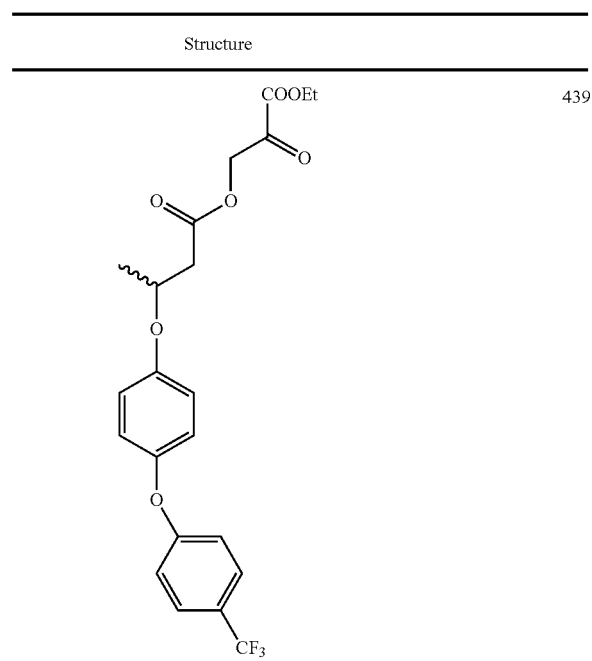 | 439 |
| 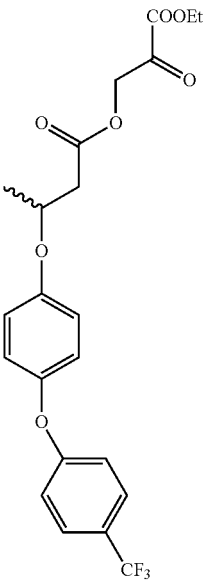 [SMILES: CCOC(=O)C(=O)COC(=O)CC(C)Oc1ccc(Oc2ccc(C(F)(F)F)cc2)cc1] | 440 |

TABLE 9-continued
| Structure | |
|---|---|
| 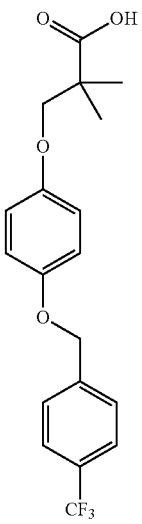 [SMILES: CC(C)(COc1ccc(OCc2ccc(C(F)(F)F)cc2)cc1)C(=O)O] | 441 |
| 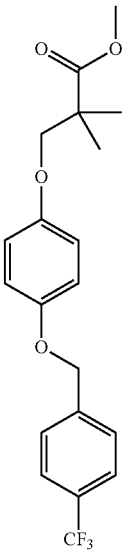 | 442 |
| 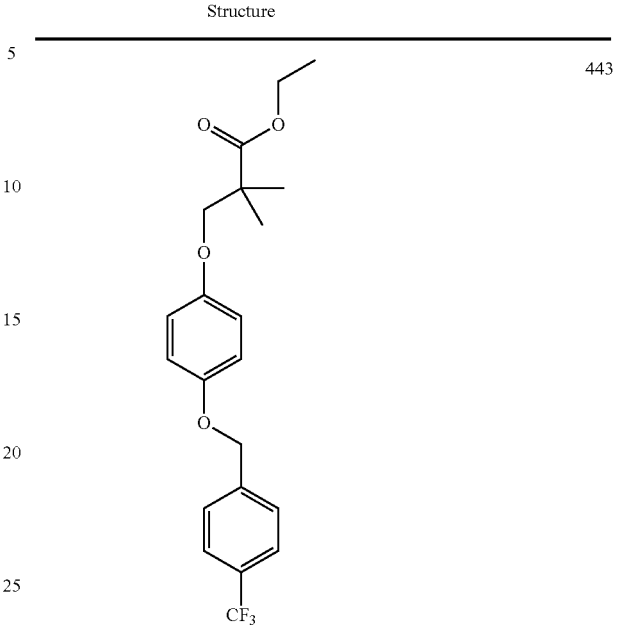 | 443 |
| 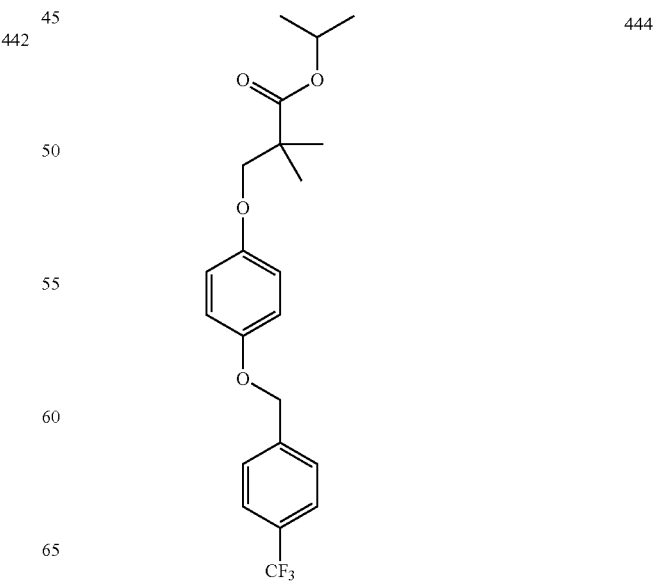 | 444 |

TABLE 9-continued
| Structure | |
|---|---|
| 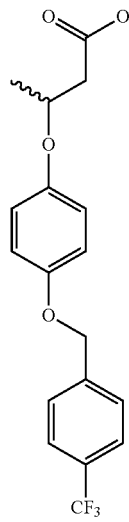 | 445 |
| 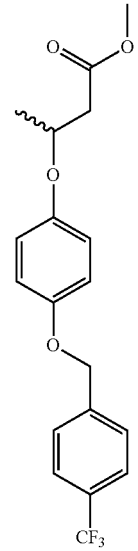 | 446 |
TABLE 9-continued
| Structure | |
|---|---|
| 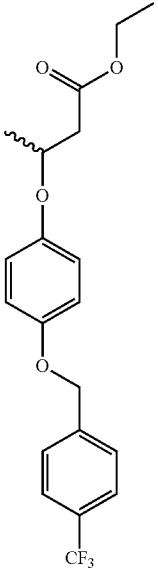 [SMILES: CCOC(=O)CC(C)Oc1ccc(OCc2ccc(C(F)(F)F)cc2)cc1] | 447 |
| 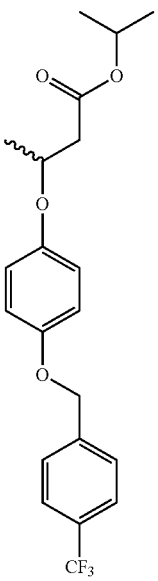 [SMILES: CC(C)OC(=O)CC(C)Oc1ccc(OCc2ccc(C(F)(F)F)cc2)cc1] | 448 |

TABLE 9-continued
| Structure | |
|---|---|
| 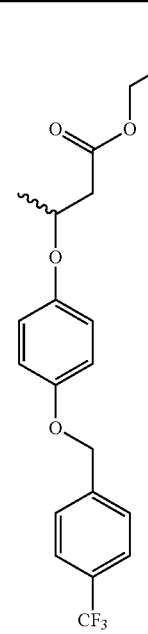 | 449 |
| 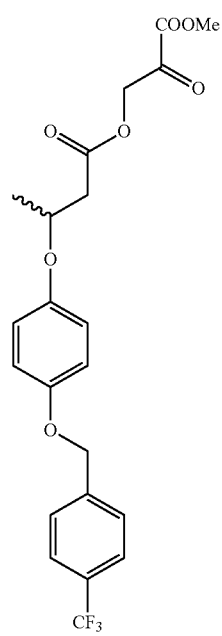 | 450 |
| 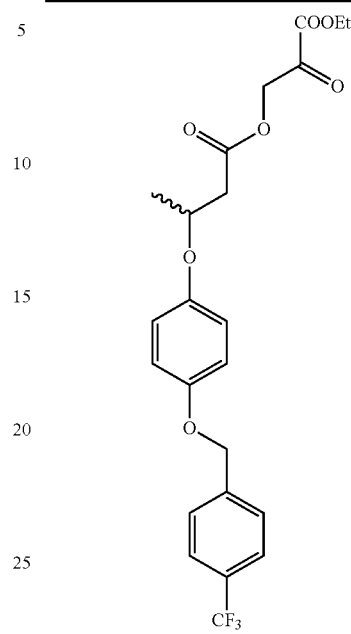 | 451 |
| 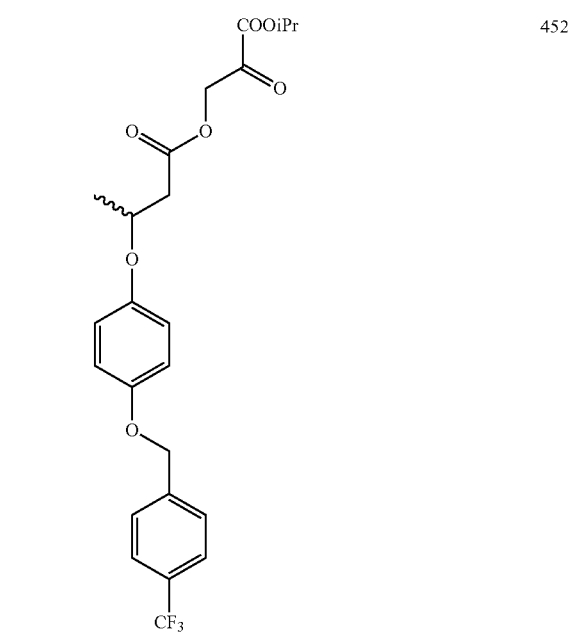 | 452 |

TABLE 9-continued
| Structure | |
|---|---|
| 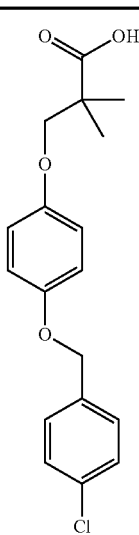 | 453 |
| 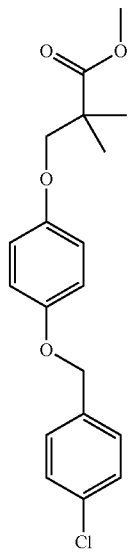 | 454 |
TABLE 9-continued
| Structure | |
|---|---|
| 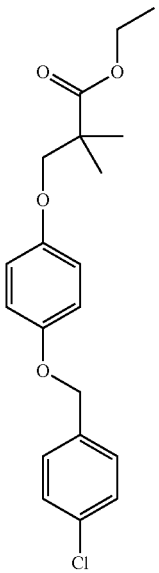 [SMILES: CCOC(=O)C(C)(C)COc1ccc(OCc2ccc(Cl)cc2)cc1] | 455 |
| 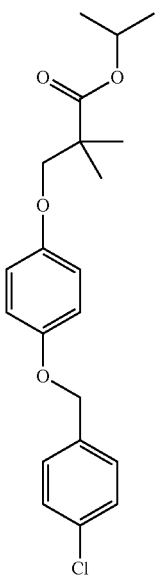 [SMILES: CC(C)OC(=O)C(C)(C)COc1ccc(OCc2ccc(Cl)cc2)cc1] | 456 |

TABLE 9-continued
| Structure | |
|---|---|
| 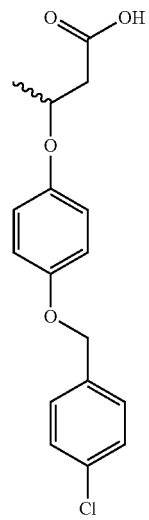 [SMILES: CC(CC(=O)O)Oc1ccc(OCc2ccc(Cl)cc2)cc1] | 457 |
| 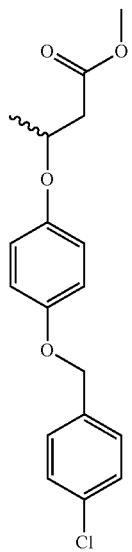 | 458 |
TABLE 9-continued
| Structure | |
|---|---|
| 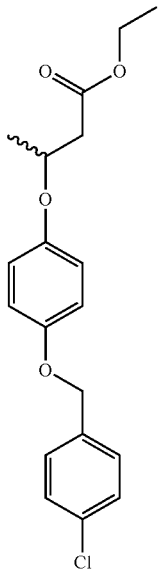 [SMILES: CCOC(=O)CC(C)Oc1ccc(OCc2ccc(Cl)cc2)cc1] | 459 |
| 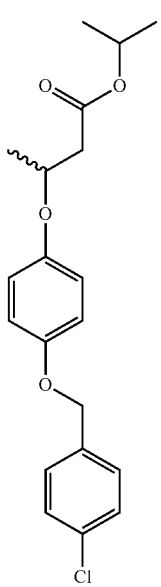 [SMILES: CC(C)OC(=O)CC(C)Oc1ccc(OCc2ccc(Cl)cc2)cc1] | 460 |

TABLE 9-continued
| Structure | |
|---|---|
| 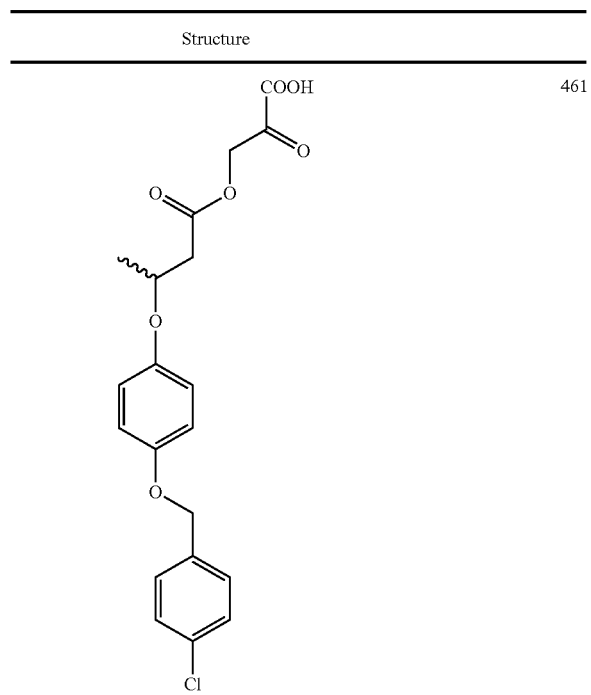 | 461 |
| 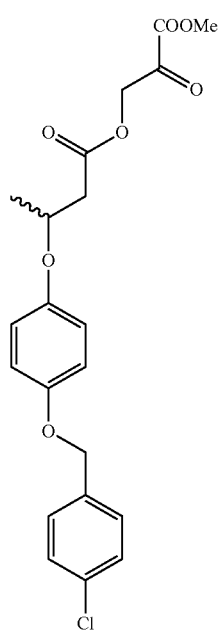 | 472 |
TABLE 9-continued
| Structure | |
|---|---|
| 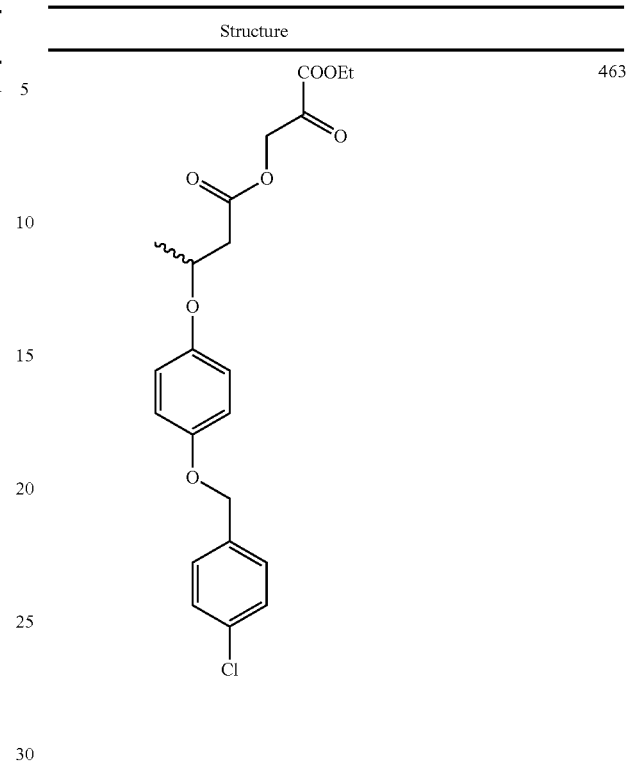 | 463 |
| 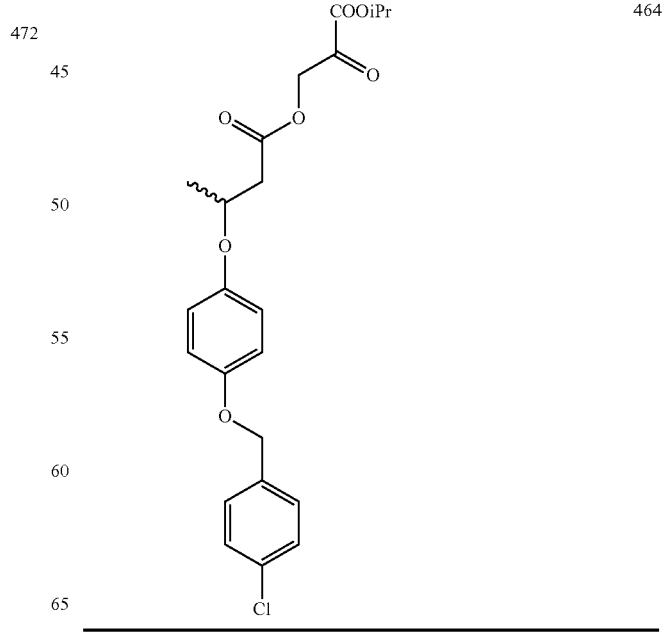 | 464 |

TABLE 10
| Structure | |
|---|---|
| 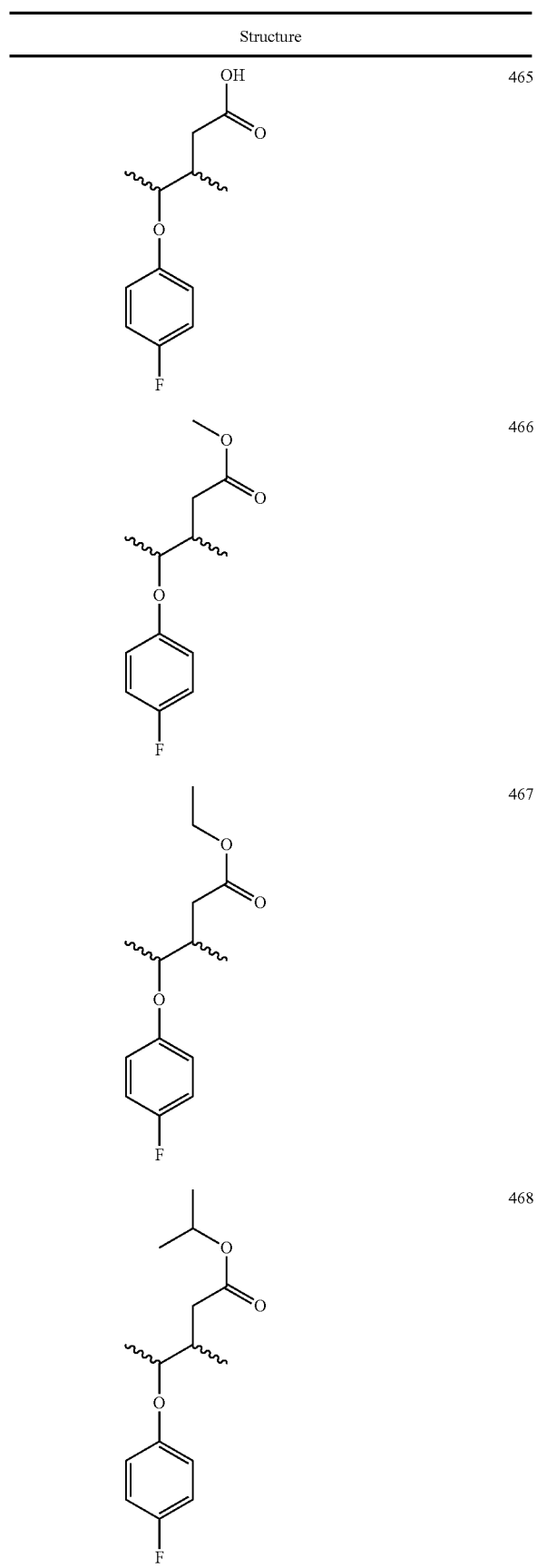 | 465<br><br>466<br><br>467<br><br>468 |
TABLE 10-continued
| Structure | |
|---|---|
| 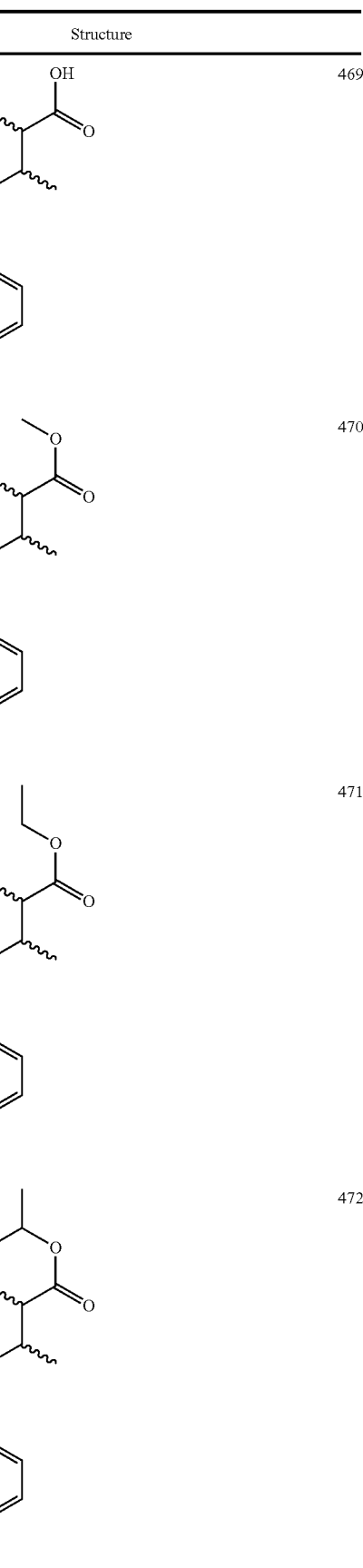 | 469<br><br>470<br><br>471<br><br>472 |

TABLE 10-continued
| Structure | |
|---|---|
| 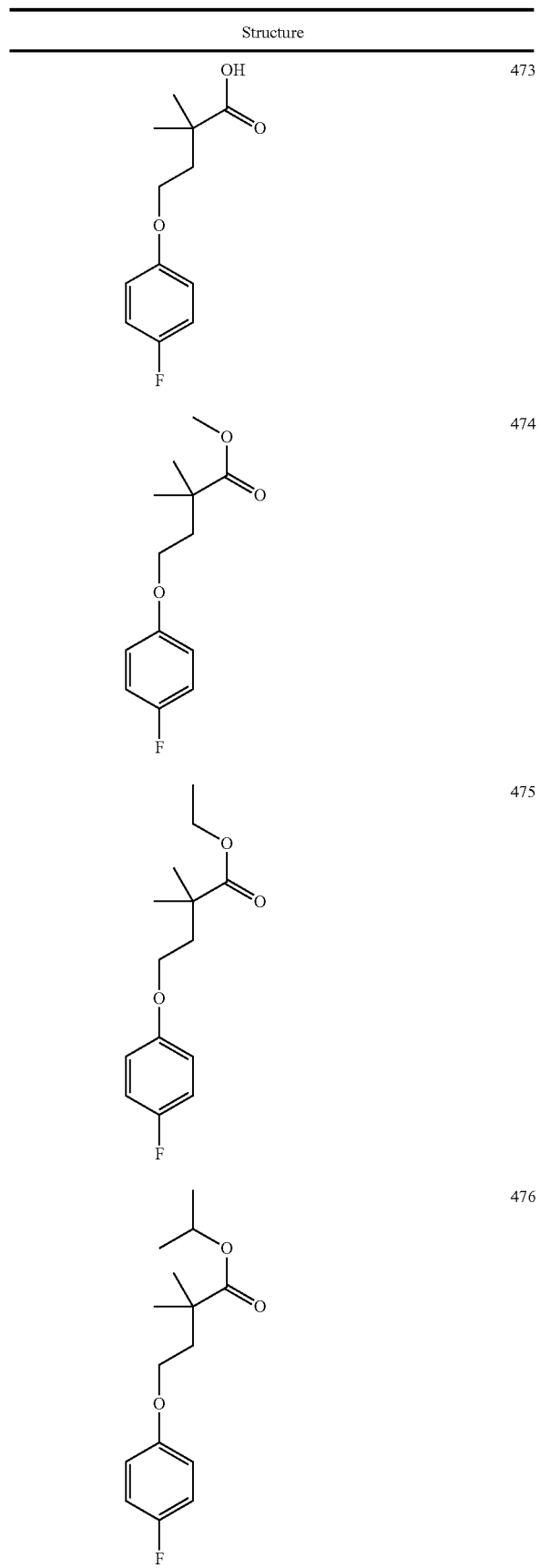 | 473<br><br>474<br><br>475<br><br>476 |
| 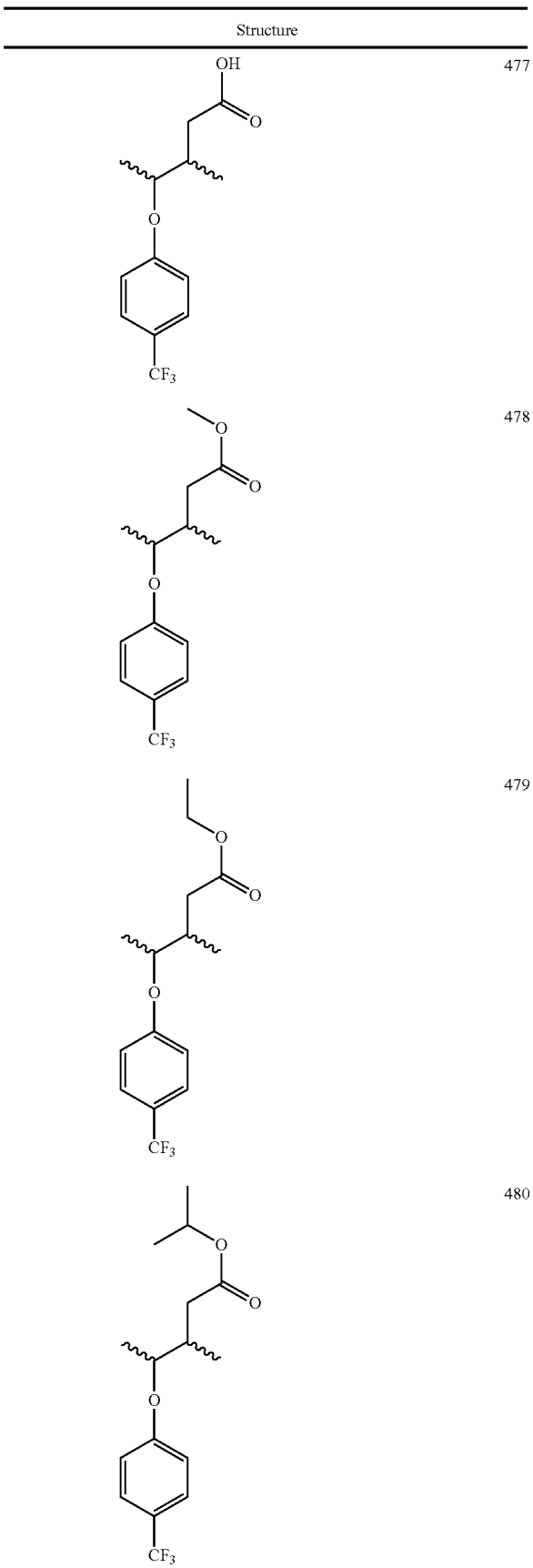 | 477<br><br>478<br><br>479<br><br>480 |

TABLE 10-continued
| Structure | |
|---|---|
| 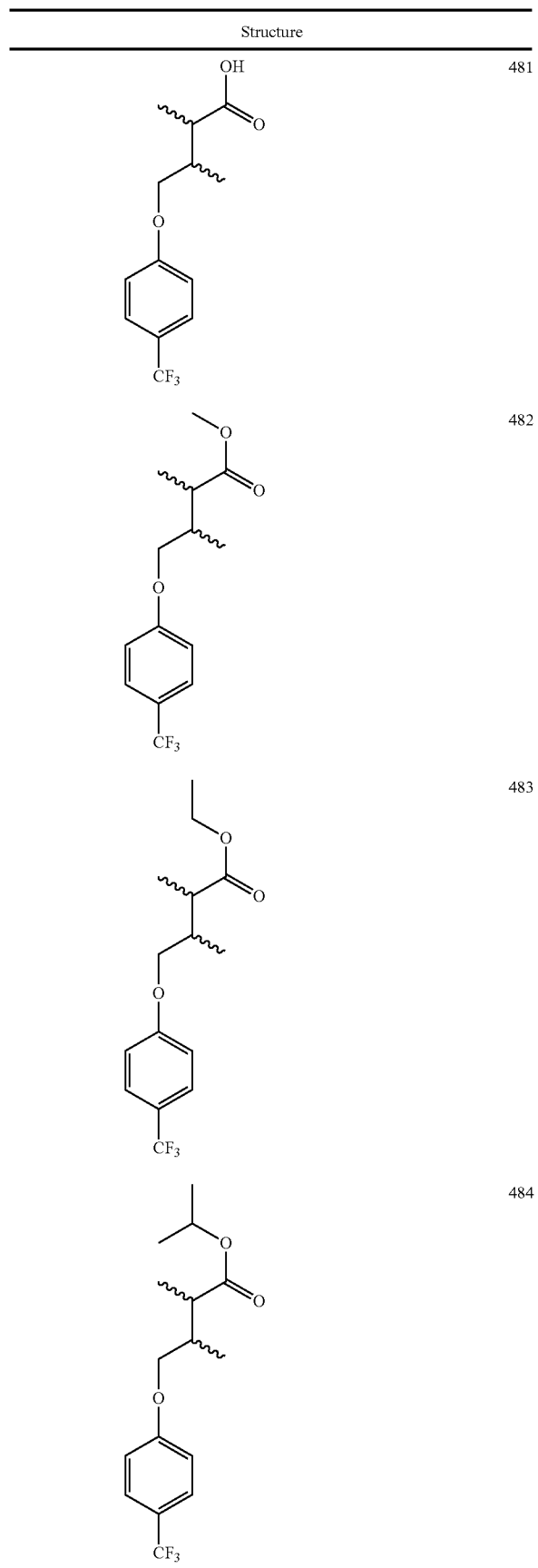 | 481 |
| 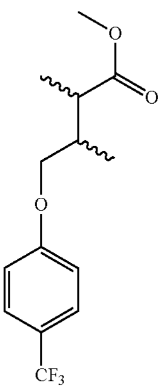 | 482 |
| 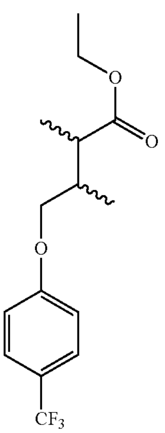 | 483 |
| 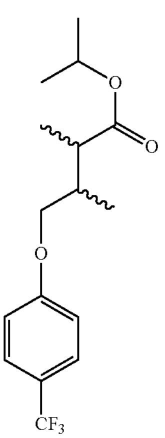 | 484 |
TABLE 10-continued
| Structure | |
|---|---|
| 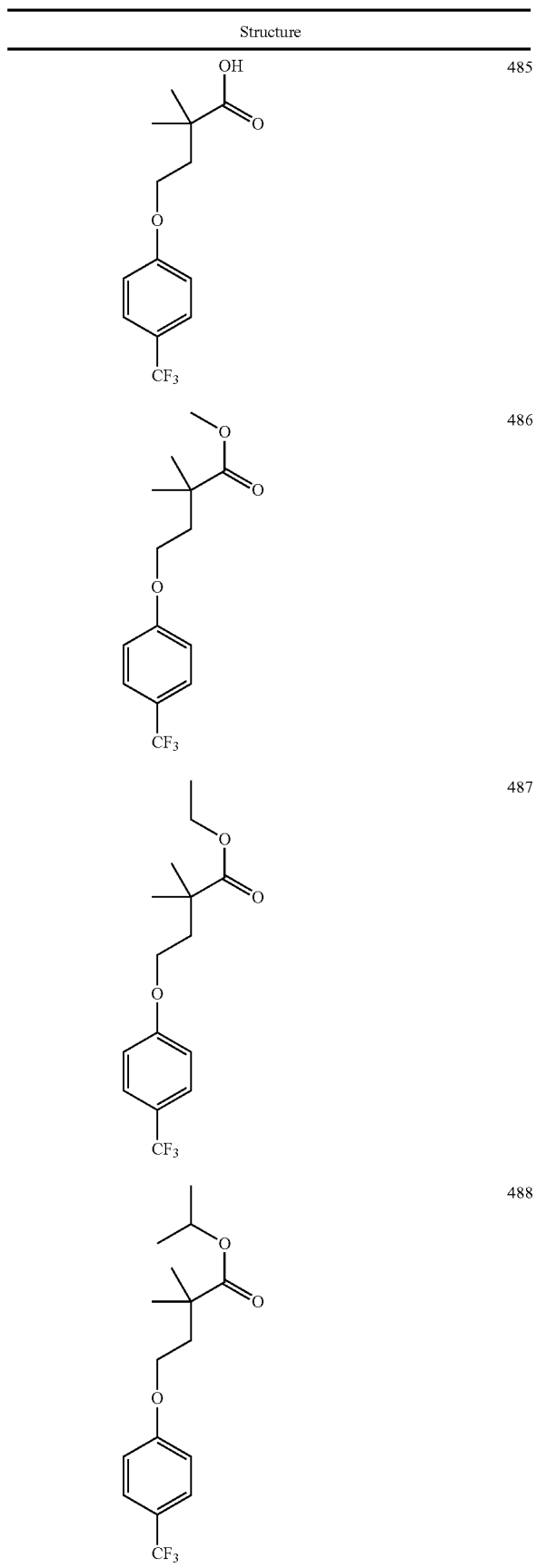 | 485 |
| | 486 |
| | 487 |
| | 488 |

TABLE 10-continued
| Structure | |
|---|---|
| 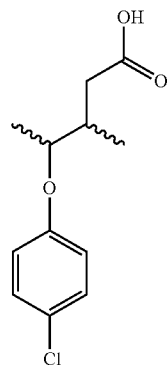 | 489 |
| 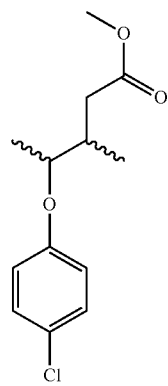 | 490 |
| 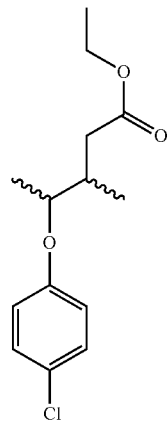 | 491 |
| 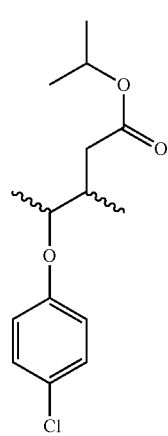 | 492 |
TABLE 10-continued
| Structure | |
|---|---|
| 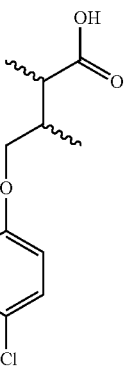 | 493 |
| 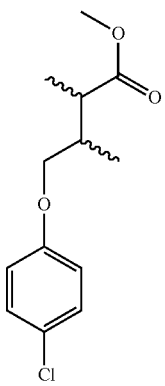 | 494 |
| 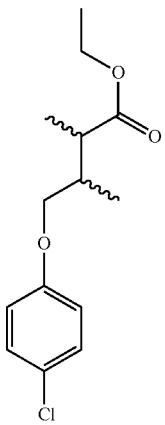 | 495 |
| 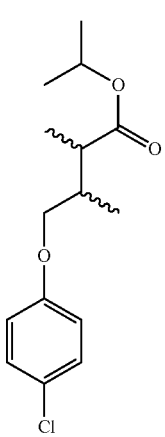 | 496 |

TABLE 10-continued
| Structure | |
|---|---|
| 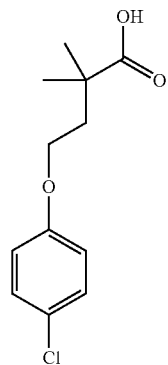 [SMILES: CC(C)(CCOc1ccc(Cl)cc1)C(=O)O] | 497 |
| 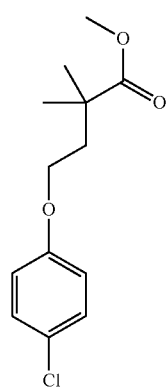 [SMILES: COC(=O)C(C)(C)CCOc1ccc(Cl)cc1] | 498 |
| 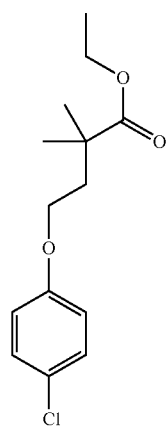 [SMILES: CCOC(=O)C(C)(C)CCOc1ccc(Cl)cc1] | 499 |
| 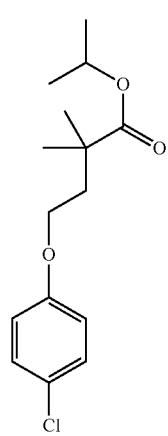 [SMILES: CC(C)OC(=O)C(C)(C)CCOc1ccc(Cl)cc1] | 500 |
TABLE 10-continued
| Structure | |
|---|---|
| 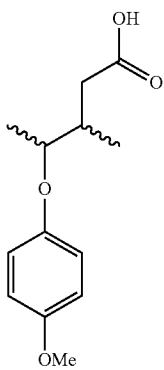 | 501 |
| 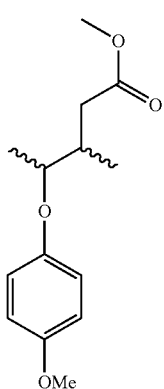 | 502 |
| 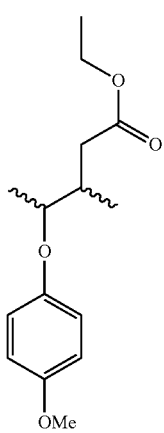 | 503 |
| 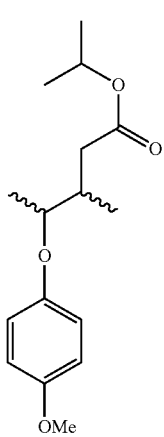 | 504 |

TABLE 10-continued
| Structure | |
|---|---|
| 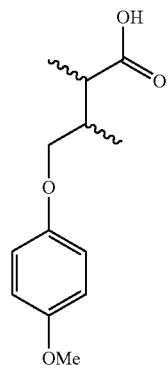 | 505 |
| 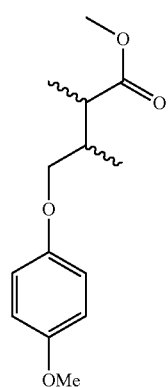 | 506 |
| 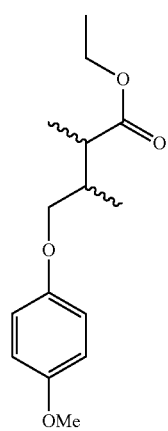 | 507 |
| 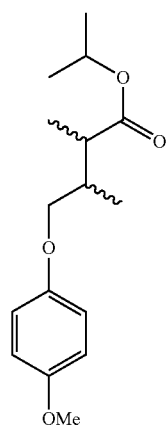 | 508 |
TABLE 10-continued
| Structure | |
|---|---|
| 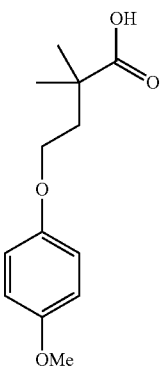 [SMILES: COc1ccc(OCCC(C)(C)C(=O)O)cc1] | 509 |
| 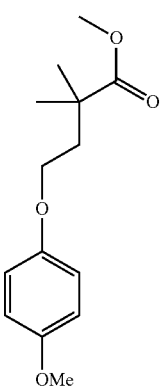 [SMILES: COC(=O)C(C)(C)CCOc1ccc(OC)cc1] | 510 |
| 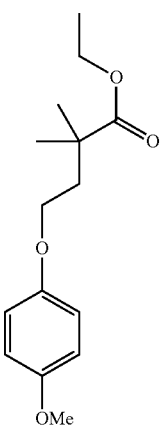 [SMILES: CCOC(=O)C(C)(C)CCOc1ccc(OC)cc1] | 511 |
| 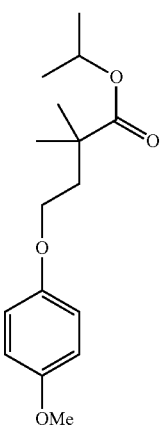 [SMILES: COc1ccc(OCCC(C)(C)C(=O)OC(C)C)cc1] | 512 |

TABLE 10-continued
| Structure | |
|---|---|
| 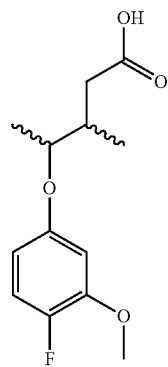 | 513 |
| 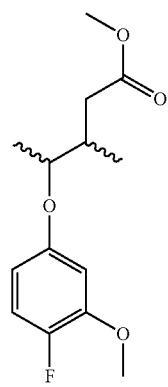 | 514 |
| 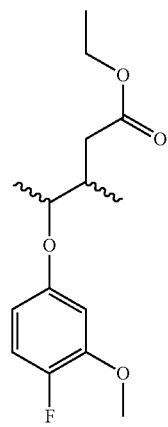 | 515 |
| 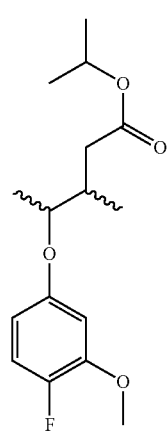 | 516 |
| 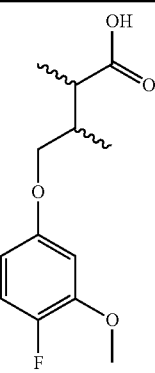 | 517 |
| 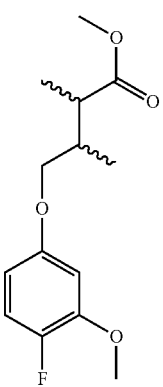 | 518 |
| 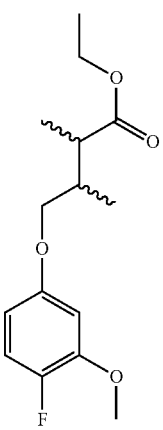 | 519 |
| 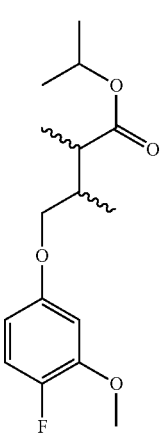 | 520 |

TABLE 10-continued
| Structure | |
|---|---|
| 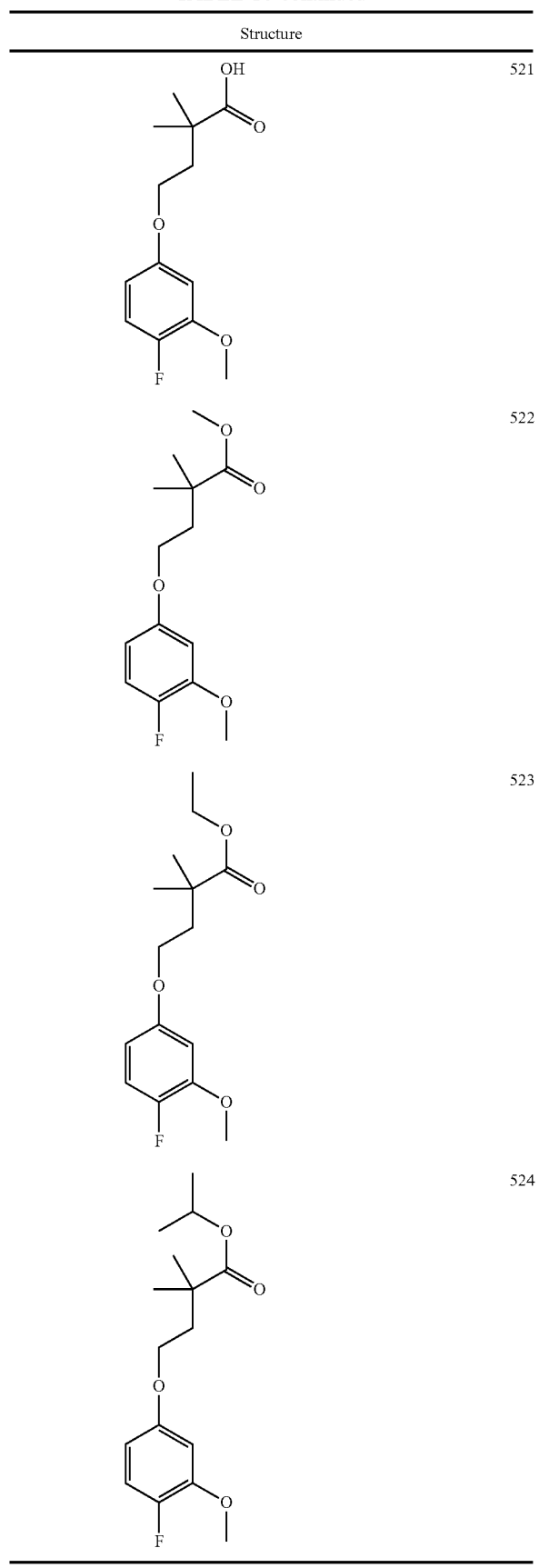 | 521<br><br>522<br><br>523<br><br>524 |
TABLE 11
| Structure | |
|---|---|
| 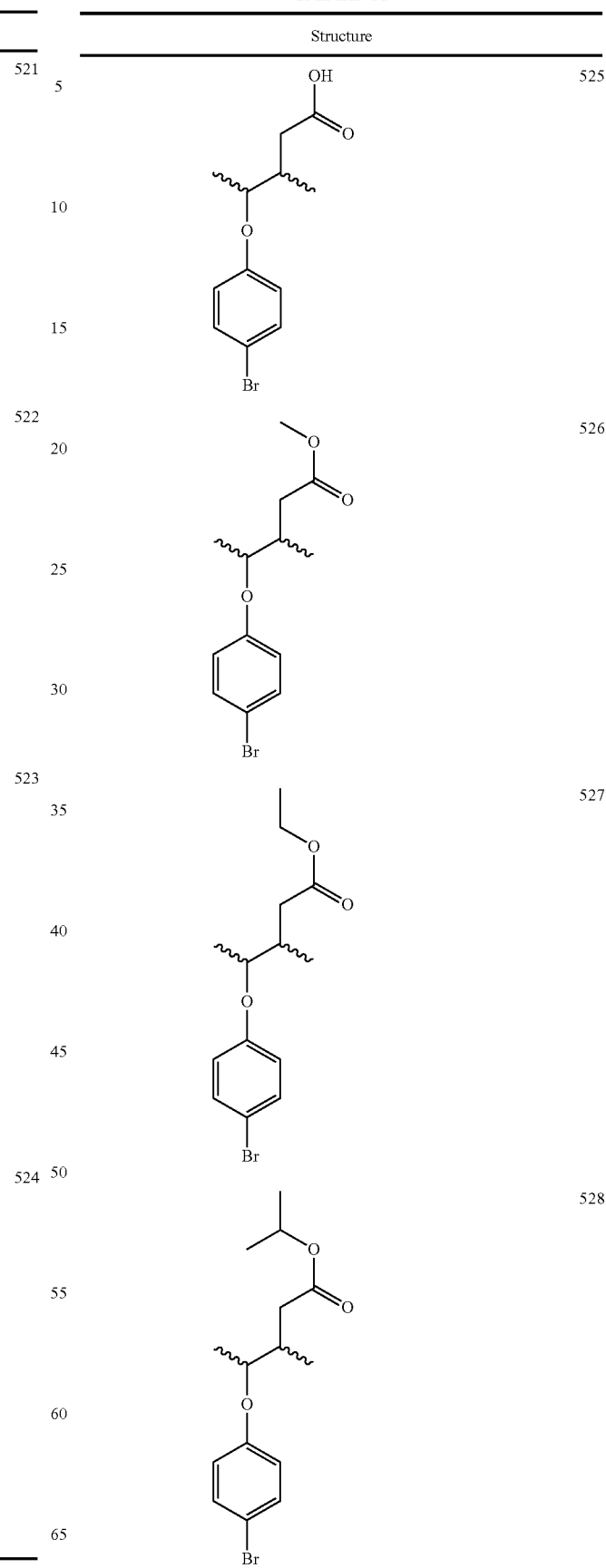 | 525<br><br>526<br><br>527<br><br>528 |

TABLE 11-continued
| Structure | |
|---|---|
| 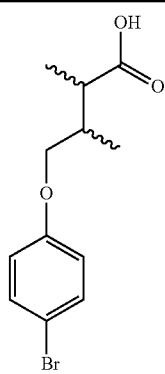 | 529 |
| 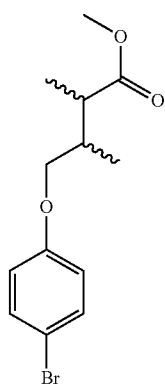 | 530 |
| 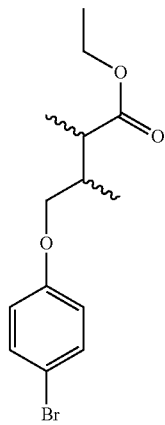 | 531 |
| 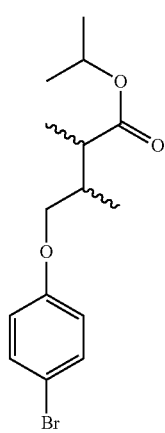 | 532 |
TABLE 11-continued
| Structure | |
|---|---|
| 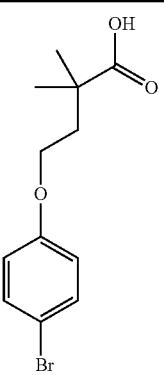 | 533 |
| 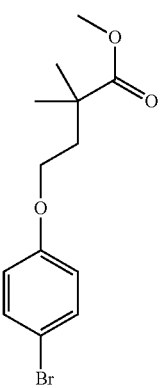 [SMILES: COC(=O)C(C)(C)CCOc1ccc(Br)cc1] | 534 |
| 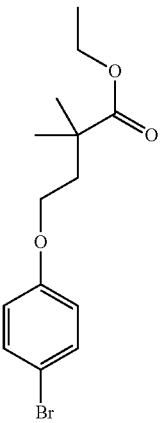 [SMILES: CCOC(=O)C(C)(C)CCOc1ccc(Br)cc1] | 535 |
| 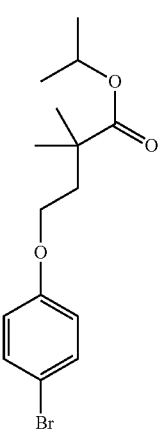 [SMILES: CC(C)OC(=O)C(C)(C)CCOc1ccc(Br)cc1] | 536 |

TABLE 11-continued
| Structure | |
|---|---|
| 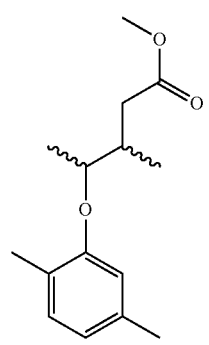 | 537 |
| 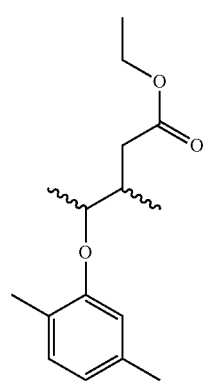 | 538 |
| 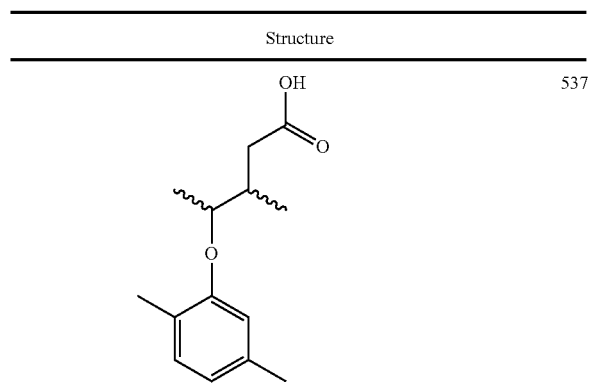 | 539 |
| 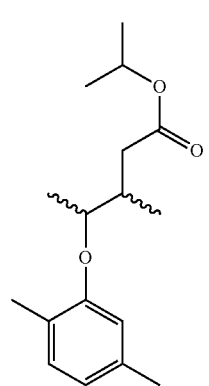 | 540 |
TABLE 11-continued
| Structure | |
|---|---|
| 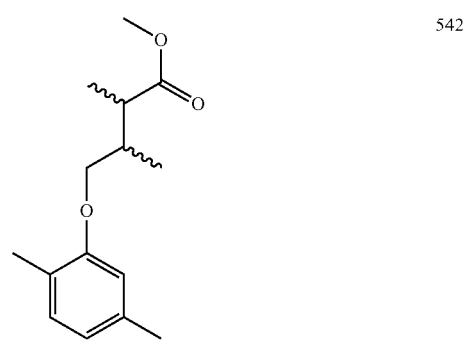 | 541 |
| 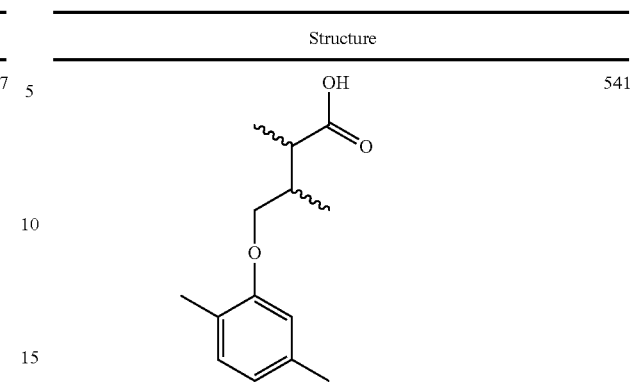 | 542 |
| 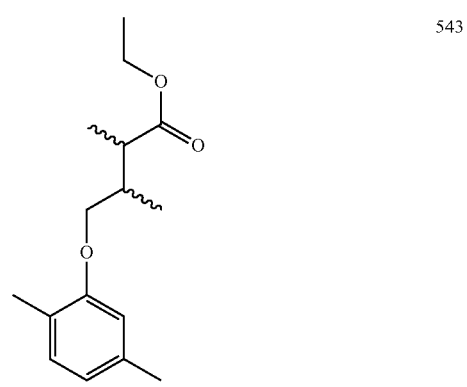 | 543 |
| 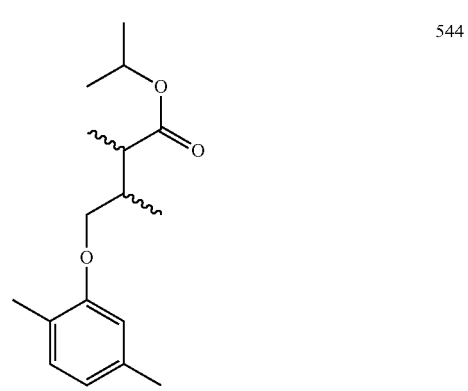 | 544 |

TABLE 11-continued
| Structure | |
|---|---|
| 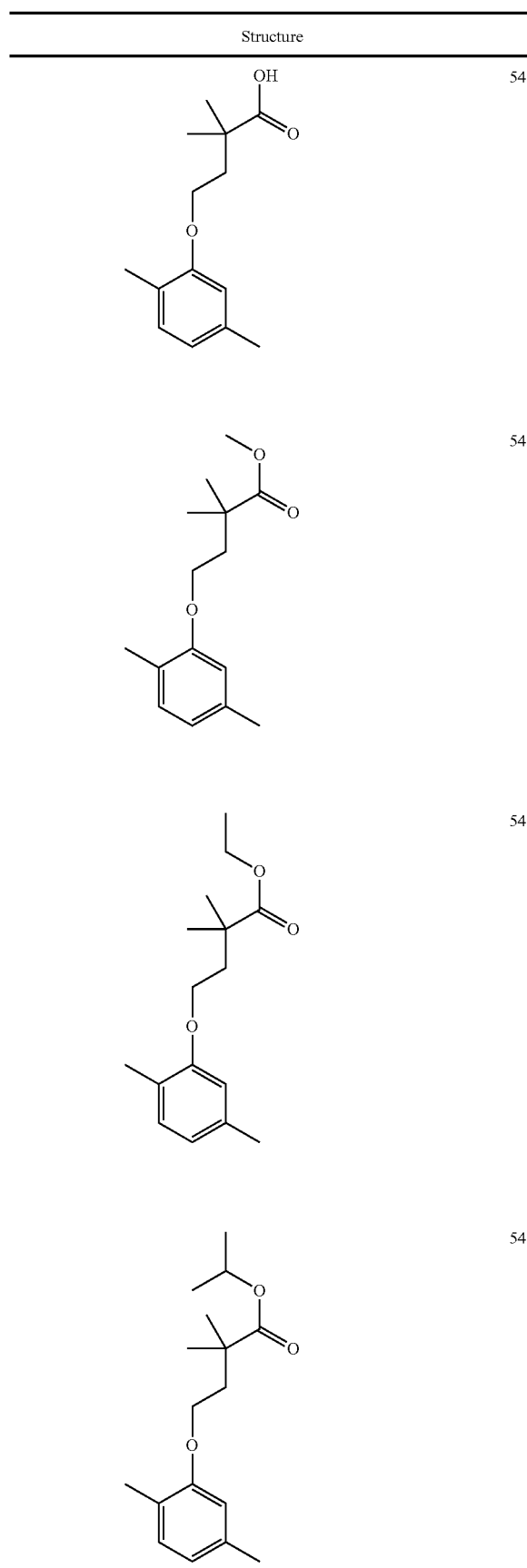 | 545 |
| 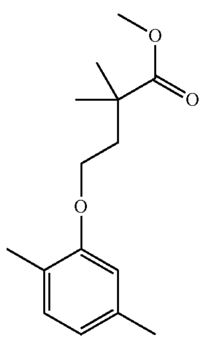 [SMILES: COC(=O)C(C)(C)CCOc1cc(C)ccc1C] | 546 |
| 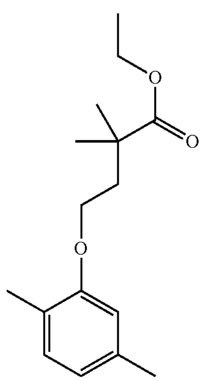 [SMILES: CCOC(=O)C(C)(C)CCOc1cc(C)ccc1C] | 547 |
| 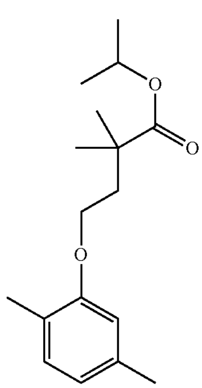 [SMILES: Cc1ccc(C)c(OCCC(C)(C)C(=O)OC(C)C)c1] | 548 |
TABLE 11-continued
| Structure | |
|---|---|
| 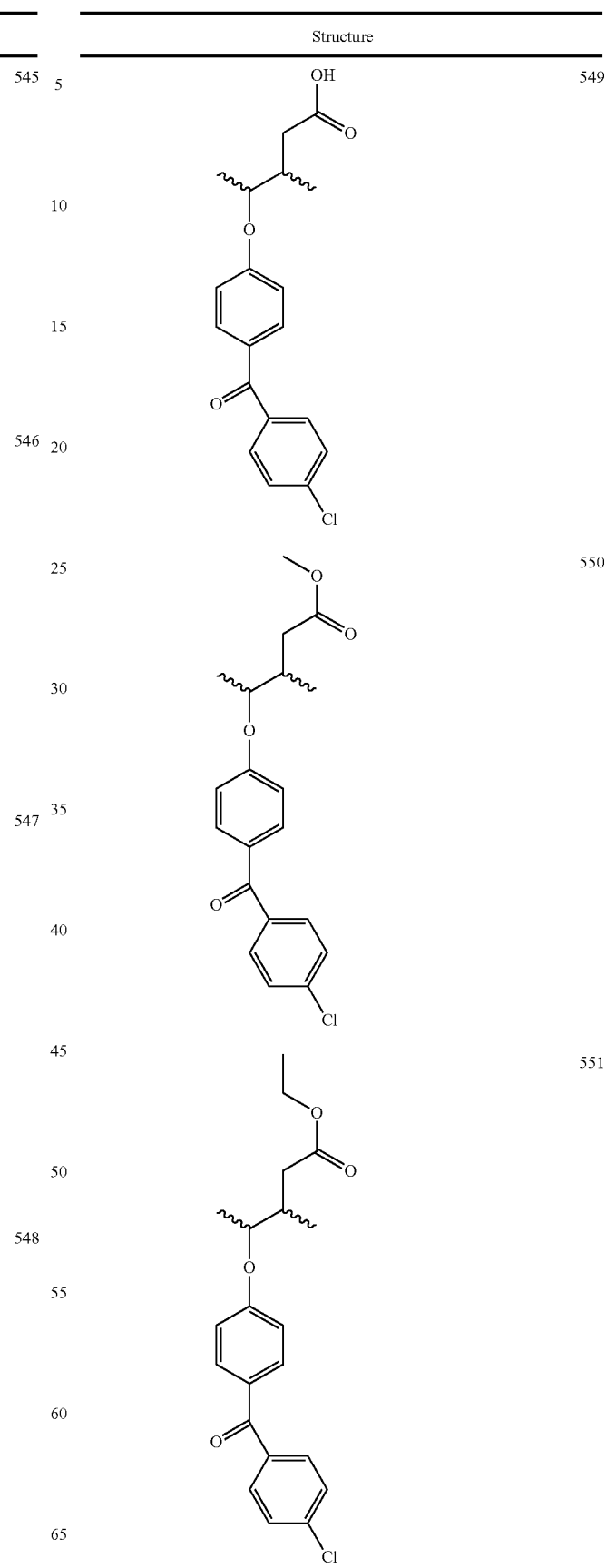 | 549 |
| 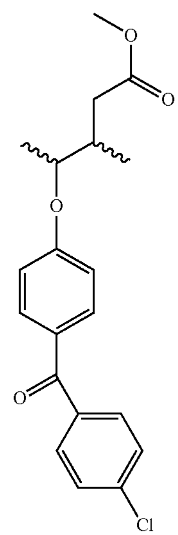 | 550 |
| 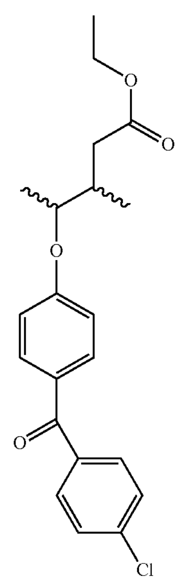 | 551 |

TABLE 11-continued
| Structure | |
|---|---|
| 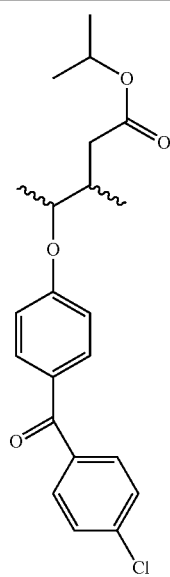 | 552 |
| 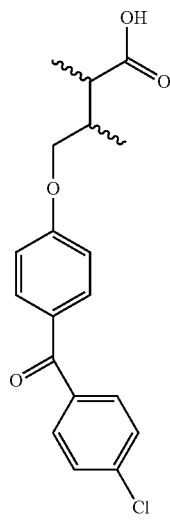 | 553 |
| 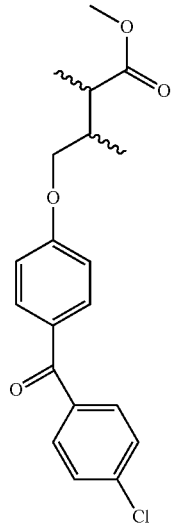 | 554 |
TABLE 11-continued
| Structure | |
|---|---|
| 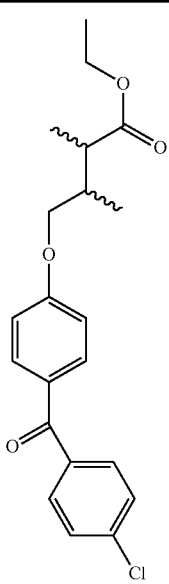 | 555 |
| 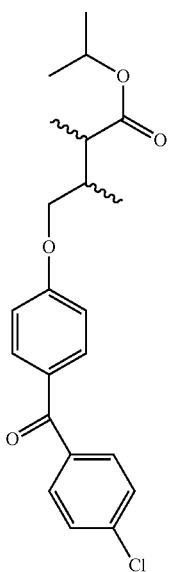 | 556 |

TABLE 11-continued
Structure
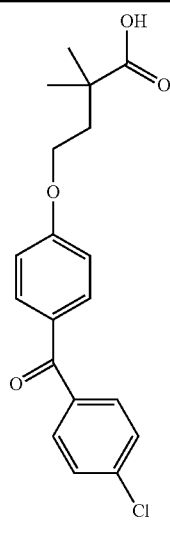
557
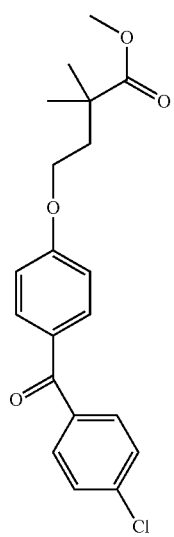 [SMILES: COC(=O)C(C)(C)CCOc1ccc(C(=O)c2ccc(Cl)cc2)cc1]
558
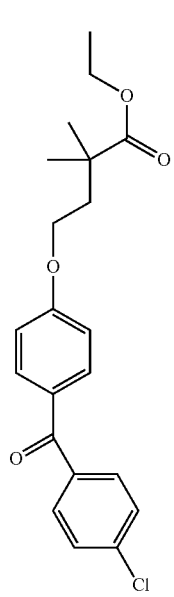 [SMILES: CCOC(=O)C(C)(C)CCOc1ccc(C(=O)c2ccc(Cl)cc2)cc1]
559
TABLE 11-continued
Structure
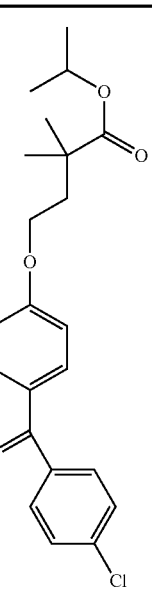
560
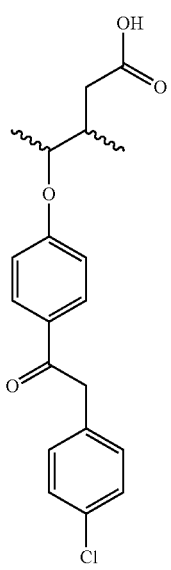
561

TABLE 11-continued
| Structure | |
|---|---|
| 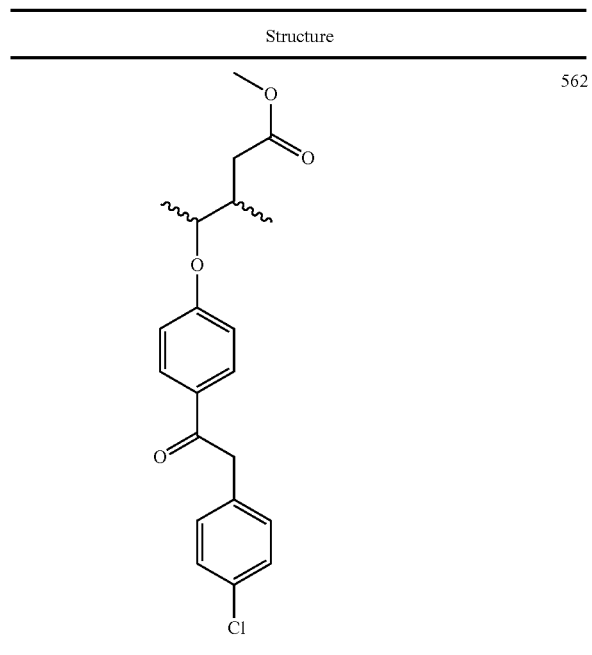 | 562 |
| 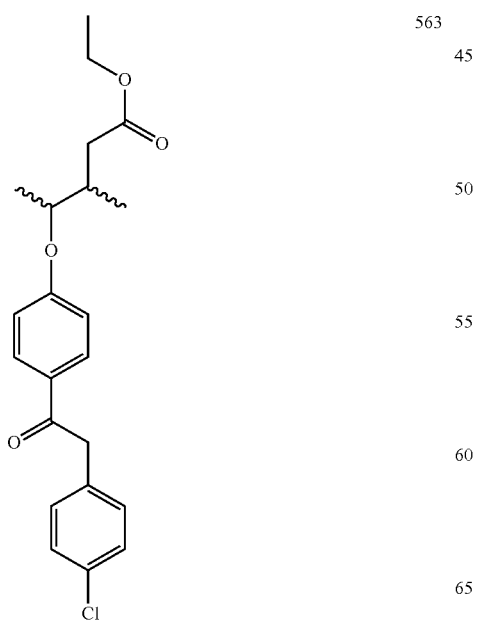 | 563 |
| 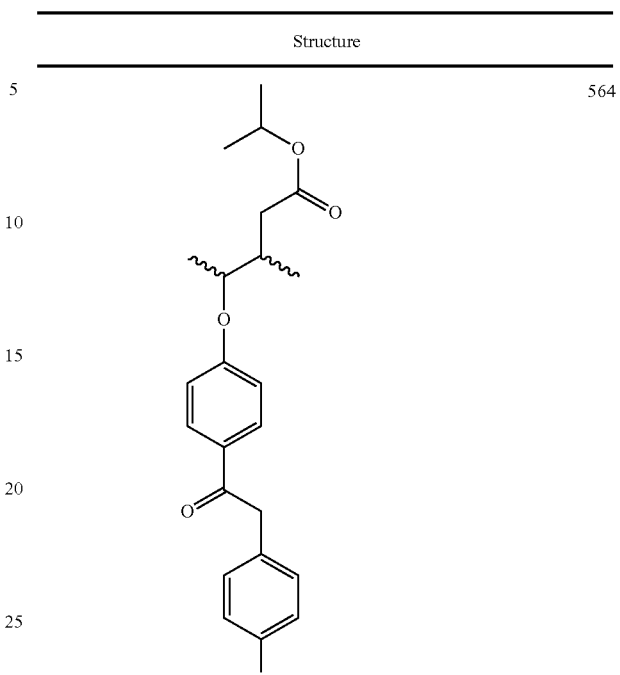 | 564 |
| 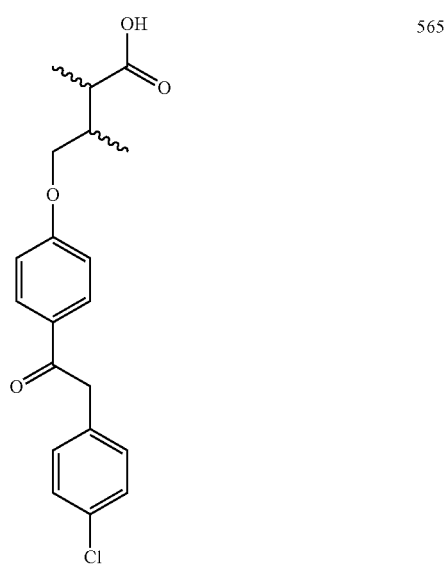 | 565 |

TABLE 11-continued
| Structure | |
|---|---|
| 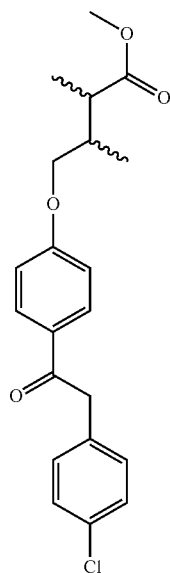 | 566 |
| 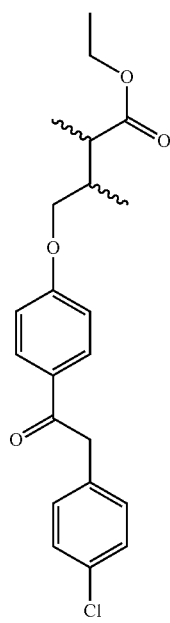 | 567 |
| 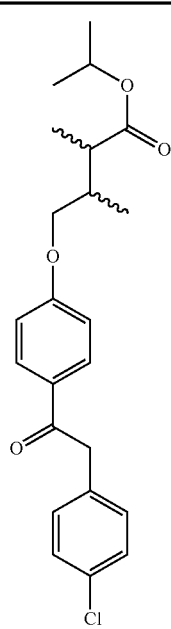 | 568 |
| 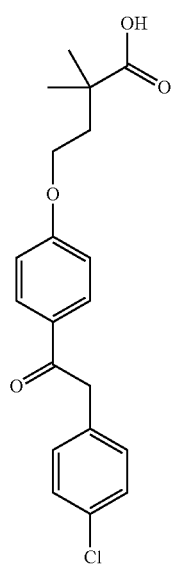 | 569 |

TABLE 11-continued
| Structure | |
|---|---|
| 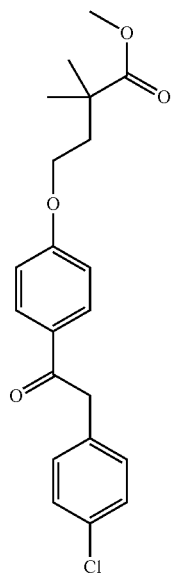 | 570 |
| 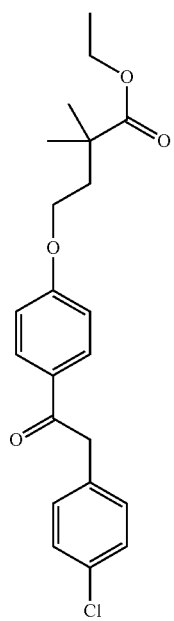 | 571 |
TABLE 11-continued
| Structure | |
|---|---|
| 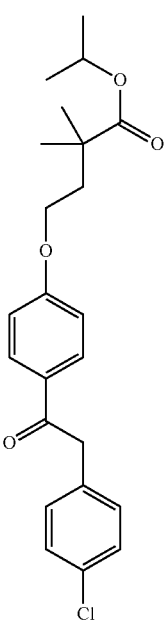 | 572 |
TABLE 12
| Structure | |
|---|---|
| 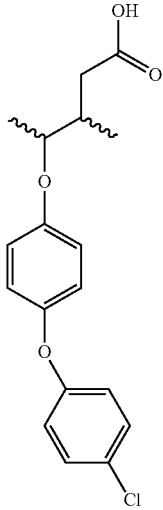 | 573 |

TABLE 12-continued
| Structure | |
|---|---|
| 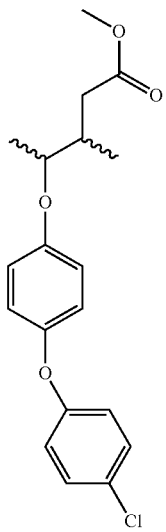 | 574 |
| 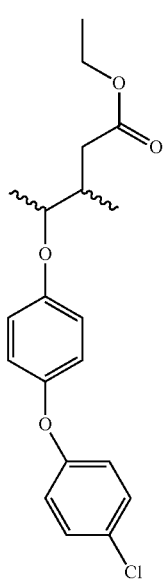 | 575 |
| 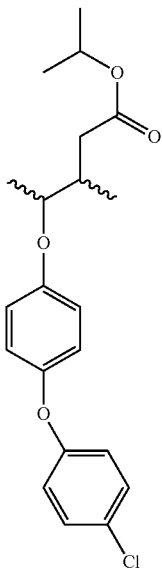 | 576 |
| 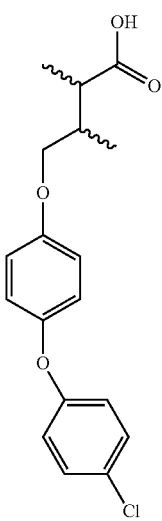 | 577 |
| 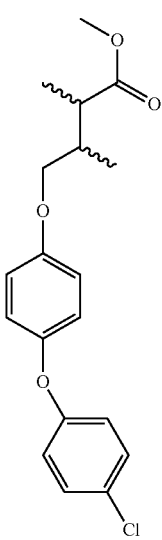 | 578 |

TABLE 12-continued
| Structure | |
|---|---|
| 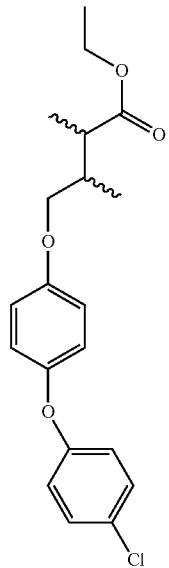 | 579 |
| 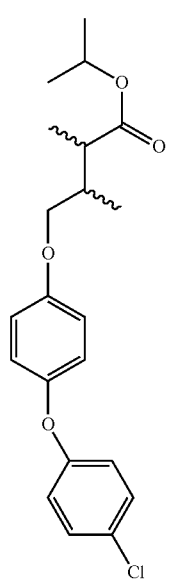 | 580 |
TABLE 12-continued
| Structure | |
|---|---|
| 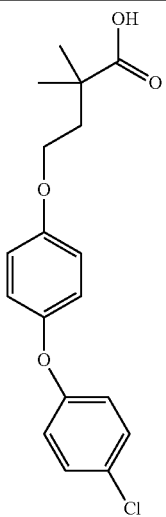 | 581 |
| | 582 |
| 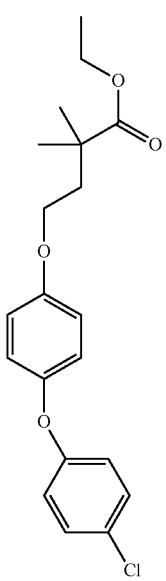 | 583 |

TABLE 12-continued
Structure
584
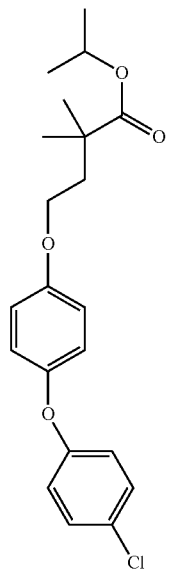 [SMILES: CC(C)OC(=O)C(C)(C)CCOc1ccc(Oc2ccc(Cl)cc2)cc1]
585
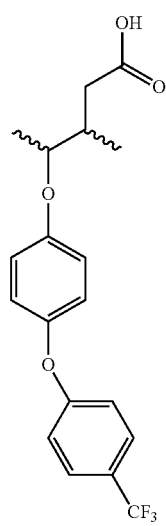
586
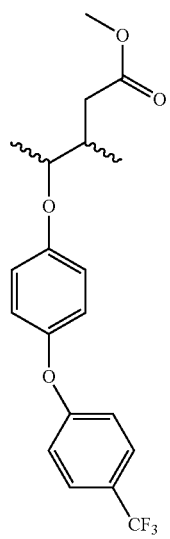
TABLE 12-continued
Structure
587
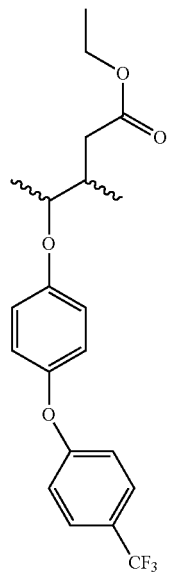
588
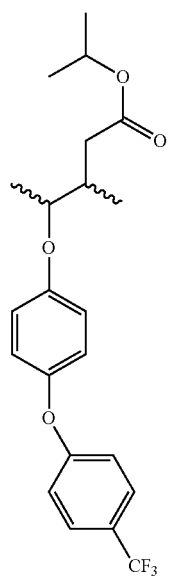

TABLE 12-continued
| Structure | |
|---|---|
| 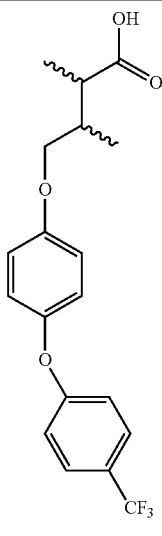 | 589 |
| 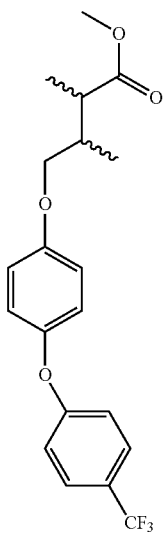 | 590 |
| 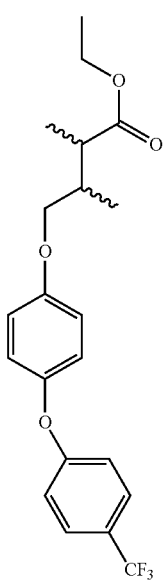 | 591 |
TABLE 12-continued
| Structure | |
|---|---|
| 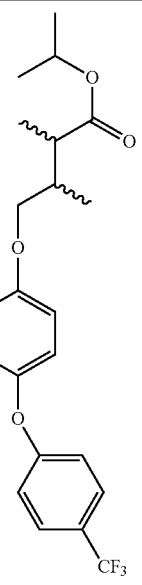 | 592 |
| 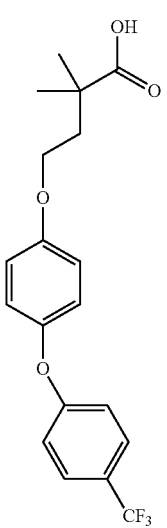 [SMILES: CC(C)(CCOc1ccc(Oc2ccc(C(F)(F)F)cc2)cc1)C(=O)O] | 593 |
| 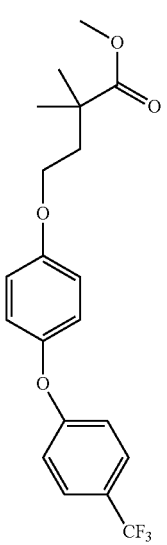 [SMILES: COC(=O)C(C)(C)CCOc1ccc(Oc2ccc(C(F)(F)F)cc2)cc1] | 594 |

TABLE 12-continued
Structure
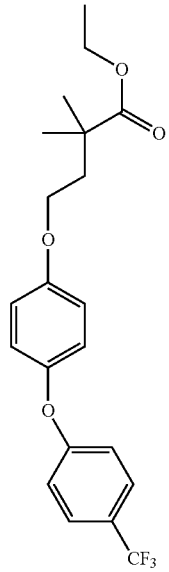 [SMILES: CCOC(=O)C(C)(C)CCOc1ccc(Oc2ccc(C(F)(F)F)cc2)cc1]
595
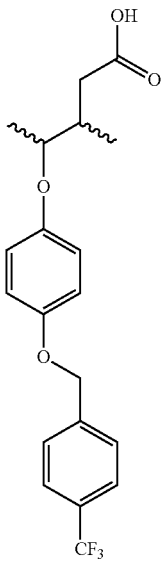
597
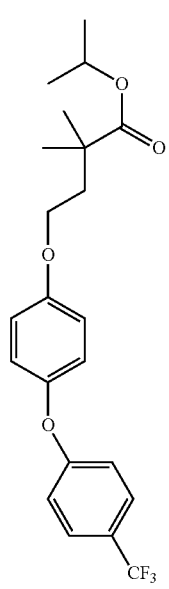 [SMILES: CC(C)OC(=O)C(C)(C)CCOc1ccc(Oc2ccc(C(F)(F)F)cc2)cc1]
596
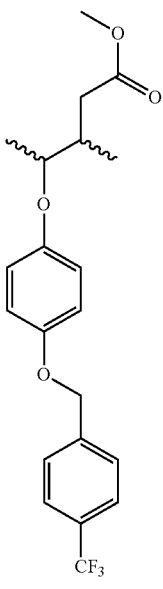
598

TABLE 12-continued
| Structure | |
|---|---|
| 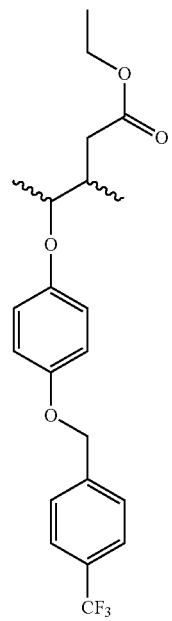 | 599 |
| 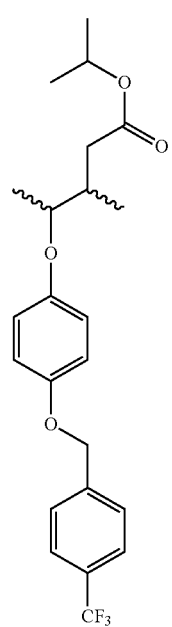 | 600 |
| 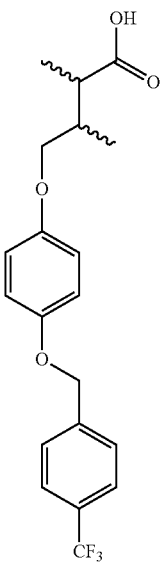 | 601 |
| 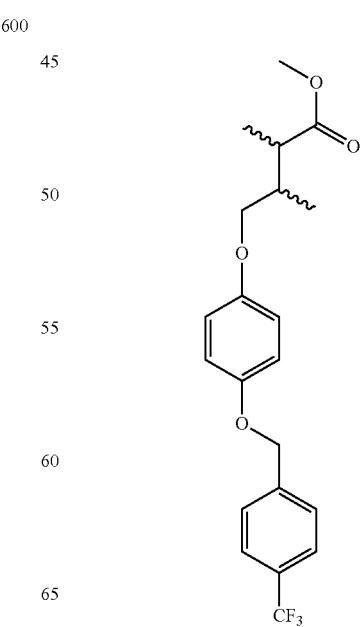 | 602 |

TABLE 12-continued
| Structure | |
|---|---|
| 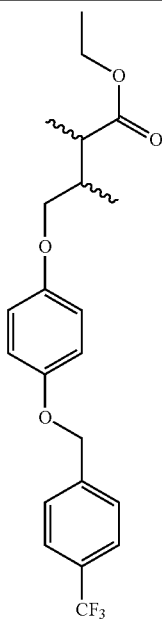 | 603 |
| 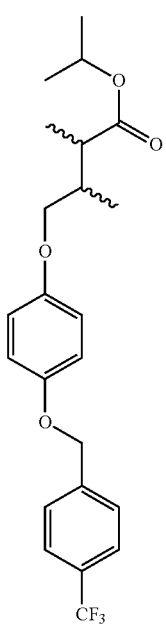 | 604 |
TABLE 12-continued
| Structure | |
|---|---|
| 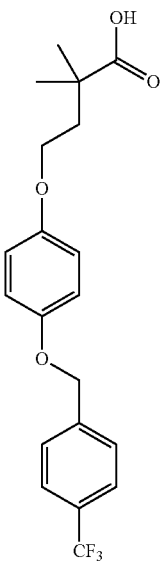 [SMILES: CC(C)(CCOc1ccc(OCc2ccc(C(F)(F)F)cc2)cc1)C(=O)O] | 605 |
| 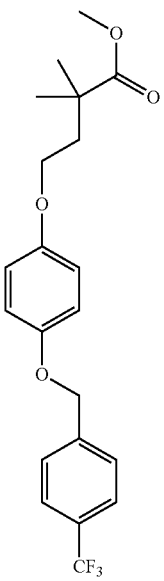 [SMILES: COC(=O)C(C)(C)CCOc1ccc(OCc2ccc(C(F)(F)F)cc2)cc1] | 606 |

TABLE 12-continued
Structure
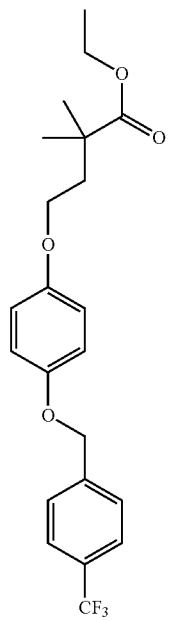 [SMILES: CCOC(=O)C(C)(C)CCOc1ccc(OCc2ccc(C(F)(F)F)cc2)cc1]
607
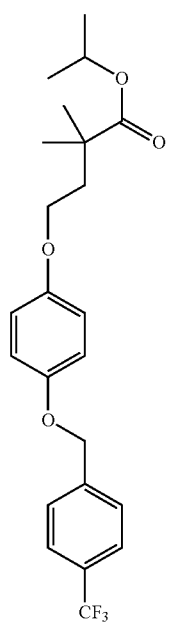 [SMILES: CC(C)OC(=O)C(C)(C)CCOc1ccc(OCc2ccc(C(F)(F)F)cc2)cc1]
608
TABLE 12-continued
Structure
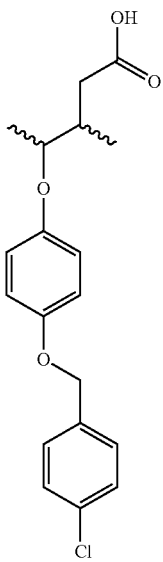
609
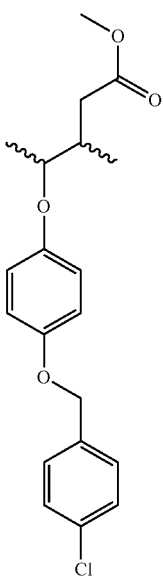
610

TABLE 12-continued
| Structure | |
|---|---|
| 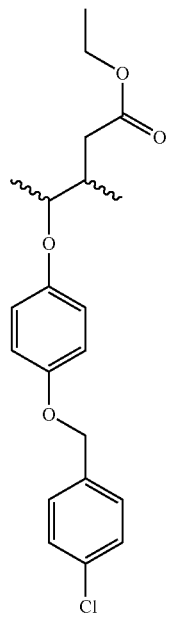 | 611 |
| 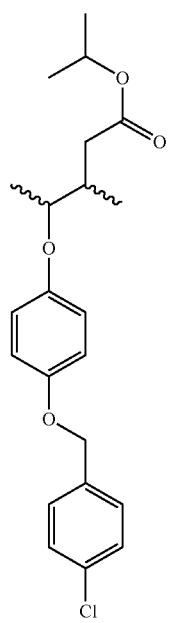 | 612 |
TABLE 12-continued
| Structure | |
|---|---|
| 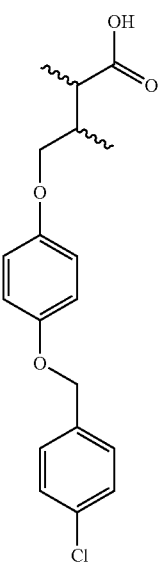 | 613 |
| 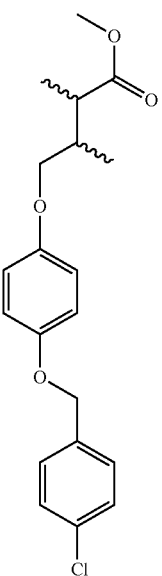 | 614 |

TABLE 12-continued
| Structure | |
|---|---|
| 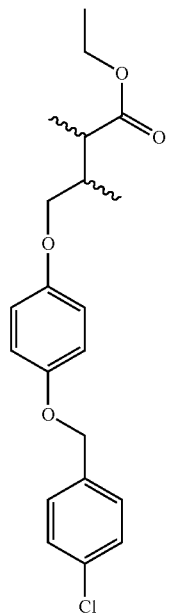 | 615 |
| 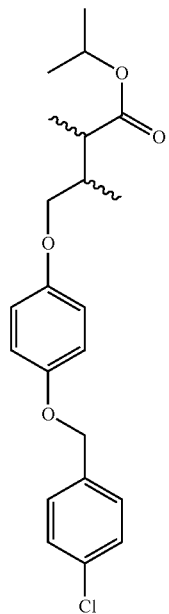 | 616 |
| 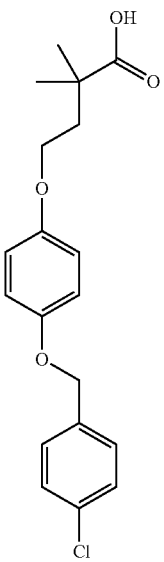 [SMILES: CC(C)(CCOc1ccc(OCc2ccc(Cl)cc2)cc1)C(=O)O] | 617 |
| 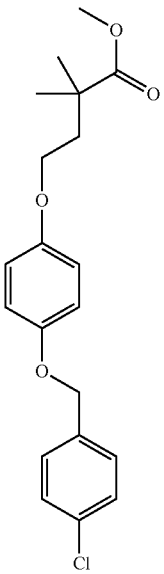 [SMILES: COC(=O)C(C)(C)CCOc1ccc(OCc2ccc(Cl)cc2)cc1] | 618 |

TABLE 12-continued
| Structure | |
|---|---|
| 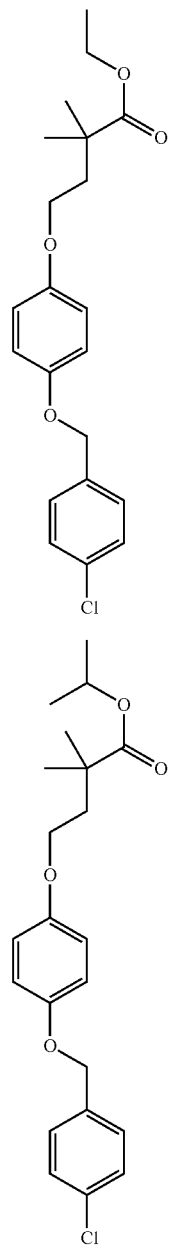 | 619 |
| | 620 |
TABLE 13
| Structure | |
|---|---|
| 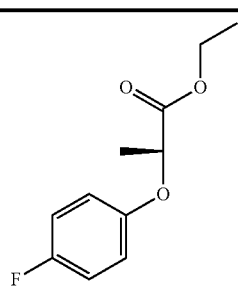 | 621 |
| 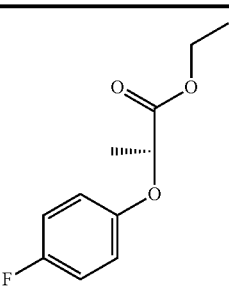 | 622 |
| 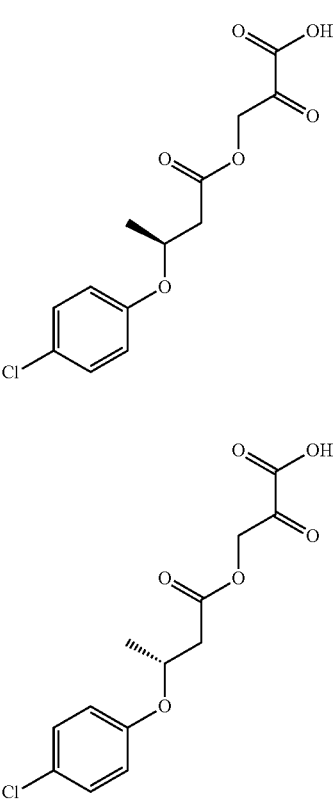 | 623 |
| | 624 |
| | 625 |
| 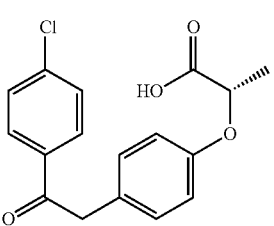 [SMILES: C[C@H](Oc1ccc(CC(=O)c2ccc(Cl)cc2)cc1)C(=O)O] | 626 |

TABLE 13-continued
Structure
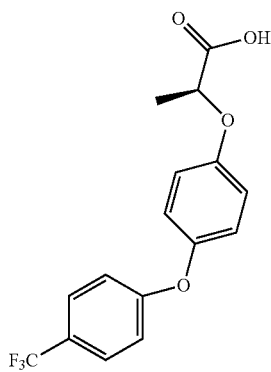 [SMILES: C[C@H](Oc1ccc(Oc2ccc(C(F)(F)F)cc2)cc1)C(=O)O]
627
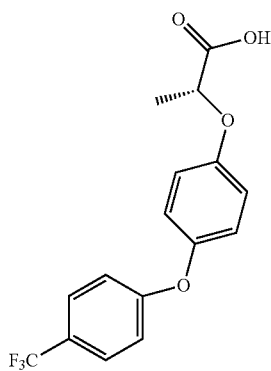 [SMILES: C[C@@H](Oc1ccc(Oc2ccc(C(F)(F)F)cc2)cc1)C(=O)O]
628
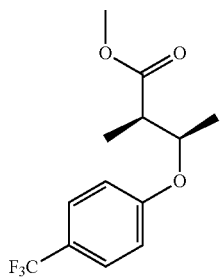 [SMILES: COC(=O)[C@H](C)[C@@H](C)Oc1ccc(C(F)(F)F)cc1]
629
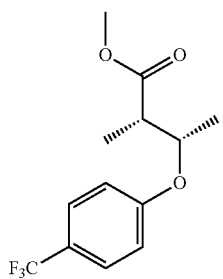 [SMILES: COC(=O)[C@@H](C)[C@H](C)Oc1ccc(C(F)(F)F)cc1]
630
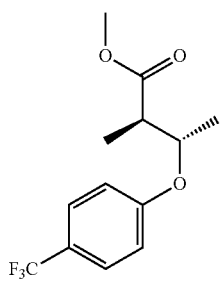 [SMILES: COC(=O)[C@H](C)[C@H](C)Oc1ccc(C(F)(F)F)cc1]
631
TABLE 13-continued
Structure
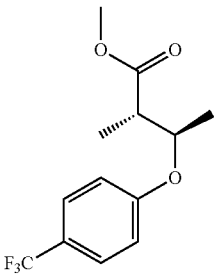 [SMILES: COC(=O)[C@@H](C)[C@@H](C)Oc1ccc(C(F)(F)F)cc1]
632
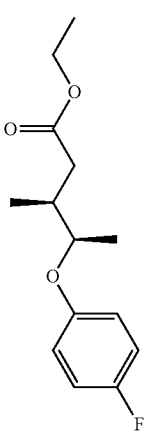 [SMILES: CCOC(=O)C[C@H](C)[C@@H](C)Oc1ccc(F)cc1]
633
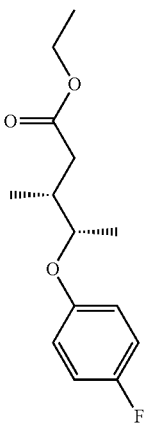 [SMILES: CCOC(=O)C[C@@H](C)[C@H](C)Oc1ccc(F)cc1]
634
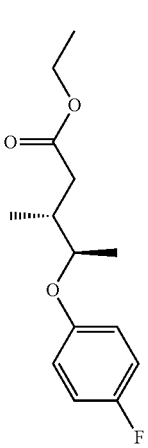 [SMILES: CCOC(=O)C[C@@H](C)[C@@H](C)Oc1ccc(F)cc1]
645

TABLE 13-continued
| Structure | |
|---|---|
| 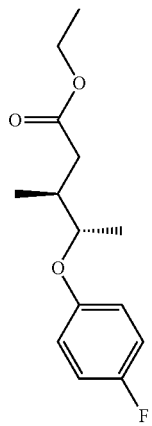 [SMILES: CCOC(=O)C[C@H](C)[C@H](C)Oc1ccc(F)cc1] | 636 |
| 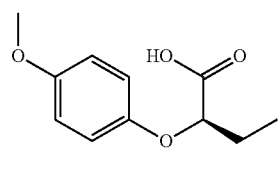 | 637 |
| 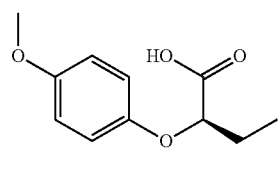 | 638 |
| 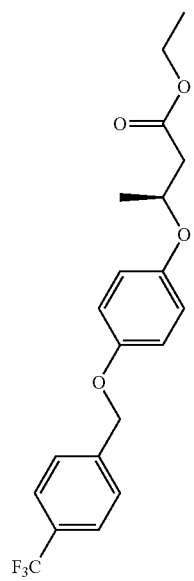 [SMILES: CCOC(=O)C[C@H](C)Oc1ccc(OCc2ccc(C(F)(F)F)cc2)cc1] | 639 |
TABLE 13-continued
| Structure | |
|---|---|
| 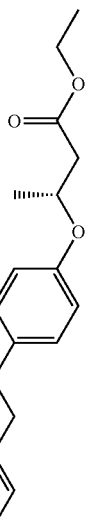 | 640 |
| 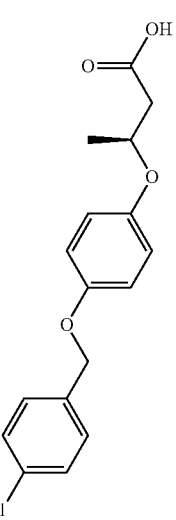 | 641 |
| 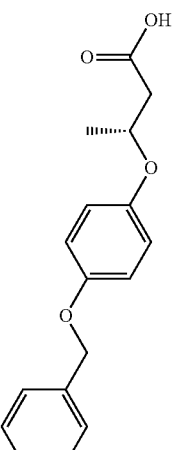 | 642 |

The formulations described in this application are useful for dermatological and cosmetic conditions and may be formulated as a pharmaceutical composition and administered to a mammal, such as a human patient, in a variety of forms adapted to a chosen route of administration, i.e. topically, intralesionally, or subcutaneously. The formulations described in this application useful for endothelial tissue conditions may also be formulated as a pharmaceutical composition and administered to a mammal, such as a human patient, intravenously. It should be understood that the invention is not limited by the chosen route of administration. The compound present may be administered alone or in combination with one or more other therapeutic agents.

In a typical embodiment the compound is administered as a formulation in association with a pharmaceutically acceptable carrier. The choice of carrier largely depends on factors such as the particular mode of administration, the effect of the carrier on solubility and stability, and the nature of the dosage form.

In some embodiments, the compound will be formulated with a carrier suitable for administration directly to the skin or hair.

In yet another embodiment, the compound is formulated with a carrier suitable for intravenous administration.

In other embodiments, the compound is topically applied to a subject. Topical application is especially appropriate for the treatment of acne, rosacea, excess sebum, oily skin or hair, and shiny or greasy looking skin. In certain embodiments, topical application refers to application of a compound, and optional carrier, directly to the skin and/or hair. The topical composition according to the present invention can be in the form of solutions, lotions, salves, creams, ointments, liposomes, sprays, gels, foams, roller sticks, or any other formulation routinely used in dermatology.

In other embodiments, compositions of the invention may be solid or semi-solid formulations which are suitable for use as cleansing soaps, gels, or bars. These compositions are prepared according to the usual methods and may optionally contain additional excipients such as moisturizers, colorants, fragrances, and the like.

The compound may also be formulated for application to the hair in the form of aqueous, alcoholic or aqueous-alcoholic solutions, or in the form of creams, gels, emulsions or mousses, or alternatively in the form of aerosol compositions also comprising a propellant under pressure. The composition according to the invention can also be a hair care composition, and in particular a shampoo, a hair-setting lotion, a treating lotion, a styling cream or gel, a dye composition, a lotion or gel for preventing hair loss, etc. The amounts of the excipients in the various compositions according to the invention are those conventionally used in the fields considered.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Gennaro (1995)).

II. METHODS OF INHIBITION OF CCL5 PRODUCTION BY CELLS

The compounds and compositions described herein inhibit the production of CCL5 by various types of mammalian cells present in epithelial and endothelial tissues. Non-limiting examples are inhibition of production of CCL5 by keratinocytes, respiratory epithelial cells, fibroblasts, and endothelial cells under conditions known to increase CCL5 gene expression and subsequent release CCL5 into the cellular or tissue milieu, as measured by various assays including immune based protein quantitation.

III. METHODS OF TREATMENT

CCL5 acts as a cytokine when secreted by cells and participates in pro-inflammation response, angiogenesis, leukocyte adhesion, and extravasation into tissues. Increased blood and/or tissue levels of CCL5 have been shown to contribute to disease pathogenesis and progression. Increased tissue or blood levels of CCL5 are directly contributory to the pathogenesis of: autoimmune diseases; inflammatory diseases; auto-inflammatory conditions; pain conditions; respiratory ailments; airway and pulmonary conditions; gastrointestinal disorders; allergic diseases; atopic disorders; eczematous conditions; infection-based diseases; trauma and tissue injury-based conditions; fibrotic diseases; ophthalmic/ocular diseases; joint, muscle, and bone disorders; skin/dermatological diseases; renal diseases; genetic diseases; hematopoietic diseases; liver diseases; oral diseases; metabolic diseases, including diabetes (e.g. Type II) and complications thereof; proliferative diseases; cardiovascular conditions; vascular conditions including restenosis; neuro-inflammatory conditions; neurodegenerative conditions; cancer; and pulmonary conditions. Thus, inhibition of CCL5 production has implications for treatment of many disorders with diverse primary etiologies.

With regard to the increased levels of secreted pro-inflammatory cytokines and chemokines produced by leukocytes, CCL5 through its interaction with its receptor(s) (known as CCL5, CCL3, CCL3L1, and CCL4), present on many types of leukocytes, causes the increased production of cytokines produced by leukocytes and especially monocytes such as Th1 and Th2 cells. Among the pro-inflammatory cytokines induced by CCL5 are: IL-1 beta, TNF-alpha, IL-6, and IFN-gamma. These increased pro-inflammatory cytokines and chemokines act to induce pathogenic processes in various non-leukocyte cells and are responsible for acute and chronic diseases and their complications such as, but not limited to; Atopic disorders, Autoimmune diseases, Carcinoma, Cardiac disorders, Dermatologic diseases, Fibrosis, Gastrointestinal disorders, Hepatic diseases, Infectious diseases, Inflammatory disorders, Metabolic disorders (e.g. diabetes), Nephropathies, Neoplasia, Neurodegenerative disorders, Ophthalmologic disorders, Osteoporosis, Pulmonary diseases, Urinary tract disorders, Vascular conditions including restenosis, and others. Inhibitions of the production of CCL5 by the compounds of the present invention reduce the tissue levels of these pro-inflammatory cytokines and chemokines produced by leukocytes and other cell types.

As used in this application, the terms "co-administered" or "co-administration" refer to a dosing regimen where the compound of Formula 1 is administered with a second therapeutic agent, typically having a differing mechanism of action, to promote a desired result. It should be understood that "co administration" is not limited by the route(s) of administration and can refer to simultaneous dosing, dosing at different times during a single day, or even dosing on different days. The compounds can be administered separately or can be combined into a single formulation (i.e. fixed combination).

In an embodiment of the present invention the compounds according to Formula 1 may be used either simultaneously or sequentially in combination with a second compound such as, but not limited to, those listed below to reduce the production of CCL5 by certain cells such as, but not limited to: keratinocytes, fibroblasts, respiratory epithelial cells, and endothelial cells under conditions that stimulate CCL5 production by such cells.

Non-steroidal anti-inflammatory drugs, such as but not limited to: aspirin, choline salicylate, celecoxib, acetaminophen, diclofenac, flurbiprofen, ibuprofen, indomethacin, ketoprofen, meclofenamate, mefenamic acid, nabumetone, naproxen, piroxicam, rofecoxib, salicylates, sulindac, tolmetin, and valdecoxib.

Immunomodulatory agents, such as but not limited to: methotrexate, azathioprine, mitoxantrone, cladribin, cyclophosphamide, tacrorimus, methotrexate, cyclosporine, and hydroxychloroquine.

Antimalarials, such as but not limited to: chloroquine, quinine, amodiaquine, pyrimethamine, proguanil, mefloquine, atovaquone, primaquine, artemisinin, and halofantrine.

Antibiotics, such as but not limited to: sulfonamides, clindamycin, members of the tetracycline family (including minocycline and doxycycline), erythromycin, and dapsone.

Anti-TNF alpha agents, such as but not limited to: infliximab, adalimumab, certolizumab pegol, golimumab, thalidomide, lenalidomide, pomalidomide, and etanercept.

Anti-CD20 agents, such as but not limited to: rituximab, obinutuzumab, Ibritumomab tiuxetan, and tositumomab.

Antidiarrheals, such as but not limited to: lidamidine, diphenoxylate, loperamide, and quercetin.

Antidepressants, such as but not limited to: amitriptyline, clomipramine, doxepin nortriptyline, and trimipramine.

Antipsychotics, such as but not limited to: droperidol, pimozide, chlorpromazine, thiothixene, loxapine, molindone, quetiapine, risperidone, sertindole, and zotepine.

Antifungals, such as but not limited to: clotimazole, flucisoconazole, abafungin, micafugin, terbinafine, ciclopirox, and tolnaftate.

Antihelminthics, such as but not limited to: mebendazole, levamisole, abamectin, and suramine T lymphocyte activation inhibitors, such as but not limited to: voclosporin, peroxynitrite, and dasatinib.

Anti-IL-1 agents, such as but not limited to: anakinra and IL-1Ra.

Glucocorticoids, such as but not limited to: methyl prednisolone, prednisolone, dexamethasone, betamethasone, fluticasone propionate, budesonide, flunisolide, mometasone furoate, triamcinolone acetonide, rofleponide, ciclesonide, and butixocort propionate.

Anti-cytokine/chemokine monoclonal antibodies, such as but not limited to: basiliximab, daclizumab, and secukinumab.

Sex steroids and receptor modulators, such as but not limited to: progesterone, progestins, androgen, estrogen, mifepristone, and misoprostil.

Anti-cellular surface receptor monoclonal antibodies directed against cell surface receptors such as but not limited: CCR1, CCR3, CCL3L1, CCL4, CCR5, IL7Ra, and TSLPR.

Aminosalicylic acid derivatives such as but not limited to: sulfasalazine and mesalazine.

Anticholinergic agents, such as but not limited to: ipratropium, oxitropium, tiotropium, dextromethorphan, revatropate, pirenzepine, darifenacin, oxybutynin, mecamylamine, terodiline, tolterodine, otilonium, trospium chloride, and solifenacin.

Adrenergic agonists, such as but not limited to: salmeterol, salbutamol, clonidine, oxymetazoline, and dolbutamine.

Cholineric agonists, such as but not limited to: carbachol, epibatidine, galantamine, nicotine, and varenicline.

Corticosteroids, such as but not limited to: cortisone and hydrocortisone.

Antineoplastic chemotherapeutic agents, such as but not limited to: cisplatin cyclophosphamide, bleomycin, doxorubicin, etoposide, folinic acid, and vincristine.

Phosphodiesterase inhibitors, such as but not limited to: mesembrenone, rolipram, Ibudilast, piclamilast, luteolin, drotaverine, roflumilast, cilomilast, apremilast, and crisaborole.

Leukotriene pathway modulators, such as but not limited to: 3-[3-butylsulfanyl-1-[(4-chlorophenyl)methyl]-5-propan-2-yl-indol-2-yl]-2,2-dimethyl-propanoic acid, baicalein, caffeic acid, curcumin, hyperforin, and zileuton.

Monoclonal antibodies directed against human immunoglobulins, such as but not limited to: omalizumab.

Adrenergic antagonists, such as but not limited to: alfluosin, idazoxan, labetalol, phentolamine, trazadone, propranolol, and atenolol.

Calcium channel antagonists, such as but not limited to: amelodipine, nifedapine, verapamil, diltiazem, and mibefradil.

Dopamine agonists, such as but not limited to: aripiprazole, bromocriptine, bupropion, cabergoline, lisuride, and roxindole.

Serotonin agonists, such as but not limited to: cabergoline, cisapride, gepirone, lorcaserin, and naratriptan.

Dopamine antagonists, such as but not limited to: amoxipine, bromopride, butaclamol, eticlopride, olanzapine, tiapride, and ziprasidone.

Serotonin antagonists, such as but not limited to: cyproheptadine, ketanserin, metergoline, methdilazine, oxetorone, and tropisetron.

Monoamine reuptake inhibitors, such as but not limited to: amineptine, citalopram, edivoxetine, hyperforin, mazindol, and viloxazine.

Protease inhibitors, such as but not limited to: amastatin, bestatin, and gabexate.

Histamine receptor antagonists, such as but not limited to: acrivastine, brompheniramine, cetirizine, cimetidine, ciproxifan, clobenprobit, cyclizine, carebastine, cyproheptadine, ebastine, epinastine, efletirizine, fexofenadine, and thioperamide.

Proton pump inhibitors, such as but not limited to; omeprazole, lansoprazole, pantoprazole, and rabeprazole.

HMG-CoA reductase inhibitors, such as but not limited to: atorvastatin, fluastatin, lovastatin, and simvastatin.

Retinoids such as, but not limited to, etretinate, tretinoin, retinol, retinyl palmitate, adapalene, tazarotene, and alitretinoin.

Administration of the therapeutic agent may be by any suitable means. In some embodiments, the one or more therapeutic agents are administered by oral administration. In some embodiments, the one or more therapeutic agents are administered by transdermal administration. In some embodiments, the one or more therapeutic agents are administered by injection or intravenous infusion. In one embodiment, the one or more therapeutic agents are administered topically to a mucosal, dermal, or ocular tissue.

If combinations of agents are administered as separate compositions, they may be administered by the same route or by different routes. If combinations of agents are administered in a single composition, they may be administered by any suitable route. In some embodiments, combinations of agents are administered as a single composition by oral administration. In some embodiments, combinations of agents are administered as a single composition by transdermal administration. In some embodiments, the combinations of agent are administered as a single composition by injection. In some embodiments, the combinations of agent are administered as a single composition topically.

In one embodiment of the present invention the compounds of Formula 1 may contain asymmetric or chiral centers and, therefore, exist in different stereoisomeric forms. For example, 2,2,2-trifluoroethyl 2-(4-methylphenoxy)propanoate is a compound according Formula 1 that possesses a chiral center at carbon atom number 8 and thus has two stereoisomer forms. It is intended that all stereoisomeric forms of the compounds of Formula 1 form part of the present invention, including but not limited to: diastereomers, enantiomers, and atropisomers as well as mixtures thereof, such as racemic mixtures. In addition, the present invention embraces all geometric and positional isomers. For example, if a compound of Formula 1 incorporates a double bond or a fused ring, both the cis- and trans-forms, as well as mixtures, are embraced within the scope of the invention. Both the single positional isomers and mixture of positional isomers are also within the scope of the present invention.

In one embodiment of the present invention, compounds of Formula 1 may exist in different tautomeric forms, and all such forms are embraced within the scope of the invention, as defined by the claims.

The dose and dosing regimens of the compound present in the invention may be adjusted to provide the optimum desired response in accordance with methods and practices well known in the therapeutic arts. For example, a single bolus dose may be administered, or several divided doses may be administered over time. The dose may also be proportionally reduced or increased as indicated by the exigencies of the therapeutic situation. The appropriate dosing regimen, the amount of each dose administered and/or the intervals between doses will depend upon a number of factors, including: the compound, the type of pharmaceutical composition, the characteristics of the subject in need of treatment and the severity of the condition being treated.

The dose of the compound will vary, but as a general guideline for dermatological administration, the compound will be present in a dermatologically acceptable formulation in a therapeutically effective dose in an amount of from about 0.001 mg/kg to about 1000 mg/kg/body weight per day of a compound provided herein. The pharmaceutical compositions therefore should provide a dosage of from about 0.001 mg/kg/body weight to about 1000 mg/kg/body weight of the compound for some conditions. In another embodiment of the present invention the pharmaceutical dosage unit forms are prepared to provide a preparation for topical application containing 0.01 to 50 w/w %, and more typically from about 0.1 to 10 w/w %. In yet other embodiments the pharmaceutical dosage unit forms are prepared to provide a preparation for topical application containing from 0.01% to 30% (w/v) of the compounds.

In some embodiments, the formulation may be applied to the affected area from 1 to 4 times daily. A "dermatologically acceptable formulation" is one that may be applied to the skin or hair and will allow the drug to diffuse to the site of action.

The dose of the compound will also vary for endothelial tissue administration, but as a general guideline for endothelial administration, the compound will be present in an endothelially acceptable formulation in a therapeutically effective dose in an amount of from about 500 picomolar (pM) to 300 millimolar (mM).

The skilled artisan can also be expected to readily determine the maximum tolerable dose, the therapeutically effective amount which provides a detectable therapeutic benefit to a patient, and the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

The determination of optimal dosages for a particular patient is well-known to those skilled in the art. Certain non-limiting examples of pharmaceutically acceptable vehicles suitable for topical administration include propylene glycol:transcutanol:ethanol (20:20:60, v/v/v) and propylene glycol:ethanol (30:70, v/v). In some embodiments, the compound of Formula 1 may be present at concentrations of between about 1.5% to about 2.0% (w/v).

In another embodiment, the medicinal and cosmetic formulations containing the compound and any additional therapeutic agents will typically be packaged for retail distribution (i.e. an article of manufacture or a kit). Such articles will be labeled and packaged in a manner to instruct the patient how to use the product. Such instructions will include the condition to be treated, duration of treatment, dosing schedule, etc. The compound(s) of Formula 1 may also be admixed with any inert carrier and utilized in laboratory assays in order determine the concentration of the compounds within the serum, urine, etc., of the patient as is known in the art. The compound may also be used as a research tool.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention belongs. The following examples and biological data are being presented in order to further illustrate the invention. This disclosure should not be construed as limiting the invention in any manner.

For all of the foregoing embodiments, each embodiment disclosed herein is contemplated as being applicable to each of the other disclosed embodiments. Those skilled in the art will readily appreciate that the specific Experimental Details which follow are only illustrative of the invention as described more fully in the claims which follow thereafter.

IV. EXAMPLES

To determine the ability of compounds according to Formula 1 to inhibit CCL5 production using a functional assay, cultivated human keratinocytes, endothelial cells were treated with known stimulants of CCL5 production and the gene expression and production of CCL5 protein were determined by well-known methods as described below.

Human keratinocyte cells (NEHK) from healthy volunteers were obtained and cultivated at $1 \times 10^6$ cells/ml using 6 well plates in NEHK-GM media according to supplier's protocol (MatTek Inc., Ashland, Mass. 01721). Human bronchial epithelial cells (NHBE) were obtained and cultivated at $1 \times 10^6$ cells/ml using 6 well plates in NHBE-GM media according to supplier's protocol (MatTek Inc. Ashland, Mass. 01721). Human umbilical vein endothelial cells (HUVEC) were obtained and cultivated at 1×10$^6$ cells/ml using 6 well plates in supplemented Medium 200 according to supplier's protocol (ThermoFisher-Invitrogen Carlsbad Calif. 92008). Human cell suspensions without stimulation agents known to induce CCL5 production were used as a baseline control for the experiments. Cell cultures were treated with various exemplar compounds according to Formula 1 at several concentrations for 6 hours prior to stimulation by CCL5 inducing agents. The cultures of NHEK, NHBE, and HUVEC were then stimulated with various known stimulators of CCL5 production that consisted of: Poly [I:C] 10 ug/ml (see FIG. 1a and FIG. 2a), Flagellin 10 ug/ml (Invivogen, San Diego, Calif.; see FIG. 1b) and TNF alpha 1 ug/ml (Invivogen, San Diego, Calif.; see FIG. 2b, FIG. 3, and FIG. 4) for 24-48 hrs). Measurement of CCL5 gene expression was determined from total RNA extracted from cell pellets after incubation by RNAseq quantitation method standardized using expression of housekeeping genes as reference standard. CCL5 protein production was measured in the cell culture supernatants after incubation using the CCL5 ELISA kit (R&D Systems, Minneapolis, Minn.).

To determine the ability of compounds according to Formula 1 to inhibit the biological effect of CCL5 to induce the transcription of genes and production of corresponding proteins known to be upregulated by CCL5 on binding to its cellular receptors using a functional assay, freshly isolated human PBMCs or CD14+ monocytes from healthy volunteers were isolated and cultured at 1×106 cells/ml in RPMI-1640 medium (GIBCO® Inc. Carlsbad, Calif., USA) supplemented with 20% fetal bovine serum and 1% streptomycin/penicillin. The cultures of PBMC, CD+14 monocytes were stimulated with 300 ng/ml of human CCL5 (R&D SYSTEMS®, Minneapolis, Minn. USA) for 4 hrs. Cell suspensions without CCL5 stimulation were used as a baseline control for the experiments. Cell cultures were treated with various exemplar compounds according to Formula 1 at several concentrations. As a known positive control for CCL5 pathway inhibition, a blocking antibody to human CCL5 (R&D SYSTEMS®, Minneapolis, Minn. USA) was used (10 ug/ml) that prevents binding of CCL5 to its receptors, thereby blocking signal transduction through the CCL5 signaling pathways thus inhibiting its biological activity. After 24 hours total RNA was extracted from cell pellets and mRNA was quantitated using expression of housekeeping genes as reference standard. IL-8 and MMP-19 protein production was measured in the cell culture supernatants after incubation using ELISA (R&D Systems, Minneapolis, Minn.).

To test the effect of the compounds on treatment of human dermatologic disorders associated with increased CCL5 production by keratinocytes, Compound 11 and Compound 21 were formulated into a topically applied cream at a concentration of 7%. The compounds in the cream base were applied topically to human subjects suffering from dermatitis in an area of the skin with active skin lesions. The control was the topical cream base composition without the active compounds. Outcome was measured by reduction or disappearance to the lesion in the treated area vs the control area.

Hidradenitis: Three patients with discrete lesions of hidradenitis were treated with topically applied Compound 20 twice per day for a period of 21 days. An additional 4 patients were treated with Compound 16 in a similar fashion and 3 others with Compound 97 in the same way. In all treatment groups the lesions treated with the compounds in the cream base decreased and resolved by the 28th day, whereas the lesions on the same patients treated with the cream base control did not resolve.

Eczema: Four patients with hand and facial eczema were treated with Compound 97 topically applied in a cream base over a period of 14 days. By day 7 the eczema had resolved in the area treated in three of the patients and by day 12 in the fourth patient. The eczema persisted in the areas not so treated.

Rosacea: Two patients with rosacea were treated with Compound 25 for 28 days in a lotion form. At the end of the course of therapy the rosacea had nearly disappeared in the treated area, but not in the areas untreated.

To test the effect of the compounds on treatment of human endothelial disorders such as abnormal angiogenesis associated with increased CCL5 levels. Compound 10 and Compound 21 were formulated into a topically applied solution of 1%. The compounds in the solution were applied topically to cultivated human endothelial cells induced to form tubes formed in vitro by CCL5. The control was the topical base solution without the active compounds. Outcome was measured by reduction or lack of formation of the endothelial tubes in the endothelial tube formation assay, which is a human model for abnormal angiogenesis (ThermoFisher-InvitroGen Carlsbad Calif. 92008).

The results of the experiments and clinical tests herein demonstrate that compounds according to Formula 1 inhibit the production of CCL5 from human epithelial and endothelial cells and tissues. In addition, they demonstrate a clinical therapeutic effect in patients suffering from a dermatologic disorder associated with production of CCL5 from keratinocytes and on CCL5 driven angiogenesis. Therefore, the compounds according to Formula 1 are useful in treatment of inflammatory disorders associated with increased CCL5 production by epithelial and endothelial tissues including but not limited to: dermatitis, eczema, rosacea and abnormal angiogenesis induced by CCL5.

REFERENCES

1. Murphy (2002) Pharmacol Rev 54:227-229
2. Allen et al. (2007) Annu Rev Immunol 25:787-820
3. Russo et al. (2010) Curr Opin Drug Discov Devel 13:414-27
4. Murphy (1994) Annu Rev Immunol 12:593-633
   Schein et al. (1988) J Immunol 141:1018-25
6. Zhebrun et al. (2014) Bull Exp Biol Med. 158(2):192-6
7. Chihara et at (1997) J Allergy Clin Immunol. 100(6 Pt 2):S52-5
8. Toebak et al. (2006) Toxicol In Vitro. 20(1):117-24
9. Tanaka et al. (2006) Int J Immunogenet. 33(6):423-8
10. Tanaka et al. (2006) Int J Immunogenet. 33(6):423-8
11. Nickel et al. (2000) J Immunol. 164(3):1612-6
12. Antinolo et al. (2003) Mol Hum Reprod. 9(8):491-5
13. Iijima et al. (2003) Am J Pathol. 163(1):261-8
14. Yamamoto et al. (2013) Dis Markers. 34(3):153-61
15. Szodoray et al. (2004) Scand J Immunol. 59(6):592-9
16. Chen et al. (2004) Tissue Antigens 63(1):41-5
17. Turner et al. (2014) Biochem Biophys ACTA 1843(11): 2563-2582
18. Lin et al. (2012) Cancer Sci. 103(5):904-12
19. Mitchell and Olive (2010) Mol Immunol. 47(11-12): 2065-73
20. Murdoch and Finn (2000) Blood 15; 95(10):3032-43
21. Camargo et al. (2009) J Immunol. 182(1):171-82
22. Nickel et al. (2000) J Immunol. 164(3):1612-6
23. Makki et al. (2000) Clin Exp Rheumatol. 18(3):391-3

What is claimed is:

1. A method of treating a disorder or condition affecting the epithelium and/or endothelium comprising administering to an area of cells exhibiting the disorder or condition of a mammalian subject in need thereof a therapeutically effective amount of a compound according to Formula 1 or a tautomer thereof

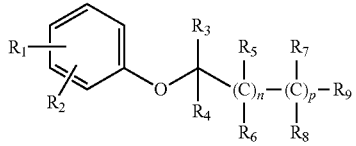

Formula 1 wherein:

n and p are independently selected from 0 or 1;

$R_1$ and $R_2$ are independently selected H, OH, F, Cl, Br, I, (halogen)alkyl, $C_1$-$C_8$ straight or branched chain alkyl, $C_1$-$C_8$ cycloalkyl, heterocycloalkyl, alkylheterocycloalkyl, optionally substituted $C_1$-$C_8$ alkenyl optionally substituted $C_1$-$C_8$ alkynyl, optionally substituted aryl, optionally substituted alkylaryl, optionally substituted heteroaryl, optionally substituted alkylheteroaryl, O-alkyl, O-cycloalkyl, O-alkylcycloalkyl, O-aryl, O-optionally substituted aryl, alkyl-O-aryl, alkyl-O-optionally substituted aryl, C(O)-aryl, C(O)-optionally substituted aryl, $CH_2C(O)$-aryl, $CH_2C(O)$-optionally substituted aryl, O-(halogen)alkyl;

$R_3$, $R_4$, $R_5$, $R_6$, $R_7$, and $R_8$, if present, are independently selected from H, $C_1$-$C_8$ straight or branded chain alkyl, $C_1$-$C_8$ cycloakyl, heterocycloalkyl, alkylheterocycloalkyl, optionally substituted $C_1$-$C_8$ alkenyl, optionally substituted $C_1$-$C_8$ alkynyl, optionally substituted aryl, optionally substituted alkylaryl, optionally substituted heteroaryl, or optionally substituted alkylheteroaryl, and/or adjacent substitutents $R_1$ and $R_2$, $R_3$ and $R_4$, $R_5$ and $R_6$, $R_7$ and $R_8$, if present, may form Ft saturated or unsaturated 3-7 membered carbocyclic or heterocyclic ring;

$R_9$ is selected front $B(OH)_2$, $B(OR_{10})(OR_{11})$;

$R_{10}$ and $R_{11}$, if present, are independently selected from optionally substituted alkyl, cycloalkyl, alkylcycloalkyl, and/or when $R_{10}$ and $R_{11}$ are present and adjacent to each other can together front an alkyl bridged 5 or 6 membered heterocyclic ring, or a pharmaceutically acceptable salt, ester or prodrug form thereof.

2. The method according to claim 1, further comprising a second compound selected from the group consisting of Non-steroidal anti-inflammatory drugs, Immunomodulatory agents, Anti-malarials, Antibiotics, Anti-TNF alpha agents, Anti-CD20 agents, Anti-diarrheal drugs, Antidepressants, Anti-psychotics, Anti-fungals, Anti-helminthics, T lymphocyte activation inhibitors, Anti-IL-1 agents, Glucocorticoids, Anti-cytokine/chemokine monoclonal antibodies, Sex steroids and receptor modulators, Anti-cellular surface receptor monoclonal antibodies, Aminosalicylic acid derivatives, Anticholinergic agents, Adrenergic agonists, Corticosteroids, Anti-neoplastic chemotherapeutic agents, Phosphodiesterase inhibitors, Leukotriene pathway modulators, Monoclonal antibodies directed against human immunoglobulins, Adrenergic antagonists, Calcium channel antagonists, Dopamine agonists, Serotonin agonists, Dopamine antagonists, Serotonin antagonists, Monoamine reuptake inhibitors, Protease inhibitors, Histamine antagonists, Proton pump inhibitors, and HMG-CoA reductase inhibitors.

3. The method according to claim 1, wherein the disorder is Alopecia, Asthma, Atopic Dermatitis (AD), Dermatitis, Bronchiolitis, Bronchiolitis Obliterans Syndrome, Chronic Obstructive Pulmonary Disease, Dry Eye Syndrome, Dermatomyositis, Eczema, Esophagitis, Colitis, Hidradenitis, Idiopathic Pulmonary Fibrosis, Macular degeneration, Nasal Polyps, Retinopathy, Rosacea, Scleroderma, Sjogren's syndrome, and/or Vitiligo.

4. The method according to claim 1, wherein the endothelial disorder is abnormal angiogenesis.

5. The method according to claim 1, wherein the cells are human cells.

6. The method according to claim 5, wherein the human cells are keratinocytes, leukocytes, or endothelial cells.

7. A method of inhibiting the biological activity of CCL5 on mammalian cells comprising administering to a mammalian subject in need thereof a therapeutically effective amount of a compound according to Formula 1 or a tautomer thereof

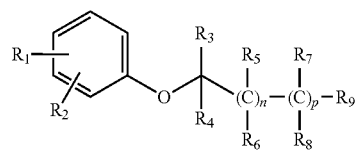

Formula 1 wherein:

n and p are independently selected from 0 or 1;

$R_1$ and $R_2$ are independently selected from H, OH, F, Cl, Br, I, (halogen)alkyl, $C_1$-$C_8$ straight or branched chain alkyl, $C_1$-$C_8$ cycloalkyl, heterocycloalkyl, alkylheterocycloalkyl, optionally substituted $C_1$-$C_8$ alkenyl, optionally substituted $C_1$-$C_8$ alkynyl, optionally substituted aryl, optionally substituted alkylaryl, optionally substituted heteroaryl, optionally substituted alkylheteroaryl, O-alkyl, O-cycloalkyl, O-alkylcycloalkyl, O-aryl, O-optionally substituted aryl, alkyl-O-aryl, alkyl-O-optionally substituted aryl, C(O)-aryl, C(O)-optionally substituted aryl, $CH_2C(O)$-aryl, $CH_2C(O)$-optionally substituted aryl, O-(halogen)alkyl;

$R_3$, $R_4$, $R_5$, $R_6$, $R_7$, and $R_8$, if present, are independently selected from H, $C_1$-$C_8$ straight or branched chain alkyl, $C_1$-$C_8$ cycloalkyl, heterocycloalkyl, alkylheterocycloalkyl, optionally substituted $C_1$-$C_8$ alkenyl, optionally substituted $C_1$-$C_8$ alkynyl, optionally substituted aryl, optionally substituted alkylaryl, optionally substituted heteroaryl, or optionally substituted alkylheteroaryl, and/or adjacent substituents $R_1$ and $R_2$, $R_3$ and $R_4$, $R_5$ and $R_6$, $R_7$ and $R_8$, if present, may form a saturated or unsaturated 3-7 membered carbocyclic or heterocyclic ring;

$R_9$ selected from $B(OH)_2$, $B(OR_{10})(OR_{11})$;

$R_{10}$ and $R_{11}$, if present, are independently selected from optionally substituted alkyl, cycloalkyl, alkylcycloalkyl, and/or when $R_{10}$ and $R_{11}$ are present and adjacent to each other can together from an alkyl bridged 5 or 6 membered heterocyclic ring, or a pharmaceutically acceptable salt, ester or prodrug form thereof.

8. A method of treating a disease or condition affecting the endothelium and/or endothelium associated with the increase levels of CCL5 by administering to the area of cells exhibiting the disease or condition of a mammalian subject in need thereof a therapeutically effective amount of a compound according to Formula 1 or a tautomer thereof

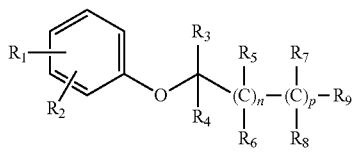

Formula 1 wherein:

n and p are independently selected from 0 or 1;

$R_1$ and $R_2$ are independently selected from H, OH, F, Cl, Br, I, (halogen)alkyl, $C_1$-$C_8$ straight or branched chain alkyl, $C_1$-$C_8$ cycloalkyl, heterocycloalkyl, alkylheterocycloalkyl, optionally substituted $C_1$-$C_8$ alkenyl, optionally substituted $C_1$-$C_8$ alkynyl, optionally substituted aryl, optionally substituted alkylaryl, optionally substituted heteroaryl, optionally substituted alkylheteroaryl, O-alkyl, O-cycloalkyl, O-alkylcycloalkyl, O-aryl, O-optionally substituted aryl, alkyl-O-aryl, alkyl-O-optionally substituted aryl, C(O)-aryl, C(O)-optionally substituted aryl, $CH_2C(O)$-aryl, $CH_2C(O)$-optionally substituted aryl, O-(halogen)alkyl;

$R_3$, $R_4$, $R_5$, $R_6$, $R_7$, and $R_8$, if present, are independently selected from H, $C_1$-$C_8$ straight or branched chain alkyl, $C_1$-$C_8$ cycloalkyl, heterocycloalkyl, alkylheterocycloalkyl, optionally substituted $C_1$-$C_8$ alkenyl, optionally substituted $C_1$-$C_8$ alkynyl, optionally substituted aryl, optionally substituted alkylaryl, optionally substituted heteroaryl, or optionally substituted alkylheteroaryl, and/or adjacent substituents $R_1$ and $R_2$, $R_3$ and $R_4$, $R_5$ and $R_6$, $R_7$ and $R_8$, if present, may form a saturated or unsaturated 3-7 membered carbocyclic or heterocyclic ring;

$R_9$ selected from $B(OH)_2$, $B(OR_{10})(OR_{11})$;

$R_{10}$ and $R_{11}$, if present, are independently selected from optionally substituted alkyl, cycloalkyl, alkylcycloalkyl, and/or when $R_{10}$ and $R_{11}$ are present and adjacent to each other can together from an alkyl bridged 5 or 6 membered heterocyclic ring, or a pharmaceutically acceptable salt, ester or prodrug form thereof.

9. The method according to claim 7, further comprising administering at least one other compound selected from the group consisting of: Non-steroidal anti-inflammatory drugs, Immunomodulatory agents, Anti-malarials, Antibiotics, Anti-TNF alpha agents, Anti-CD20 agents, Anti-diarrheal drugs, Antidepressants, Anti-psychotics, Anti-fungals, Antihelminthics, T lymphocyte activation inhibitors, Anti-IL-1 agents, Glucocorticoids, Anti-cytokine/chemokine monoclonal antibodies, Sex steroids and receptor modulators, Anti-cellular surface receptor monoclonal antibodies, Aminosalicylic acid derivatives, Anticholinergic agents, Adrenergic agonists, Corticosteroids, Anti-neoplastic chemotherapeutic agents, Glucose modulators such as insulin, glyburide, and metformin, Phosphodiesterase inhibitors, Leukotriene pathway modulators, Monoclonal antibodies directed against human immunoglobulins, Adrenergic antagonists, Calcium channel antagonists, Dopamine agonists, Serotonin agonists, Dopamine antagonists, Serotonin antagonists, Monoamine reuptake inhibitors, Protease inhibitors, Histamine antagonists, Proton pump inhibitors, and HMG-CoA reductase inhibitors.

10. The method according to claim 7, wherein the cells are human cells.

* * * * *

UNITED STATES PATENT AND TRADEMARK OFFICE
CERTIFICATE OF CORRECTION

| | | |
|---|---|---|
| PATENT NO. | : 11,497,724 B2 | Page 1 of 1 |
| APPLICATION NO. | : 17/580429 | |
| DATED | : November 15, 2022 | |
| INVENTOR(S) | : Bruce Kovacs | |

It is certified that error appears in the above-identified patent and that said Letters Patent is hereby corrected as shown below:

In the Claims

At Column 235, Claim 8, Line 2, delete first reference to "endothelium" and insert -- epithelium --

Signed and Sealed this
Tenth Day of June, 2025

Coke Morgan Stewart
*Acting Director of the United States Patent and Trademark Office*